US009446125B2

(12) United States Patent
Zhou et al.

(10) Patent No.: US 9,446,125 B2

(45) Date of Patent: *Sep. 20, 2016

(54) ANTI-EPHA2 ANTIBODIES AND METHODS OF USE THEREOF

(71) Applicant: The Regents of the University of California, Oakland, CA (US)

(72) Inventors: Yu Zhou, San Francisco, CA (US); James D. Marks, Kensington, CA (US)

(73) Assignee: THE REGENTS OF THE UNIVERSITY OF CALIFORNIA, BERKE, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,077

(22) Filed: Aug. 18, 2015

(65) Prior Publication Data

US 2015/0343081 A1 Dec. 3, 2015

Related U.S. Application Data

(63) Continuation of application No. 13/810,638, filed as application No. PCT/US2011/045069 on Jul. 22, 2011, now Pat. No. 9,220,772.

(60) Provisional application No. 61/366,823, filed on Jul. 22, 2010.

(51) Int. Cl.

| | |
|---|---|
| ***A61K 39/395*** | (2006.01) |
| ***C07K 16/30*** | (2006.01) |
| ***C07K 16/46*** | (2006.01) |
| ***A61K 47/48*** | (2006.01) |
| ***C07K 16/28*** | (2006.01) |
| ***C07K 16/40*** | (2006.01) |

(52) U.S. Cl.

CPC ... *A61K 39/39558* (2013.01); *A61K 47/48215* (2013.01); *C07K 16/2866* (2013.01); *C07K 16/2884* (2013.01); *C07K 16/30* (2013.01); *C07K 16/40* (2013.01); *C07K 16/464* (2013.01); *C07K 2317/10* (2013.01); *C07K 2317/21* (2013.01); *C07K 2317/34* (2013.01); *C07K 2317/55* (2013.01); *C07K 2317/622* (2013.01); *C07K 2317/77* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 6,001,356 | A | 12/1999 | Mikecz et al. | |
| 2003/0049683 | A1 * | 3/2003 | Bowdish | C07K 14/505 435/7.1 |
| 2003/0059937 | A1 | 3/2003 | Ruben et al. | |
| 2004/0028685 | A1 | 2/2004 | Kinch et al. | |
| 2004/0091486 | A1 | 5/2004 | Kinch et al. | |
| 2004/0110933 | A1 | 6/2004 | Rondon et al. | |
| 2005/0260710 | A1 * | 11/2005 | Suzuki | C07K 16/00 435/69.1 |
| 2006/0123504 | A1 * | 6/2006 | Leavitt | A01K 67/0275 800/19 |
| 2006/0177453 | A1 | 8/2006 | Mather et al. | |
| 2006/0246523 | A1 * | 11/2006 | Bieniarz | A61K 47/48338 435/7.92 |
| 2009/0247540 | A1 | 10/2009 | Wang et al. | |
| 2010/0143345 | A1 | 6/2010 | Kinch et al. | |
| 2010/0183618 | A1 * | 7/2010 | Hasegawa | C07K 16/2866 424/139.1 |

FOREIGN PATENT DOCUMENTS

| | | | |
|---|---|---|---|
| WO | WO 2004024750 | | 3/2004 |
| WO | WO 2006060419 | | 6/2006 |
| WO | WO 2006084226 | | 8/2006 |
| WO | WO 2007030642 | | 3/2007 |
| WO | WO 2008040348 | | 4/2008 |
| WO | WO2009/028639 | * | 3/2009 |
| WO | WO 2010054010 | | 5/2010 |

OTHER PUBLICATIONS

GenBank Accession No. NP_000601.3 "CD44 antigen isoform 1 precursor [*Homo sapiens*]" dated Jul. 18, 2010.

GenBank Accession No. NP_004422.2 "ephrin type-A receptor 2 precursor [*Homo sapiens*]" dated Jul. 18, 2010.

GenBank Deposition AF317001.1 "Synthetic construct HCV-E2 single chain Fv antibody mRNA, complete cds" dated Feb. 28, 2003.

Hamilton et al. (2007) "The hyaluronan receptors CD44 and Rhamm (CD168) form complexes with ERK1,2 that sustain high basal motility in breast cancer cells" *J Biol Chem* 282(22):16667-16680.

Neve et al. (2006) "A collection of breast cancer cell lines for the study of functionally distinct cancer subtypes" *Cancer Cell* 10(6):515-527.

UniProt Accession No. P16070 "RecName: Full=CD44 antigen; AltName: Full=Phagocytic glycoprotein I; Short=PGP-I; AltName: Full=Phagocytic glycoprotein 1; Short=PGP-1; AltName: Full=HUTCH-I; AltName: Full=Extracellular matrix receptor III; Short=ECMR-III; AltName: Full=GP90 lymphocyte homing/adhesion receptor; AltName: Full=Hermes antigen; AltName: Full=Hyaluronate receptor; AltName: Full=Heparan sulfate proteoglycan; AltName: Full=Epican; AltName: Full=CDw44; AltName: CD_antigen=CD44; Flags: Precursor" dated Jul. 13, 2010.

(Continued)

*Primary Examiner* — Michael D Allen

(74) *Attorney, Agent, or Firm* — Bozicevic, Field & Francis LLP; Carol Francis

(57) ABSTRACT

Antibodies that bind to tumor associated antigen CD44 or to tumor associated antigen EphA2, are disclosed herein, as well as related compositions and methods of use. Methods of use encompass cancer therapies, diagnostics, and screening methods.

17 Claims, 85 Drawing Sheets

(56) References Cited

OTHER PUBLICATIONS

UniProt Accession No. P29317 "RecName: Full=Ephrin type-A receptor 2; AltName: Full=Epithelial cell kinase; AltName: Full=Tyrosine-protein kinase receptor ECK; Flags: Precursor" dated Jul. 15, 2010.
Zhou et al. (2010) "Internalizing cancer antibodies from phage libraries selected on tumor cells and yeast-displayed tumor antigens" *J Mol Biol* 404(1):88-99.
Abraham, et al., (2006) "Expression of EphA2 and Ephrin A-1 in Carcinoma of the Urinary Bladder", Clinical Cancer Research, 12(2):353-360.
Baxevanis, C. (2008), "Antibody-based cancer therapy", Expert Opinion: Drug Discovery, 3(4):441-452.
Polyak, et al., (2002) "Alanine-170 and proline-172 are critical determinants for extracellular CD20 epitopes; heterogeneity in the fine specificity of CD20 monoclonal antibodies is defined by additional requirements imposed by both amino acid sequence and quaternary structure", Blood, 99(9):3256-3262.
Mundodzana, D., et al, (1998) "Conformational Dependence of Anaplasma marginale Major Surface Protein 5 Surface-Exposed B-Cell Epitopes", Infection and Immunity, 66(6):2619-2624.
Paul, William E., (1993) "Structure and Function of Immunoglobulins", Fundamental Immunilogy 3rd Edition, Raven Press, New York, Chapter 9, pp. 292-295.
Bendig, Mary M., (1995) "Humanization of rodent monoclonal antibodies by CDR grafting", Methods: A Companion to Methods in Enzymology, 8(2):83-93.
Rudikoff, Stuart, et al. (1982) "Single amino acid substitution altering antigen-binding specificity." Proceedings of the National Academy of Sciences 79(6):1979-1983.
Panka, David, J., et al., (1988) "Variable region framework differences result in decreased or increased affinity of variant anti-digoxin antibodies", Proceedings of the National Academy of Sciences USA, 85:3080-3084.
Wall, R. J. (1996) "Transgenic livestock: progress and prospects for the future." Theriogenology 45(1):57-68.
Houdebine, Louis-Marie. (1994) "Production of pharmaceutical proteins from transgenic animals." Journal of biotechnology 34(3):269-287.
Kappel, Catherine A., et al. (1992), "Regulating gene expression in transgenic animals." Current opinion in biotechnology 3(5):548-553.
O'Connell, David, et al. (2002)"Phage versus phagemid libraries for generation of human monoclonal antibodies." Journal of molecular biology 321(1):49-56.
Hatano, Manabu, et al., (2004), "Vaccination with EphA2-derived T cell epitopes promotes immunity against both EphA2-expressing and EphA2-negative tumors", J. Trans. Med., 2(1):40.

* cited by examiner

Anti-CD44: $V_H$

| Clone | FR1 | CDR1 | FR2 |
|---|---|---|---|
| F2-1A6 | QVQLVQSGAEVKKPGESLKISCKGSGYSFT | SYWIG | WVRQMPGKGLEWMG |
| F2-1H9 | QVQLQESGGGLVQPGGSLRLSCAASGFTFS | SYRMH | WVRQAPGKGLEWVA |

| | CDR2 | FR3 |
|---|---|---|
| F2-1A6 | IIYPGDSDTRYSPSFQG | QVTISADKSISTAYLQWSSLKASDTAMYYCAR |
| F2-1H9 | AVKQDGSEKYYLDSVKG | RFTISRDNAKSSLYLQMDSLSVEDTAVYYCAR |

| | CDR3 | FR4 | |
|---|---|---|---|
| F2-1A6 | RLHGPFYFDY | WGQGTLVTVSS | (SEQ ID NO:96) |
| F2-1H9 | GLRT | MGQGTLVTVSS | (SEQ ID NO:97) |

Anti-CD44: $V_L$

| | FR1 | CDR1 | FR2 |
|---|---|---|---|
| F2-1A6 | SELTQDPAVSVALGQTVRITC | QGDSLRSYYAS | WYQQKPGQAPLLVIY |
| F2-1H9 | SELTQDPAVSVALGQTVRITC | QGDSLRSYYAS | WYQRKPGQAPLLVIY |

| | CDR2 | FR3 |
|---|---|---|
| F2-1A6 | GKNIRPS | GIPDRFSGSSSGNTASLTITGAQAEDEADYYC |
| F2-1H9 | GKNIRPS | GIPDRFSGSSSGNTASLIITGAQAEDEADYYC |

| | CDR3 | FR4 | |
|---|---|---|---|
| F2-1A6 | NSRDSSGNHVV | FGGGTKLTVLG | (SEQ ID NO:98) |
| F2-1H9 | NSRDSSANQM | FGGGTKLTVLG | (SEQ ID NO:99) |

FIG. 7

Anti-EphA2: $V_H$

| Clone | FR1 | CDR1 | FR2 |
|---|---|---|---|
| 2D6 | QVQLQESGGGLVQPGGSLRLSCAASGFTFS | SYAMS | WVRQAPGKGLDWVS |
| D2-1A7 | QVQLQQSGGGVVQPGRSLRLSCAASGFTFS | SYAMH | WVRQAPGKGLEWVA |
| D2-1A9 | QVQLVESGGGLIQPGGSLKLSCAASGFTVS | NSYMS | WVRQAPGKGLEWVA |
| D2-1B1 | QVQLQESGGGVVQPGRSLRLSCAASGFTFS | SYGMH | WVRQAPGKGLEWVA |

| | CDR2 | FR3 |
|---|---|---|
| 2D6 | IIYNGDNTYYADSVKG | RFTISRDNSKNSLYLQMNSLRAEDTAVYYCAR |
| D2-1A7 | VISYDGSNKYYADSVKG | RFTISRDNSKNTLYLQMNSLRAEDTAVYYCAR |
| D2-1A9 | VIYSAGNTYYADSVKG | RFTISRDTSNNTVHLQMNSLRPEDTAVYYCAR |
| D2-1B1 | VISYDGSNKYYADSVKG | RFTISRDNSKNTLYLQMNSLRAEDTAVYYCAK |

| | CDR3 | FR4 |
|---|---|---|
| 2D6 | WSGTSYDY | WGQGTLVTVSS (SEQ ID NO:100) |
| D2-1A7 | ASVGATGPFDI | WGQGTMVTVSS (SEQ ID NO:101) |
| D2-1A9 | EGSFGYDY | RGQGTLVTVSS (SEQ ID NO:102) |
| D2-1B1 | VIAGGAYYGSADY | WGQGTLVTVSS (SEQ ID NO:103) |

Anti-EphA2: $V_L$

| Clone | FR1 | CDR1 | FR2 |
|---|---|---|---|
| 2D6 | SELTQDPAVSVALGQTVRITC | QGDSLRSYYAS | WYQQKPGQAPLLVIY |
| D2-1A7 | SELTQDPAVSVALGQTVSITC | QGDSLRSYYAS | WYQQKPGQAPLLVIY |
| D2-1A9 | DIVMTQSPGTLSLSPGERATLSC | RASQSVSSSFLG | WYQQKPGQAPRLLIY |
| D2-1B1 | SELTQDPAVSVALGQTVKITC | QGDSLRTYYAS | WYQQKPGQAPVLVIY |

| | CDR2 | FR3 |
|---|---|---|
| 2D6 | GENNRPS | GIPDRFSGSSSGNTASLTITGAQAEDEADYYC |
| D2-1A7 | GENNRPS | GIPDRFSGSSSGNTASLTITGAQAEDEADYYC |
| D2-1A9 | GASSRAT | GIPDRFSGSGSGTDFTLTISRLEPEDFAVYYC |
| D2-1B1 | GENSRPS | GIPDRFSGSSSGNTASLTITGAQAEDEADYYC |

| | CDR3 | FR4 |
|---|---|---|
| 2D6 | HSRDSSGTHLRV | FGGGTKVTVLG (SEQ ID NO:104) |
| D2-1A7 | NSRDSSGTHLTV | FGGGTKLTVLG (SEQ ID NO:105) |
| D2-1A9 | QQYGISPLT | FGGGTKVEIKR (SEQ ID NO:106) |
| D2-1B1 | HSRDSSGTHLRV | FGGGTKLTVLG (SEQ ID NO:107) |

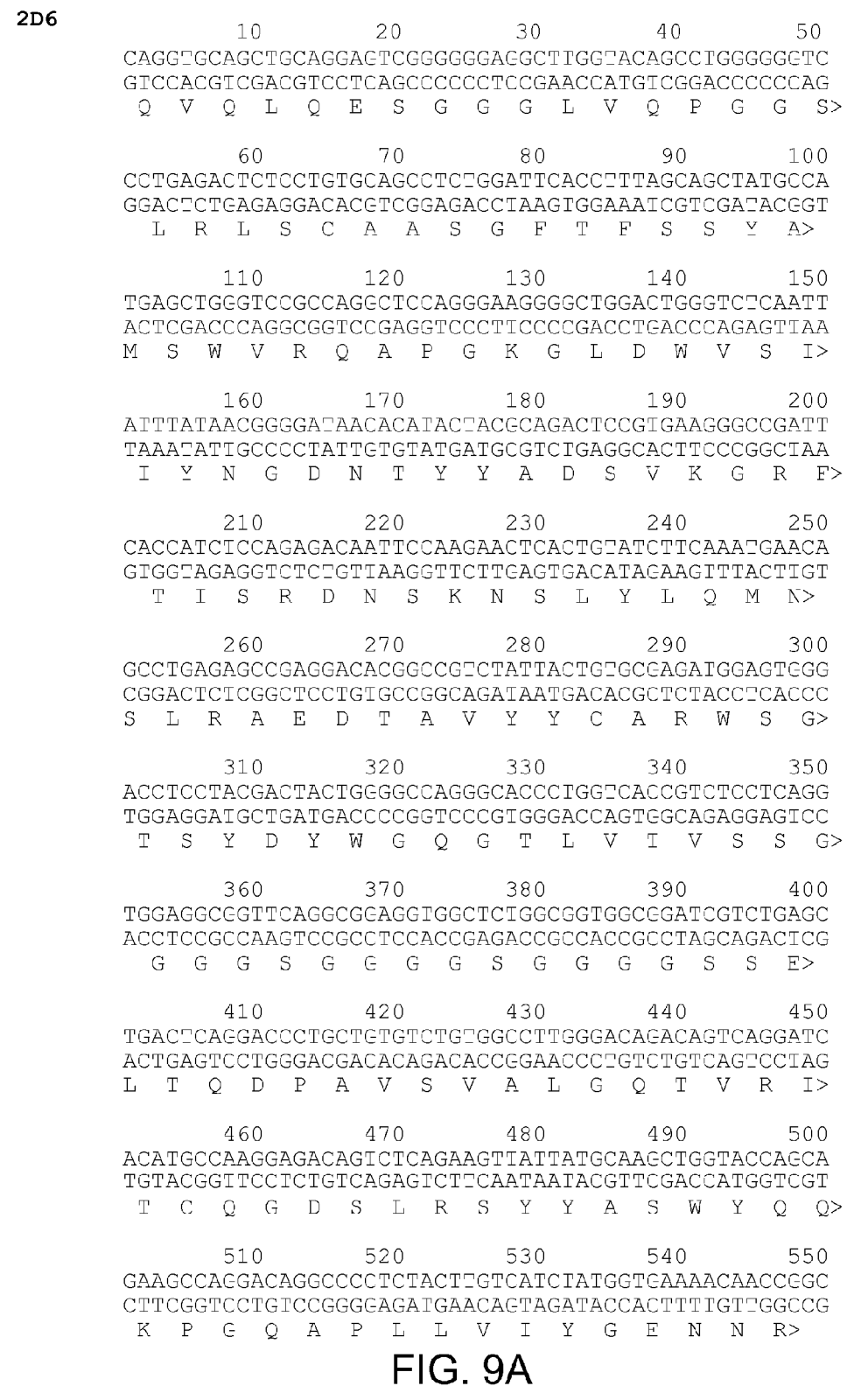

```
        10        20        30        40        50
CAGGTGCAGCTGCAGGAGTCGGGGGGAGGCTTGGTACAGCCTGGGGGGTC
GTCCACGTCGACGTCCTCAGCCCCCCTCCGAACCATGTCGGACCCCCCAG
 Q  V  Q  L  Q  E  S  G  G  G  L  V  Q  P  G  G  S>

        60        70        80        90       100
CCTGAGACTCTCCTGTGCAGCCTCTGGATTCACCTTTAGCAGCTATGCCA
GGACTCTGAGAGGACACGTCGGAGACCTAAGTGGAAATCGTCGATACGGT
  L  R  L  S  C  A  A  S  G  F  T  F  S  S  Y  A>

       110       120       130       140       150
TGAGCTGGGTCCGCCAGGCTCCAGGGAAGGGGCTGGACTGGGTCTCAATT
ACTCGACCCAGGCGGTCCGAGGTCCCTTCCCCGACCTGACCCAGAGTTAA
M  S  W  V  R  Q  A  P  G  K  G  L  D  W  V  S  I>

       160       170       180       190       200
ATTTATAACGGGGATAACACATACTACGCAGACTCCGTGAAGGGCCGATT
TAAATATTGCCCCTATTGTGTATGATGCGTCTGAGGCACTTCCCGGCTAA
 I  Y  N  G  D  N  T  Y  Y  A  D  S  V  K  G  R  F>

       210       220       230       240       250
CACCATCTCCAGAGACAATTCCAAGAACTCACTGTATCTTCAAATGAACA
GTGGTAGAGGTCTCTGTTAAGGTTCTTGAGTGACATAGAAGTTTACTTGT
  T  I  S  R  D  N  S  K  N  S  L  Y  L  Q  M  N>

       260       270       280       290       300
GCCTGAGAGCCGAGGACACGGCCGTCTATTACTGTGCGAGATGGAGTGGG
CGGACTCTCGGCTCCTGTGCCGGCAGATAATGACACGCTCTACCTCACCC
S  L  R  A  E  D  T  A  V  Y  Y  C  A  R  W  S  G>

       310       320       330       340       350
ACCTCCTACGACTACTGGGGCCAGGGCACCCTGGTCACCGTCTCCTCAGG
TGGAGGATGCTGATGACCCCGGTCCCGTGGGACCAGTGGCAGAGGAGTCC
 T  S  Y  D  Y  W  G  Q  G  T  L  V  T  V  S  S  G>

       360       370       380       390       400
TGGAGGCGGTTCAGGCGGAGGTGGCTCTGGCGGTGGCGGATCGTCTGAGC
ACCTCCGCCAAGTCCGCCTCCACCGAGACCGCCACCGCCTAGCAGACTCG
  G  G  G  S  G  G  G  G  S  G  G  G  G  S  S  E>

       410       420       430       440       450
TGACTCAGGACCCTGCTGTGTCTGTGGCCTTGGGACAGACAGTCAGGATC
ACTGAGTCCTGGGACGACACAGACACCGGAACCCTGTCTGTCAGTCCTAG
L  T  Q  D  P  A  V  S  V  A  L  G  Q  T  V  R  I>

       460       470       480       490       500
ACATGCCAAGGAGACAGTCTCAGAAGTTATTATGCAAGCTGGTACCAGCA
TGTACGGTTCCTCTGTCAGAGTCTTCAATAATACGTTCGACCATGGTCGT
 T  C  Q  G  D  S  L  R  S  Y  Y  A  S  W  Y  Q  Q>

       510       520       530       540       550
GAAGCCAGGACAGGCCCCTCTACTTGTCATCTATGGTGAAAACAACCGGC
CTTCGGTCCTGTCCGGGGAGATGAACAGTAGATACCACTTTTGTTGGCCG
 K  P  G  Q  A  P  L  L  V  I  Y  G  E  N  N  R>
```

FIG. 9A

```
        560       570       580       590       600
CCTCAGGGATCCCAGACCGATTCTCTGGCTCCAGCTCAGGAAACACAGCT
GGAGTCCCTAGGGTCTGGCTAAGAGACCGAGGTCGAGTCCTTTGTGTCGA
P  S  G  I  P  D  R  F  S  G  S  S  S  G  N  T  A>

        610       620       630       640       650
TCCTTGACCATCACTGGGGCTCAGGCGGAAGATGAGGCTGACTATTACTG
AGGAACTGGTAGTGACCCCGAGTCCGCCTTCTACTCCGACTGATAATGAC
 S  L  T  I  T  G  A  Q  A  E  D  E  A  D  Y  Y  C>

        660       670       680       690       700
TCACTCCCGGGACAGCAGTGGTACCCATCTAAGGGTGTTCGGCGGAGGGA
AGTGAGGGCCCTGTCGTCACCATGGGTAGATTCCCACAAGCCGCCTCCCT
  H  S  R  D  S  S  G  T  H  L  R  V  F  G  G  G>

        710       720
CCAAGGTCACCGTCCTAGGT (SEQ ID NO:108)
GGTTCCAGTGGCAGGATCCA (SEQ ID NO:109)
T  K  V  T  V  L  G> (SEQ ID NO:110)
```

FIG. 9B

```
D2-1A7          10        20        30        40        50
        CAGGTACAGCTGCAGCAGTCAGGGGGAGGCGTGGTCCAGCCTGGGAGGTC
        GTCCATGTCGACGTCGTCAGTCCCCCTCCGCACCAGGTCGGACCCTCCAG
         Q  V  Q  L  Q  Q  S  G  G  G  V  V  Q  P  G  R  S>

                60        70        80        90       100
        CCTGAGACTCTCCTGTGCAGCCTCTGGATTCACCTTCAGTAGCTATGCTA
        GGACTCTGAGAGGACACGTCGGAGACCTAAGTGGAAGTCATCGATACGAT
          L  R  L  S  C  A  A  S  G  F  T  F  S  S  Y  A>

               110       120       130       140       150
        TGCACTGGGTCCGCCAGGCTCCAGGCAAGGGGCTGGAGTGGGTGGCAGTT
        ACGTGACCCAGGCGGTCCGAGGTCCGTTCCCCGACCTCACCCACCGTCAA
        M  H  W  V  R  Q  A  P  G  K  G  L  E  W  V  A  V>

               160       170       180       190       200
        ATATCATATGATGGAAGCAATAAATACTACGCAGACTCCGTGAAGGGCCG
        TATAGTATACTACCTTCGTTATTTATGATGCGTCTGAGGCACTTCCCGGC
         I  S  Y  D  G  S  N  K  Y  Y  A  D  S  V  K  G  R>

               210       220       230       240       250
        ATTCACCATCTCCAGAGACAATTCCAAGAACACGCTGTATCTGCAAATGA
        TAAGTGGTAGAGGTCTCTGTTAAGGTTCTTGTGCGACATAGACGTTTACT
          F  T  I  S  R  D  N  S  K  N  T  L  Y  L  Q  M>

               260       270       280       290       300
        ACAGCCTGAGAGCTGAGGACACGGCTGTGTATTACTGTGCGAGAGCTAGC
        TGTCGGACTCTCGACTCCTGTGCCGACACATAATGACACGCTCTCGATCG
        N  S  L  R  A  E  D  T  A  V  Y  Y  C  A  R  A  S>

               310       320       330       340       350
        GTCGGGGCTACGGGGCCTTTTGATATCTGGGGCCAAGGGACAATGGTCAC
        CAGCCCCGATGCCCCGGAAAACTATAGACCCCGGTTCCCTGTTACCAGTG
         V  G  A  T  G  P  F  D  I  W  G  Q  G  T  M  V  T>

               360       370       380       390       400
        CGTCTCTTCAGGTGGAGGCGGTTCAGGCGGAGGTGGCTCTGGCGGTGGCG
        GCAGAGAAGTCCACCTCCGCCAAGTCCGCCTCCACCGAGACCGCCACCGC
          V  S  S  G  G  G  G  S  G  G  G  G  S  G  G  G>

               410       420       430       440       450
        GATCGTCTGAGCTGACTCAGGACCCTGCTGTGTCTGTGGCCTTGGGACAG
        CTAGCAGACTCGACTGAGTCCTGGGACGACACAGACACCGGAACCCTGTC
        G  S  S  E  L  T  Q  D  P  A  V  S  V  A  L  G  Q>

               460       470       480       490       500
        ACAGTCAGCATCACATGCCAAGGAGACAGCCTCAGAAGCTATTATGCAAG
        TGTCAGTCGTAGTGTACGGTTCCTCTGTCGGAGTCTTCGATAATACGTTC
         T  V  S  I  T  C  Q  G  D  S  L  R  S  Y  Y  A  S>
```

FIG. 10A

```
       510       520       530       540       550
CTGGTACCAGCAGAAGCCAGGACAGGCCCCTCTACTTGTCATCTATGGTG
GACCATGGTCGTCTTCGGTCCTGTCCGGGGAGATGAACAGTAGATACCAC
  W  Y  Q  Q  K  P  G  Q  A  P  L  L  V  I  Y  G>

       560       570       580       590       600
AAAACAACCGGCCCTCAGGGATCCCAGACCGATTTTCTGGCTCCAGCTCA
TTTTGTTGGCCGGGAGTCCCTAGGGTCTGGCTAAAAGACCGAGGTCGAGT
E  N  N  R  P  S  G  I  P  D  R  F  S  G  S  S  S>

       610       620       630       640       650
GGAAACACAGCTTCCTTGACCATCACTGGGGCTCAGGCGGAAGATGAGGC
CCTTTGTGTCGAAGGAACTGGTAGTGACCCCGAGTCCGCCTTCTACTCCG
 G  N  T  A  S  L  T  I  T  G  A  Q  A  E  D  E  A>

       660       670       680       690       700
TGACTATTACTGTAACTCCCGGGACAGCAGTGGTACGCATTTGACGGTGT
ACTGATAATGACATTGAGGGCCCTGTCGTCACCATGCGTAAACTGCCACA
  D  Y  Y  C  N  S  R  D  S  S  G  T  H  L  T  V>

       710       720
TCGGCGGAGGGACCAAGCTGACCGTCCTAGGT (SEQ ID NO:111)
AGCCGCCTCCCTGGTTCGACTGGCAGGATCCA (SEQ ID NO:112)
F  G  G  G  T  K  L  T  V  L  G> (SEQ ID NO:113)
```

```
         10        20        30        40        50
CAGGTGCAGCTGGTGGAGTCTGGAGGAGGCTTGATCCAGCCTGGGGGGTC
GTCCACGTCGACCACCTCAGACCTCCTCCGAACTAGGTCGGACCCCCCAG
 Q  V  Q  L  V  E  S  G  G  G  L  I  Q  P  G  G  S>

         60        70        80        90       100
CCTGAAACTCTCCTGTGCAGCCTCTGGGTTCACCGTCAGTAACAGCTACA
GGACTTTGAGAGGACACGTCGGAGACCCAAGTGGCAGTCATTGTCGATGT
  L  K  L  S  C  A  A  S  G  F  T  V  S  N  S  Y>

        110       120       130       140       150
TGAGCTGGGTCCGCCAGGCTCCAGGGAAGGGGCTGGAGTGGGTCGCAGTT
ACTCGACCCAGGCGGTCCGAGGTCCCTTCCCCGACCTCACCCAGCGTCAA
M  S  W  V  R  Q  A  P  G  K  G  L  E  W  V  A  V>

        160       170       180       190       200
ATTTATAGCGCTGGTAACACATACTACGCAGACTCCGTGAAGGGCCGATT
TAAATATCGCGACCATTGTGTATGATGCGTCTGAGGCACTTCCCGGCTAA
 I  Y  S  A  G  N  T  Y  Y  A  D  S  V  K  G  R  F>

        210       220       230       240       250
CACCATCTCCAGAGACACTTCCAACAACACGGTGCATCTTCAAATGAACA
GTGGTAGAGGTCTCTGTGAAGGTTGTTGTGCCACGTAGAAGTTTACTTGT
  T  I  S  R  D  T  S  N  N  T  V  H  L  Q  M  N>

        260       270       280       290       300
GCCTGAGACCCGAAGACACGGCCGTGTATTACTGTGCGAGAGAGGGCAGC
CGGACTCTGGGCTTCTGTGCCGGCACATAATGACACGCTCTCTCCCGTCG
S  L  R  P  E  D  T  A  V  Y  Y  C  A  R  E  G  S>

        310       320       330       340       350
TTTGGTTACGACTACAGGGGCCAGGGAACCCTGGTCACCGTCTCCTCAGG
AAACCAATGCTGATGTCCCCGGTCCCTTGGGACCAGTGGCAGAGGAGTCC
 F  G  Y  D  Y  R  G  Q  G  T  L  V  T  V  S  S  G>

        360       370       380       390       400
TGGAGGCGGTTCAGGCGGAGGTGGCTCTGGCGGTGGCGGATCGGACATCG
ACCTCCGCCAAGTCCGCCTCCACCGAGACCGCCACCGCCTAGCCTGTAGC
  G  G  G  S  G  G  G  G  S  G  G  G  G  S  D  I>

        410       420       430       440       450
TGATGACCCAGTCTCCAGGCACCCTGTCTTTGTCTCCAGGGGAAAGAGCC
ACTACTGGGTCAGAGGTCCGTGGGACAGAAACAGAGGTCCCCTTTCTCGG
V  M  T  Q  S  P  G  T  L  S  L  S  P  G  E  R  A>

        460       470       480       490       500
ACCCTCTCCTGCAGGGCCAGTCAGAGTGTTAGCAGCAGCTTCTTAGGCTG
TGGGAGAGGACGTCCCGGTCAGTCTCACAATCGTCGTCGAAGAATCCGAC
 T  L  S  C  R  A  S  Q  S  V  S  S  S  F  L  G  W>
```

FIG. 11A

```
       510       520       530       540       550
GTACCAACAGAAACCTGGCCAGGCTCCCAGGCTCCTCATCTATGGTGCAT
CATGGTTGTCTTTGGACCGGTCCGAGGGTCCGAGGAGTAGATACCACGTA
  Y  Q  Q  K  P  G  Q  A  P  R  L  L  I  Y  G  A>

       560       570       580       590       600
CCAGCAGGGCCACTGGCATCCCAGACAGGTTCAGTGGCAGTGGGTCTGGG
GGTCGTCCCGGTGACCGTAGGGTCTGTCCAAGTCACCGTCACCCAGACCC
S  S  R  A  T  G  I  P  D  R  F  S  G  S  G  S  G>

       610       620       630       640       650
ACAGACTTCACTCTCACCATCAGCAGACTGGAGCCTGAAGATTTTGCAGT
TGTCTGAAGTGAGAGTGGTAGTCGTCTGACCTCGGACTTCTAAAACGTCA
 T  D  F  T  L  T  I  S  R  L  E  P  E  D  F  A  V>

       660       670       680       690       700
GTATTACTGTCAGCAGTATGGTATCTCACCGCTCACTTTCGGCGGAGGGA
CATAATGACAGTCGTCATACCATAGAGTGGCGAGTGAAAGCCGCCTCCCT
  Y  Y  C  Q  Q  Y  G  I  S  P  L  T  F  G  G  G>

       710       720
CCAAGGTGGAAATCAAACGT (SEQ ID NO:114)
GGTTCCACCTTTAGTTTGCA (SEQ ID NO:115)
T  K  V  E  I  K  R> (SEQ ID NO:116)
```

```
        10        20        30        40        50
CAGGTGCAGCTGCAGGAGTCGGGGGGAGGCGTGGTCCAGCCTGGGAGGTC
GTCCACGTCGACGTCCTCAGCCCCCCTCCGCACCAGGTCGGACCCTCCAG
 Q  V  Q  L  Q  E  S  G  G  G  V  V  Q  P  G  R  S>

        60        70        80        90       100
CCTGAGACTCTCCTGTGCAGCCTCTGGATTCACCTTCAGTAGCTATGGCA
GGACTCTGAGAGGACACGTCGGAGACCTAAGTGGAAGTCATCGATACCGT
  L  R  L  S  C  A  A  S  G  F  T  F  S  S  Y  G>

       110       120       130       140       150
TGCACTGGGTCCGCCAGGCTCCAGGCAAGGGGCTGGAGTGGGTGGCAGTT
ACGTGACCCAGGCGGTCCGAGGTCCGTTCCCCGACCTCACCCACCGTCAA
M  H  W  V  R  Q  A  P  G  K  G  L  E  W  V  A  V>

       160       170       180       190       200
ATATCATATGATGGAAGTAATAAATACTATGCAGACTCCGTGAAGGGCCG
TATAGTATACTACCTTCATTATTTATGATACGTCTGAGGCACTTCCCGGC
 I  S  Y  D  G  S  N  K  Y  Y  A  D  S  V  K  G  R>

       210       220       230       240       250
ATTCACCATCTCCAGAGACAATTCCAAGAACACGCTGTATCTGCAAATGA
TAAGTGGTAGAGGTCTCTGTTAAGGTTCTTGTGCGACATAGACGTTTACT
  F  T  I  S  R  D  N  S  K  N  T  L  Y  L  Q  M>

       260       270       280       290       300
ACAGCCTGAGAGCTGAGGACACGGCTGTGTATTACTGTGCGAAAGTAATA
TGTCGGACTCTCGACTCCTGTGCCGACACATAATGACACGCTTTCATTAT
N  S  L  R  A  E  D  T  A  V  Y  Y  C  A  K  V  I>

       310       320       330       340       350
GCGGGGGGGGCTTACTATGGTTCAGCTGACTACTGGGGCCAGGGAACCCT
CGCCCCCCCCGAATGATACCAAGTCGACTGATGACCCCGGTCCCTTGGGA
 A  G  G  A  Y  Y  G  S  A  D  Y  W  G  Q  G  T  L>

       360       370       380       390       400
GGTCACCGTCTCCTCAGGTGGAGGCGGTTCAGGCGGAGGTGGCTCTGGCG
CCAGTGGCAGAGGAGTCCACCTCCGCCAAGTCCGCCTCCACCGAGACCGC
  V  T  V  S  S  G  G  G  G  S  G  G  G  G  S  G>

       410       420       430       440       450
GTGGCGGATCGTCTGAGCTGACTCAGGACCCTGCTGTGTCTGTGGCCTTG
CACCGCCTAGCAGACTCGACTGAGTCCTGGGACGACACAGACACCGGAAC
G  G  G  S  S  E  L  T  Q  D  P  A  V  S  V  A  L>

       460       470       480       490       500
GGACAGACAGTCAAGATCACATGCCAAGGAGACAGCCTCAGAACCTATTA
CCTGTCTGTCAGTTCTAGTGTACGGTTCCTCTGTCGGAGTCTTGGATAAT
 G  Q  T  V  K  I  T  C  Q  G  D  S  L  R  T  Y  Y>
```

FIG. 12A

```
        510         520         530         540         550
TGCAAGCTGGTACCAGCAGAAGCCAGGACAGGCCCCTGTACTTGTCATCT
ACGTTCGACCATGGTCGTCTTCGGTCCTGTCCGGGGACATGAACAGTAGA
  A  S  W  Y  Q  Q  K  P  G  Q  A  P  V  L  V  I>

        560         570         580         590         600
ATGGTGAAAACAGCCGGCCCTCCGGGATCCCAGACCGATTCTCTGGCTCC
TACCACTTTTGTCGGCCGGGAGGCCCTAGGGTCTGGCTAAGAGACCGAGG
Y  G  E  N  S  R  P  S  G  I  P  D  R  F  S  G  S>

        610         620         630         640         650
AGCTCAGGAAACACAGCTTCCTTGACCATCACTGGGGCTCAGGCGGAAGA
TCGAGTCCTTTGTGTCGAAGGAACTGGTAGTGACCCCGAGTCCGCCTTCT
 S  S  G  N  T  A  S  L  T  I  T  G  A  Q  A  E  D>

        660         670         680         690         700
TGAGGCTGACTATTACTGTCACTCCCGGGACAGCAGTGGTACCCATCTAA
ACTCCGACTGATAATGACAGTGAGGGCCCTGTCGTCACCATGGGTAGATT
  E  A  D  Y  Y  C  H  S  R  D  S  S  G  T  H  L>

        710         720         730
GGGTGTTCGGCGGAGGGACCAAGCTGACCGTCCTAGGT (SEQ ID NO:117)
CCCACAAGCCGCCTCCCTGGTTCGACTGGCAGGATCCA (SEQ ID NO:118)
R  V  F  G  G  G  T  K  L  T  V  L  G> (SEQ ID NO:119)
```

FIG. 12B

```
F2-1A6          10         20         30         40         50
        CAGGTGCAGCTGGTGCAGTCTGGGGCAGAGGTGAAAAAGCCCGGGGAGTC
        GTCCACGTCGACCACGTCAGACCCCGTCTCCACTTTTTCGGGCCCCTCAG
         Q  V  Q  L  V  Q  S  G  A  E  V  K  K  P  G  E  S>

                60         70         80         90        100
        TCTGAAGATCTCCTGTAAGGGTTCTGGATACAGCTTTACCAGTTACTGGA
        AGACTTCTAGAGGACATTCCCAAGACCTATGTCGAAATGGTCAATGACCT
          L  K  I  S  C  K  G  S  G  Y  S  F  T  S  Y  W>

               110        120        130        140        150
        TCGGCTGGGTGCGCCAGATGCCCGGGAAAGGCCTGGAGTGGATGGGGATC
        AGCCGACCCACGCGGTCTACGGGCCCTTTCCGGACCTCACCTACCCCTAG
        I  G  W  V  R  Q  M  P  G  K  G  L  E  W  M  G  I>

               160        170        180        190        200
        ATCTATCCTGGTGACTCTGATACCAGATACAGCCCGTCCTTCCAAGGCCA
        TAGATAGGACCACTGAGACTATGGTCTATGTCGGGCAGGAAGGTTCCGGT
         I  Y  P  G  D  S  D  T  R  Y  S  P  S  F  Q  G  Q>

               210        220        230        240        250
        GGTCACCATCTCAGCCGACAAGTCCATCAGCACCGCCTACCTGCAGTGGA
        CCAGTGGTAGAGTCGGCTGTTCAGGTAGTCGTGGCGGATGGACGTCACCT
          V  T  I  S  A  D  K  S  I  S  T  A  Y  L  Q  W>

               260        270        280        290        300
        GCAGCCTCAAGGCCTCGGACACCGCCATGTATTACTGTGCGAGGCGACTA
        CGTCGGAGTTCCGGAGCCTGTGGCGGTACATAATGACACGCTCCGCTGAT
        S  S  L  K  A  S  D  T  A  M  Y  Y  C  A  R  R  L>

               310        320        330        340        350
        CACGGACCTTTCTACTTTGACTACTGGGGCCAGGGAACCCTGGTCACCGT
        GTGCCTGGAAAGATGAAACTGATGACCCCGGTCCCTTGGGACCAGTGGCA
         H  G  P  F  Y  F  D  Y  W  G  Q  G  T  L  V  T  V>

               360        370        380        390        400
        CTCCTCAGGTGGAGGCGGTTCAGGCGGAGGTGGCTCTGGCGGTGGCGGAT
        GAGGAGTCCACCTCCGCCAAGTCCGCCTCCACCGAGACCGCCACCGCCTA
          S  S  G  G  G  G  S  G  G  G  G  S  G  G  G  G>

               410        420        430        440        450
        CGTCTGAGCTGACTCAGGACCCTGCTGTGTCTGTGGCCTTGGGACAGACA
        GCAGACTCGACTGAGTCCTGGGACGACACAGACACCGGAACCCTGTCTGT
        S  S  E  L  T  Q  D  P  A  V  S  V  A  L  G  Q  T>

               460        470        480        490        500
        GTCAGAATCACATGCCAAGGAGACAGCCTCAGAAGCTATTATGCAAGTTG
        CAGTCTTAGTGTACGGTTCCTCTGTCGGAGTCTTCGATAATACGTTCAAC
         V  R  I  T  C  Q  G  D  S  L  R  S  Y  Y  A  S  W>
```

FIG. 13A

```
        510         520         530         540         550
GTACCAGCAGAAGCCAGGACAGGCCCCTCTCCTTGTCATCTATGGTAAAA
CATGGTCGTCTTCGGTCCTGTCCGGGGAGAGGAACAGTAGATACCATTTT
  Y  Q  Q  K  P  G  Q  A  P  L  L  V  I  Y  G  K>

        560         570         580         590         600
ACATCCGGCCCTCAGGGATCCCAGACCGATTCTCTGGCTCCAGCTCAGGA
TGTAGGCCGGGAGTCCCTAGGGTCTGGCTAAGAGACCGAGGTCGAGTCCT
N  I  R  P  S  G  I  P  D  R  F  S  G  S  S  S  G>

        610         620         630         640         650
AACACAGCTTCCTTGACCATCACTGGGGCTCAGGCGGAAGATGAGGCTGA
TTGTGTCGAAGGAACTGGTAGTGACCCCGAGTCCGCCTTCTACTCCGACT
 N  T  A  S  L  T  I  T  G  A  Q  A  E  D  E  A  D>

        660         670         680         690         700
CTATTACTGTAACTCCCGGGACAGCAGTGGTAACCATGTGGTATTCGGCG
GATAATGACATTGAGGGCCCTGTCGTCACCATTGGTACACCATAAGCCGC
  Y  Y  C  N  S  R  D  S  S  G  N  H  V  V  F  G>

        710         720
GAGGGACCAAGCTGACCGTCCTAGGT (SEQ ID NO:120)
CTCCCTGGTTCGACTGGCAGGATCCA (SEQ ID NO:121)
G  G  T  K  L  T  V  L  G> (SEQ ID NO:122)
```

```
         10        20        30        40        50
CAGGTGCAGCTGCAGGAGTCGGGGGGAGGCTTGGTCCAGCCTGGGGGGTC
GTCCACGTCGACGTCCTCAGCCCCCCTCCGAACCAGGTCGGACCCCCCAG
 Q  V  Q  L  Q  E  S  G  G  G  L  V  Q  P  G  G  S>

         60        70        80        90       100
CCTGAGACTCTCCTGTGCAGCCTCTGGATTCACCTTTAGTAGCTATCGGA
GGACTCTGAGAGGACACGTCGGAGACCTAAGTGGAAATCATCGATAGCCT
  L  R  L  S  C  A  A  S  G  F  T  F  S  S  Y  R>

        110       120       130       140       150
TGCACTGGGTCCGCCAGGCTCCAGGGAAGGGGCTGGAGTGGGTGGCCGCC
ACGTGACCCAGGCGGTCCGAGGTCCCTTCCCCGACCTCACCCACCGGCGG
M  H  W  V  R  Q  A  P  G  K  G  L  E  W  V  A  A>

        160       170       180       190       200
GTAAAGCAAGATGGAAGTGAGAAGTACTATTTGGACTCTGTGAAGGGCCG
CATTTCGTTCTACCTTCACTCTTCATGATAAACCTGAGACACTTCCCGGC
 V  K  Q  D  G  S  E  K  Y  Y  L  D  S  V  K  G  R>

        210       220       230       240       250
ATTCACCATCTCCAGAGACAACGCCAAGAGCTCACTGTATCTGCAAATGG
TAAGTGGTAGAGGTCTCTGTTGCGGTTCTCGAGTGACATAGACGTTTACC
  F  T  I  S  R  D  N  A  K  S  S  L  Y  L  Q  M>

        260       270       280       290       300
ACAGCCTGAGCGTCGAGGACACGGCCGTCTATTACTGTGCGAGAGGTCTG
TGTCGGACTCGCAGCTCCTGTGCCGGCAGATAATGACACGCTCTCCAGAC
D  S  L  S  V  E  D  T  A  V  Y  Y  C  A  R  G  L>

        310       320       330       340       350
CGTACCATGGGCCAGGGCACCCTGGTCACCGTCTCCTCAGGTGGAGGCGG
GCATGGTACCCGGTCCCGTGGGACCAGTGGCAGAGGAGTCCACCTCCGCC
 R  T  M  G  Q  G  T  L  V  T  V  S  S  G  G  G  G>

        360       370       380       390       400
TTCAGGCGGAGGTGGCTCTGGCGGTGGCGGATCGTCTGAGCTGACTCAGG
AAGTCCGCCTCCACCGAGACCGCCACCGCCTAGCAGACTCGACTGAGTCC
  S  G  G  G  G  S  G  G  G  G  S  S  E  L  T  Q>

        410       420       430       440       450
ACCCTGCTGTGTCTGTGGCCTTGGGACAGACAGTCAGGATCACATGCCAA
TGGGACGACACAGACACCGGAACCCTGTCTGTCAGTCCTAGTGTACGGTT
D  P  A  V  S  V  A  L  G  Q  T  V  R  I  T  C  Q>

        460       470       480       490       500
GGAGACAGCCTCAGAAGCTATTATGCAAGTTGGTACCAGCGGAAGCCAGG
CCTCTGTCGGAGTCTTCGATAATACGTTCAACCATGGTCGCCTTCGGTCC
 G  D  S  L  R  S  Y  Y  A  S  W  Y  Q  R  K  P  G>
```

FIG. 14A

```
        510       520       530       540       550
ACAGGCCCCTCTCCTTGTCATCTATGGTAAAAACATCCGGCCCTCAGGGA
TGTCCGGGGAGAGGAACAGTAGATACCATTTTTGTAGGCCGGGAGTCCCT
  Q  A  P  L  L  V  I  Y  G  K  N  I  R  P  S  G>

        560       570       580       590       600
TCCCAGACCGATTCTCTGGCTCCAGCTCAGGAAACACAGCTTCCTTGATC
AGGGTCTGGCTAAGAGACCGAGGTCGAGTCCTTTGTGTCGAAGGAACTAG
I  P  D  R  F  S  G  S  S  S  G  N  T  A  S  L  I>

        610       620       630       640       650
ATCACTGGGGCTCAGGCGGAAGATGAGGCTGACTATTACTGTAATTCTCG
TAGTGACCCCGAGTCCGCCTTCTACTCCGACTGATAATGACATTAAGAGC
 I  T  G  A  Q  A  E  D  E  A  D  Y  Y  C  N  S  R>

        660       670       680       690       700
GGACAGCAGTGCTAACCAGATGTTCGGCGGAGGGACCAAGCTGACCGTCC
CCTGTCGTCACGATTGGTCTACAAGCCGCCTCCCTGGTTCGACTGGCAGG
  D  S  S  A  N  Q  M  F  G  G  G  T  K  L  T  V>

TAGGT (SEQ ID NO:123)
ATCCA (SEQ ID NO:124)
L  G> (SEQ ID NO:125)
```

```
        10        20        30        40        50
CAGGTGCAGCTGGTGGAGTCTGGGGGAGGCGTGGTCCAGCCTGGGAGGTC
 Q  V  Q  L  V  E  S  G  G  G  V  V  Q  P  G  R  S>

        60        70        80        90       100
CCTGAGACTCTCCTGTGCAGCCTCTGGATTCACCTTCAGTAGCTATGGCA
  L  R  L  S  C  A  A  S  G  F  T  F  S  S  Y  G>

       110       120       130       140       150
TGCACTGGGTCCGCCAGGCTCCAGGCAAGGGGCTGGAGTGGGTGGCAGTT
M  H  W  V  R  Q  A  P  G  K  G  L  E  W  V  A  V>

       160       170       180       190       200
ATATCATATGATGGAAGTAATAAATACTATGCAGACTCCGTGAAGGGCCG
 I  S  Y  D  G  S  N  K  Y  Y  A  D  S  V  K  G  R>

       210       220       230       240       250
ATTCACCATCTCCAGAGACAATTCCAAGAACACGCTGTATCTGCAAATGA
  F  T  I  S  R  D  N  S  K  N  T  L  Y  L  Q  M>

       260       270       280       290       300
ACAGCCTGAGAGCTGAGGACACGGCTGTGTATTACTGTGCGAAAGATTAT
N  S  L  R  A  E  D  T  A  V  Y  Y  C  A  K  D  Y>

       310       320       330       340       350
GGCTATTGTAGTGGTGGTAGCTGCTACTCGCCCTTTGACTACTGGGGCCA
 G  Y  C  S  G  G  S  C  Y  S  P  F  D  Y  W  G  Q>

       360       370       380       390       400
GGGCACCCTGGTCACCGTCTCCTCAGGTGGAGGCGGTTCAGGCGGAGGTG
  G  T  L  V  T  V  S  S  G  G  G  G  S  G  G  G>

       410       420       430       440       450
GCTCTGGCGGTGGCGGATCGAATTTTATGCTGACTCAGGACCCTGCTGTG
G  S  G  G  G  G  S  N  F  M  L  T  Q  D  P  A  V>

       460       470       480       490       500
TCTGTGGCCTTGGGACAGACAGTCAGGATCACATGCCAAGGAGACAGCCT
 S  V  A  L  G  Q  T  V  R  I  T  C  Q  G  D  S  L>

       510       520       530       540       550
CAGAAGCTATTATGCAAGCTGGTACCAGCAGAAGCCAGGACAGGCCCCTG
  R  S  Y  Y  A  S  W  Y  Q  Q  K  P  G  Q  A  P>

       560       570       580       590       600
TACTTGTCATCTATGGTAAAAACAACCGGCCCTCAGGGATCCCAGACCGG
V  L  V  I  Y  G  K  N  N  R  P  S  G  I  P  D  R>
```

FIG. 15A

```
        610        620        630        640        650
TTCTCTGGCTCCAGCTCAGGAAACACAGCTTCCTTGACCATCACTGGGGC
 F  S  G  S  S  S  G  N  T  A  S  L  T  I  T  G  A>

        660        670        680        690        700
TCAGGCGGAAGATGAGGCTGACTATTACTGTCACTCCCGGGACAGCAGTG
  Q  A  E  D  E  A  D  Y  Y  C  H  S  R  D  S  S>

        710        720        730        740
GTAACTATCTCTTCGGAGGTGGGACCAAGCTGACCGTCCTAGGT(SEQ ID NO:91)
G  N  Y  L  F  G  G  G  T  K  L  T  V  L  G>(SEQ ID NO:90)
```

```
         10        20        30        40        50
CAGGTGCAGCTGCAGGAGTCGGGGGGAGGCTTGGTCCAGCCTGGGGGGTC
 Q  V  Q  L  Q  E  S  G  G  G  L  V  Q  P  G  G  S>

         60        70        80        90       100
CCTGAGACTCTCCTGTTCAGCCTCTGGATTCACCTTCAGTAGCTATGCTA
  L  R  L  S  C  S  A  S  G  F  T  F  S  S  Y  A>

        110       120       130       140       150
TGCACTGGGTCCGCCAGGCTCCAGGGAAGGGACTGGAATATGTTTCAGCT
M  H  W  V  R  Q  A  P  G  K  G  L  E  Y  V  S  A>

        160       170       180       190       200
ATTAGTAGTAATGGGGGTAGCACATACTACGCAGACTCCGTGAAGGGCAG
 I  S  S  N  G  G  S  T  Y  Y  A  D  S  V  K  G  R>

        210       220       230       240       250
ATTCACCATCTCCAGAGACAATTCCAAGAACACGCTGTATCTTCAAATGA
  F  T  I  S  R  D  N  S  K  N  T  L  Y  L  Q  M>

        260       270       280       290       300
GCAGTCTGAGAGCTGAGGACACGGCTGTGTATTACTGTGTCGCGCGTTTG
S  S  L  R  A  E  D  T  A  V  Y  Y  C  V  A  R  L>

        310       320       330       340       350
GAGTGGTTACCACTAGCCTGGGACTACTGGGGCCAGGGCACCCTGGTCAC
 E  W  L  P  L  A  W  D  Y  W  G  Q  G  T  L  V  T>

        360       370       380       390       400
CGTCTCCTCAGGTGGAGGCGGTTCAGGCGGAGGTGGCTCTGGCGGTGGCG
  V  S  S  G  G  G  G  S  G  G  G  G  S  G  G  G>

        410       420       430       440       450
GATCGTCTGAGCTGACTCAGGACCCTGCTGTGTCTGTGGCCTTGGGACAG
G  S  S  E  L  T  Q  D  P  A  V  S  V  A  L  G  Q>

        460       470       480       490       500
ACAGTCAGGATCACATGCCAAGGAGACAGCCTCAGAAGCTATTATGCAAG
 T  V  R  I  T  C  Q  G  D  S  L  R  S  Y  Y  A  S>

        510       520       530       540       550
CTGGTACCAGCAGAAGCCAGGACAGGCCCCTGTACTTGTCATCTATGGTA
  W  Y  Q  Q  K  P  G  Q  A  P  V  L  V  I  Y  G>

        560       570       580       590       600
AAAACAACCGGCCCTCAGGGATCCCAGACCGATTCTCTGGCTCCAGCTCA
K  N  N  R  P  S  G  I  P  D  R  F  S  G  S  S  S>
```

FIG. 16A

```
         610       620       630       640       650
GGAAACACAGCTTCCTTGACCATCACTGGGGCTCAGGCGGAAGATGAGGC
 G  N  T  A  S  L  T  I  T  G  A  Q  A  E  D  E  A>

         660       670       680       690       700
TGACTATTACTGTAACTCCCGGGACAGCAGTGGTAACCATAAGGTGTTCG
  D  Y  Y  C  N  S  R  D  S  S  G  N  H  K  V  F>

         710       720
GCGGAGGGACCAAGCTGACCGTCCTAGGT (SEQ ID NO:59)
G  G  G  T  K  L  T  V  L  G> (SEQ ID NO:58)
```

```
         10        20        30        40        50
CAGGTGCAGCTGGTGCAGTCTGGGGGAGGCTTGGTACAGCCTGGGGGGTC
 Q  V  Q  L  V  Q  S  G  G  G  L  V  Q  P  G  G  S>

         60        70        80        90       100
CCTGAGACTCTCCTGTGCAGCCTCTGGATTCACCTTTAGCAGCTATGCCA
  L  R  L  S  C  A  A  S  G  F  T  F  S  S  Y  A>

        110       120       130       140       150
TGAGCTGGGTCCGCCAGGCTCCAGGGAAGGGGCTGGAGTGGGTCTCAGCT
M  S  W  V  R  Q  A  P  G  K  G  L  E  W  V  S  A>

        160       170       180       190       200
ATTAGTGGTAGTGGTGGTAGCACATACTACGCAGACTCCGTGAAGGGCCG
 I  S  G  S  G  G  S  T  Y  Y  A  D  S  V  K  G  R>

        210       220       230       240       250
GTTCACCATCTCCAGAGACAATTCCAAGAACACGCTGTATCTGCAAATGA
  F  T  I  S  R  D  N  S  K  N  T  L  Y  L  Q  M>

        260       270       280       290       300
ACAGCCTGAGAGCTGAGGACACGGCTGTGTATTACTGTGCGAAAGCAGCC
N  S  L  R  A  E  D  T  A  V  Y  Y  C  A  K  A  A>

        310       320       330       340       350
AGGATAGCAGCTCGTCCTGGACCCCTTGACTACTGGGGCCAGGGAACCCT
 R  I  A  A  R  P  G  P  L  D  Y  W  G  Q  G  T  L>

        360       370       380       390       400
GGTCACCGTCTCCTCAGGTGGAGGCGGTTCAGGCGGAGGTGGCTCTGGCG
  V  T  V  S  S  G  G  G  G  S  G  G  G  G  S  G>

        410       420       430       440       450
GTGGCGGATCGTCTGAGCTGACTCAGGACCCTGCTGTGTCTGTGGCCGTG
G  G  G  S  S  E  L  T  Q  D  P  A  V  S  V  A  V>

        460       470       480       490       500
GGACAGACAGTCAAGATCACATGCCAAGGAGACAGCCTCAGAAACTATTA
 G  Q  T  V  K  I  T  C  Q  G  D  S  L  R  N  Y  Y>

        510       520       530       540       550
TGCAAGCTGGTACCAGCAGAAGCCAAGACAGGCCCCTGTACTTGTCATCT
  A  S  W  Y  Q  Q  K  P  R  Q  A  P  V  L  V  I>

        560       570       580       590       600
ATGGTAAAAACAACCGGCCCTCAGGGATCCCAGACCGATTCTCTGGCTCC
Y  G  K  N  N  R  P  S  G  I  P  D  R  F  S  G  S>
```

FIG. 17A

```
        610         620         630         640         650
AGCTCAGGAAACACAGCTTCCTTGACCATCACTGGGGCTCAGGCGGAAGA
 S  S  G  N  T  A  S  L  T  I  T  G  A  Q  A  E  D>

        660         670         680         690         700
TGAGGCTGACTATTACTGTAACTCCCGGGACAGAAGTAATAACCATCTAC
  E  A  D  Y  Y  C  N  S  R  D  R  S  N  N  H  L>

        710         720         730
TATTCGGCGGAGGGACCAAGCTGACCGTCCTAGGT (SEQ ID NO:93)
L  F  G  G  G  T  K  L  T  V  L  G> (SEQ ID NO:92)
```

```
        10        20        30        40        50
CAGGTACAGCTGCAGCAGTCAGGGGGAGGCTTGGTCCAGCCTGGGGGGTC
 Q  V  Q  L  Q  Q  S  G  G  G  L  V  Q  P  G  G  S>

        60        70        80        90       100
CCTGAGACTCTCCTGTGCAGCCTCTGGATTCACCTTTAGCAGCTATGCCA
  L  R  L  S  C  A  A  S  G  F  T  F  S  S  Y  A>

       110       120       130       140       150
TGAGCTGGGTCCGCCAGGCTCCAGTGAAGGGGCTGGAGTGGGTCTCAGCT
M  S  W  V  R  Q  A  P  V  K  G  L  E  W  V  S  A>

       160       170       180       190       200
ATTAGTGGTAGTGGTGGTAGCACATACTACGCAGACTCCGTGAAGGGCCG
 I  S  G  S  G  G  S  T  Y  Y  A  D  S  V  K  G  R>

       210       220       230       240       250
GTTCACCATCTCCAGAGACAATTCCAAGAACACGCTGTATCTGCAAATGA
  F  T  I  S  R  D  N  S  K  N  T  L  Y  L  Q  M>

       260       270       280       290       300
ACAGCCTGAGAATTGAGGACACGGCTGTCTATTACTGTGGGAGACATCTT
N  S  L  R  I  E  D  T  A  V  Y  Y  C  G  R  H  L>

       310       320       330       340       350
AGTAGCGGCTCGAGCGTTGACTACTGGGGCCAGGGAACCCTGGTCACCGT
 S  S  G  S  S  V  D  Y  W  G  Q  G  T  L  V  T  V>

       360       370       380       390       400
CTCCTCAGGTGGAGGCGGTTCAGGCGGAGGTGGCTCTGGCGGTGGCGGAT
  S  S  G  G  G  G  S  G  G  G  G  S  G  G  G  G>

       410       420       430       440       450
CGTCTGAGCTGACTCAGCCTCCCTCCGCGTCCGGGTCTCCTGGACAGTCA
S  S  E  L  T  Q  P  P  S  A  S  G  S  P  G  Q  S>

       460       470       480       490       500
GTCACCATCTCCTGCACTGGAACCAGCAGTGACGTTGGTGGTTATAACTA
 V  T  I  S  C  T  G  T  S  S  D  V  G  G  Y  N  Y>

       510       520       530       540       550
TGTCTCCTGGTACCAACAGCGCCCAGGCTACGCCCCCAAACTCATGATTT
  V  S  W  Y  Q  Q  R  P  G  Y  A  P  K  L  M  I>

       560       570       580       590       600
ATGATGTCAGTAATCGGCCCTCAGGGGTTTCTAATCGCTTCTCTGGCTCC
Y  D  V  S  N  R  P  S  G  V  S  N  R  F  S  G  S>
```

FIG. 18A

```
       610        620        630        640        650
AAGTCTGGCAACTCAGCCTCCCTGGACATCAGTGGGCTCCAGTCTGAGGA
 K  S  G  N  S  A  S  L  D  I  S  G  L  Q  S  E  D>

       660        670        680        690        700
TGAGGCTGATTACTATTGTGCAGCATGGGATGACAGCCTGCGTGAATTTC
  E  A  D  Y  Y  C  A  A  W  D  D  S  L  R  E  F>

       710        720        730
TCTTTGGAACTGGGACCAAGGTCACCGTCCTAGGT (SEQ ID NO:64)
L  F  G  T  G  T  K  V  T  V  L  G> (SEQ ID NO:63)
```

```
        10         20         30         40         50
CAGGTCAACTTAAGGGAGTCTGGGGGAGGCCTGGTCAAGCCTGGGGGGTC
 Q  V  N  L  R  E  S  G  G  G  L  V  K  P  G  G  S>

        60         70         80         90        100
CCTGAGACTCTCCTGTGCAGCCTCTGGATTCACCTTTAGCAGCTATGCCA
  L  R  L  S  C  A  A  S  G  F  T  F  S  S  Y  A>

       110        120        130        140        150
TGAGCTGGGTCCGCCAGGCTCCAGGGAAGGGGCTGGAGTGGGTCTCAGTC
M  S  W  V  R  Q  A  P  G  K  G  L  E  W  V  S  V>

       160        170        180        190        200
ATTAGTGATGGTAGTACCACATATTACGCAGACTCCGTGAAGGGCCGGTT
 I  S  D  G  S  T  T  Y  Y  A  D  S  V  K  G  R  F>

       210        220        230        240        250
CACCATCTCCAGAGACAATTCCAAGAACATGCTGTATCTGCAAACGAACA
  T  I  S  R  D  N  S  K  N  M  L  Y  L  Q  T  N>

       260        270        280        290        300
GCCTGAGAGCCGAGGACACGGCCGTATATTACTGTGCGAAAGCCGGCCCT
S  L  R  A  E  D  T  A  V  Y  Y  C  A  K  A  G  P>

       310        320        330        340        350
CGAACTACAGTAACTACGGTTGACTCCTGGGGCCAGGGAACCCTGGTCAC
 R  T  T  V  T  T  V  D  S  W  G  Q  G  T  L  V  T>

       360        370        380        390        400
CGTCTCCTCAGGTGGAGGCGGTTCAGGCGGAGGTGGCTCTGGCGGTGGCG
  V  S  S  G  G  G  G  S  G  G  G  G  S  G  G  G>

       410        420        430        440        450
GATCGCAGTCTGTGCTGACTCAGCCGCCCTCAGTGTCTGGGGCCCCAGGG
G  S  Q  S  V  L  T  Q  P  P  S  V  S  G  A  P  G>

       460        470        480        490        500
CAGAGGGTCACCATCTCCTGCACTGGGAGCAGCTCCAACATCGGGGCAGG
 Q  R  V  T  I  S  C  T  G  S  S  S  N  I  G  A  G>

       510        520        530        540        550
TTATGATGTACACTGGTACCAGCAGCTTCCAGGAACAGCCCCCAAACTCC
  Y  D  V  H  W  Y  Q  Q  L  P  G  T  A  P  K  L>

       560        570        580        590        600
TCACCTATGGTAACAGCAATCGGCCCTCAGGGGTCCCTGACCGATTCTCT
L  T  Y  G  N  S  N  R  P  S  G  V  P  D  R  F  S>
```

FIG. 19A

```
        610        620        630        640        650
GGCTCCAAGTCTGGCACCTCAGCCTCCCTGGCCATCACTGGGCTCCAGGC
 G  S  K  S  G  T  S  A  S  L  A  I  T  G  L  Q  A>

        660        670        680        690        700
TGAGGATGAGGCTGACTATTACCGCTCAGCATGGGACAGCAGCCTCTTTA
  E  D  E  A  D  Y  Y  R  S  A  W  D  S  S  L  F>

        710        720        730        740
ATTGGGTGTTCGGCGGAGGGACCAAGCTGACCGTCCTAGGT (SEQ ID NO:73)
N  W  V  F  G  G  G  T  K  L  T  V  L  G> (SEQ ID NO:72)
```

```
       10        20        30        40        50
CAGGTGCAGCTGGTGGAGTCTGGGGGAGGCTTGGTACAGCCAGGGGGGTC
 Q  V  Q  L  V  E  S  G  G  G  L  V  Q  P  G  G  S>

       60        70        80        90       100
CCTGAGACTCTCCTGTGCAGCCTCTGGATTCACCTTTAGCAGCTATGCCA
  L  R  L  S  C  A  A  S  G  F  T  F  S  S  Y  A>

      110       120       130       140       150
TGGGCTGGGTCCGCCAGGCTCCAGGGAAGGGGCTGGAGTGGGTCTCAGCT
M  G  W  V  R  Q  A  P  G  K  G  L  E  W  V  S  A>

      160       170       180       190       200
ATTAGTGCTAGTGGTGGTAGCACATATTACGCAGACTCCGTGAAGGGCCG
 I  S  A  S  G  G  S  T  Y  Y  A  D  S  V  K  G  R>

      210       220       230       240       250
GTTCACCATCTCCAGAGACAATTCCAAGAACACGCTGTATTTGCAACTGA
  F  T  I  S  R  D  N  S  K  N  T  L  Y  L  Q  L>

      260       270       280       290       300
ACAGCCTGAGAGCCGAGGACACGGCCGTATATTACTGTGCAAAAGGATTG
N  S  L  R  A  E  D  T  A  V  Y  Y  C  A  K  G  L>

      310       320       330       340       350
AAAGATAGTAGTGGTTTTGACTACTGGGGCCAGGGAACCCTGGTCACTGT
 K  D  S  S  G  F  D  Y  W  G  Q  G  T  L  V  T  V>

      360       370       380       390       400
CTCCTCAGGTGGAGGCGGTTCAGGCGGAGGTGGCTCTGGCGGTGGCGGAT
  S  S  G  G  G  G  S  G  G  G  G  S  G  G  G  G>

      410       420       430       440       450
CGAATTTTATGCTGACTCAGGACCCTGCTGTGTCTGTGGCCTTGGGACAG
S  N  F  M  L  T  Q  D  P  A  V  S  V  A  L  G  Q>

      460       470       480       490       500
ACAGTCAGGATCACATGCCAAGGAGACAGCCTCAGAAGCTATTATGCAAG
 T  V  R  I  T  C  Q  G  D  S  L  R  S  Y  Y  A  S>

      510       520       530       540       550
CTGGTACCAGCAGAAGCCAGGACAGGCCCCTGTACTTGTCATCTATGGTA
  W  Y  Q  Q  K  P  G  Q  A  P  V  L  V  I  Y  G>

      560       570       580       590       600
AAAACAACCGGCCCTCAGGGATCCCAGACCGATTCTCTGGCTCCAGCTCA
K  N  N  R  P  S  G  I  P  D  R  F  S  G  S  S  S>
```

FIG. 20A

```
        610       620       630       640       650
GGAAACACAGCTTCCTTGACCATCACTGGGGCTCAGGCGGAAGATGAGGC
 G  N  T  A  S  L  T  I  T  G  A  Q  A  E  D  E  A>

        660       670       680       690       700
TGACTATTACTGTAACTCCCGGGACAGCAGTGCCAAACGGGTGGTATTCG
  D  Y  Y  C  N  S  R  D  S  S  A  K  R  V  V  F>

        710       720
GCGGAGGGACCAAGGTCACCGTCCTAGGT(SEQ ID NO:86)
G  G  G  T  K  V  T  V  L  G>(SEQ ID NO:85)
```

```
        10        20        30        40        50
CAGGTGCAGCTGCAGGAGTCGGGGGGAGGCTTGGTACAGCCTGGGGGGTC
 Q  V  Q  L  Q  E  S  G  G  G  L  V  Q  P  G  G  S>

        60        70        80        90       100
CCTGAGACTCTCCTGTGCAGCCTCTGGATTCACCTTTAGCAGCTATGCCA
  L  R  L  S  C  A  A  S  G  F  T  F  S  S  Y  A>

       110       120       130       140       150
TGAGCTGGGTCCGCCAGGCTCCAGGGAAGGGGCTGGAGTGGGTCTCAGCT
M  S  W  V  R  Q  A  P  G  K  G  L  E  W  V  S  A>

       160       170       180       190       200
ATTACTAGTAGCGGTGGTAGGACATACTACGCAGACTCCGTGAGGGGCCG
 I  T  S  S  G  G  R  T  Y  Y  A  D  S  V  R  G  R>

       210       220       230       240       250
GCTCACCATCTCCAGAGACAATTCCAAGAACACGCTGTATCTGCAAATGA
  L  T  I  S  R  D  N  S  K  N  T  L  Y  L  Q  M>

       260       270       280       290       300
ACACCCTGAGAGCCGAGGACACGGCCGTATATTACTGTGCAAAAGGAATA
N  T  L  R  A  E  D  T  A  V  Y  Y  C  A  K  G  I>

       310       320       330       340       350
GTGGGAGCTACTGCCTTTGACTACTGGGGCCAGGGAACCCTGGTCACCGT
 V  G  A  T  A  F  D  Y  W  G  Q  G  T  L  V  T  V>

       360       370       380       390       400
CTCCTCAGGTGGAGGCGGTTCAGGCGGAGGTGGCTCTGGCGGTGGCGGAT
  S  S  G  G  G  G  S  G  G  G  G  S  G  G  G  G>

       410       420       430       440       450
CGTCTGAGCTGACTCAGGACCCTGCTGTGTCTGTGGCCTTGGGACAGACA
S  S  E  L  T  Q  D  P  A  V  S  V  A  L  G  Q  T>

       460       470       480       490       500
GTCAGAATCACATGCCAGGGAGACAGCCTCAGAAGCTATTATGCAAGCTG
 V  R  I  T  C  Q  G  D  S  L  R  S  Y  Y  A  S  W>

       510       520       530       540       550
GTACCAGCAGAAGCCAGGACAGGCCCCTGTACTTGTCATCTATGGTAAAA
  Y  Q  Q  K  P  G  Q  A  P  V  L  V  I  Y  G  K>

       560       570       580       590       600
ACAACCGGCCCTCAGGGATCCCAGACCGATTCTCTGGCTCCAGCTCAGGA
N  N  R  P  S  G  I  P  D  R  F  S  G  S  S  S  G>
```

FIG. 21A

```
        610       620       630       640       650
AACACAGCTTCCTTGACCATCACTGGGGCTCAGGCGGAAGATGAGGCTGA
 N  T  A  S  L  T  I  T  G  A  Q  A  E  D  E  A  D>

        660       670       680       690       700
CTATTACTGTAACTCCCGGGACAGCAGTGGTAACTCTGTGGTATTCGGCG
  Y  Y  C  N  S  R  D  S  S  G  N  S  V  V  F  G>

        710       720
GAGGGACCAAGGTCACCGTCCTAGGT(SEQ ID NO:128)
G  G  T  K  V  T  V  L  G>(SEQ ID NO:127)
```

```
        10        20        30        40        50
CAGGTGCTGCTGGTGGAGTCCGGGGGAGGCGTGGTCCAGGCCGGGGCATC
 Q  V  L  L  V  E  S  G  G  G  V  V  Q  A  G  A  S>

        60        70        80        90       100
CCTGAGAGTCTCCTGTGCAGCATCTGGATTCAGTTTGACTAGCTATGGGA
  L  R  V  S  C  A  A  S  G  F  S  L  T  S  Y  G>

       110       120       130       140       150
TGCACTGGGTCCGCCAGGCTCCAGGCAAGGGACTGGAGTGGGTGGCTTTT
M  H  W  V  R  Q  A  P  G  K  G  L  E  W  V  A  F>

       160       170       180       190       200
ATTTCGTCTGATGGTAGTGATAAGTACTATGTAGACTCTGTGAAGGGCCG
 I  S  S  D  G  S  D  K  Y  Y  V  D  S  V  K  G  R>

       210       220       230       240       250
ATTCACCATCTCCAGAGACACTTCCAAGAACATGATGTATCTGCAAATGA
  F  T  I  S  R  D  T  S  K  N  M  M  Y  L  Q  M>

       260       270       280       290       300
ACAGCCTGACAACTGAGGATACGGCTGTGTATTACTGTGCGAAAGACTGG
N  S  L  T  T  E  D  T  A  V  Y  Y  C  A  K  D  W>

       310       320       330       340       350
GGCAGCAACTGGTACCTCTTTGACTACTGGGGCCAGGGAACCCTGGTCAC
 G  S  N  W  Y  L  F  D  Y  W  G  Q  G  T  L  V  T>

       360       370       380       390       400
CGTCTCCTCAGGTGGAGGCGGTTCAGGCGGAGGTGGCTCTGGCGGTGGCG
  V  S  S  G  G  G  G  S  G  G  G  G  S  G  G  G>

       410       420       430       440       450
GATCGCAGTCTGTGCTGACTCAGCCACCCTCAGCGTCTGAGACCCCCGGG
G  S  Q  S  V  L  T  Q  P  P  S  A  S  E  T  P  G>

       460       470       480       490       500
CAGAGGGTCACCATCTCTTGTTCTGGAAGCAGCTCCAACATCGGAGCGAA
 Q  R  V  T  I  S  C  S  G  S  S  S  N  I  G  A  N>

       510       520       530       540       550
TACTGTACACTGGTACCAGCAGTTCCCAGGAACGGCCCCCAAACTTCTCA
  T  V  H  W  Y  Q  Q  F  P  G  T  A  P  K  L  L>
```

FIG. 22A

```
        560       570       580       590       600
TCTATAGTTATAGTCAGCGGCCCTCAGGGGTCCCTGACCGATTCTCTGAC
I  Y  S  Y  S  Q  R  P  S  G  V  P  D  R  F  S  D>

        610       620       630       640       650
TCCAAGTCTGGTACCTCAGCCTCCCTGGCCATCAGTGGGCTCCAGTCTGA
 S  K  S  G  T  S  A  S  L  A  I  S  G  L  Q  S  E>

        660       670       680       690       700
GGATGAGGCTGATTATTACTGTGCAGCATGGGATGACATCCTGAATGGTT
  D  E  A  D  Y  Y  C  A  A  W  D  D  I  L  N  G>

        710       720       730
GGGTGTTCGGCGGAGGGACCAAGGTAACCGTCCTAGGT(SEQ ID NO:130)
W  V  F  G  G  G  T  K  V  T  V  L  G>(SEQ ID NO:129)
```

```
        10         20         30         40         50
CAGGTGCAGCTGGTGGAGTCCGGGGGAGGCGTGGTCCAGCCTGGGAGGTC
 Q  V  Q  L  V  E  S  G  G  G  V  V  Q  P  G  R  S>

        60         70         80         90        100
CCTGAGACTCTCCTGTGCAGCCTCTGGATTCACCTTTAGCAGCTATGCCA
  L  R  L  S  C  A  A  S  G  F  T  F  S  S  Y  A>

       110        120        130        140        150
TGGGGTGGGTCCGCCAGGCTCCAGGCAAGGGGCTGGAGTGGGTGGCTGTT
M  G  W  V  R  Q  A  P  G  K  G  L  E  W  V  A  V>

       160        170        180        190        200
ATTTATAGAGATGGTCACGGATATTACGCAGACTCCGTGAAGGGCCGATT
 I  Y  R  D  G  H  G  Y  Y  A  D  S  V  K  G  R  F>

       210        220        230        240        250
CACCGTCTCCAGAGACAGTTCCGAGAACACGGTGTATCTTCAAATGAACA
  T  V  S  R  D  S  S  E  N  T  V  Y  L  Q  M  N>

       260        270        280        290        300
GCCTGAGAGCCGAGGACACGGCCATATATTACTGCGCGAGCCATGACTAC
S  L  R  A  E  D  T  A  I  Y  Y  C  A  S  H  D  Y>

       310        320        330        340        350
GCTGGTAATCCCGCAGGCTCGGCATCTGGCTACTGGGGCCAGGGCACCCT
 A  G  N  P  A  G  S  A  S  G  Y  W  G  Q  G  T  L>

       360        370        380        390        400
GGTCACCGTCTCCTCAGGTGGAGGCGGTTCAGGCGGAGGTGGCTCTGGCG
  V  T  V  S  S  G  G  G  G  S  G  G  G  G  S  G>

       410        420        430        440        450
GTGGCGGATCGCAGTCTGCCCTGACTCAGCCTGCCTCCGTGTCTGCGTCT
G  G  G  S  Q  S  A  L  T  Q  P  A  S  V  S  A  S>

       460        470        480        490        500
CCTGGACAGTCGATCACCATCTCCTGCACTGGAACCAGCAGTGATGTTGG
 P  G  Q  S  I  T  I  S  C  T  G  T  S  S  D  V  G>

       510        520        530        540        550
TGGTTATGACTATGTCTCCTGGTACCAACAGCACCCAGGCAAAGCCCCCA
  G  Y  D  Y  V  S  W  Y  Q  Q  H  P  G  K  A  P>
```

FIG. 23A

```
       560       570       580       590       600
AACTCGTCATGTATAGTCACAATCAGCGGTCCTCAGGGGTCCCTGACCGA
K  L  V  M  Y  S  H  N  Q  R  S  S  G  V  P  D  R>

       610       620       630       640       650
TTCTCTGGCTCCAAGTCTGGCAACTCAGCCTCCCTGGACATCAGTGGGCT
 F  S  G  S  K  S  G  N  S  A  S  L  D  I  S  G  L>

       660       670       680       690       700
CCAGTCTGAGGATGAGGCTGATTATTACCGTGCAGCATGGGATGACAGCC
  Q  S  E  D  E  A  D  Y  Y  R  A  A  W  D  D  S>

       710       720       730       740 (SEQ ID NO:136)
TGAGTGAATTTCTCTTCGGAACTGGGACCAAGCTGACCGTCCTAGGT
L  S  E  F  L  F  G  T  G  T  K  L  T  V  L  G>
                                    (SEQ ID NO:135)
```

```
        10        20        30        40        50
CTGGTGCAGCTGGTGCAGTCTGGGGGAGGCCTGGTCAAGCCTGGGGGGTC
 L  V  Q  L  V  Q  S  G  G  G  L  V  K  P  G  G  S>

        60        70        80        90       100
CCTGAGACTCTCCTGTGCAGCCTCTGGATTCACCTTCAGTACCTATAGCA
  L  R  L  S  C  A  A  S  G  F  T  F  S  T  Y  S>

       110       120       130       140       150
TGAACTGGGTCCGCCAGGCTCCAGGGAAGGGCCTGGAGTGGGTCTCATCC
M  N  W  V  R  Q  A  P  G  K  G  L  E  W  V  S  S>

       160       170       180       190       200
ATTAGTAGTAGTAGTAGTTACATATACTACGCAGACTCAGTGAAGGGCCG
 I  S  S  S  S  S  Y  I  Y  Y  A  D  S  V  K  G  R>

       210       220       230       240       250
ATTCACCATCTCCAGAGACAACGCCAACAACTCACTGTATCTGCAAATGA
  F  T  I  S  R  D  N  A  N  N  S  L  Y  L  Q  M>

       260       270       280       290       300
ACAGCCTGAGAGCCGAGGACACGGCTGTCTATTACTGTGCGAGAGGGAAT
N  S  L  R  A  E  D  T  A  V  Y  Y  C  A  R  G  N>

       310       320       330       340       350
ACGGTGGCCCAAAGACTGGACGTCTTTGACTACTGGGGCCAGGGAACCCT
 T  V  A  Q  R  L  D  V  F  D  Y  W  G  Q  G  T  L>

       360       370       380       390       400
GGTCACCGTCTCCTCAGGTGGAGGCGGTTCAGGCGGAGGTGGCCCTGGCG
  V  T  V  S  S  G  G  G  G  S  G  G  G  G  P  G>

       410       420       430       440       450
GTGGCGGATCGCAGTCTGTGTTGACGCAGCCGCCCTCAGTGTCTGGGGCC
G  G  G  S  Q  S  V  L  T  Q  P  P  S  V  S  G  A>

       460       470       480       490       500
CCAGGGCAGAGGGTCACCATCTCCTGCACTGGGGGCAGCTCCAACGTCGG
 P  G  Q  R  V  T  I  S  C  T  G  G  S  S  N  V  G>

       510       520       530       540       550
GGCAGGTTTTGATGTACACTGGTACCAGCAGCTTCCAGGAACAGCCCCCA
  A  G  F  D  V  H  W  Y  Q  Q  L  P  G  T  A  P>
```

FIG. 24A

```
        560       570       580       590       600
AACTCCTCATCTATGGTGACAAGAATCGGCCCTCAGGGGTCCCTGACCGA
K  L  L  I  Y  G  D  K  N  R  P  S  G  V  P  D  R>

        610       620       630       640       650
TTCTCTGGCTCCAGGTCTGGCACCTCAGCCTCCCTGGCCATCACTGGGCT
 F  S  G  S  R  S  G  T  S  A  S  L  A  I  T  G  L>

        660       670       680       690       700
CCAGGCTGAGGATGAGGCTGATTATTACTGCCAGGCCTATGACAGCAGCC
  Q  A  E  D  E  A  D  Y  Y  C  Q  A  Y  D  S  S>

        710       720       730       740(SEQ ID NO:138)
TGCGTGGTTCGGTATTCGGCGGAGGGACCAAGCTGACCGTCCTAGGT
L  R  G  S  V  F  G  G  G  T  K  L  T  V  L  G>
                                             (SEQ ID NO:137)
```

```
         10        20        30        40        50
CAGGTGCAGCTGGTGCAGTCTGGGGGAGGCTTGGTACAGCCTGGGGGGTC
 Q  V  Q  L  V  Q  S  G  G  G  L  V  Q  P  G  G  S>

         60        70        80        90       100
CCTGAGACTCTCCTGTGCAGCGTCTGGATTCACCTTCAGTAGCTATGGCA
  L  R  L  S  C  A  A  S  G  F  I  F  S  S  Y  G>

        110       120       130       140       150
TGCACTGGGTCCGCCAGGCTCCAGGCAAGGGGCTGGAGTGGGTGGCAGTT
M  H  W  V  R  Q  A  P  G  K  G  L  E  W  V  A  V>

        160       170       180       190       200
ATATGGTATGATGGAAGTAATAAATACTATGCAGACTCCGTGAAGGGCCG
 I  W  Y  D  G  S  N  K  Y  Y  A  D  S  V  K  G  R>

        210       220       230       240       250
ATTCACCATCTCCAGAGACAATTCCAGGAACACATTGTATTTGGAAATGA
  F  T  I  S  R  D  N  S  R  N  I  L  Y  L  E  M>

        260       270       280       290       300
ACAGCCTGAGGGCCGAGGACACGGCCGTTTATTATTGTGTGAAAGATCGT
N  S  L  R  A  E  D  T  A  V  Y  Y  C  V  K  D  R>

        310       320       330       340       350
CAACCGGACGGGAGATGGCCATTTGACTTATGGGGCCAGGGAACCCTGGT
 Q  P  D  G  R  W  P  F  D  L  W  G  Q  G  T  L  V>

        360       370       380       390       400
CACCGTCTCCTCAGGTGGAGGCGGTTCAGGCGGAGGTGGCTCTGGCGGTG
  T  V  S  S  G  G  G  G  S  G  G  G  G  S  G  G>

        410       420       430       440       450
GCGGATCGCAGTCTGCCCTGACTCAGCCTGCCTCCGTGTCGGGGTCTCCT
G  G  S  Q  S  A  L  T  Q  P  A  S  V  S  G  S  P>

        460       470       480       490       500
GGACAGTCGGTCACCATCTCCTGCACAGGAGCCAACAGTGACCTTGGTGG
 G  Q  S  V  T  I  S  C  T  G  A  N  S  D  L  G  G>

        510       520       530       540       550
TTATAACTATGTCTCCTGGTACCAACATCACCCAGCCAAAGCCCCCAAAC
  Y  N  Y  V  S  W  Y  Q  H  H  P  A  K  A  P  K>
```

FIG. 25A

```
        560         570         580         590         600
TCATAATTTATGAGGTCAATAATCGGCCCTCAGGGGTTTCTCATCGCTTC
L   I   I   Y   E   V   N   N   R   P   S   G   V   S   H   R   F>

        610         620         630         640         650
TCTGGCTCCAAGTCTGCCAACACGGCCTCCCTGACCATCTCTGGGCTCCA
 S   G   S   K   S   A   N   T   A   S   L   T   I   S   G   L   Q>

        660         670         680         690         700
GGCTGAGGACGAGGCTGATTATTACTGCAGCTCATATAGAAGCGGCGGCA
  A   E   D   E   A   D   Y   Y   C   S   S   Y   R   S   G   G>

        710         720         730         740
CTTATGTTTTCGGAACTGGGACCAAGCTGACCGTCCTAGGT(SEQ ID NO:306)
T   Y   V   F   G   T   G   T   K   L   T   V   L   G> (SEQ ID NO:305)
```

```
          10        20        30        40        50
CAGTTGCAGCTGGTGGAGTCTGGGGGAGGCTTGGTACAGCCTGGGGGGTC
 Q  L  Q  L  V  E  S  G  G  G  L  V  Q  P  G  G  S>

          60        70        80        90       100
CCTGAGACTCTCCTGTGCAGCCTCTGGATTCACTTTTAGCAGCTATGCCA
  L  R  L  S  C  A  A  S  G  F  T  F  S  S  Y  A>

         110       120       130       140       150
TGAACTGGGTCCGCCAGGCTCCAGGGAAGGGGCTGGAGTGGGTCTCAGCT
M  N  W  V  R  Q  A  P  G  K  G  L  E  W  V  S  A>

         160       170       180       190       200
ATTAGTGGTAGTGGTGGTAACACATACTATGCAGACTCCGTGAAGGGCCG
 I  S  G  S  G  G  N  T  Y  Y  A  D  S  V  K  G  R>

         210       220       230       240       250
GTTCACCATCTCCAGAGACAATTCCAACAACGCCCTGTATCTGCAAATGA
  F  T  I  S  R  D  N  S  N  N  A  L  Y  L  Q  M>

         260       270       280       290       300
ACAGCCTGAGAGTCGAGGACACGGCTGTGTATTACTGTGCGAGAGATGCC
N  S  L  R  V  E  D  T  A  V  Y  Y  C  A  R  D  A>

         310       320       330       340       350
AGTTACTATGCTGATGACTACTGGGGCCAGGGAACCCTGGTCACCGTCTC
 S  Y  Y  A  D  D  Y  W  G  Q  G  T  L  V  T  V  S>

         360       370       380       390       400
CTCAGGTGGAGGCGGTTCAGGCGGAGGTGGCTCTGGCGGTGGCGGATCGT
  S  G  G  G  G  S  G  G  G  G  S  G  G  G  G  S>

         410       420       430       440       450
CTGAGCTGACTCAGGACCCTGCTGTGTCTGTGGCCTTGGGACAGACAGTC
S  E  L  T  Q  D  P  A  V  S  V  A  L  G  Q  T  V>

         460       470       480       490       500
AGGATCACATGCCAAGGAGACAGCCTCAAAAGCTACTATGCAAGTTGGTA
 R  I  T  C  Q  G  D  S  L  K  S  Y  Y  A  S  W  Y>

         510       520       530       540       550
CCAGCAGAAGCCAGGACAGGCCCCTGTACTTGTCATCTATGGTAAAAACA
  Q  Q  K  P  G  Q  A  P  V  L  V  I  Y  G  K  N>
```

FIG. 26A

```
       560        570        580        590        600
ACCGGCCCTCAGGGATCCCAGACCGATTCTCTGGCTCCAGCTCAGGAAAC
N  R  P  S  G  I  P  D  R  F  S  G  S  S  S  G  N>

       610        620        630        640        650
ACAGCTTCCTTGACCATCACTGGGGCTCAGGCGGAAGATGAGGCTGACTA
 T  A  S  L  T  I  T  G  A  Q  A  E  D  E  A  D  Y>

       660        670        680        690        700
TTACTGTCACTCCCGGGACAGCAGTGGTAACCATCCGGTGGTATTCGGCG
  Y  C  H  S  R  D  S  S  G  N  H  P  V  V  F  G>

       710        720
GAGGGACCAAGGTCACCGTCCTAGGT(SEQ ID NO:308)
G  G  T  K  V  T  V  L  G>(SEQ ID NO:307)
```

```
         10        20        30        40        50        60        70        80        90
CAGGTACAGCTGCAGCAGTCAGGTCCAGGACTGGTGAAGCCCTCGCAGACCCTCTCACTCACCTGTGCCATCTCCGGGGACAGTGTCTCT
GTCCATGTCGACGTCGTCAGTCCAGGTCCTGACCACTTCGGGAGCGTCTGGGAGAGTGAGTGGACACGGTAGAGGCCCCTGTCACAGAGA
 Q  V  Q  L  Q  Q  S  G  P  G  L  V  K  P  S  Q  T  L  S  L  T  C  A  I  S  G  D  S  V  S>

        100       110       120       130       140       150       160       170       180
AGCAACAGTGCTGCTTGGAACTGGATCAGGCAGTCCCCATCGAGAGGCCTTGAGTGGCTGGGAAGGACATACTACAGGTCCAAGTGGTAT
TCGTTGTCACGACGAACCTTGACCTAGTCCGTCAGGGGTAGCTCTCCGGAACTCACCGACCCTTCCTGTATGATGTCCAGGTTCACCATA
 S  N  S  A  A  W  N  W  I  R  Q  S  P  S  R  G  L  E  W  L  G  R  T  Y  Y  R  S  K  W  Y>

        190       200       210       220       230       240       250       260       270
AATGATTATGCAGTATCTGTGAAAAGTCGAATAACCATCAACCCAGACACGTCCAAGAACCTCTTCTCCCTGCAGCTGAACTCTGTGACT
TTACTAATACGTCATAGACACTTTTCAGCTTATTGGTAGTTGGGTCTGTGCAGGTTCTTGGAGAAGAGGGACGTCGACTTGAGACACTGA
 N  D  Y  A  V  S  V  K  S  R  I  T  I  N  P  D  T  S  K  N  L  F  S  L  Q  L  N  S  V  T>

        280       290       300       310       320       330       340       350       360
CCCGAGGACACGGCTCTGTATTACTGTGCAAGAGAGGAGGATTACAGTGGCTTCCAGCACTGGGGCCAGGGCACCCTGGTCACCGTCTCT
GGGCTCCTGTGCCGAGACATAATGACACGTTCTCTCCTCCTAATGTCACCGAAGGTCGTGACCCCGGTCCCGTGGGACCAGTGGCAGAGA
 P  E  D  T  A  L  Y  Y  C  A  R  E  E  D  Y  S  G  F  Q  H  W  G  Q  G  T  L  V  T  V  S>

        370       380       390       400       410       420       430       440       450
TCAGGTGGAGGCGGTTCAGGCGGAGGTGGCTCTGGCGGTGGCGGATCGCAGTCTGCTCTGACTCAGCCTGCCTCCGTGTCTGGGTCTCCT
AGTCCACCTCCGCCAAGTCCGCCTCCACCGAGACCGCCACCGCCTAGCGTCAGACGAGACTGAGTCGGACGGAGGCACAGACCCAGAGGA
 S  G  G  G  G  S  G  G  G  G  S  G  G  G  G  S  Q  S  A  L  T  Q  P  A  S  V  S  G  S  P>

        460       470       480       490       500       510       520       530       540
GGACAGTCGATCACCATCTCCTGCACTGGAACCAGCAGTGACGTTGGTGGTTATAACTATGTCTCCTGGTATCAACAGCACCCAGGCAAA
CCTGTCAGCTAGTGGTAGAGGACGTGACCTTGGTCGTCACTGCAACCACCAATATTGATACAGAGGACCATAGTTGTCGTGGGTCCGTTT
 G  Q  S  I  T  I  S  C  T  G  T  S  S  D  V  G  G  Y  N  Y  V  S  W  Y  Q  Q  H  P  G  K>
```

FIG. 27A

```
        550       560       570       580       590       600       610       620       630
GCCCCCAAACTCATGATTTATGAGGGCAGTAAGCGGCCCTCAGGGGTCCCTGAGCGATTCTCTGGCTCCAACTCTGGGAACACGGCCACC
CGGGGGTTTGAGTACTAAATACTCCCGTCATTCGCCGGGAGTCCCCAGGGACTCGCTAAGAGACCGAGGTTGAGACCCTTGTGCCGGTGG
 A  P  K  L  M  I  Y  E  G  S  K  R  P  S  G  V  P  E  R  F  S  G  S  N  S  G  N  T  A  T>

        640       650       660       670       680       690       700       710       720
CTGACCATCGGCAGGGTCGAAGCCGGGGATGAGGCCGACTATTACTGTCAGGCGTGGGATAGTACTAGTGATCATGTGGTTTTCGGCGGA
GACTGGTAGCCGTCCCAGCTTCGGCCCCTACTCCGGCTGATAATGACAGTCCGCACCCTATCATGATCACTAGTACACCAAAAGCCGCCT
 L  T  I  G  R  V  E  A  G  D  E  A  D  Y  Y  C  Q  A  W  D  S  T  S  D  H  V  V  F  G  G>

        730       740
GGGACCAAGGTCACCGTCCTAGGT (SEQ ID NO:310)
CCCTGGTTCCAGTGGCAGGATCCA (SEQ ID NO:416)
 G  T  K  V  T  V  L  G> (SEQ ID NO:309)
```

```
         10        20        30        40        50        60        70        80        90
CAGGTGCAGCTGCAGGAGTCGGGGGGAGGCGTGGTCCAGCCTGGGGGGTCCCTGAGACTCTCCTGTGCAGCGTCTGGATTCACCTTCAGT
GTCCACGTCGACGTCCTCAGCCCCCCTCCGCACCAGGTCGGACCCCCCAGGGACTCTGAGAGGACACGTCGCAGACCTAAGTGGAAGTCA
 Q  V  Q  L  Q  E  S  G  G  G  V  V  Q  P  G  G  S  L  R  L  S  C  A  A  S  G  F  T  F  S>

        100       110       120       130       140       150       160       170       180
AACTATGCTATGCACTGGGTCCGCCAGGCTCCAGGGAAGGGACTGGAATATGTTTCATCTATTAGTAGTAATGGGGGTGGCACATATTAT
TTGATACGATACGTGACCCAGGCGGTCCGAGGTCCCTTCCCTGACCTTATACAAAGTAGATAATCATCATTACCCCCACCGTGTATAATA
 N  Y  A  M  H  W  V  R  Q  A  P  G  K  G  L  E  Y  V  S  S  I  S  S  N  G  G  G  T  Y  Y>

        190       200       210       220       230       240       250       260       270
GCAGACTCTGTGAAGGGCAGATTCACCATCTCCAGAGACGACGCCAAGAACACACTGTATCTACAACTGAACAGTCTGAGAGACGAGGAC
CGTCTGAGACACTTCCCGTCTAAGTGGTAGAGGTCTCTGCTGCGGTTCTTGTGTGACATAGATGTTGACTTGTCAGACTCTCTGCTCCTG
 A  D  S  V  K  G  R  F  T  I  S  R  D  D  A  K  N  T  L  Y  L  Q  L  N  S  L  R  D  E  D>

        280       290       300       310       320       330       340       350       360
ACGGCTGTGTATTACTGCGCTAAAGATTACTTTGGTTCTATTGACTACTGGGGCCAGGGAACCCTGGTCACCGTCTCCTCAGGTGGAGGC
TGCCGACACATAATGACGCGATTTCTAATGAAACCAAGATAACTGATGACCCCGGTCCCTTGGGACCAGTGGCAGAGGAGTCCACCTCCG
 T  A  V  Y  Y  C  A  K  D  Y  F  G  S  I  D  Y  W  G  Q  G  T  L  V  T  V  S  S  G  G  G>

        370       380       390       400       410       420       430       440       450
GGTTCAGGCGGAGGTGGCTCTGGCGGTGGCGGATCGCCTGAGCTGACTCAGGACCCTGCTGTGTCTGTGGCCTTGGGACAGACAGTCACG
CCAAGTCCGCCTCCACCGAGACCGCCACCGCCTAGCGGACTCGACTGAGTCCTGGGACGACACAGACACCGGAACCCTGTCTGTCAGTGC
 G  S  G  G  G  G  S  G  G  G  G  S  P  E  L  T  Q  D  P  A  V  S  V  A  L  G  Q  T  V  T>

        460       470       480       490       500       510       520       530       540
ATCACATGCCAAGGAGACAGCCTCAGAAGCTATTATGCAAGTTGGTACCAGCAGAAGCCAGGACAGGCCCCTCTCCTTGTCATCTATGGT
TAGTGTACGGTTCCTCTGTCGGAGTCTTCGATAATACGTTCAACCATGGTCGTCTTCGGTCCTGTCCGGGGAGAGGAACAGTAGATACCA
 I  T  C  Q  G  D  S  L  R  S  Y  Y  A  S  W  Y  Q  Q  K  P  G  Q  A  P  L  L  V  I  Y  G>

        550       560       570       580       590       600       610       620       630
AAAAACATCCGGCCCTCAGGGATCCCAGACCGATTCTCTGGCTCCAGCTCAGGAAACTCAGCTTCCTTGACCATCACTGGGGCTCAGGCG
TTTTTGTAGGCCGGGAGTCCCTAGGGTCTGGCTAAGAGACCGAGGTCGAGTCCTTTGAGTCGAAGGAACTGGTAGTGACCCCGAGTCCGC
 K  N  I  R  P  S  G  I  P  D  R  F  S  G  S  S  S  G  N  S  A  S  L  T  I  T  G  A  Q  A>
```

FIG. 28A

```
           640        650        660        670        680        690        700        710        720
GAAGATGAGGCTGACTATTACTGTCACTCCCGGGACAGCAGTGGTACCCATCTAAGGGTATTCGGCGGAGGGACCAAGCTGACCGTCCTA
CTTCTACTCCGACTGATAATGACAGTGAGGGCCCTGTCGTCACCATGGGTAGATTCCCATAAGCCGCCTCCCTGGTTCGACTGGCAGGAT
 E  D  E  A  D  Y  Y  C  H  S  R  D  S  S  G  T  H  L  R  V  F  G  G  G  T  K  L  T  V  L>

GGT (SEQ ID NO:312)
CCA (SEQ ID NO:417)
G>  (SEQ ID NO:311)
```

```
         10        20        30        40        50        60        70        80        90
CAGGTACAGCTGCAGCAGTCAGGGGGAGGCTTGGTCCAGCCTGGGGGGTCCCTGAGACTCTCCTGTTCAGCCTCTGGATTCACCTTCAGT
GTCCATGTCGACGTCGTCAGTCCCCCTCCGAACCAGGTCGGACCCCCCAGGGACTCTGAGAGGACAAGTCGGAGACCTAAGTGGAAGTCA
 Q  V  Q  L  Q  Q  S  G  G  G  L  V  Q  P  G  G  S  L  R  L  S  C  S  A  S  G  F  T  F  S>

        100       110       120       130       140       150       160       170       180
AACTATGCTATTCACTGGGTCCGCCAGGCTCCAGGGAAGGGACTGGAATATGTTTCAGCTATTAATAGTAATGGGGGCAGCACATACTAC
TTGATACGATAAGTGACCCAGGCGGTCCGAGGTCCCTTCCCTGACCTTATACAAAGTCGATAATTATCATTACCCCCGTCGTGTATGATG
 N  Y  A  I  H  W  V  R  Q  A  P  G  K  G  L  E  Y  V  S  A  I  N  S  N  G  G  S  T  Y  Y>

        190       200       210       220       230       240       250       260       270
GCAGACTCCGTGAAGGGCAGATCCATCATCTCCAGAGACAATTCCATGAACACGGTGTATCTTCAAATGAGCAGTCTGAGAGCTGAGGAC
CGTCTGAGGCACTTCCCGTCTAGGTAGTAGAGGTCTCTGTTAAGGTACTTGTGCCACATAGAAGTTTACTCGTCAGACTCTCGACTCCTG
 A  D  S  V  K  G  R  S  I  I  S  R  D  N  S  M  N  T  V  Y  L  Q  M  S  S  L  R  A  E  D>

        280       290       300       310       320       330       340       350       360
ACGGCTGTCTATTACTGTGTGAAGGAGGAGAATGGTTCGGGGTTTGACTCCTGGGGCCAGGGCACCCTGGTCACCGTCTCCTCAGGTGGA
TGCCGACAGATAATGACACACTTCCTCCTCTTACCAAGCCCCAAACTGAGGACCCCGGTCCCGTGGGACCAGTGGCAGAGGAGTCCACCT
 T  A  V  Y  Y  C  V  K  E  E  N  G  S  G  F  D  S  W  G  Q  G  T  L  V  T  V  S  S  G  G>

        370       380       390       400       410       420       430       440       450
GGCGGTTCAGGCGGAGGTGGCTCTGGCGGTGGCGGATCGGAAATTGTGCTGACTCAGTCTCCATCTTCCGTGTCTGCTTCTGTAGGAGAC
CCGCCAAGTCCGCCTCCACCGAGACCGCCACCGCCTAGCCTTTAACACGACTGAGTCAGAGGTAGAAGGCACAGACGAAGACATCCTCTG
 G  G  S  G  G  G  G  S  G  G  G  G  S  E  I  V  L  T  Q  S  P  S  S  V  S  A  S  V  G  D>

        460       470       480       490       500       510       520       530       540
AGAGTCACCATCACTTGTCGGGCGAGTCAGGATATAAGCAAGTGGTTAGCCTGGTATCAGCAGAGACCAGGGAAAGTCCCTAGACTCCTC
TCTCAGTGGTAGTGAACAGCCCGCTCAGTCCTATATTCGTTCACCAATCGGACCATAGTCGTCTCTGGTCCCTTTCAGGGATCTGAGGAG
 R  V  T  I  T  C  R  A  S  Q  D  I  S  K  W  L  A  W  Y  Q  Q  R  P  G  K  V  P  R  L  L>

        550       560       570       580       590       600       610       620       630
ATTTATTCTGCATCCAGTTTGCAAAGTGGGGTCCCATCAAGATTCAGCGGCAGTGGATCTGGGACAGATTTCACTCTCACCATCAGCAGC
TAAATAAGACGTAGGTCAAACGTTTCACCCCAGGGTAGTTCTAAGTCGCCGTCACCTAGACCCTGTCTAAAGTGAGAGTGGTAGTCGTCG
 I  Y  S  A  S  S  L  Q  S  G  V  P  S  R  F  S  G  S  G  S  G  T  D  F  T  L  T  I  S  S>
```

FIG. 29A

```
         640       650       660       670       680       690       700       710       720
CTGCAGCCTGAAGATTTTGCATCTTATTTTTGTCAACAGGCTAGTGTTTTCCCGGTCACTTTCGGCGGAGGGACCAAGCTGGAGATCAAA
GACGTCGGACTTCTAAAACGTAGAATAAAAACAGTTGTCCGATCACAAAAGGGCCAGTGAAAGCCGCCTCCCTGGTTCGACCTCTAGTTT
 L  Q  P  E  D  F  A  S  Y  F  C  Q  Q  A  S  V  F  P  V  T  F  G  G  G  T  K  L  E  I  K>

CGT (SEQ ID NO:314)
GCA (SEQ ID NO:418)
 R> (SEQ ID NO:313)
```

```
        10        20        30        40        50        60        70        80        90
CAGGTGCAGCTGCAGGAGTCGGGGGGAGGCTTGGTCCAGCCTGGGGGGTTCCTGAGACTCTCCTGTGCAGCGTCTGGATTCACCTTCAGC
GTCCACGTCGACGTCCTCAGCCCCCCTCCGAACCAGGTCGGACCCCCCAAGGACTCTGAGAGGACACGTCGCAGACCTAAGTGGAAGTCG
 Q  V  Q  L  Q  E  S  G  G  G  L  V  Q  P  G  G  F  L  R  L  S  C  A  A  S  G  F  T  F  S>

       100       110       120       130       140       150       160       170       180
AGCTATGGCATGCACTGGGTCCGCCAGACTCCAGGGAAGGGGCTGGAGTGGGTTTCATACATTAGTAGTAGTAGTAGTTACACAAACTAC
TCGATACCGTACGTGACCCAGGCGGTCTGAGGTCCCTTCCCCGACCTCACCCAAAGTATGTAATCATCATCATCATCAATGTGTTTGATG
 S  Y  G  M  H  W  V  R  Q  T  P  G  K  G  L  E  W  V  S  Y  I  S  S  S  S  S  Y  T  N  Y>

       190       200       210       220       230       240       250       260       270
GCAGACTCTGTGAAGGGCCGGTTCACCATCTCCAGAGACAATTCCAAGAACACGCTGTATCTGCAGATGAACAGCCTGAGAGCTGAGGAC
CGTCTGAGACACTTCCCGGCCAAGTGGTAGAGGTCTCTGTTAAGGTTCTTGTGCGACATAGACGTCTACTTGTCGGACTCTCGACTCCTG
 A  D  S  V  K  G  R  F  T  I  S  R  D  N  S  K  N  T  L  Y  L  Q  M  N  S  L  R  A  E  D>

       280       290       300       310       320       330       340       350       360
ACGGCTGTGTATTACTGTGCGAGAGATAACTGGTACTTCGATCTCTGGGGCCGTGGCACCCTGGTCACCGTCTCCTCAGGTGGAGGCGGT
TGCCGACACATAATGACACGCTCTCTATTGACCATGAAGCTAGAGACCCCGGCACCGTGGGACCAGTGGCAGAGGAGTCCACCTCCGCCA
 T  A  V  Y  Y  C  A  R  D  N  W  Y  F  D  L  W  G  R  G  T  L  V  T  V  S  S  G  G  G  G>

       370       380       390       400       410       420       430       440       450
TCAGGCGGAGGTGGCTCTGGCGGTGGCGGATCGGATGTTGTGATGACTCAGTCTCCTTCCACCCTGTCTGCATCTGTAGGAGACAGAGTC
AGTCCGCCTCCACCGAGACCGCCACCGCCTAGCCTACAACACTACTGAGTCAGAGGAAGGTGGGACAGACGTAGACATCCTCTGTCTCAG
 S  G  G  G  G  S  G  G  G  G  S  D  V  V  M  T  Q  S  P  S  T  L  S  A  S  V  G  D  R  V>

       460       470       480       490       500       510       520       530       540
AGTATCACTTGCCGGGCCAGTGAGAGTATTAGTAGGTGGTTGGCCTGGTATCAGCAGAAACCAGGAAAAGCCCCTAAGGCCCTGATCTAT
TCATAGTGAACGGCCCGGTCACTCTCATAATCATCCACCAACCGGACCATAGTCGTCTTTGGTCCTTTTCGGGGATTCCGGGACTAGATA
 S  I  T  C  R  A  S  E  S  I  S  R  W  L  A  W  Y  Q  Q  K  P  G  K  A  P  K  A  L  I  Y>

       550       560       570       580       590       600       610       620       630
AAGGCATCTAGTTTAGAAAGTGGGGTCCCATCAAGGTTCAGCGGCAGTGGATCTGCGACAGAGTTCACTCTCACCATCAACAGCCTGCAG
TTCCGTAGATCAAATCTTTCACCCCAGGGTAGTTCCAAGTCGCCGTCACCTAGACGCTGTCTCAAGTGAGAGTGGTAGTTGTCGGACGTC
 K  A  S  S  L  E  S  G  V  P  S  R  F  S  G  S  G  S  A  T  E  F  T  L  T  I  N  S  L  Q>
```

FIG. 30A

```
         640       650       660       670       680       690       700       710(SEQ ID NO:316)
CCTGATGATTTTGCAACTTATTACTGCCAACAGTATAGTAGTTATCCGTTGACGTTCGGCCAAGGGACCAAAGTGGATATCAAACGT
GGACTACTAAAACGTTGAATAATGACGGTTGTCATATCATCAATAGGCAACTGCAAGCCGGTTCCCTGGTTTCACCTATAGTTTGCA
 P  D  D  F  A  T  Y  Y  C  Q  Q  Y  S  S  Y  P  L  T  F  G  Q  G  T  K  V  D  I  K  R>
                                                                            (SEQ ID NO:315)

                                                                                  (SEQ ID NO:419)
```

```
        10        20        30        40        50        60        70        80        90
CAGGTGCAGCTGGTGGAGTCTGGGGGAGGCGTGGTCCAACCTGGGAGGTCCCTGAGACTCTCCTGTGCAGCCTCTGGATTCACCTTCAGT
GTCCACGTCGACCACCTCAGACCCCCTCCGCACCAGGTTGGACCCTCCAGGGACTCTGAGAGGACACGTCGGAGACCTAAGTGGAAGTCA
 Q  V  Q  L  V  E  S  G  G  G  V  V  Q  P  G  R  S  L  R  L  S  C  A  A  S  G  F  T  F  S>

       100       110       120       130       140       150       160       170       180
AGCTATGGCATGCACTGGGTCCGCCAGGCTCCAGGCAAGGGGCTGGAGTGGGTGGCAGTTATATCATATGATGGAAGTAATAAATACTAT
TCGATACCGTACGTGACCCAGGCGGTCCGAGGTCCGTTCCCCGACCTCACCCACCGTCAATATAGTATACTACCTTCATTATTTATGATA
 S  Y  G  M  H  W  V  R  Q  A  P  G  K  G  L  E  W  V  A  V  I  S  Y  D  G  S  N  K  Y  Y>

       190       200       210       220       230       240       250       260       270
GCAGACTCCGTGAAGGGCCGATTCACCATCTCCAGAGACAATTCCAAGAACACGCTGTATCTGCAAATGAACAGCCTGAGAGCTGAGGAC
CGTCTGAGGCACTTCCCGGCTAAGTGGTAGAGGTCTCTGTTAAGGTTCTTGTGCGACATAGACGTTTACTTGTCGGACTCTCGACTCCTG
 A  D  S  V  K  G  R  F  T  I  S  R  D  N  S  K  N  T  L  Y  L  Q  M  N  S  L  R  A  E  D>

       280       290       300       310       320       330       340       350       360
ACGGCTGTGTATTACTGTGCGAGAGCCCTGTACTATGATGAAGCCCTTGACTACTGGGGCCAGGGAACCCTGGTCACCGTCTCTTCAGGT
TGCCGACACATAATGACACGCTCTCGGGACATGATACTACTTCGGGAACTGATGACCCCGGTCCCTTGGGACCAGTGGCAGAGAAGTCCA
 T  A  V  Y  Y  C  A  R  A  L  Y  Y  D  E  A  L  D  Y  W  G  Q  G  T  L  V  T  V  S  S  G>

       370       380       390       400       410       420       430       440       450
GGAGGCGGTTCAGGCGGAGGTGGCTCTGGCGGTGGCGGATCGGAAATTGTGTTGACGCAGTCTCCATCCTCACTGTCTGCATCTGTAGGA
CCTCCGCCAAGTCCGCCTCCACCGAGACCGCCACCGCCTAGCCTTTAACACAACTGCGTCAGAGGTAGGAGTGACAGACGTAGACATCCT
 G  G  G  S  G  G  G  G  S  G  G  G  G  S  E  I  V  L  T  Q  S  P  S  S  L  S  A  S  V  G>

       460       470       480       490       500       510       520       530       540
GACAGAGTCACCATCACTTGTCGGGCGAGTCAGGATATGAGCAGGTGGTTAGCCTGGTATCAGCAGAAACCAGGGAAAGCCCCTAAGCTC
CTGTCTCAGTGGTAGTGAACAGCCCGCTCAGTCCTATACTCGTCCACCAATCGGACCATAGTCGTCTTTGGTCCCTTTCGGGGATTCGAG
 D  R  V  T  I  T  C  R  A  S  Q  D  M  S  R  W  L  A  W  Y  Q  Q  K  P  G  K  A  P  K  L>
```

FIG. 31A

```
        550       560       570       580       590       600       610       620       630
CTGATCCATTCTGCATCCACTTTGCAAAGTGGGGTCCCATCAAGATTCAGCGGCAGTGGATCTGGGACAGAATTCACTCTGACAATAAGC
GACTAGGTAAGACGTAGGTGAAACGTTTCACCCCAGGGTAGTTCTAAGTCGCCGTCACCTAGACCCTGTCTTAAGTGAGACTGTTATTCG
 L  I  H  S  A  S  T  L  Q  S  G  V  P  S  R  F  S  G  S  G  S  G  T  E  F  T  L  T  I  S>

        640       650       660       670       680       690       700       710       720
AGCCTGCAGCCTGAAGATTTTGCAACTTACTATTGTCAACAACTTGGCGTTTACCCGCTCACTATCGGCGGGGGGACCAAGGTGGAAATC
TCGGACGTCGGACTTCTAAAACGTTGAATGATAACAGTTGTTGAACCGCAAATGGGCGAGTGATAGCCGCCCCCCTGGTTCCACCTTTAG
 S  L  Q  P  E  D  F  A  T  Y  Y  C  Q  Q  L  G  V  Y  P  L  T  I  G  G  G  T  K  V  E  I>

AAACGT (SEQ ID NO:318)
TTTGCA (SEQ ID NO:420)
 K  R> (SEQ ID NO:317)
```

```
        10        20        30        40        50        60        70        80        90
CAGGTGCAGCTGCAGGAGTCGGGGGGAGGCCTGGTCAAGCCTGGGGGGTCCCTGAGACTCTCCTGTGCAGGCTCTGGATTCATCTTCAAT
GTCCACGTCGACGTCCTCAGCCCCCCTCCGGACCAGTTCGGACCCCCCAGGGACTCTGAGAGGACACGTCCGAGACCTAAGTAGAAGTTA
 Q  V  Q  L  Q  E  S  G  G  G  L  V  K  P  G  G  S  L  R  L  S  C  A  G  S  G  F  I  F  N>

       100       110       120       130       140       150       160       170       180
ACCTATAGCATGAACTGGGTCCGCCAGTCTCCAGGGAAGGGGCTGGAGTGGGTCTCGTCCACTGGTGGTAGTGGTAAAAACACATTTTAT
TGGATATCGTACTTGACCCAGGCGGTCAGAGGTCCCTTCCCCGACCTCACCCAGAGCAGGTGACCACCATCACCATTTTTGTGTAAAATA
 T  Y  S  M  N  W  V  R  Q  S  P  G  K  G  L  E  W  V  S  S  T  G  G  S  G  K  N  T  F  Y>

       190       200       210       220       230       240       250       260       270
GCAGACTCAGTGAGGGGCCGATTCACCATCTCCAGAGACAACGCCAAGAACTCACTGTATCTGCAAATGAACAGCCTGAGAGCCGAAGAC
CGTCTGAGTCACTCCCCGGCTAAGTGGTAGAGGTCTCTGTTGCGGTTCTTGAGTGACATAGACGTTTACTTGTCGGACTCTCGGCTTCTG
 A  D  S  V  R  G  R  F  T  I  S  R  D  N  A  K  N  S  L  Y  L  Q  M  N  S  L  R  A  E  D>

       280       290       300       310       320       330       340       350       360
ACGGCTGTATATTACTGTGCGAGAGAGGATAGTAGTGGTTCCTTTGACTACTGGGGCCAGGGGACCCTGGTCACCGTCTCCTCAGGTGGA
TGCCGACATATAATGACACGCTCTCTCCTATCATCACCAAGGAAACTGATGACCCCGGTCCCCTGGGACCAGTGGCAGAGGAGTCCACCT
 T  A  V  Y  Y  C  A  R  E  D  S  S  G  S  F  D  Y  W  G  Q  G  T  L  V  T  V  S  S  G  G>

       370       380       390       400       410       420       430       440       450
GGCGGTTCAGGCGGAGGTGGCTCTGGCGGTGGCGGATCGGACATCCAGATGACCCAGTCTCCTTCCACCCTGTCTGCATCTATTGGAGAC
CCGCCAAGTCCGCCTCCACCGAGACCGCCACCGCCTAGCCTGTAGGTCTACTGGGTCAGAGGAAGGTGGGACAGACGTAGATAACCTCTG
 G  G  S  G  G  G  G  S  G  G  G  G  S  D  I  Q  M  T  Q  S  P  S  T  L  S  A  S  I  G  D>

       460       470       480       490       500       510       520       530       540
AGAGTCACCATCACCTGCCGGGCCAGTGAGGGTATTTATCACTGGTTGGCCTGGTATCAGCAGAAGCCAGGGAAAGCCCCTAAACTCCTG
TCTCAGTGGTAGTGGACGGCCCGGTCACTCCCATAAATAGTGACCAACCGGACCATAGTCGTCTTCGGTCCCTTTCGGGGATTTGAGGAC
 R  V  T  I  T  C  R  A  S  E  G  I  Y  H  W  L  A  W  Y  Q  Q  K  P  G  K  A  P  K  L  L>
```

FIG. 32A

```
        550       560       570       580       590       600       610       620       630
ATCTATAAGGCCTCTAGTTTAGCCAGTGGGGCCCCATCAAGGTTCAGCGGCAGTGGATCTGGGACAGATTTCACTCTCACCATCAGCAGC
TAGATATTCCGGAGATCAAATCGGTCACCCCGGGGTAGTTCCAAGTCGCCGTCACCTAGACCCTGTCTAAAGTGAGAGTGGTAGTCGTCG
 I  Y  K  A  S  S  L  A  S  G  A  P  S  R  F  S  G  S  G  S  G  T  D  F  T  L  T  I  S  S>

        640       650       660       670       680       690       700       710       720
CTGCAGCCTGATGATTTTGCAACTTATTACTGCCAGCAATATCATACTATTTCGAGGACGTTCGGCCCANGGACCAAGCTGGAGATCAAA
GACGTCGGACTACTAAAACGTTGAATAATGACGGTCGTTATAGTATGATAAAGCTCCTGCAAGCCGGGTNCCTGGTTCGACCTCTAGTTT
 L  Q  P  D  D  F  A  T  Y  Y  C  Q  Q  Y  H  T  I  S  R  T  F  G  P  X  T  K  L  E  I  K>

CGT (SEQ ID NO:320)
GCA (SEQ ID NO:421)
 R> (SEQ ID NO:319)
```

```
        10        20        30        40        50        60        70        80        90
CAGGTGCAGCTGGTGGAGTCTGGGGGAGGCGTGGTCCAGCCTGGGAGGTCCCTGAGACTCTCCTGTGCAGCGTCTGGATTCACCTTCAGT
GTCCACGTCGACCACCTCAGACCCCCTCCGCACCAGGTCGGACCCTCCAGGGACTCTGAGAGGACACGTCGCAGACCTAAGTGGAAGTCA
 Q  V  Q  L  V  E  S  G  G  G  V  V  Q  P  G  R  S  L  R  L  S  C  A  A  S  G  F  T  F  S>

       100       110       120       130       140       150       160       170       180
AGCTATGGCATGCACTGGGTCCGCCAGGCTCCAGGCAAGGGGCTGGAGTGGGTTTCATACATTAGTAGTAGTGGTAGTTACACAAACTAC
TCGATACCGTACGTGACCCAGGCGGTCCGAGGTCCGTTCCCCGACCTCACCCAAAGTATGTAATCATCATCACCATCAATGTGTTTGATG
 S  Y  G  M  H  W  V  R  Q  A  P  G  K  G  L  E  W  V  S  Y  I  S  S  S  G  S  Y  T  N  Y>

       190       200       210       220       230       240       250       260       270
GCAGACTCTGTGAAGGGCCGATTCACCATCTCCAGAGACAACGCCAAGAACACGCTGTATCTGCAAATGAACAGCCTGAGAGCCGAGGAC
CGTCTGAGACACTTCCCGGCTAAGTGGTAGAGGTCTCTGTTGCGGTTCTTGTGCGACATAGACGTTTACTTGTCGGACTCTCGGCTCCTG
 A  D  S  V  K  G  R  F  T  I  S  R  D  N  A  K  N  T  L  Y  L  Q  M  N  S  L  R  A  E  D>

       280       290       300       310       320       330       340       350       360
ACGGCCGTATATTACTGTGCGAAAGTCCGTGGGTGGGACGGTGACTACTTAGACTACTGGGGCCAGGGAACCCTGGTCACCGTCTCCTCA
TGCCGGCATATAATGACACGCTTTCAGGCACCCACCCTGCCACTGATGAATCTGATGACCCCGGTCCCTTGGGACCAGTGGCAGAGGAGT
 T  A  V  Y  Y  C  A  K  V  R  G  W  D  G  D  Y  L  D  Y  W  G  Q  G  T  L  V  T  V  S  S>

       370       380       390       400       410       420       430       440       450
GGTGGAGGCGGTTCAGGCGGAGGTGGCTCTGGCGGTGCCGGATCGGACATCCAGATGACCCAGTCTCCATCCCTCCTGTCTGCATCTGTA
CCACCTCCGCCAAGTCCGCCTCCACCGAGACCGCCACGGCCTAGCCTGTAGGTCTACTGGGTCAGAGGTAGGGAGGACAGACGTAGACAT
 G  G  G  G  S  G  G  G  G  S  G  G  A  G  S  D  I  Q  M  T  Q  S  P  S  L  L  S  A  S  V>

       460       470       480       490       500       510       520       530       540
GGAGACAGAGTCACCATCACTTGCCGGGCCAGTCAGGGCATTAACAATTATTTAGCCTGGTATCAGCAAAAACCAGGGAAAGCCCCTAAA
CCTCTGTCTCAGTGGTAGTGAACGGCCCGGTCAGTCCCGTAATTGTTAATAAATCGGACCATAGTCGTTTTTGGTCCCTTTCGGGGATTT
 G  D  R  V  T  I  T  C  R  A  S  Q  G  I  N  N  Y  L  A  W  Y  Q  Q  K  P  G  K  A  P  K>
```

FIG. 33A

```
        550       560       570       580       590       600       610       620       630
CTCCTGATCTATGCTGCATCCACTTTGCAAAGTGGGGTCCCGTCAAGGTTCAGCGGCAGTGGATCTGGGACAGAATTCACTCTCACAATC
GAGGACTAGATACGACGTAGGTGAAACGTTTCACCCCAGGGCAGTTCCAAGTCGCCGTCACCTAGACCCTGTCTTAAGTGAGAGTGTTAG
 L  L  I  Y  A  A  S  T  L  Q  S  G  V  P  S  R  F  S  G  S  G  S  G  T  E  F  T  L  T  I>

        640       650       660       670       680       690       700       710       720
AGCGGCCTGCAGCCTGAAGATTTTGCAACTTATTACTGTCAAAACCTTAATAGTTACCCGCTCACTTTCGGCGGAGGGACCAAGGTGGAA
TCGCCGGACGTCGGACTTCTAAAACGTTGAATAATGACAGTTTTGGAATTATCAATGGGCGAGTGAAAGCCGCCTCCCTGGTTCCACCTT
 S  G  L  Q  P  E  D  F  A  T  Y  Y  C  Q  N  L  N  S  Y  P  L  T  F  G  G  G  T  K  V  E>

ATCAAACGT (SEQ ID NO:322)
TAGTTTGCA (SEQ ID NO:422)
 I  K  R> (SEQ ID NO:321)
```

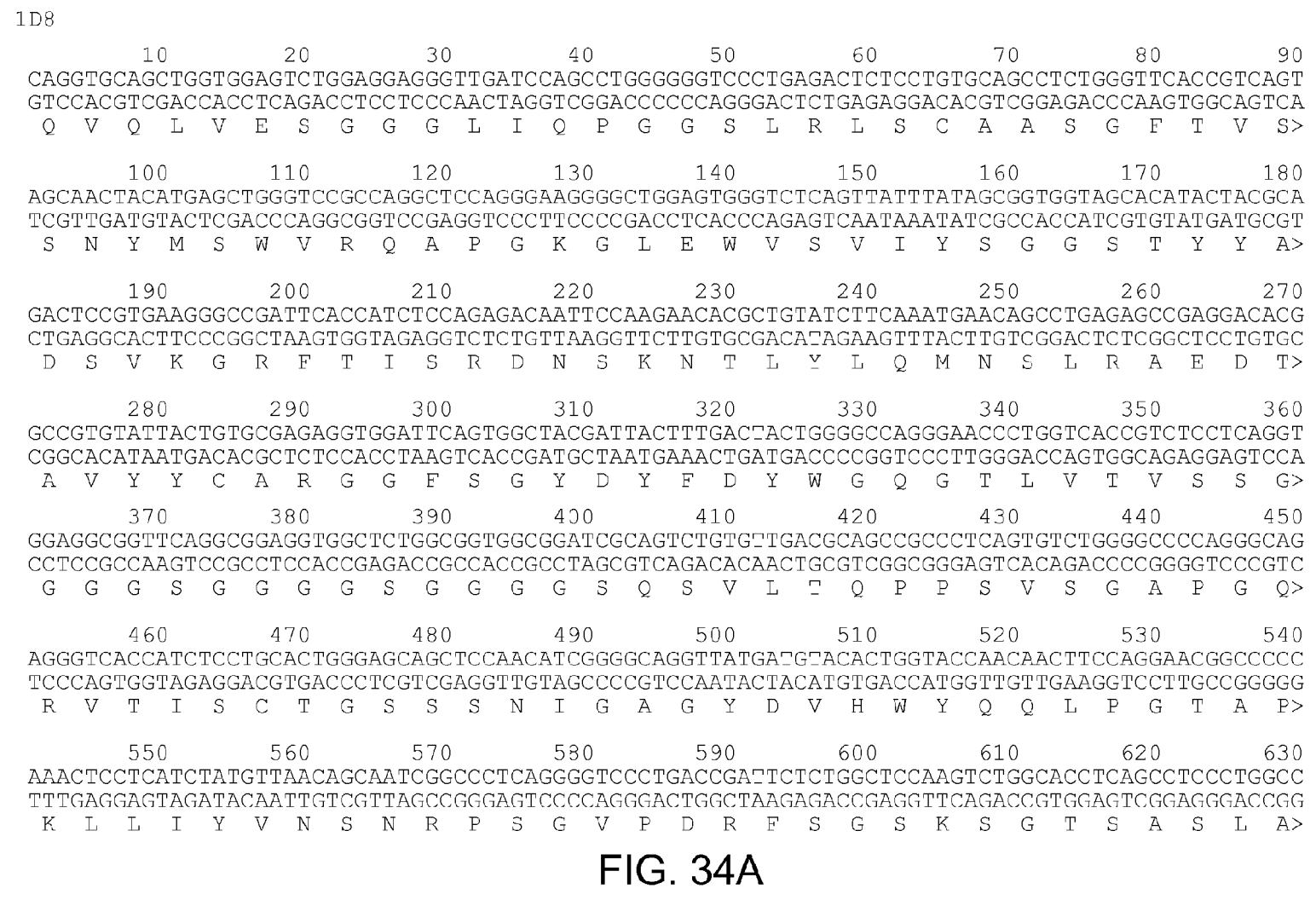

```
         10        20        30        40        50        60        70        80        90
CAGGTGCAGCTGGTGGAGTCTGGAGGAGGGTTGATCCAGCCTGGGGGGTCCCTGAGACTCTCCTGTGCAGCCTCTGGGTTCACCGTCAGT
GTCCACGTCGACCACCTCAGACCTCCTCCCAACTAGGTCGGACCCCCCAGGGACTCTGAGAGGACACGTCGGAGACCCAAGTGGCAGTCA
 Q  V  Q  L  V  E  S  G  G  G  L  I  Q  P  G  G  S  L  R  L  S  C  A  A  S  G  F  T  V  S>

        100       110       120       130       140       150       160       170       180
AGCAACTACATGAGCTGGGTCCGCCAGGCTCCAGGGAAGGGGCTGGAGTGGGTCTCAGTTATTTATAGCGGTGGTAGCACATACTACGCA
TCGTTGATGTACTCGACCCAGGCGGTCCGAGGTCCCTTCCCCGACCTCACCCAGAGTCAATAAATATCGCCACCATCGTGTATGATGCGT
 S  N  Y  M  S  W  V  R  Q  A  P  G  K  G  L  E  W  V  S  V  I  Y  S  G  G  S  T  Y  Y  A>

        190       200       210       220       230       240       250       260       270
GACTCCGTGAAGGGCCGATTCACCATCTCCAGAGACAATTCCAAGAACACGCTGTATCTTCAAATGAACAGCCTGAGAGCCGAGGACACG
CTGAGGCACTTCCCGGCTAAGTGGTAGAGGTCTCTGTTAAGGTTCTTGTGCGACATAGAAGTTTACTTGTCGGACTCTCGGCTCCTGTGC
 D  S  V  K  G  R  F  T  I  S  R  D  N  S  K  N  T  L  Y  L  Q  M  N  S  L  R  A  E  D  T>

        280       290       300       310       320       330       340       350       360
GCCGTGTATTACTGTGCGAGAGGTGGATTCAGTGGCTACGATTACTTTGACTACTGGGGCCAGGGAACCCTGGTCACCGTCTCCTCAGGT
CGGCACATAATGACACGCTCTCCACCTAAGTCACCGATGCTAATGAAACTGATGACCCCGGTCCCTTGGGACCAGTGGCAGAGGAGTCCA
 A  V  Y  Y  C  A  R  G  G  F  S  G  Y  D  Y  F  D  Y  W  G  Q  G  T  L  V  T  V  S  S  G>

        370       380       390       400       410       420       430       440       450
GGAGGCGGTTCAGGCGGAGGTGGCTCTGGCGGTGGCGGATCGCAGTCTGTGTTGACGCAGCCGCCCTCAGTGTCTGGGGCCCCAGGGCAG
CCTCCGCCAAGTCCGCCTCCACCGAGACCGCCACCGCCTAGCGTCAGACACAACTGCGTCGGCGGGAGTCACAGACCCCGGGGTCCCGTC
 G  G  G  S  G  G  G  G  S  G  G  G  G  S  Q  S  V  L  T  Q  P  P  S  V  S  G  A  P  G  Q>

        460       470       480       490       500       510       520       530       540
AGGGTCACCATCTCCTGCACTGGGAGCAGCTCCAACATCGGGGCAGGTTATGATGTACACTGGTACCAACAACTTCCAGGAACGGCCCCC
TCCCAGTGGTAGAGGACGTGACCCTCGTCGAGGTTGTAGCCCCGTCCAATACTACATGTGACCATGGTTGTTGAAGGTCCTTGCCGGGGG
 R  V  T  I  S  C  T  G  S  S  S  N  I  G  A  G  Y  D  V  H  W  Y  Q  Q  L  P  G  T  A  P>

        550       560       570       580       590       600       610       620       630
AAACTCCTCATCTATGTTAACAGCAATCGGCCCTCAGGGGTCCCTGACCGATTCTCTGGCTCCAAGTCTGGCACCTCAGCCTCCCTGGCC
TTTGAGGAGTAGATACAATTGTCGTTAGCCGGGAGTCCCCAGGGACTGGCTAAGAGACCGAGGTTCAGACCGTGGAGTCGGAGGGACCGG
 K  L  L  I  Y  V  N  S  N  R  P  S  G  V  P  D  R  F  S  G  S  K  S  G  T  S  A  S  L  A>
```

FIG. 34A

```
        640       650       660       670       680       690       700       710       720
ATCACTGGGCTCCAGGCTGAGGATGAGGCTGATTATTACTGCCAGTCCTATGACAGCAGCCTGAGTGGTTGGGTGTTCGGCGGAGGGACC
TAGTGACCCGAGGTCCGACTCCTACTCCGACTAATAATGACGGTCAGGATACTGTCGTCGGACTCACCAACCCACAAGCCGCCTCCCTGG
 I  T  G  L  Q  A  E  D  E  A  D  Y  Y  C  Q  S  Y  D  S  S  L  S  G  W  V  F  G  G  G  T>

        730
AAGCTGACCGTCCTAGGT (SEQ ID NO:324)
TTCGACTGGCAGGATCCA (SEQ ID NO:423)
 K  L  T  V  L  G> (SEQ ID NO:323)
```

```
         10         20         30         40         50
CAGGTGCAGC TGCAGGAGTC GGGGGGAGGC CTGGTCAAGC CTGGGGGGTC
GTCCACGTCG ACGTCCTCAG CCCCCCTCCG GACCAGTTCG GACCCCCCAG
 Q  V  Q   L  Q  E  S   G  G  G   L  V  K   P  G  G  S>

         60         70         80         90        100
CCTGAGACTC TCCTGTGCAG CCTCTGGATT CACCTTCAGT AGCTATAGCA
GGACTCTGAG AGGACACGTC GGAGACCTAA GTGGAAGTCA TCGATATCGT
  L  R  L   S  C  A   A  S  G  F   T  F  S   S  Y  S>

        110        120        130        140        150
TGAACTGGGT CCGCCAGGCT CCAGGGAAGG GGCTGGAGTG GGTCTCATCC
ACTTGACCCA GGCGGTCCGA GGTCCCTTCC CCGACCTCAC CCAGAGTAGG
M  N  W  V   R  Q  A   P  G  K   G  L  E  W   V  S  S>

        160        170        180        190        200
ATTAGTAGTA GTAGTTACAT ATACTACGCA GACTCAGTGA AGGGCCGATT
TAATCATCAT CATCAATGTA TATGATGCGT CTGAGTCACT TCCCGGCTAA
 I  S  S   S  S  Y  I   Y  Y  A   D  S  V   K  G  R  F>

        210        220        230        240        250
CACCATCTCC AGAGACAACG CCAAGAACTC ACTGTATCTG CAAATGAACA
GTGGTAGAGG TCTCTGTTGC GGTTCTTGAG TGACATAGAC GTTTACTTGT
  T  I  S   R  D  N   A  K  N  S   L  Y  L   Q  M  N>

        260        270        280        290        300
GCCTGAGAGC CGAGGACACG GCTGTGTATT ACTGTGCGAG AGGGGCCTAT
CGGACTCTCG GCTCCTGTGC CGACACATAA TGACACGCTC TCCCCGGATA
S  L  R  A   E  D  T   A  V  Y   Y  C  A  R   G  A  Y>

        310        320        330        340        350
TACGATTTTT GGGGTGGTGA TTACTTTGAC TACTGGGGCC AGGGCACCCT
ATGCTAAAAA CCCCACCACT AATGAAACTG ATGACCCCGG TCCCGTGGGA
 Y  D  F   W  G  G  D   Y  F  D   Y  W  G   Q  G  T  L>

        360        370        380        390        400
GGTCACCGTC TCCTCAGGTG GAGGCGGTTC AGGCGGAGGT GGCTCTGGCG
CCAGTGGCAG AGGAGTCCAC CTCCGCCAAG TCCGCCTCCA CCGAGACCGC
  V  T  V   S  S  G   G  G  G  S   G  G  G   G  S  G>

        410        420        430        440        450
GTGGCGGATC GTCTGAGCTG ACTCAGGACC CTGCTGTGTC TGTGGCCTTG
CACCGCCTAG CAGACTCGAC TGAGTCCTGG GACGACACAG ACACCGGAAC
G  G  G  S   S  E  L   T  Q  D   P  A  V  S   V  A  L>

        460        470        480        490        500
GGAGAGACAG TCACAATCAC GTGCCAAGGA GACATTCTCA GAGGCTATTA
CCTCTCTGTC AGTGTTAGTG CACGGTTCCT CTGTAAGAGT CTCCGATAAT
 G  E  T   V  T  I  T   C  Q  G   D  I  L   R  G  Y  Y>
```

FIG. 35A

```
        510        520        530        540        550
TGCAAGCTGG TACCAGCAGA AGCCAGGACA GGCCCCTATA CTTGTCATCT
ACGTTCGACC ATGGTCGTCT TCGGTCCTGT CCGGGGATAT GAACAGTAGA
  A  S  W   Y  Q  Q   K  P  G  Q   A  P  I   L  V  I>

        560        570        580        590        600
ATAATAAAAA CAACCGGCCC TCAGGGATCC CAGACCGATT CTCTGGCTCC
TATTATTTTT GTTGGCCGGG AGTCCCTAGG GTCTGGCTAA GAGACCGAGG
Y  N  K  N   N  R  P   S  G  I   P  D  R  F   S  G  S>

        610        620        630        640        650
AGCTCAGGAA ACACAGCTTC CTTGACCATC ACTGGGGCTC AGGCGGAAGA
TCGAGTCCTT TGTGTCGAAG GAACTGGTAG TGACCCCGAG TCCGCCTTCT
 S  S  G   N  T  A  S   L  T  I   T  G  A   Q  A  E  D>

        660        670        680        690        700
TGAGGCTGAC TATTACTGTA ACTCCCGGGA CAGCAGTAGT ACCCATCGAG
ACTCCGACTG ATAATGACAT TGAGGGCCCT GTCGTCATCA TGGGTAGCTC
  E  A  D   Y  Y  C   N  S  R  D   S  S  S   T  H  R>

        710        720        730
GGGTGTTCGG CGGAGGGACC AAGCTGACCG TCCTGGGT (SEQ ID NO: 326)
CCCACAAGCC GCCTCCCTGG TTCGACTGGC AGGACCCA (SEQ ID NO: 424)
G  V  F  G   G  G  T   K  L  T   V  L  G> (SEQ ID NO: 325)
```

```
         10        20        30        40        50        60        70        80        90
CAGGTACAGCTGCAGCAGTCAGGGGGAGGCGTGGTCCAGCCTGGGAGGTCCCTGAGACTCTCCTGTGCAGCCTCTGGATTCACCTTCAGT
GTCCATGTCGACGTCGTCAGTCCCCCTCCGCACCAGGTCGGACCCTCCAGGGACTCTGAGAGGACACGTCGGAGACCTAAGTGGAAGTCA
 Q  V  Q  L  Q  Q  S  G  G  G  V  V  Q  P  G  R  S  L  R  L  S  C  A  A  S  G  F  T  F  S>

        100       110       120       130       140       150       160       170       180
AGCTATGGCATTCACTGGGTCCGCCAGGCTCCAGGCAAGGGGCTGGAGTGGGTGGCAGTTATATCATATGATGGAAGTAATAAATACTAT
TCGATACCGTAAGTGACCCAGGCGGTCCGAGGTCCGTTCCCCGACCTCACCCACCGTCAATATAGTATACTACCTTCATTATTTATGATA
 S  Y  G  I  H  W  V  R  Q  A  P  G  K  G  L  E  W  V  A  V  I  S  Y  D  G  S  N  K  Y  Y>

        190       200       210       220       230       240       250       260       270
GCAGACTCCGTGAAGGGCCGATTCACCATCTCCAGAGACAATTCCAAGAACACGCTGTATCTGCAAATGAACAGCCTGAGAGCTGAGGAC
CGTCTGAGGCACTTCCCGGCTAAGTGGTAGAGGTCTCTGTTAAGGTTCTTGTGCGACATAGACGTTTACTTGTCGGACTCTCGACTCCTG
 A  D  S  V  K  G  R  F  T  I  S  R  D  N  S  K  N  T  L  Y  L  Q  M  N  S  L  R  A  E  D>

        280       290       300       310       320       330       340       350       360
ACGGCTGTGTATTACTGTGCGAAAGGCTATGGTTCAGGGAGTTATTGGTCGGGTGCTTTTGATATCTGGGGCCAAGGGACAATGGTCACC
TGCCGACACATAATGACACGCTTTCCGATACCAAGTCCCTCAATAACCAGCCCACGAAAACTATAGACCCCGGTTCCCTGTTACCAGTGG
 T  A  V  Y  Y  C  A  K  G  Y  G  S  G  S  Y  W  S  G  A  F  D  I  W  G  Q  G  T  M  V  T>

        370       380       390       400       410       420       430       440       450
GTCTCCTCAGGTGGAGGCGGTTCAGGCGGAGGTGGCTCTGGCGGTGGCGGATCGGAAATTGTGTTGACGCAGTCTCCACTCTCCCTGCCC
CAGAGGAGTCCACCTCCGCCAAGTCCGCCTCCACCGAGACCGCCACCGCCTAGCCTTTAACACAACTGCGTCAGAGGTGAGAGGGACGGG
 V  S  S  G  G  G  G  S  G  G  G  G  S  G  G  G  G  S  E  I  V  L  T  Q  S  P  L  S  L  P>

        460       470       480       490       500       510       520       530       540
GTCACCCCTGGAGAGCCGGCCTCCATCTCCTGCAGGTCTAGTCAGAGCCTCCTGCATACTAATGGATACAACTATTTGGATTGGTACCTG
CAGTGGGGACCTCTCGGCCGGAGGTAGAGGACGTCCAGATCAGTCTCGGAGGACGTATGATTACCTATGTTGATAAACCTAACCATGGAC
 V  T  P  G  E  P  A  S  I  S  C  R  S  S  Q  S  L  L  H  T  N  G  Y  N  Y  L  D  W  Y  L>

        550       560       570       580       590       600       610       620       630
CAGAAGCCAGGGCAGTCTCCACAACTCCTGATCTACTTGGGTTCTAATCGGGCCTCCGGGGTCCCTGACAGGTTCAGTGGCAGTGGATCA
GTCTTCGGTCCCGTCAGAGGTGTTGAGGACTAGATGAACCCAAGATTAGCCCGGAGGCCCCAGGGACTGTCCAAGTCACCGTCACCTAGT
 Q  K  P  G  Q  S  P  Q  L  L  I  Y  L  G  S  N  R  A  S  G  V  P  D  R  F  S  G  S  G  S>
```

FIG. 36A

```
        640       650       660       670       680       690       700       710       720
GGCACAGATTTTACACTGAAAATCAGCAGAGTGGAGGCTGAGGATGTTGGGGTTTATTACTGCATGCAAGGTCGACAAAGTCCGCTCACT
CCGTGTCTAAAATGTGACTTTTAGTCGTCTCACCTCCGACTCCTACAACCCCAAATAATGACGTACGTTCCAGCTGTTTCAGGCGAGTGA
 G  T  D  F  T  L  K  I  S  R  V  E  A  E  D  V  G  V  Y  Y  C  M  Q  G  R  Q  S  P  L  T>

        730       740       750
TTCGGCGGAGGGACCAAGGTGGAAATCAAACGT (SEQ ID NO:328)
AAGCCGCCTCCCTGGTTCCACCTTTAGTTTGCA (SEQ ID NO:425)
 F  G  G  G  T  K  V  E  I  K  R> (SEQ ID NO:327)
```

FIG. 36B

```
D1D1
         10        20        30        40        50        60        70        80        90
CAGGTGCAGCTGGTCGAGTCTGGGGGAGGCCTGGTCAAGCCTGGGGGGTCCCTGAGACTCTCCTGTGCAGCCTCTGGATTCACCTTCAGC
GTCCACGTCGACCAGCTCAGACCCCCTCCGGACCAGTTCGGACCCCCCAGGGACTCTGAGAGGACACGTCGGAGACCTAAGTGGAAGTCG
 Q  V  Q  L  V  E  S  G  G  G  L  V  K  P  G  G  S  L  R  L  S  C  A  A  S  G  F  T  F  S>

        100       110       120       130       140       150       160       170       180
ACCTATACCATGAGCTGGGCCCGCCAGGCTCCAGGGAAGGGGCTGGAATGGGTCTCAGCTATTAGTGCTGATGGTGCTGGCACATACTAC
TGGATATGGTACTCGACCCGGGCGGTCCGAGGTCCCTTCCCCGACCTTACCCAGAGTCGATAATCACGACTACCACGACCGTGTATGATG
 T  Y  T  M  S  W  A  R  Q  A  P  G  K  G  L  E  W  V  S  A  I  S  A  D  G  A  G  T  Y  Y>

        190       200       210       220       230       240       250       260       270
GGAGACTCCGTGAAGGGCCGGTTCACCGTCTCCAGAGACAATTTCAAGAGCACGCTGTATCTGCAAATGAACAGACTGAGAGCCGAAGAC
CCTCTGAGGCACTTCCCGGCCAAGTGGCAGAGGTCTCTGTTAAAGTTCTCGTGCGACATAGACGTTTACTTGTCTGACTCTCGGCTTCTG
 G  D  S  V  K  G  R  F  T  V  S  R  D  N  F  K  S  T  L  Y  L  Q  M  N  R  L  R  A  E  D>

        280       290       300       310       320       330       340       350       360
ACGGCCGTATATTACTGTGCGAAGCTGGGCGGTGAGAGCTACTCTGCCGACTGGGGCCAGGGCACCCTGGTCACCGTCTCCTCAAGTGGA
TGCCGGCATATAATGACACGCTTCGACCCGCCACTCTCGATGAGACGGCTGACCCCGGTCCCGTGGGACCAGTGGCAGAGGAGTTCACCT
 T  A  V  Y  Y  C  A  K  L  G  G  E  S  Y  S  A  D  W  G  Q  G  T  L  V  T  V  S  S  S

        370       380       390       400       410       420       430       440       450
GGCGGTTCAGGCGGAGGTGGCTCTGGCGGTGGCGGATCGCACGTTATACTGACTCAGGACCCTGCTGTGTCTGTGGCCTTGGGACAGACA
CCGCCAAGTCCGCCTCCACCGAGACCGCCACCGCCTAGCGTGCAATATGACTGAGTCCTGGGACGACACAGACACCGGAACCCTGTCTGT
 G  G  S  G  G  G  G  S  G  G  G  G  S  H  V  I  L  T  Q  D  P  A  V  S  V  A  L  G  Q  T>

        460       470       480       490       500       510       520       530       540
GTCAAGATCACATGCCAAGGAGACAGCCTCAGAAGCTATTATGCAAGCTGGTACCAGCAGAAGCCAGGACAGGCCCCTCTCCTTGTCTTG
CAGTTCTAGTGTACGGTTCCTCTGTCGGAGTCTTCGATAATACGTTCGACCATGGTCGTCTTCGGTCCTGTCCGGGGAGAGGAACAGAAC
 V  K  I  T  C  Q  G  D  S  L  R  S  Y  Y  A  S  W  Y  Q  Q  K  P  G  Q  A  P  L  L  V  L>

        550       560       570       580       590       600       610       620       630
TATGGTGAAAACAACCGGCCCTCAGGGATCCCAGACCGATTCTCTGGCTCCGGCTCAGGAAACACAGCTTCCTTGACCATCACTGGGGCT
ATACCACTTTTGTTGGCCGGGAGTCCCTAGGGTCTGGCTAAGAGACCGAGGCCGAGTCCTTTGTGTCGAAGGAACTGGTAGTGACCCCGA
 Y  G  E  N  N  R  P  S  G  I  P  D  R  F  S  G  S  G  S  G  N  T  A  S  L  T  I  T  G  A>
```

FIG. 37A

```
        640       650       660       670       680       690       700       710       720
CAGGCGGAAGATGAGGCTGACTATTACTGTCACTCCCGGGACAGCAGTGGGAAGTATGTCTTCGGAGTTGGGACCAAGGTCACCGTCCTA
GTCCGCCTTCTACTCCGACTGATAATGACAGTGAGGGCCCTGTCGTCACCCTTCATACAGAAGCCTCAACCCTGGTTCCAGTGGCAGGAT
 Q  A  E  D  E  A  D  Y  Y  C  H  S  R  D  S  S  G  K  Y  V  F  G  V  G  T  K  V  T  V  L

GGT (SEQ ID NO:330)
CCA (SEQ ID NO:426)
 G> (SEQ ID NO:329)
```

```
         10        20        30        40        50        60        70        80        90
CAGGTGCAGTTGGTGGAGTCTGGGGGAGGCGTGGTCCAGCCTGGGAGGTCCCTGAGACTCTCCTGTGCAGCCTCTGGATTCACCTTTAGC
GTCCACGTCAACCACCTCAGACCCCCTCCGCACCAGGTCGGACCCTCCAGGGACTCTGAGAGGACACGTCGGAGACCTAAGTGGAAATCG
 Q  V  Q  L  V  E  S  G  G  G  V  V  Q  P  G  R  S  L  R  L  S  C  A  A  S  G  F  T  F  S>

        100       110       120       130       140       150       160       170       180
AACTATGCCATGATCTGGGTCCGCCAGGCTCCAGGGAAGGGGCTGGAGTGGGTCTCAGCTATTACTGGTGGTGGTGGTAGCACATACTAC
TTGATACGGTACTAGACCCAGGCGGTCCGAGGTCCCTTCCCCGACCTCACCCAGAGTCGATAATGACCACCACCACCATCGTGTATGATG
 N  Y  A  M  I  W  V  R  Q  A  P  G  K  G  L  E  W  V  S  A  I  T  G  G  G  G  S  T  Y  Y>

        190       200       210       220       230       240       250       260       270
GCAGACTCCGTGAAGGGCCGGTTCACCATCTCCAGAGACAATTCCAAGAACACGCTGTATCTGCAAATGAACAGCCTGAGAGCCGAGGAC
CGTCTGAGGCACTTCCCGGCCAAGTGGTAGAGGTCTCTGTTAAGGTTCTTGTGCGACATAGACGTTTACTTGTCGGACTCTCGGCTCCTG
 A  D  S  V  K  G  R  F  T  I  S  R  D  N  S  K  N  T  L  Y  L  Q  M  N  S  L  R  A  E  D>

        280       290       300       310       320       330       340       350       360
ACGGCCTTGTATTATTGTGCAAAAACTTTGGGACGTTCAACAGTGGCTACTGACTACTGGGGCCAGGGCACCCTGGTCACCGTCTCCTCA
TGCCGGAACATAATAACACGTTTTTGAAACCCTGCAAGTTGTCACCGATGACTGATGACCCCGGTCCCGTGGGACCAGTGGCAGAGGAGT
 T  A  L  Y  Y  C  A  K  T  L  G  R  S  T  V  A  T  D  Y  W  G  Q  G  T  L  V  T  V  S  S>

        370       380       390       400       410       420       430       440       450
GGTGGAGGCGGTTCAGGCGGAGGTGGCTCTGGCGGTGGCGGATCGTCTGAGCTGACTCAGGACCCTGCTGTGTCTGTGGCCTTGGGACAG
CCACCTCCGCCAAGTCCGCCTCCACCGAGACCGCCACCGCCTAGCAGACTCGACTGAGTCCTGGGACGACACAGACACCGGAACCCTGTC
 G  G  G  G  S  G  G  G  G  S  G  G  G  G  S  S  E  L  T  Q  D  P  A  V  S  V  A  L  G  Q>

        460       470       480       490       500       510       520       530       540
ACAGTCAGGATCACATGCCAAGGAGACAGCCTCAGAAGCTATTATGCAAGCTGGTACCAGCAGAAGCCAGGACAGGCCCCTGTACTTGTC
TGTCAGTCCTAGTGTACGGTTCCTCTGTCGGAGTCTTCGATAATACGTTCGACCATGGTCGTCTTCGGTCCTGTCCGGGGACATGAACAG
T  V  R  I  T  C  Q  G  D  S  L  R  S  Y  Y  A  S  W  Y  Q  Q  K  P  G  Q  A  P  V  L  V>
```

FIG. 38A

```
         550       560       570       580       590       600       610       620       630
ATCTATGGTAAAAACAACCGGCCCTCAGGGATCCCAGACCGATTCTCTGGCTCCAGCTCAGGAAACACAGCTTCCTTGACCATCACTGGG
TAGATACCATTTTTGTTGGCCGGGAGTCCCTAGGGTCTGGCTAAGAGACCGAGGTCGAGTCCTTTGTGTCGAAGGAACTGGTAGTGACCC
 I  Y  G  K  N  N  R  P  S  G  I  P  D  R  F  S  G  S  S  S  G  N  T  A  S  L  T  I  T  G>

         640       650       660       670       680       690       700       710       720
GCTCAGGCGGAAGATGAGGCTGACTATTACTGTAACTCCCGGGACAGCAGTGGTAACCCTCATGTGGTATTCGGCGGAGGGACAAAGCTG
CGAGTCCGCCTTCTACTCCGACTGATAATGACATTGAGGGCCCTGTCGTCACCATTGGGAGTACACCATAAGCCGCCTCCCTGTTTCGAC
 A  Q  A  E  D  E  A  D  Y  Y  C  N  S  R  D  S  S  G  N  P  H  V  V  F  G  G  G  T  K  L>

ACCGTCCTAGGT (SEQ ID NO:332)
TGGCAGGATCCA (SEQ ID NO:427)
 T  V  L  G> (SEQ ID NO:331)
```

FIG. 38B

```
H1C2
          10        20        30        40        50        60        70        80        90
CAGGTGCAGCGGGTGGAGTCTGGGGGAGGCGTGGTCCAGCCTGGGAGGTCCCTGAGACTCTCCTGTGCAGCCTCTGGATTCACCTTTAGC
GTCCACGTCGCCCACCTCAGACCCCCTCCGCACCAGGTCGGACCCTCCAGGGACTCTGAGAGGACACGTCGGAGACCTAAGTGGAAATCG
 Q  V  Q  R  V  E  S  G  G  G  V  V  Q  P  G  R  S  L  R  L  S  C  A  A  S  G  F  T  F  S>

         100       110       120       130       140       150       160       170       180
AGCTATGCCATGAGCTGGGTCCGCCAGGCTCCAGGGAAGGGGCTGGAGTGGGTCTCAGCTATTAGTGGTAGTGGTGGTAGCACATACTAC
TCGATACGGTACTCGACCCAGGCGGTCCGAGGTCCCTTCCCCGACCTCACCCAGAGTCGATAATCACCATCACCACCATCGTGTATGATG
 S  Y  A  M  S  W  V  R  Q  A  P  G  K  G  L  E  W  V  S  A  I  S  G  S  G  G  S  T  Y  Y>

         190       200       210       220       230       240       250       260       270
GCAGACTCCGTGAAGGGCCGGTTCACCATCTCCAGAGACAATTCCAAGAACACGCTGTATCTGCAAATGAACAGCCTGAGAGCCGAGGAC
CGTCTGAGGCACTTCCCGGCCAAGTGGTAGAGGTCTCTGTTAAGGTTCTTGTGCGACATAGACGTTTACTTGTCGGACTCTCGGCTCCTG
 A  D  S  V  K  G  R  F  T  I  S  R  D  N  S  K  N  T  L  Y  L  Q  M  N  S  L  R  A  E  D>

         280       290       300       310       320       330       340       350       360
ACGGCCGTATATTACTGTGCGAAAGGCCCGGGGGCAGCTCAAGACTACTGGGGCCAGGGAACCCTGGTCACCGTCTCCTCAGGTGGAGGC
TGCCGGCATATAATGACACGCTTTCCGGGCCCCCGTCGAGTTCTGATGACCCCGGTCCCTTGGGACCAGTGGCAGAGGAGTCCACCTCCG
 T  A  V  Y  Y  C  A  K  G  P  G  A  A  Q  D  Y  W  G  Q  G  T  L  V  T  V  S  S  G  G  G>

         370       380       390       400       410       420       430       440       450
GGTTCAGGCGGAGGTGGCTCTGGCAGTGGCGGATCGCAGTCTGTGTTGACTCAGGACCCTGCTGTGTCTGTGGCCTTGGGACAGACAGTC
CCAAGTCCGCCTCCACCGAGACCGTCACCGCCTAGCGTCAGACACAACTGAGTCCTGGGACGACACAGACACCGGAACCCTGTCTGTCAG
 G  S  G  G  G  G  S  G  S  G  G  S  Q  S  V  L  T  Q  D  P  A  V  S  V  A  L  G  Q  T  V>

         460       470       480       490       500       510       520       530       540
ACGATCACATGCCAAGGAGACAGCCTCAGAAGCTATTATGCAAGCTGGTACCAGCAGAAGCCAGGACAGGCCCCTGTACTTGTCATCTAT
TGCTAGTGTACGGTTCCTCTGTCGGAGTCTTCGATAATACGTTCGACCATGGTCGTCTTCGGTCCTGTCCGGGGACATGAACAGTAGATA
 T  I  T  C  Q  G  D  S  L  R  S  Y  Y  A  S  W  Y  Q  Q  K  P  G  Q  A  P  V  L  V  I  Y>
```

FIG. 39A

```
        550       560       570       580       590       600       610       620       630
GGTAAAAACAACCGGCCCTCAGGGATCCCAGACCGATTCTCTGGCTCCAGCTCAGGAAACACAGCTTCCTTGACCATCACTGGGGCTCAG
CCATTTTTGTTGGCCGGGAGTCCCTAGGGTCTGGCTAAGAGACCGAGGTCGAGTCCTTTGTGTCGAAGGAACTGGTAGTGACCCCGAGTC
 G  K  N  N  R  P  S  G  I  P  D  R  F  S  G  S  S  S  G  N  T  A  S  L  T  I  T  G  A  Q>

        640       650       660       670       680       690       700       710       720
GCGGAAGATGAGGCTGACTATTACTGTAACTCCCGGGACAGCAGTGGTAACCATGTGGTATTCGGCGGAGGGACCAAGGTCACCGTCCTA
CGCCTTCTACTCCGACTGATAATGACATTGAGGGCCCTGTCGTCACCATTGGTACACCATAAGCCGCCTCCCTGGTTCCAGTGGCAGGAT
 A  E  D  E  A  D  Y  Y  C  N  S  R  D  S  S  G  N  H  V  V  F  G  G  G  T  K  V  T  V  L>
```

GGT (SEQ ID NO:334)
CCA (SEQ ID NO:428)
G> (SEQ ID NO:333)

FIG. 39B

```
H1C4
         10        20        30        40        50        60        70        80        90
CAGGTGCAGCTGGTGGAGTCTGGGGGAGGCTTGGTACAGCCTGGGGGGTCCCTGAGACTCTCCTGTGCAGCCTCTGGATTCACCTTTAGC
GTCCACGTCGACCACCTCAGACCCCCTCCGAACCATGTCGGACCCCCCAGGGACTCTGAGAGGACACGTCGGAGACCTAAGTGGAAATCG
 Q  V  Q  L  V  E  S  G  G  G  L  V  Q  P  G  G  S  L  R  L  S  C  A  A  S  G  F  T  F  S>

        100       110       120       130       140       150       160       170       180
ACCTTGGCCATGGGGTGGGTCCGCCAGGCTCCAGGGAAGGGGCTGGAGTGGGTCTCAGCTATTAGTGGTAGTGGTGGTAGCACATACTAC
TGGAACCGGTACCCCACCCAGGCGGTCCGAGGTCCCTTCCCCGACCTCACCCAGAGTCGATAATCACCATCACCACCATCGTGTATGATG
 T  L  A  M  G  W  V  R  Q  A  P  G  K  G  L  E  W  V  S  A  I  S  G  S  G  G  S  T  Y  Y>

        190       200       210       220       230       240       250       260       270
GCAGACTCCGTGAAGGGCCGGTTCACCATCTCCAGAGACAATTCCAAGAACACGCTGTATCTGCAAATGAACAGCCTGAGAGCCGAAGAC
CGTCTGAGGCACTTCCCGGCCAAGTGGTAGAGGTCTCTGTTAAGGTTCTTGTGCGACATAGACGTTTACTTGTCGGACTCTCGGCTTCTG
 A  D  S  V  K  G  R  F  T  I  S  R  D  N  S  K  N  T  L  Y  L  Q  M  N  S  L  R  A  E  D>

        280       290       300       310       320       330       340       350       360
ACGGCCGTGTATTACTGTGCGAGAGGGGCGGTGGGAGCTACTACCGCCTTTGACTACTGGGGCCAGGGAACCCTGGTCACCGTCTCCTCG
TGCCGGCACATAATGACACGCTCTCCCCGCCACCCTCGATGATGGCGGAAACTGATGACCCCGGTCCCTTGGGACCAGTGGCAGAGGAGC
 T  A  V  Y  Y  C  A  R  G  A  V  G  A  T  T  A  F  D  Y  W  G  Q  G  T  L  V  T  V  S  S>

        370       380       390       400       410       420       430       440       450
GGTGGAGGCGGTTCAGGCGGAGGTGGCTCTGGCGGTGGCGGATCGTCTGAGCTGACTCAGGACCCTGCTGTGTCTGTGGCCTTGGGACAG
CCACCTCCGCCAAGTCCGCCTCCACCGAGACCGCCACCGCCTAGCAGACTCGACTGAGTCCTGGGACGACACAGACACCGGAACCCTGTC
 G  G  G  G  S  G  G  G  G  S  G  G  G  G  S  S  E  L  T  Q  D  P  A  V  S  V  A  L  G  Q>

        460       470       480       490       500       510       520       530       540
ACAGTCAAGATCACATGCCAAGGAGACAGCCTCAGAAGCTATTATGCAAGCTGGTACCAGCAGAAGCCAGGACAGGCCCCTGTACTTGTC
TGTCAGTTCTAGTGTACGGTTCCTCTGTCGGAGTCTTCGATAATACGTTCGACCATGGTCGTCTTCGGTCCTGTCCGGGGACATGAACAG
 T  V  K  I  T  C  Q  G  D  S  L  R  S  Y  Y  A  S  W  Y  Q  Q  K  P  G  Q  A  P  V  L  V>
```

FIG. 40A

```
        55C       560       570       580       590       600       610       620       630
ATCTATGGTAAAAACAACCGGCCCTCAGGGATCCCAGACCGATTCTCTGGCTCCAGCTCAGGGAACACAGCTTCCTTGACCATCACTGGG
TAGATACCATTTTTGTTGGCCGGGAGTCCCTAGGGTCTGGCTAAGAGACCGAGGTCGAGTCCCTTGTGTCGAAGGAACTGGTAGTGACCC
 I  Y  G  K  N  N  R  P  S  G  I  P  D  R  F  S  G  S  S  S  G  N  T  A  S  L  T  I  T  G>

        64C       650       660       670       680       690       700       710       720
GCTCAGGCGGAAGATGAGGCTGACTATTACTGTAACTCCCGGGACAGCAGTGGTAACCATCTCGTATTCGGCGGAGGGACCAAGCTGACC
CGAGTCCGCCTTCTACTCCGACTGATAATGACATTGAGGGCCCTGTCGTCACCATTGGTAGAGCATAAGCCGCCTCCCTGGTTCGACTGG
 A  Q  A  E  D  E  A  D  Y  Y  C  N  S  R  D  S  S  G  N  H  L  V  F  G  G  G  T  K  L  T>

GTCCTAGGT (SEQ ID NO:336)
CAGGATCCA (SEQ ID NO:429)
 V  L  G> (SEQ ID NO:335)
```

FIG. 40B

```
h1E3
        10        20        30        40        50        60        70        80        90
CAGGTGCAGCTGCAGGAGTCGGGGGGAGGCCTGGTCAAGCCTGGGGGGTCCCTGAGACTCTCCTGTGAAGCCTCTGGATTCACCTTCAGT
GTCCACGTCGACGTCCTCAGCCCCCCTCCGGACCAGTTCGGACCCCCCAGGGACTCTGAGAGGACACTTCGGAGACCTAAGTGGAAGTCA
 Q  V  Q  L  Q  E  S  G  G  G  L  V  K  P  G  G  S  L  R  L  S  C  E  A  S  G  F  T  F  S>

       100       110       120       130       140       150       160       170       180
AGCTATAGCATGAACTGGGTCCGCCAGGCTCCAGGGAAGGGGCTGGAGTGGGTCTCAGCTATTAGTGGTAGTGGTGGTAGCACATACTAC
TCGATATCGTACTTGACCCAGGCGGTCCGAGGTCCCTTCCCCGACCTCACCCAGAGTCGATAATCACCATCACCACCATCGTGTATGATG
 S  Y  S  M  N  W  V  R  Q  A  P  G  K  G  L  E  W  V  S  A  I  S  G  S  G  G  S  T  Y  Y>

       190       200       210       220       230       240       250       260       270
GCAGACTCCGTGAAGGGCCGGTTCACCATCTCCAGAGACAATTCCAAGAACACGCTGTATCTGCAAATGAACAGCCTGAGAGCCGAGGAC
CGTCTGAGGCACTTCCCGGCCAAGTGGTAGAGGTCTCTGTTAAGGTTCTTGTGCGACATAGACGTTTACTTGTCGGACTCTCGGCTCCTG
 A  D  S  V  K  G  R  F  T  I  S  R  D  N  S  K  N  T  L  Y  L  Q  M  N  S  L  R  A  E  D>

       280       290       300       310       320       330       340       350       360
ACGGCCGTGTATTACTGTGCGAAAGTGGCTAGCAGCTCGTCGCTAGGTATGGACGTCTGGGGCCAAGGGACCACGGTCACCGTCTCCTCA
TGCCGGCACATAATGACACGCTTTCACCGATCGTCGAGCAGCGATCCATACCTGCAGACCCCGGTTCCCTGGTGCCAGTGGCAGAGGAGT
 T  A  V  Y  Y  C  A  K  V  A  S  S  S  S  L  G  M  D  V  W  G  Q  G  T  T  V  T  V  S  S>

       370       380       390       400       410       420       430       440       450
GGTGGAGGCGGTTCAGGCGGAGGTGGCTCTGGCGGTGGCGGATCGTCTGAGCTGACTCAGGACCCTGCTGTGTCTGTGGCCTTGGGACAG
CCACCTCCGCCAAGTCCGCCTCCACCGAGACCGCCACCGCCTAGCAGACTCGACTGAGTCCTGGGACGACACAGACACCGGAACCCTGTC
 G  G  G  G  S  G  G  G  G  S  G  G  G  G  S  S  E  L  T  Q  D  P  A  V  S  V  A  L  G  Q>

       460       470       480       490       500       510       520       530       540
ACAGTCAGGATCACATGCCAAGGAGACAGCCTCAGAAGCTATTATGCAAGCTGGTACCAGCAGAAGCCAGGACAGGCCCCTGTACTTGTC
TGTCAGTCCTAGTGTACGGTTCCTCTGTCGGAGTCTTCGATAATACGTTCGACCATGGTCGTCTTCGGTCCTGTCCGGGGACATGAACAG
 T  V  R  I  T  C  Q  G  D  S  L  R  S  Y  Y  A  S  W  Y  Q  Q  K  P  G  Q  A  P  V  L  V>

       550       560       570       580       590       600       610       620       630
ATCTATGGTAAAAACAACCGGCCCTCAGGGATCCCAGACCGATTCTCTGGCTCCAGCTCAGGAAACACAGCTTCCTTGACCATCACTGGG
TAGATACCATTTTTGTTGGCCGGGAGTCCCTAGGGTCTGGCTAAGAGACCGAGGTCGAGTCCTTTGTGTCGAAGGAACTGGTAGTGACCC
 I  Y  G  K  N  N  R  P  S  G  I  P  D  R  F  S  G  S  S  S  G  N  T  A  S  L  T  I  T  G>
```

FIG. 41A

```
      640       650       660       670       680       690       700       710       720
GCTCGGGCGGAGGATGAGGCTGACTATTACTGTACGTCCCGGGACAGCAGTGGTAAGCAACTGGTGTTCGGCGGAGGGACCAAGCTGACC
CGAGCCCGCCTCCTACTCCGACTGATAATGACATGCAGGGCCCTGTCGTCACCATTCGTTGACCACAAGCCGCCTCCCTGGTTCGACTGG
 A  R  A  E  D  E  A  D  Y  Y  C  T  S  R  D  S  S  G  K  Q  L  V  F  G  G  G  T  K  L  T>

GTCCTAGGT (SEQ ID NO:338)
CAGGATCCA (SEQ ID NO:430)
 V  L  G> (SEQ ID NO:337)
```

FIG. 41B

```
H1F1
         10        20        30        40        50        60        70        80        90
CAGGTGCAGCTGGTGGAGTCTGGGGGAGGCTTGGTATAGCCTGGGGGGTCCCTGAGACTCTCCTGTGCAGCCTCTGGATTCACCTTTAGC
GTCCACGTCGACCACCTCAGACCCCCTCCGAACCATATCGGACCCCCCAGGGACTCTGAGAGGACACGTCGGAGACCTAAGTGGAAATCG
 Q  V  Q  L  V  E  S  G  G  G  L  V  *  P  G  G  S  L  R  L  S  C  A  A  S  G  F  T  F  S>

        100       110       120       130       140       150       160       170       180
AACTATGCCTTGATCTGGGTCCGCCAGGCTCCAGGGAAGGGGCTGGAGTGGGTCTCCGCTATCAGTGGTAGTGGTAGTGGCACATACTAC
TTGATACGGAACTAGACCCAGGCGGTCCGAGGTCCCTTCCCCGACCTCACCCAGAGGCGATAGTCACCATCACCATCACCGTGTATGATG
 N  Y  A  L  I  W  V  R  Q  A  P  G  K  G  L  E  W  V  S  A  I  S  G  S  G  S  G  T  Y  Y>

        190       200       210       220       230       240       250       260       270
GCAGACTCCGTGAAGGGCCGGTTCACCATCTCCAGAGACAATTCCAAGAACACACTGTATCTGCAAATGAACACCCTGAGAGCCGAAGAC
CGTCTGAGGCACTTCCCGGCCAAGTGGTAGAGGTCTCTGTTAAGGTTCTTGTGTGACATAGACGTTTACTTGTGGGACTCTCGGCTTCTG
 A  D  S  V  K  G  R  F  T  I  S  R  D  N  S  K  N  T  L  Y  L  Q  M  N  T  L  R  A  E  D>

        280       290       300       310       320       330       340       350       360
ACGGCCCTATATTACTGTGCGAAATCTGTAGTGGGAGCTACCTCTTTGGACTACTGGGGCCAGGGAACCCTGGTCACCGTCTCCTCAGGT
TGCCGGGATATAATGACACGCTTTAGACATCACCCTCGATGGAGAAACCTGATGACCCCGGTCCCTTGGGACCAGTGGCAGAGGAGTCCA
 T  A  L  Y  Y  C  A  K  S  V  V  G  A  T  S  L  D  Y  W  G  Q  G  T  L  V  T  V  S  S  G>

        370       380       390       400       410       420       430       440       450
GGAGGCGGTTCAGGCGGAGGTGGCTCTGGCGGTGGCGGATCGCAGTCTGTGCTGACTCAGGACCCTGCTGTGTCTGTGGCCTTGGGACAG
CCTCCGCCAAGTCCGCCTCCACCGAGACCGCCACCGCCTAGCGTCAGACACGACTGAGTCCTGGGACGACACAGACACCGGAACCCTGTC
 G  G  G  S  G  G  G  G  S  G  G  G  G  S  Q  S  V  L  T  Q  D  P  A  V  S  V  A  L  G  Q>

        460       470       480       490       500       510       520       530       540
ACAGTCAGGATCACATGTCAAGGAGACAGCCTCAGAGACTATTATGCAAGCTGGTACAAGCAGAAGCCAGGACAGGCCCCTCTACTTGTC
TGTCAGTCCTAGTGTACAGTTCCTCTGTCGGAGTCTCTGATAATACGTTCGACCATGTTCGTCTTCGGTCCTGTCCGGGGAGATGAACAG
 T  V  R  I  T  C  Q  G  D  S  L  R  D  Y  Y  A  S  W  Y  K  Q  K  P  G  Q  A  P  L  L  V>
```

FIG. 42A

```
        550       560       570       580       590       600       610       620       630
TTCTTTGGTAAAAGCAATCGGCCCTCAGGGATCCCAAACCGATTCTCTGGCTCCACCTCAGGAAGCACAGCTACCTTGACCGTCACTGGG
AAGAAACCATTTTCGTTAGCCGGGAGTCCCTAGGGTTTGGCTAAGAGACCGAGGTGGAGTCCTTCGTGTCGATGGAACTGGCAGTGACCC
 F  F  G  K  S  N  R  P  S  G  I  P  N  R  F  S  G  S  T  S  G  S  T  A  T  L  T  V  T  G>

        640       650       660       670       680       690       700       710       720
GCTCAGGCGGAAGATGAGGCTGACTATTTCTGCAGCTCTCGGGACAGCAGTGGTAGGCTTATCCTATTCGGCGGAGGGACCAAGCTGACC
CGAGTCCGCCTTCTACTCCGACTGATAAAGACGTCGAGAGCCCTGTCGTCACCATCCGAATAGGATAAGCCGCCTCCCTGGTTCGACTGG
 A  Q  A  E  D  E  A  D  Y  F  C  S  S  R  D  S  S  G  R  L  I  L  F  G  G  G  T  K  L  T>

GTCCTAGGT (SEQ ID NO:340)
CAGGATCCA (SEQ ID NO:431)
 V  L  G> (SEQ ID NO:339)
```

```
        10        20        30        40        50        60        70        80        90
CAGGTGCAGCTGCAGGAGTCGGGGGGAGGCTTGGTACAGCCTGGGGGGTCCCTGAGACTCTCCTGTGCAGCCTCTGGATTCACCTTTAGC
GTCCACGTCGACGTCCTCAGCCCCCCTCCGAACCATGTCGGACCCCCCAGGGACTCTGAGAGGACACGTCGGAGACCTAAGTGGAAATCG
 Q  V  Q  L  Q  E  S  G  G  G  L  V  Q  P  G  G  S  L  R  L  S  C  A  A  S  G  F  T  F  S>

       100       110       120       130       140       150       160       170       180
AGCTATGCCATGAGCTGGGTCCGCCAGGCTCCAGGGAAGGGGCTGGAGTGGGTCTCAGCTATTACTAGTAGCGGTGGTAGGACATACTAC
TCGATACGGTACTCGACCCAGGCGGTCCGAGGTCCCTTCCCCGACCTCACCCAGAGTCGATAATGATCATCGCCACCATCCTGTATGATG
 S  Y  A  M  S  W  V  R  Q  A  P  G  K  G  L  E  W  V  S  A  I  T  S  S  G  G  R  T  Y  Y>

       190       200       210       220       230       240       250       260       270
GCAGACTCCGTGAGGGGCCGGCTCACCATCTCCAGAGACAATTCCAAGAACACGCTGTATCTGCAAATGAACACCCTGAGAGCCGAGGAC
CGTCTGAGGCACTCCCCGGCCGAGTGGTAGAGGTCTCTGTTAAGGTTCTTGTGCGACATAGACGTTTACTTGTGGGACTCTCGGCTCCTG
 A  D  S  V  R  G  R  L  T  I  S  R  D  N  S  K  N  T  L  Y  L  Q  M  N  T  L  R  A  E  D>

       280       290       300       310       320       330       340       350       360
ACGGCCGTATATTACTGTGCAAAAGGAATAGTGGGAGCTACTGCCTTTGACTACTGGGGCCAGGGAACCCTGGTCACCGTCTCCTCAGGT
TGCCGGCATATAATGACACGTTTTCCTTATCACCCTCGATGACGGAAACTGATGACCCCGGTCCCTTGGGACCAGTGGCAGAGGAGTCCA
 T  A  V  Y  Y  C  A  K  G  I  V  G  A  T  A  F  D  Y  W  G  Q  G  T  L  V  T  V  S  S  G>

       370       380       390       400       410       420       430       440       450
GGAGGCGGTTCAGGCGGAGGTGGCTCTGGCGGTGGCGGATCGTCTGAGCTGACTCAGGACCCTGCTGTGTCTGTGGCCTTGGGACAGACA
CCTCCGCCAAGTCCGCCTCCACCGAGACCGCCACCGCCTAGCAGACTCGACTGAGTCCTGGGACGACACAGACACCGGAACCCTGTCTGT
 G  G  G  S  G  G  G  G  S  G  G  G  G  S  S  E  L  T  Q  D  P  A  V  S  V  A  L  G  Q  T>

       460       470       480       490       500       510       520       530       540
GTCAGAATCACATGCCAGGGAGACAGCCTCAGAAGCTATTATGCAAGCTGGTACCAGCAGAAGCCAGGACAGGCCCCTGTACTTGTCATC
CAGTCTTAGTGTACGGTCCCTCTGTCGGAGTCTTCGATAATACGTTCGACCATGGTCGTCTTCGGTCCTGTCCGGGGACATGAACAGTAG
 V  R  I  T  C  Q  G  D  S  L  R  S  Y  Y  A  S  W  Y  Q  Q  K  P  G  Q  A  P  V  L  V  I>

       550       560       570       580       590       600       610       620       630
TATGGTAAAAACAACCGGCCCTCAGGGATCCCAGACCGATTCTCTGGCTCCAGCTCAGGAAACACAGCTTCCTTGACCATCACTGGGGCT
ATACCATTTTTGTTGGCCGGGAGTCCCTAGGGTCTGGCTAAGAGACCGAGGTCGAGTCCTTTGTGTCGAAGGAACTGGTAGTGACCCCGA
 Y  G  K  N  N  R  P  S  G  I  P  D  R  F  S  G  S  S  S  G  N  T  A  S  L  T  I  T  G  A>
```

FIG. 43A

```
       640       650       660       670       680       690       700       710       720
CAGGCGGAAGATGAGGCTGACTATTACTGTAACTCCCGGGACAGCAGTGGTAACTCTGTGGTATTCGGCGGAGGGACCAAGGTCACCGTC
GTCCGCCTTCTACTCCGACTGATAATGACATTGAGGGCCCTGTCGTCACCATTGAGACACCATAAGCCGCCTCCCTGGTTCCAGTGGCAG
 Q  A  E  D  E  A  D  Y  Y  C  N  S  R  D  S  S  G  N  S  V  V  F  G  G  G  T  K  V  T  V>

CTAGGT (SEQ ID NO:128)
GATCCA (SEQ ID NO:432)
 L  G> (SEQ ID NO:127)

#
```

Sequences of anti-CD44 scFv from fd phage library (E8 for CD44 link domain, D6 for CD44)

| VH | FR1 | CDR1 | FR2 | CDR2 |
|---|---|---|---|---|
| E8H11 | QVQLVESGGGVVQPGRSLRLSCAASGFTFS | SYGMH | WVRQAPGKGLEWVA | VISYDGSNKYYADSVKG |
| E8H7 | QVQLQESGGGLVQPGGSLRLSCSASGFTFS | SYAMH | WVRQAPGKGLEYVS | AISSNGGSTYYADSVKG |
| E8G12 | QVQLVQSGGGLVQPGGSLRLSCAASGFTFS | SYAMS | WVRQAPGKGLEWVS | AISGSGGSTYYADSVKG |
| E8F11 | QVQLQQSGGGLVQPGGSLRLSCAASGFTFS | SYAMS | WVRQAPVKGLEWVS | AISGSGGSTYYADSVKG |
| E8C9 | QVNLRESGGGLVKPGGSLRLSCAASGFTFS | SYAMS | WVRQAPGKGLEWVS | VIS-DGSTTYYADSVKG |
| D6G9 | QVQLVESGGGLVQPGGSLRLSCAASGFTFS | SYAMG | WVRQAPGKGLEWVS | AISASGGSTYYADSVKG |
| D6D3 | QVQLQESGGGLVQPGGSLRLSCAASGFTFS | SYAMS | WVRQAPGKGLEWVS | AITSSGGRTYYADSVRG |

| | FR3 | CDR3 | FR4 | |
|---|---|---|---|---|
| E8H11 | RFTISRDNSKNTLYLQMNSLRAEDTAVYYCAK | DYGYCSGGSCYSPFDY | WGQGTLVTVSS | (SEQ ID NO:90) |
| E8H7 | RFTISRDNSKNTLYLQMSSLRAEDTAVYYCVA | RLEWL-----PLAWDY | WGQGTLVTVSS | (SEQ ID NO:342) |
| E8G12 | RFTISRDNSKNTLYLQMNSLRAEDTAVYYCAK | AARIAAR---PGPLDY | WGQGTLVTVSS | (SEQ ID NO:343) |
| E8F11 | RFTISRDNSKNTLYLQMNSLRIEDTAVYYCGR | H--LSSG----SSVDY | WGQGTLVTVSS | (SEQ ID NO:344) |
| E8C9 | RFTISRDNSKNMLYLQTNSLRAEDTAVYYCAK | AGPRTTV----TTVDS | WGQGTLVTVSS | (SEQ ID NO:345) |
| D6G9 | RFTISRDNSKNTLYLQLNSLRAEDTAVYYCAK | GLKDSSG------FDY | WGQGTLVTVSS | (SEQ ID NO:346) |
| D6D3 | RLTISRDNSKNTLYLQMNTLRAEDTAVYYCAK | GIVGATA------FDY | WGQGTLVTVSS | (SEQ ID NO:347) |

| VL | FR1 | CDR1 | FR2 | CDR2 |
|---|---|---|---|---|
| E8H11 | NFMLTQDPAVSVALGQTVRITC | QGDSLRS---YYAS | WYQQKPGQAPVLVIY | GKNNRPS |
| E8H7 | S-ELTQDPAVSVALGQTVRITC | QGDSLRS---YYAS | WYQQKPGQAPVLVIY | GKNNRPS |
| E8G12 | S-ELTQDPAVSVAVGQTVKITC | QGDSLRN---YYAS | WYQQKPRQAPVLVIY | GKNNRPS |
| E8F11 | -SELTQPPSASGSPGQSVTISC | TGTSSDVGGYNYVS | WYQQRPGYAPKLMIY | DVSNRPS |
| E8C9 | QSVLTQPPSVSGAPGQRVTISC | TGSSSNIGAGYDVH | WYQQLPGTAPKLLIY | GNSNRPS |
| D6G9 | NFMLTQDPAVSVALGQTVRITC | QGDSLRS---YYAS | WYQQKPGQAPVLVIY | GKNNRPS |
| D6D3 | S-ELTQDPAVSVALGQTVRITC | QGDSLRS---YYAS | WYQQKPGQAPVLVIY | GKNNRPS |

| | FR3 | CDR3 | FR4 | |
|---|---|---|---|---|
| E8H11 | GIPDRFSGSSSGNTASLTITGAQAEDEADYYC | HSRDSSGN-YL | FGGGTKLTVLG | (SEQ ID NO:348) |
| E8H7 | GIPDRFSGSSSGNTASLTITGAQAEDEADYYC | NSRDSSGNHKV | FGGGTKLTVLG | (SEQ ID NO:349) |
| E8G12 | GIPDRFSGSSSGNTASLTITGAQAEDEADYYC | NSRDRSNNHLL | FGGGTKLTVLG | (SEQ ID NO:350) |
| E8F11 | GVSNRFSGSKSGNSASLDISGLQSEDEADYYC | AAWDDSLREFL | FGTGTKVTVLG | (SEQ ID NO:351) |
| E8C9 | GVPDRFSGSKSGTSASLAITGLQAEDEADYYR | SAWDSSLFNWV | FGGGTKLTVLG | (SEQ ID NO:352) |
| D6G9 | GIPDRFSGSSSGNTASLTITGAQAEDEADYYC | NSRDSSAKRVV | FGGGTKVTVLG | (SEQ ID NO:353) |
| D6D3 | GIPDRFSGSSSGNTASLTITGAQAEDEADYYC | NSRDSSGNSVV | FGGGTKVTVLG | (SEQ ID NO:354) |

Sequences of anti-CD44 scFv from phagemid library (D1 for CD44 link domain, H for CD44s)

| VH | FR1 | CDR1 | FR2 | CDR2 |
|---|---|---|---|---|
| D1-1C5 | QVQLQQSGGGVVQPGRSLRLSCAASGFTFS | SYGIH | WVRQAPGKGLEWVA | VISYDGSNKYYADSVKG |
| D1D1 | QVQLVESGGGLVKPGGSLRLSCAASGFTFS | TYTMS | WARQAPGKGLEWVS | AISADGAGTYYGDSVKG |
| HB8 | QVQLVESGGGVVQPGRSLRLSCAASGFTFS | NYAMI | WVRQAPGKGLEWVS | AITGGGGSTYYADSVKG |
| HC2 | QVQRVESGGGVVQPGRSLRLSCAASGFTFS | SYAMS | WVRQAPGKGLEWVS | AISGSGGSTYYADSVKG |
| HC4 | QVQLVESGGGLVQPGGSLRLSCAASGFTFS | TLAMG | WVRQAPGKGLEWVS | AISGSGGSTYYADSVKG |
| HE3 | QVQLQESGGGLVKPGGSLRLSCEASGFTFS | SYSMN | WVRQAPGKGLEWVS | AISGSGGSTYYADSVKG |
| HF1 | QVQLVESGGGLV*PGGSLRLSCAASGFTFS | NYALI | WVRQAPGKGLEWVS | AISGSGSGTYYADSVKG |
| HH3 | QVQLQESGGGLVQPGGSLRLSCAASGFTFS | SYAMS | WVRQAPGKGLEWVS | AITSSGGRTYYADSVRG |

| | FR3 | CDR3 | FR4 | |
|---|---|---|---|---|
| D1C5 | RFTISRDNSKNTLYLQMNSLRAEDTAVYYCAK | GYGSGSYWSGAFDI | WGQGTMVTVSS | (SEQ ID NO:355) |
| D1D1 | RFTVSRDNFKSTLYLQMNRLRAEDTAVYYCAK | LGGESYSAD | WGQGTLVTVSS | (SEQ ID NO:356) |
| HB8 | RFTISRDNSKNTLYLQMNSLRAEDTALYYCAK | TLGRSTVATDY | WGQGTLVTVSS | (SEQ ID NO:357) |
| HC2 | RFTISRDNSKNTLYLQMNSLRAEDTAVYYCAK | GPGAAQDY | WGQGTLVTVSS | (SEQ ID NO:358) |
| HC4 | RFTISRDNSKNTLYLQMNSLRAEDTAVYYCAR | GAVGATTAFDY | WGQGTLVTVSS | (SEQ ID NO:359) |
| HE3 | RFTISRDNSKNTLYLQMNSLRAEDTAVYYCAK | VASSSSLGMDV | WGQGTTVTVSS | (SEQ ID NO:360) |
| HF1 | RFTISRDNSKNTLYLQMNTLRAEDTALYYCAK | SVVGATSLDY | WGQGTLVTVSS | (SEQ ID NO:361) |
| HH3 | RLTISRDNSKNTLYLQMNTLRAEDTAVYYCAK | GIVGATAFDY | WGQGTLVTVSS | (SEQ ID NO:347) |

| VL | FR1 | CDR1 | FR2 | CDR2 |
|---|---|---|---|---|
| D1C5 | EIVLTQSPLSLPVTPGEPASISC | RSSQSLLHTNGYNYLD | WYLQKPGQSPQLLIY | LGSNRAS |
| D1D1 | HVILTQDPAVSVALGQTVKITC | QGDSLRSYYAS | WYQQKPGQAPLLVLY | GENNRPS |
| HB8 | SELTQDPAVSVALGQTVRITC | QGDSLRSYYAS | WYQQKPGQAPVLVIY | GKNNRPS |
| HC2 | QSVLTQDPAVSVALGQTVTITC | QGDSLRSYYAS | WYQQKPGQAPVLVIY | GKNNRPS |
| HC4 | SELTQDPAVSVALGQTVKITC | QGDSLRSYYAS | WYQQKPGQAPVLVIY | GKNNRPS |
| HE3 | SELTQDPAVSVALGQTVRITC | QGDSLRSYYAS | WYQQKPGQAPVLVIY | GKNNRPS |
| HF1 | QSVLTQDPAVSVALGQTVRITC | QGDSLRDYYAS | WYKQKPGQAPLLVFF | GKSNRPS |
| HH3 | SELTQDPAVSVALGQTVRITC | QGDSLRSYYAS | WYQQKPGQAPVLVIY | GKNNRPS |

FIG. 45A

Sequences of anti-CD44 scFv from phagemid library (D1 for CD44 link domain, H for CD44s)

| | FR3 | CDR3 | FR4 | |
|---|---|---|---|---|
| D1C5 | GVPDRFSGSGSGTDFTLKISRVEAEDVGVYYC | MQGRQSPLT | FGGGTKVEIKR | (SEQ ID NO:362) |
| D1D1 | GIPDRFSGSGSGNTASLTITGAQAEDEADYYC | HSRDSSGKYV | FGVGTKVTVLG | (SEQ ID NO:363) |
| HB8 | GIPDRFSGSSSGNTASLTITGAQAEDEADYYC | NSRDSSGNPHVV | FGGGTKLTVLG | (SEQ ID NO:364) |
| HC2 | GIPDRFSGSSSGNTASLTITGAQAEDEADYYC | NSRDSSGNHVV | FGGGTKVTVLG | (SEQ ID NO:365) |
| HC4 | GIPDRFSGSSSGNTASLTITGAQAEDEADYYC | NSRDSSGNHLV | FGGGTKLTVLG | (SEQ ID NO:366) |
| HE3 | GIPDRFSGSSSGNTASLTITGARAEDEADYYC | TSRDSSGKQLV | FGGGTKLTVLG | (SEQ ID NO:367) |
| HF1 | GIPNRFSGSTSGSTATLTVTGAQAEDEADYFC | SSRDSSGRLIL | FGGGTKLTVLG | (SEQ ID NO:368) |
| HH3 | GIPDRFSGSSSGNTASLTITGAQAEDEADYYC | NSRDSSGNSVV | FGGGTKVTVLG | (SEQ ID NO:354) |

Sequences of anti-EphA2 scFv from fd phage library

| VH | FR1 | CDR1 | FR2 | CDR2 |
|---|---|---|---|---|
| A3H9 | QVLLVESGGGVVQAGASLRVSCAASGFSLT | SYGMH | WVRQAPGKGLEWVA | FISSDGSDKYYVDSVKG |
| A3G3 | QVQLVESGGGVVQPGRSLRLSCAASGFTFS | SYAMG | WVRQAPGKGLEWVA | VIYRDGHGYYADSVKG |
| A3D10 | LVQLVQSGGGLVKPGGSLRLSCAASGFTFS | TYSMN | WVRQAPGKGLEWVS | SISSSSSYIYYADSVKG |
| A3D1 | QVQLVQSGGGLVQPGGSLRLSCAASGFTFS | SYGMH | WVRQAPGKGLEWVA | VIWYDGSNKYYADSVKG |
| A3C8 | QLQLVESGGGLVQPGGSLRLSCAASGFTFS | SYAMN | WVRQAPGKGLEWVS | AISGSGGNTYYADSVKG |

| | FR3 | CDR3 | FR4 | |
|---|---|---|---|---|
| A3H9 | RFTISRDTSKNMMYLQMNSLTTEDTAVYYCAR | DWGSNWYLFDY | WGQGTLVTVSS | (SEQ ID NO:369) |
| A3G3 | RFTVSRDSSENTVYLQMNSLRAEDTAIYYCAS | HDYAGNPAGSASGY | WGQGTLVTVSS | (SEQ ID NO:370) |
| A3D10 | RFTISRDNANNSLYLQMNSLRAEDTAVYYCAR | GNTVAQRLDVFDY | WGQGTLVTVSS | (SEQ ID NO:371) |
| A3D1 | RFTISRDNSRNTLYLEMNSLRAEDTAVYYCVK | DRQPDGRWPFDL | WGQGTLVTVSS | (SEQ ID NO:372) |
| A3C8 | RFTISRDNSNNALYLQMNSLRVEDTAVYYCAR | DASYYADDY | WGQGTLVTVSS | (SEQ ID NO:373) |

| VL | FR1 | CDR1 | FR2 | CDR2 |
|---|---|---|---|---|
| A3H9 | SVLTQPPSASETPGQRVTISC | SGSSSNIGANTVH | WYQQFPGTAPKLLIY | SYSQRPS |
| A3G3 | SALTQPASVSASPGQSITISC | TGTSSDVGGYDYVS | WYQQHPGKAPKLVMY | SHNQRSS |
| A3D10 | SVLTQPPSVSGAPGQRVTISC | TGGSSNVGAGFDVH | WYQQLPGTAPKLLIY | GDKNRPS |
| A3D1 | SALTQPASVSGSPGQSVTISC | TGANSDLGGYNYVS | WYQHHPAKAPKLIIY | EVNNRPS |
| A3C8 | SELTQDPAVSVALGQTVRITC | QGDSLKSYYAS | WYQQKPGQAPVLVIY | GKNNRPS |

| | FR3 | CDR3 | FR4 | |
|---|---|---|---|---|
| A3H9 | GVPDRFSDSKSGTSASLAISGLQSEDEADYYC | AAWDDILNGWV | FGGGTKVTVLG | (SEQ ID NO:374) |
| A3G3 | GVPDRFSGSKSGNSASLDISGLQSEDEADYYR | AAWDDSLSEFL | FGTGTKLTVLG | (SEQ ID NO:375) |
| A3D10 | GVPDRFSGSRSGTSASLAITGLQAEDEADYYC | QAYDSSLRGSV | FGGGTKLTVLG | (SEQ ID NO:376) |
| A3D1 | GVSHRFSGSKSANTASLTISGLQAEDEADYYC | SSYRSGGTYV | FGTGTKLTVLG | (SEQ ID NO:377) |
| A3C8 | GIPDRFSGSSSGNTASLTITGAQAEDEADYYC | HSRDSSGNHPVV | FGGGTKVTVLG | (SEQ ID NO:378) |

FIG. 47

Sequences of anti-EphA2 scFv from phagemid library

| VH | FR1 | CDR1 | FR2 | CDR2 |
|---|---|---|---|---|
| 1A3 | QVQLQQSGPGLVKPSQTLSLTCAISGDSVS | SNSAA | WNWIRQSPSRGLEWLG | RTYYRSKWYNDYAVSVKS |
| 1A5 | QVQLQESGGGVVQPGGSLRLSCAASGFTFS | NYAMH | WVRQAPGKGLEYVS | SISSNGGGTYYADSVKG |
| 1A8 | QVQLQQSGGGLVQPGGSLRLSCSASGFTFS | NYAIH | WVRQAPGKGLEYVS | AINSNGGSTYYADSVKG |
| 1A12 | QVQLQESGGGLVQPGGFLRLSCAASGFTFS | SYGMH | WVRQTPGKGLEWVS | YISSSSSYTNYADSVKG |
| 1B2 | QVQLVESGGGVVQPGRSLRLSCAASGFTFS | SYGMH | WVRQAPGKGLEWVA | VISYDGSNKYYADSVKG |
| 1C2 | QVQLQESGGGLVKPGGSLRLSCAGSGFIFN | TYSMN | WVRQSPGKGLEWVS | STGGSGKNTFYADSVRG |
| 1C7 | QVQLVESGGGVVQPGRSLRLSCAASGFTFS | SYGMH | WVRQAPGKGLEWVS | YISSSGSYTNYADSVKG |
| 1D8 | QVQLVESGGGLIQPGGSLRLSCAASGFTVS | SNYMS | WVRQAPGKGLEWVS | VIYSGGSTYYADSVKG |

| | FR3 | CDR3 | FR4 | |
|---|---|---|---|---|
| 1A3 | RITINPDTSKNLFSLQLNSVTPEDTALYYCAR | EEDYSGFQH | WGQGTLVTVSS | (SEQ ID NO:379) |
| 1A5 | RFTISRDDAKNTLYLQLNSLRDEDTAVYYCAK | DYFGSIDY | WGQGTLVTVSS | (SEQ ID NO:380) |
| 1A8 | RSIISRDNSMNTVYLQMSSLRAEDTAVYYCVK | EENGSGFDS | WGQGTLVTVSS | (SEQ ID NO:381) |
| 1A12 | RFTISRDNSKNTLYLQMNSLRAEDTAVYYCAR | DNWYFDL | WGRGTLVTVSS | (SEQ ID NO:382) |
| 1B2 | RFTISRDNSKNTLYLQMNSLRAEDTAVYYCAR | ALYYDEALDY | WGQGTLVTVSS | (SEQ ID NO:383) |
| 1C2 | RFTISRDNAKNSLYLQMNSLRAEDTAVYYCAR | EDSSGSFDY | WGQGTLVTVSS | (SEQ ID NO:384) |
| 1C7 | RFTISRDNAKNTLYLQMNSLRAEDTAVYYCAK | VRGWDGDYLDY | WGQGTLVTVSS | (SEQ ID NO:385) |
| 1D8 | RFTISRDNSKNTLYLQMNSLRAEDTAVYYCAR | GGFSGYDYFDY | WGQGTLVTVSS | (SEQ ID NO:386) |

| VL | FR1 | CDR1 | FR2 | CDR2 |
|---|---|---|---|---|
| 1A3 | QSALTQPASVSGSPGQSITISC | TGTSSDVGGYNYVS | WYQQHPGKAPKLMIY | EGSKRPS |
| 1A5 | FELTQDPAVSVALGQTVTITC | QGDSLRSYYAS | WYQQKPGQAPLLVIY | GKNIRPS |
| 1A8 | EIVLTQSPSSVSASVGDRVTITC | RASQDISKWLA | WYQQRPGKVPRLLIY | SASSLQS |
| 1A12 | DVVMTQSPSTLSASVGDRVSITC | RASESISRWLA | WYQQKPGKAPKALIY | KASSLES |
| 1B2 | EIVLTQSPSSLSASVGDRVTITC | RASQDMSRWLA | WYQQKPGKAPKLLIH | SASTLQS |
| 1C2 | DIQMTQSPSTLSASIGDRVTITC | RASEGIYHWLA | WYQQKPGKAPKLLIY | KASSLAS |
| 1C7 | DIQMTQSPSLLSASVGDRVTITC | RASQGINNYLA | WYQQKPGKAPKLLIY | AASTLQS |
| 1D8 | QSVLTQPPSVSGAPGQRVTISC | TGSSSNIGAGYDVH | WYQQLPGTAPKLLIY | VNSNRPS |

| | FR3 | CDR3 | FR4 | |
|---|---|---|---|---|
| 1A3 | GVPERFSGSNSGNTATLTIGRVEAGDEADYYC | QAWDSTSDHVV | FGGGTKVTVLG | (SEQ ID NO:387) |
| 1A5 | GIPDRFSGSSSGNSASLTITGAQAEDEADYYC | HSRDSSGTHLRV | FGGGTKLTVLG | (SEQ ID NO:388) |
| 1A8 | GVPSRFSGSGSGTDFTLTISSLQPEDFASYFC | QQASVFPVT | FGGGTKLEIKR | (SEQ ID NO:389) |
| 1A12 | GVPSRFSGSGSATEFTLTINSLQPDDFATYYC | QQYSSYPLT | FGQGTKVDIKR | (SEQ ID NO:390) |
| 1B2 | GVPSRFSGSGSGTEFTLTISSLQPEDFATYYC | QQLGVYPLT | IGGGTKVEIKR | (SEQ ID NO:391) |
| 1C2 | GAPSRFSGSGSGTDFTLTISSLQPDDFATYYC | QQYHTISRT | FGPXTKLEIKR | (SEQ ID NO:392) |
| 1C7 | GVPSRFSGSGSGTEFTLTISGLQPEDFATYYC | QNLNSYPLT | FGGGTKVEIKR | (SEQ ID NO:393) |
| 1D8 | GVPDRFSGSKSGTSASLAITGLQAEDEADYYC | QSYDSSLSGWV | FGGGTKLTVLG | (SEQ ID NO:394) |

ANTI-EPHA2 ANTIBODIES AND METHODS OF USE THEREOF

CROSS-REFERENCE

This application is a continuation of U.S. application Ser. No. 13/810,638, filed Apr. 30, 2013, which claims the benefit of International Application Serial No. PCT/US2011/045069, filed Jul. 22, 2011, which claims the benefit of U.S. Provisional Patent Application No. 61/366,823, filed Jul. 22, 2010, each of which application is incorporated herein by reference in its entirety.

STATEMENT AS TO FEDERALLY SPONSORED RESEARCH

This invention was made with government support under grant no. CA058207 awarded by the National Institutes of Health. The government has certain rights in the invention.

INTRODUCTION

Extensive studies of cancer transcriptional patterns have led to the discovery of molecular targets to distinguish the malignant from the benign and the most aggressive cancers from those that are less aggressive. Cancers often overexpress a number of proteins, including certain cell surface antigens, e.g., cell surface receptors. Antibodies that bind such overexpressed cell surface antigens can facilitate detection and treatment of such cancers. A number of approaches have been utilized to generate antibodies to cancer cell surface receptors which can be used as potential therapeutics. Identification of overexpressed cell surface receptors and antibodies which bind them provide a route to the development of cancer therapies, especially for those cancer subtypes with poor prognosis and resistance to traditional therapies. CD44 and EphA2 are two such overexpressed cell surface receptors, and are known from transcriptional profiling and proteomic analysis to be overexpressed in basal breast cancers.

Antibodies specific to cell surface receptors overexpressed on a number of cancers have been utilized for development of targeted immunotherapeutics. For example, HER2, CD20, and EGFR are overexpressed on a number of tumors and antibodies recognizing these receptors have been developed to treat metastatic breast cancer (trastuzamab), lymphoma (rituximab), and colorectal cancer (cetuximab). Several therapeutic approaches, including antibody-drug conjugates, immunotoxins, and targeted nucleic acid delivery, require antibodies that not only bind receptor, but that also undergo internalization into the cell upon binding.

SUMMARY

Antibodies that bind to tumor associated antigen CD44 or to tumor associated antigen EphA2, are disclosed herein, as well as related compositions and methods of use. Methods of use encompass cancer therapies, diagnostics, and screening methods. In certain embodiments, antibodies bind mammalian cell surface antigen (e.g., yeast displayed mammalian cell surface antigen), in others they are endocytosed upon binding to mammalian cells.

In one embodiment, an isolated monoclonal antibody is provided that specifically binds an epitope of CD44 that is specifically bound by antibody F2-1A6 or that competes with antibody F2-1A6 for binding to CD44. Said antibody may, when bound to CD44 on the surface of a living mammalian cell, be endocytosed (by the cell). In one embodiment, said antibody comprises a $V_H$ CDR1 of F2-1A6, a $V_H$ CDR2 of F2-1A6 and a $V_H$ CDR3 of F2-1A6. In another embodiment, said antibody comprises a $V_L$ CDR1 of F2-1A6, a $V_L$ CDR2 of F2-1A6, and a $V_L$ CDR3 of F2-1A6. In yet another embodiment, said antibody competes for binding to an epitope of CD44 with an antibody comprising, a full length $V_H$ of F2-1A6, and a full length $V_L$ of F2-1A6.

In another embodiment, an isolated monoclonal antibody is provided that specifically binds an epitope of CD44 that is specifically bound by antibody F2-1H9 or that competes with antibody F2-1H9 for binding to CD44. Said antibody may, when bound to CD44 on the surface of a living mammalian cell, be endocytosed. In one embodiment, said antibody comprises a $V_H$ CDR1 of F2-1H9, a $V_H$ CDR2 of F2-1H9, and a $V_H$ CDR3 of F2-1H9. In another embodiment, said antibody comprises a $V_L$ CDR1 of F2-1H9, a $V_L$ CDR2 of F2-1H9, and a $V_L$ CDR3 of F2-1H9. In yet another embodiment, said antibody comprises a full length $V_H$ of F2-1H9 and a full length $V_L$ of F2-1H9.

In another embodiment, an isolated monoclonal antibody is provided that specifically binds an epitope of CD44 that is specifically bound by an antibody selected from E8H11, E8H7, E8G12, E8F11, E8C9, D6G9, D6D3, D1C5, D1D1, HB8, HC2, HC4, HE3, HF1, and HH3; or that competes with an antibody selected from E8H11, E8H7, E8G12, E8F11, E8C9, D6G9, D6D3, D1C5, D1D1, HB8, HC2, HC4, HE3, HF1, and HH3 for binding to CD44. In one embodiment, said antibody comprises: a $V_H$ CDR1 of E8H11, E8H7, E8G12, E8F11, E8C9, D6G9, D6D3, D1C5, D1D1, HB8, HC2, HC4, HE3, HF1, or HH3; a $V_H$ CDR2 of E8H11, E8H7, E8G12, E8F11, E8C9, D6G9, D6D3, D1C5, D1D1, HB8, HC2, HC4, HE3, HF1, or HH3; and a $V_H$ CDR3 of E8H11, E8H7, E8G12, E8F11, E8C9, D6G9, D6D3, D1C5, D1D1, HB8, HC2, HC4, HE3, HF1, or HH3. In another embodiment said antibody comprises: a $V_L$ CDR1 of E8H11, E8H7, E8G12, E8F11, E8C9, D6G9, D6D3, D1C5, D1D1, HB8, HC2, HC4, HE3, HF1, or HH3; a $V_L$ CDR2 of E8H11, E8H7, E8G12, E8F11, E8C9, D6G9, D6D3, D1C5, D1D1, HB8, HC2, HC4, HE3, HF1, or HH3; and a $V_L$ CDR3 of E8H11, E8H7, E8G12, E8F11, E8C9, D6G9, D6D3, D1C5, D1D1, HB8, HC2, HC4, HE3, HF1, or HH3. In another embodiment said antibody comprises: a full length $V_H$ of E8H11, E8H7, E8G12, E8F11, E8C9, D6G9, D6D3, D1C5, D1D1, HB8, HC2, HC4, HE3, HF1, or HH3; and a full length $V_L$ of E8H11, E8H7, E8G12, E8F11, E8C9, D6G9, D6D3, D1C5, D1D1, HB8, HC2, HC4, HE3, HF1, or HH3.

In another embodiment, an isolated monoclonal antibody is provided that specifically binds an epitope of EphA2 that is specifically bound by antibody 2D6 or that competes with antibody 2D6 for binding to EphA2. Said antibody may, when bound to EphA2 on the surface of a living mammalian cell, be endocytosed.

In another embodiment, an isolated monoclonal antibody is provided that specifically binds an epitope of EphA2 that is specifically bound by antibody D2-1A7 or that competes with antibody D2-1A7 for binding to EphA2. Said antibody may, when bound to EphA2 on the surface of a living mammalian cell, be endocytosed.

In another embodiment, an isolated monoclonal antibody is provided that specifically binds an epitope of EphA2 that is specifically bound by antibody D2-1A9 or that competes with antibody D2-1A9 for binding to EphA2. Said antibody may, when bound to EphA2 on the surface of a living mammalian cell, be endocytosed.

In another aspect, an isolated monoclonal antibody is provided that specifically binds an epitope of EphA2 that is specifically bound by antibody D2-1B1 or that competes with antibody D2-1B1 for binding to EphA2. Said antibody may, when bound to EphA2 on the surface of a living mammalian cell, be endocytosed.

In another embodiment, an isolated monoclonal antibody is provided that specifically binds an epitope of EphA2 that is specifically bound by an antibody selected from A3H9, A3G3, A3D10, A3D1, A3C8, 1A3, 1A5, 1A8, 1A12, 1B2, 1C2, 1C7, 1D8, and 15H11 or that competes with an antibody selected from A3H9, A3G3, A3D10, A3D1, A3C8, 1A3, 1A5, 1A8, 1A12, 1B2, 1C2, 1C7, 1D8, and 15H11 for binding to EphA2. In one embodiment, said antibody comprises: a $V_H$ CDR1 of A3H9, A3G3, A3D10, A3D1, A3C8, 1A3, 1A5, 1A8, 1A12, 1B2, 1C2, 1C7, 1D8, or 15H11; a $V_H$ CDR2 of A3H9, A3G3, A3D10, A3D1, A3C8, 1A3, 1A5, 1A8, 1A12, 1B2, 1C2, 1C7, 1D8, or 15H11; and a $V_H$ CDR3 of A3H9, A3G3, A3D10, A3D1, A3C8, 1A3, 1A5, 1A8, 1A12, 1B2, 1C2, 1C7, 1D8, or 15H11. In another embodiment, said antibody comprises: a $V_L$ CDR1 of A3H9, A3G3, A3D10, A3D1, A3C8, 1A3, 1A5, 1A8, 1A12, 1B2, 1C2, 1C7, 1D8, or 15H11; a $V_L$ CDR2 of A3H9, A3G3, A3D10, A3D1, A3C8, 1A3, 1A5, 1A8, 1A12, 1B2, 1C2, 1C7, 1D8, or 15H11; and a $V_L$ CDR3 of A3H9, A3G3, A3D10, A3D1, A3C8, 1A3, 1A5, 1A8, 1A12, 1B2, 1C2, 1C7, 1D8, or 15H11.

In certain embodiments, any of the aforementioned monoclonal antibodies is a single chain Fv (scFv), IgG, Fab, $(Fab')_2$, or $(scFv')_2$. Any of said antibodies may be labeled and/or be conjugated to an anti-cancer agent.

In one embodiment, a lipidic nanoparticle comprising a surface and an interior space is provided, said interior space comprising an anti-cancer agent, wherein any one or more of the aforementioned isolated antibodies is attached to the surface of said lipidic nanoparticle. In one embodiment, when the lipidic nanoparticle is contacted with a cell expressing cell surface EphA2 or cell surface CD44, said antibody binds to the cell surface EphA2 or cell surface CD44 and the lipidic nanoparticle is endocytosed.

In one embodiment, a composition is provided comprising a pharmaceutically acceptable carrier and any one of the aforementioned antibodies or any one of the aforementioned lipidic nanoparticles. Said composition may be formulated for parenteral administration. Alternatively, said composition may be formulated for intravenous, intrathecal, or intraventricular administration or for convection enhanced delivery. In one embodiment, a kit comprising the composition is provided.

In another embodiment, a method of treating a subject having cancer is provided, said method comprising administering to said subject an amount of any one of the aforementioned antibodies or any one of the aforementioned lipidic nanoparticles, wherein said amount is sufficient to slow the growth of the cancer. In one embodiment said antibody is internalized into a cancer cell In one embodiment, a method of detecting a cancer cell in a subject is provided, comprising contacting an antibody of any one of the aforementioned antibodies with a cell of said subject suspected of being cancerous and detecting said antibody bound to said cell.

In another embodiment, an isolated nucleic acid is provided, comprising a nucleotide sequence encoding an amino acid sequence of: a $V_H$ comprising a $V_H$ CDR1, a $V_H$ CDR2 and a $V_H$ CDR3 of an antibody from clone F2-1A6; a $V_L$ comprising a $V_L$ CDR1, a $V_L$ CDR2 and a $V_L$ CDR3 of an antibody from clone F2-1A6; a $V_H$ comprising a $V_H$ CDR1, a $V_H$ CDR2 and a $V_H$ CDR3 of an antibody from clone F2-1H9; a $V_L$ comprising a $V_L$ CDR1, a $V_L$ CDR2 and a $V_L$ CDR3 of an antibody from clone F2-1H9; a $V_H$ comprising a $V_H$ CDR1, a $V_H$ CDR2 and a $V_H$ CDR3 of an antibody selected from E8H11, E8H7, E8G12, E8F11, E8C9, D6G9, D6D3, D1C5, D1D1, HB8, HC2, HC4, HE3, HF1, and HH3; or a $V_L$ comprising a $V_L$ CDR1, a $V_L$ CDR2 and a $V_L$ CDR3 of an antibody selected from E8H11, E8H7, E8G12, E8F11, E8C9, D6G9, D6D3, D1C5, D1D1, HB8, HC2, HC4, HE3, HF1, and HH3. In one embodiment, said nucleic acid comprises a nucleotide sequence encoding an amino acid sequence of: a $V_H$ comprising a $V_H$ CDR1, a $V_H$ CDR2 and a $V_H$ CDR3 of an antibody from clone F2-1A6 and a $V_L$ comprising a $V_L$ CDR1, a $V_L$ CDR2 and a $V_L$ CDR3 of an antibody from clone F2-1A6; a $V_H$ comprising a $V_H$ CDR1, a $V_H$ CDR2 and a $V_H$ CDR3 of an antibody from clone F2-1H9 and a $V_L$ comprising a $V_L$ CDR1, a $V_L$ CDR2 and a $V_L$ CDR3 of an antibody from clone F2-1H9; or a $V_H$ comprising a $V_H$ CDR1, a $V_H$ CDR2 and a $V_H$ CDR3 of an antibody selected from E8H11, E8H7, E8G12, E8F11, E8C9, D6G9, D6D3, D1C5, D1D1, HB8, HC2, HC4, HE3, HF1, and HH3 and a $V_L$ comprising a $V_L$ CDR1, a $V_L$ CDR2 and a $V_L$ CDR3 of an antibody selected from E8H11, E8H7, E8G12, E8F11, E8C9, D6G9, D6D3, D1C5, D1D1, HB8, HC2, HC4, HE3, HF1, and HH3.

In another embodiment, an isolated nucleic acid is provided, comprising a nucleotide sequence encoding an amino acid sequence of: a $V_H$ comprising a $V_H$ CDR1, a $V_H$ CDR2 and a $V_H$ CDR3 of an antibody from clone 2D6, a $V_L$ comprising a $V_L$ CDR1, a $V_L$ CDR2 and a $V_L$ CDR3 of an antibody from clone 2D6, a $V_H$ comprising a $V_H$ CDR1, a $V_H$ CDR2 and a $V_H$ CDR3 of an antibody from clone D2-1A7, a $V_L$ comprising a $V_L$ CDR1, a $V_L$ CDR2 and a $V_L$ CDR3 of an antibody from clone D2-1A7, a $V_H$ comprising a $V_H$ CDR1, a $V_H$ CDR2 and a $V_H$ CDR3 of an antibody from clone D2-1A9, a $V_L$ comprising a $V_L$ CDR1, a $V_L$ CDR2 and a $V_L$ CDR3 of an antibody from clone D2-1A9, a $V_H$ comprising a $V_H$ CDR1, a $V_H$ CDR2 and a $V_H$ CDR3 of an antibody from clone D2-1B1, a $V_L$ comprising a $V_L$ CDR1, a $V_L$ CDR2 and a $V_L$ CDR3 of an antibody from clone D2-1B1; a $V_H$ comprising a $V_H$ CDR1, a $V_H$ CDR2 and a $V_H$ CDR3 of an antibody selected from A3H9, A3G3, A3D10, A3D1, A3C8, 1A3, 1A5, 1A8, 1A12, 1B2, 1C2, 1C7, 1D8, and 15H11; a $V_L$ comprising a $V_L$ CDR1, a $V_L$ CDR2 and a $V_L$ CDR3 of an antibody selected from A3H9, A3G3, A3D10, A3D1, A3C8, 1A3, 1A5, 1A8, 1A12, 1B2, 1C2, 1C7, 1D8, and 15H11; or an isolated nucleic acid comprising nucleotide sequences encoding the amino acid sequences of 1) and 2); 3) and 4); 5) and 6); 7) and 8); or 9) and 10).

In one embodiment, an expression vector is provided that comprises any of the aforementioned nucleic acids. In another embodiment, a recombinant host cell (a "genetically modified host cell") is provided comprising said vector. In one embodiment the cell expresses an anti-EphA2 antibody or an anti-CD44 antibody.

BRIEF DESCRIPTION OF THE DRAWINGS

FIG. 7. Amino acid sequences of full length $V_H$ and $V_L$ of antibodies specific for CD44 from various clones. The framework and complementary determining regions are also indicated. SEQ ID NOs refers to the full length variable region.

FIG. 8. Amino acid sequences of full length $V_H$ and $V_L$ of antibodies specific for EphA2 from various clones. The framework and complementary determining regions are also indicated. SEQ ID NOs refers to the full length variable region.

FIGS. 9A and 9B. Amino acid sequences and encoding nucleic acid sequences for full length antibodies from clone 2D6.

FIGS. 10A and 10B. Amino acid sequences and encoding nucleic acid sequences for full length scFv antibodies from clone D2-1A7.

FIGS. 11A and 11B. Amino acid sequences and encoding nucleic acid sequences for full length scFv antibodies from clone D2-1A9.

FIGS. 12A and 12B. Amino acid sequences and encoding nucleic acid sequences for full length scFv antibodies from clone D2-1B1.

FIGS. 13A and 13B. Amino acid sequences and encoding nucleic acid sequences for full length scFv antibodies from clone F2-1A6.

FIGS. 14A and 14B. Amino acid sequences and encoding nucleic acid sequences for full length scFv antibodies from clone F2-1H9.

FIGS. 15A and 15B. Amino acid (SEQ ID NO:90) and encoding nucleic acid (SEQ ID NO:91) sequences for full length scFv antibodies from clone E8H11.

FIGS. 16A and 16B. Amino acid (SEQ ID NO:58) and encoding nucleic acid (SEQ ID NO:59) sequences for full length scFv antibodies from clone E8H7.

FIGS. 17A and 17B. Amino acid (SEQ ID NO:92) and encoding nucleic acid (SEQ ID NO:93) sequences for full length scFv antibodies from clone E8G12.

FIGS. 18A and 18B. Amino acid (SEQ ID NO:63) and encoding nucleic acid (SEQ ID NO:64) sequences for full length scFv antibodies from clone E8F11.

FIGS. 19A and 19B. Amino acid (SEQ ID NO:72) and encoding nucleic acid (SEQ ID NO:73) sequences for full length scFv antibodies from clone E8C9.

FIGS. 20A and 20B. Amino acid (SEQ ID NO:85) and encoding nucleic acid (SEQ ID NO:86) sequences for full length scFv antibodies from clone D6G9.

FIGS. 21A and 21B. Amino acid (SEQ ID NO:127) and encoding nucleic acid (SEQ ID NO:128) sequences for full length scFv antibodies from clone D6D3.

FIGS. 22A and 22B. Amino acid (SEQ ID NO:129) and encoding nucleic acid (SEQ ID NO:130) sequences for full length scFv antibodies from clone A3H9.

FIGS. 23A and 23B. Amino acid (SEQ ID NO:135) and encoding nucleic acid (SEQ ID NO:136) sequences for full length scFv antibodies from clone A3G3.

FIGS. 24A and 24B. Amino acid (SEQ ID NO:137) and encoding nucleic acid (SEQ ID NO:138) sequences for full length scFv antibodies from clone A3D10.

FIGS. 25A and 25B. Amino acid (SEQ ID NO:305) and encoding nucleic acid (SEQ ID NO:306) sequences for full length scFv antibodies from clone A3D1.

FIGS. 26A and 26B. Amino acid (SEQ ID NO:307) and encoding nucleic acid (SEQ ID NO:308) sequences for full length scFv antibodies from clone A3C8.

FIGS. 27A and 27B. Amino acid (SEQ ID NO:309) and encoding nucleic acid (top strand—SEQ ID NO:310; bottom strand—SEQ ID NO:416) sequences for full length scFv antibodies from clone 1A3.

FIGS. 28A and 28B. Amino acid (SEQ ID NO:311) and encoding nucleic acid (top strand—SEQ ID NO:312; bottom strand—SEQ ID NO:417) sequences for full length scFv antibodies from clone 1A5.

FIGS. 29A and 29B. Amino acid (SEQ ID NO:313) and encoding nucleic acid (top strand—SEQ ID NO:314; bottom strand—SEQ ID NO:418) sequences for full length scFv antibodies from clone 1A8.

FIGS. 30A and 30B. Amino acid (SEQ ID NO:315) and encoding nucleic acid (top strand—SEQ ID NO:316; bottom strand—SEQ ID NO:419) sequences for full length scFv antibodies from clone 1A12.

FIGS. 31A and 31B. Amino acid (SEQ ID NO:317) and encoding nucleic acid (top strand—SEQ ID NO:318; bottom strand—SEQ ID NO:420) sequences for full length scFv antibodies from clone 1B2.

FIGS. 32A and 32B. Amino acid (SEQ ID NO:319) and encoding nucleic acid (top strand—SEQ ID NO:320; bottom strand—SEQ ID NO:421) sequences for full length scFv antibodies from clone 1C2.

FIGS. 33A and 33B. Amino acid (SEQ ID NO:321) and encoding nucleic acid (top strand—SEQ ID NO:322; bottom strand—SEQ ID NO:422) sequences for full length scFv antibodies from clone 1C7.

FIGS. 34A and 34B. Amino acid (SEQ ID NO:323) and encoding nucleic acid (top strand—SEQ ID NO:324; bottom strand—SEQ ID NO:423) sequences for full length scFv antibodies from clone 1D8.

FIGS. 35A and 35B. Amino acid (SEQ ID NO:325) and encoding nucleic acid (top strand—SEQ ID NO:326; bottom strand—SEQ ID NO:424) sequences for full length scFv antibodies from clone 15H11.

FIGS. 36A and 36B. Amino acid (SEQ ID NO:327) and encoding nucleic acid (top strand—SEQ ID NO:328; bottom strand—SEQ ID NO:425) sequences for full length scFv antibodies from clone D1C5.

FIGS. 37A and 37B. Amino acid (SEQ ID NO:329) and encoding nucleic acid (top strand—SEQ ID NO:330; bottom strand—SEQ ID NO:426) sequences for full length scFv antibodies from clone D1D1.

FIGS. 38A and 38B. Amino acid (SEQ ID NO:331) and encoding nucleic acid (top strand—SEQ ID NO:332; bottom strand—SEQ ID NO:427) sequences for full length scFv antibodies from clone H1B8 (also referred to herein as "HB8").

FIGS. 39A and 39B. Amino acid (SEQ ID NO:333) and encoding nucleic acid (top strand—SEQ ID NO:334; bottom strand—SEQ ID NO:428) sequences for full length scFv antibodies from clone H1C2 (also referred to herein as "HC2").

FIGS. 40A and 40B. Amino acid (SEQ ID NO:335) and encoding nucleic acid (top strand—SEQ ID NO:336; bottom strand—SEQ ID NO:429) sequences for full length scFv antibodies from clone H1C4 (also referred to herein as "HC4").

FIGS. 41A and 41B. Amino acid (SEQ ID NO:337) and encoding nucleic acid (top strand—SEQ ID NO:338; bottom strand—SEQ ID NO:430) sequences for full length scFv antibodies from clone H1E3 (also referred to herein as "HE3").

FIGS. 42A and 42B. Amino acid (SEQ ID NO:339) and encoding nucleic acid (top strand—SEQ ID NO:340; bottom strand—SEQ ID NO:431) sequences for full length scFv antibodies from clone H1F1 (also referred to herein as "HF1").

FIGS. 43A and 43B. Amino acid (SEQ ID NO:127) and encoding nucleic acid (top strand—SEQ ID NO:128; bottom strand—SEQ ID NO:432) sequences for full length scFv antibodies from clone H1H3 (also referred to herein as "HH3").

FIG. 44. Amino acid sequences of full length $V_H$ and $V_L$ of antibodies specific for CD44 from various clones. The framework and complementary determining regions are also indicated. SEQ ID NOs refer to the full length variable region. $V_H$ sequences of E8H11 (SEQ ID NO:90); E8H7 (SEQ ID NO:342); E8G12 (SEQ ID NO:343); E8F11 (SEQ ID NO:344); E8C9 (SEQ ID NO:345); D6G9 (SEQ ID NO:346); and D6D3 (SEQ ID NO:347) are provided. $V_L$ sequences of E8H11 (SEQ ID NO:348); E8H7 (SEQ ID NO:349); E8G12 (SEQ ID NO:350); E8F11 (SEQ ID NO:351); E8C9 (SEQ ID NO:352); D6G9 (SEQ ID NO:353); and D6D3 (SEQ ID NO:354) are provided.

FIGS. 45A and 45B. Amino acid sequences of full length $V_H$ and $V_L$ of antibodies specific for CD44 from various clones. The framework and complementary determining regions are also indicated. SEQ ID NOs refer to the full length variable region. $V_H$ sequences of D1C5 (SEQ ID NO:355); D1D1 (SEQ ID NO:356); HB8 (SEQ ID NO:357); HC2 (SEQ ID NO:358); HC4 (SEQ ID NO:359); HE3 (SEQ ID NO:360); HF1 (SEQ ID NO:361); and HH3 (SEQ ID NO:347) are provided. $V_L$ sequences of D1C5 (SEQ ID NO:362); D1D1 (SEQ ID NO:363); HB8 (SEQ ID NO:364); HC2 (SEQ ID NO:365); HC4 (SEQ ID NO:366); HE3 (SEQ ID NO:367); HF1 (SEQ ID NO:368); and HH3 (SEQ ID NO:354) are provided.

FIG. 46. Amino acid sequences of full length $V_H$ and $V_L$ of antibodies specific for EphA2 from various clones. The framework and complementary determining regions are also indicated. SEQ ID NOs refer to the full length variable region. $V_H$ sequences of A3H9 (SEQ ID NO:369); A3G3 (SEQ ID NO:370); A3D10 (SEQ ID NO:371); A3D1 (SEQ ID NO:372); and A3C8 (SEQ ID NO:373) are provided. $V_L$ sequences of A3H9 (SEQ ID NO:374); A3G3 (SEQ ID NO:375); A3D10 (SEQ ID NO:376); A3D1 (SEQ ID NO:377); and A3C8 (SEQ ID NO:378) are provided.

FIG. 47. Amino acid sequences of full length $V_H$ and $V_L$ of antibodies specific for EphA2 from various clones. The framework and complementary determining regions are also indicated. SEQ ID NOs refer to the full length variable region. $V_H$ sequences of 1A3 (SEQ ID NO:379); 1A5 (SEQ ID NO:380); 1A8 (SEQ ID NO:381); 1A12 (SEQ ID NO:382); 1B2 (SEQ ID NO:383); 1C2 (SEQ ID NO:384); 1C7 (SEQ ID NO:385); and 1D8 (SEQ ID NO:386) are provided. $V_L$ sequences of 1A3 (SEQ ID NO:387); 1A5 (SEQ ID NO:388); 1A8 (SEQ ID NO:389); 1A12 (SEQ ID NO:390); 1B2 (SEQ ID NO:391); 1C2 (SEQ ID NO:392); 1C7 (SEQ ID NO:393); and 1D8 (SEQ ID NO:394) are provided.

DEFINITIONS

Figure 1:
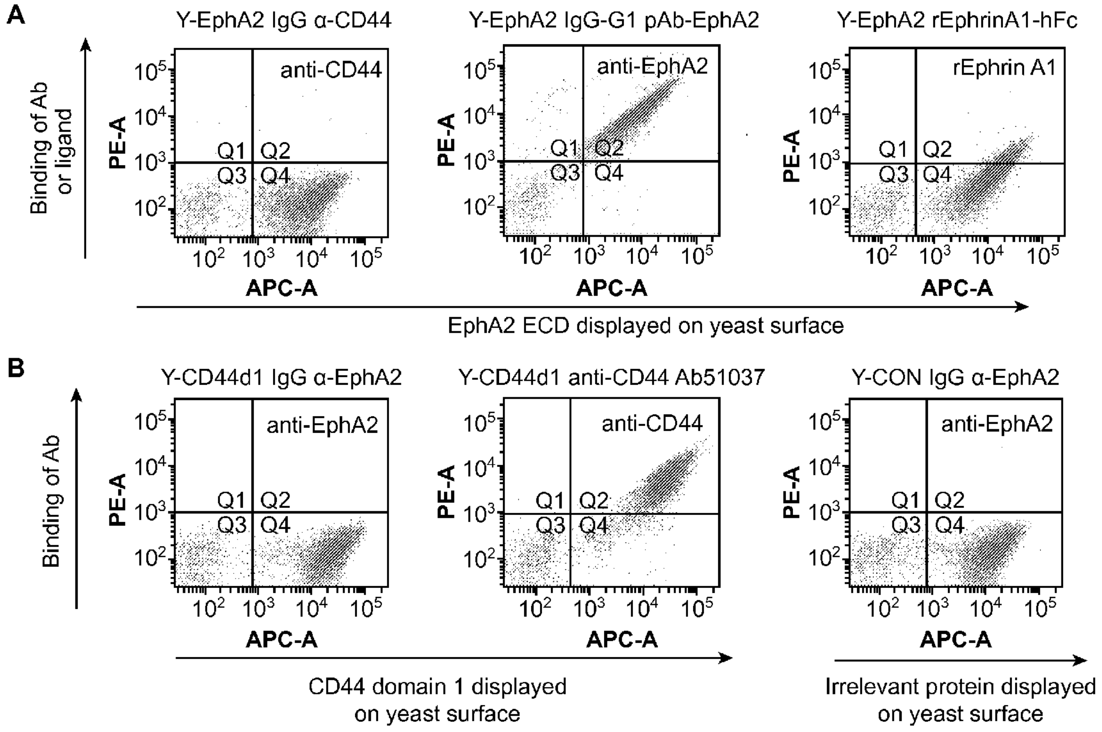
FIG. 1. Display of antigen domains on the surface of yeast. Panel A, The extracellular domain (ECD) of receptor EphA2 was displayed on the yeast surface and was recognized by an anti-EphA2 antibody and recombinant mouse Ephrin A1 (R&D, Minneapolis) as determined by flow cytometry analysis. Panel B, The link domain of CD44 (domain 1, or D1) was displayed on the yeast surface and recognized by an anti-CD44 rabbit monoclonal antibody as determined by flow cytometry analysis. Both anti-EphA2 and anti-CD44 antibodies did not recognize an irrelevant protein displayed on the yeast surface.

The following abbreviations may be used herein: CDR, complementarity determining region; Fab, antigen binding fragment of immunoglobulin with variable domain and first constant domain; FACS, fluorescent activated cell sorting; IgG, immunoglobulin G; $K_D$, dissociation equilibrium constant; $k_{on}$, association rate constant; $k_{off}$, dissociation rate constant; mAb, monoclonal antibody; MFI, mean fluorescent intensity; PBS, phosphate buffered saline; PCR, polymerase chain reaction; scFv, single chain format of antibody variable regions; $V_H$, heavy chain variable region; $V_L$, light chain variable region; TAA, tumor associated antigen; EGFR, epidermal growth factor receptor; ECD, extracellular domain; IMAC, immobilized metal affinity chromatography; ILs, immunoliposomes; IPTG, Isopropyl-β-D-thiogalactopyranoside; 2-MEA, 2-Mercaptoethylamine; DTT, Dithiothreitol; TEA, triethylamine; TBS-T, Tris-buffered saline polysorbate 20/TWEEN® 20; Ni-NTA, Nickel-nitrilotriacetic acid; PE, phycoerythrin; HMEC, human mammary epithelial cell.

As used herein, "EphA2" refers to a member of the receptor tyrosine kinase family that can bind EphrinA ligands, and can also be named "epithelial cell kinase (ECK)". The term "EphA2" can refer to any naturally occurring isoforms of a EphA2. The amino acid sequence of EphA2 is known and can be found as GenBank Accession No. NP_004422.2.

As used herein, "CD44" refers to receptor for hyaluronic acid (HA), and can also be called "phagocytic glycoprotein I", "hyaluronate receptor", or "CD44 antigen". For example, the term "CD44" can refer to either any one of naturally-occurring isoforms of a CD44. The amino acid sequence of CD44 is known and the longest isoform of CD44 can be found as GenBank Accession No. NP_000601.3.

The terms "polypeptide", "peptide", or "protein" are used interchangeably herein to designate a linear series of amino acid residues connected one to the other by peptide bonds between the alpha-amino and carboxy groups of adjacent residues. In addition, the amino acids, in addition to the 20 "standard" genetically encodable amino acids, include amino acid analogs. Furthermore, it should be noted that a dash at the beginning or end of an amino acid residue sequence indicates either a peptide bond to a further sequence of one or more amino acid residues or a covalent bond to a carboxyl or hydroxyl end group. However, the absence of a dash should not be taken to mean that such peptide bonds or covalent bond to a carboxyl or hydroxyl end group is not present, as it is conventional in representation of amino acid sequences to omit such.

"Antibody" encompasses compositions comprising an antigen-binding protein, individually or as a preparation comprising a plurality thereof, having one or more polypeptides that can be genetically encodable by immunoglobulin genes, or fragments of immunoglobulin genes, or that comprise CDRs obtained or derived from immunoglobulins, and which bind an antigen of interest. Light chains are classified as either kappa or lambda. Heavy chains can be classified as gamma, mu, alpha, delta, or epsilon, which in turn define the immunoglobulin classes, IgG, IgM, IgA, IgD and IgE, respectively.

An example of an antibody is one having a structural unit of a tetramer composed of two pairs of polypeptide chains, each pair having one "light" and one "heavy" chain. The N-terminal portion of each chain defines a variable region that mediates antigen binding. The terms variable light chain ($V_L$) and variable heavy chain ($V_H$) refer to light and heavy chains respectively.

"Antibody" also encompasses single-chain antibodies that contain a heavy chain and a light chain linked together as a single polypeptide, each of such linked heavy or light chains nonetheless being referred to herein as a heavy chain or a light chain. Antibody may also refer to heavy chain-only antibodies such as heavy chain antibodies or HCAbs.

As noted above, "antibody" encompasses intact immunoglobulins as well antigen-binding fragments of antibodies. Thus, the term "antibody", as used herein also includes an antigen-binding portion of an antibody, which can be produced by the modification of whole antibodies or synthesized de novo using recombinant DNA methodologies. Examples include, but are not limited to, Fab', Fab'$_2$, scFv, nanobodies, unibodies, and diabodies. A "nanobody" refers to the smallest antigen-binding fragment of a single chain antibody, also referred to as a $V_H$H or single-domain antibodies (dAbs).

"Monoclonal antibody" refers to a composition comprising one or more antibodies obtained from a population of substantially homogeneous antibodies, i.e., a population the individual antibodies of which are identical except for any naturally occurring mutations that may be present in minor amounts. Monoclonal antibodies are highly specific, being directed against a single antigenic site and generally to a single epitope on an antigen. The modifier "monoclonal" indicates the character of the antibody as being obtained from a substantially homogeneous population of antibodies, and does not require that the antibody be produced by any particular method or be the only antibody in the composition.

A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker (Huston, et al. (1988) *Proc. Nat. Acad. Sci. USA,* 85: 5879-5883). A number of structures are available for converting the light and heavy polypeptide chains from an antibody V region into a scFv molecule which will fold into a three dimensional structure substantially similar to the structure of an antigen-binding site. In addition to being diabodies, the scFvs can also be present as tribodies or tetrabodies.

It should be noted that while various antibody fragments are defined in terms of the digestion of an intact antibody, one of skill will appreciate that such fragments may be synthesized de novo either chemically or by utilizing recombinant DNA methodology.

The term "antibody" encompasses polyclonal and monoclonal antibodies, and further encompasses antibodies of any class (e.g., IgM, IgG, and subclasses thereof). "Antibody" also encompasses hybrid antibodies, bispecific antibodies, heteroantibodies, chimeric antibodies, humanized antibodies, and functional fragments thereof which retain antigen binding. "Bispecific antibodies" may resemble single antibodies (or antibody fragments) but have two different antigen binding sites (variable regions). Heteroantibodies refers to two or more antibodies, or antibody binding fragments (e.g., Fab) linked together, each antibody or fragment having a different specificity. The antibodies may be conjugated to other moieties, and/or may be bound to a support (e.g., a solid support), such as a polystyrene plate or bead, test strip, and the like.

An immunoglobulin light or heavy chain variable region is composed of a "framework" region (FR) interrupted by three hypervariable regions, also called "complementarity determining regions" or "CDRs". The extent of the framework region and CDRs can be defined based on databases known in the art. See, for example, "Sequences of Proteins of Immunological Interest," E. Kabat et al., *Sequences of proteins of immunological interest,* 4th ed. U.S. Dept. Health and Human Services, Public Health Services, Bethesda, Md. (1987), Lefranc et al. IMGT, the international ImMunoGeneTics information System®. *Nucl. Acids Res.,* 2005, 33:D593-D597 ((worldwideweb(dot)imgt(dot)org)/textes/IMGTScientificChart/), and/or V Base at vbase(dot)mrc-cpe(dot)cam(dot)ac(dot)uk/). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to Kabat et al., supra, unless otherwise indicated.

An "anti-EphA2 antibody" or "anti-CD44 antibody" refers to an antibody that, specifically binds to EphA2 or CD44, preferably with high affinity. A specific antibody for EphA2 or CD44 does not exhibit comparable binding to other antigens unrelated to EphA2 or CD44 relative to the binding of EphA2 or CD44.

The term "high affinity" when used with respect to an antibody refers to an antibody that specifically binds to ("recognizes") its target(s) with an affinity ($K_D$) value less than or equal to $10^{-6}$ M, less than $10^{-7}$ M, less than $10^{-8}$ M, preferably less than $10^{-9}$ M, less than $10^{-10}$ M, or less than $10^{-11}$ M. A lower $K_D$ value corresponds to a higher binding affinity (i.e., stronger binding) so that a $K_D$ value of $10^{-7}$ indicates a higher binding affinity than a $K_D$ value of $10^{-6}$.

An "antigen-binding site" or "binding portion" refers to a part of an antibody molecule (e.g. fragment of an immunoglobulin molecule or scFv) that participates in immunoreactive antigen binding. The antigen binding site is formed by amino acid residues of the N-terminal variable ("V") regions of the heavy ("H") and/or light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In a tertrameric antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and/or light chains are referred to as "complementarity determining regions" or "CDRs" and are determined, for example based on Kabat et al., supra.

A "F2-1A6 antibody" refers to an antibody expressed by clone F2-1A6 or to an antibody synthesized in other manners, but having the same CDRs and optionally, the same framework regions as the antibody expressed by clone F2-1A6, and having substantially the same antigen binding specificity. Similarly, antibodies 2D6, D2-1A7, D2-1A9, D2-1B1, F2-1H9, and the like (e.g., antibodies E8H11, E8H7, E8G12, E8F11, and E8C9; antibodies D6G9 and D6D3; antibodies D1C5 and D1D1; antibodies HB8, HC2, HC4, HE3, HF1, and HH3; antibodies A3H9, A3G3, A3D10, A3D1, and A3C8; antibodies 1A3, 1A5, 1A8, 1A12, 1B2, 1C2, 1C7, and 1D8; and antibody 15H11) refer to antibodies expressed by the corresponding clone(s) and/or to antibodies synthesized in other manners, but having the same CDRs and optionally, the same framework regions as the referenced antibodies, and having substantially the same antigen binding specificity. The CDRs of these antibodies are defined by Kabat et al., supra, as shown in FIGS. 7, 8, and 44-47, and tables below.

An "epitope" is a site on an antigen (e.g. a site on the EphA2 extracellular domain (ECD)) to which an antibody binds. Epitopes can be formed both from contiguous amino acids or noncontiguous amino acids juxtaposed by folding (e.g., tertiary folding) of a protein. Epitopes formed from contiguous amino acids are typically retained on exposure to denaturing solvents whereas epitopes formed by folding are typically lost on treatment with denaturing solvents. An epitope typically includes at least 3, and more usually, at least 5 or 8-10 amino acids in a linear or spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996). Several commercial laboratories offer epitope mapping services. Epitopes bound by an antibody immunoreactive with a membrane associated antigen can reside on the surface of the cell (e.g. in the extracellular region of a transmembrane protein), so that such epitopes are considered cell-surface accessible, solvent accessible, and/or cell-surface exposed.

"Isolated" refers to an entity of interest (e.g., a protein, e.g., an antibody) that is in an environment different from that in which the entity may naturally occur. An "isolated" entity is separated from all or some of the components that accompany it in nature and may be substantially enriched. "Isolated" also refers to the state of an entity separated from all or some of the components that accompany it during manufacture (e.g., chemical synthesis, recombinant expression, culture medium, and the like). A subject antibody can be substantially pure. "Substantially pure" can refer to compositions in which at least 75%, at least 85%, at least 90%, at least 95%, at least 98%, at least 99%, or more than 99%, of the total composition is the entity of interest (e.g., a subject antibody).

The phrases "specifically bind(s) to," "specific for," "immunoreactive" and "immunoreactivity," and "antigen binding specificity," when referring to an antibody, refer to a binding reaction with an antigen which is highly preferential to the antigen or a fragment thereof, so as to be determinative of the presence of the antigen in the presence of a heterogeneous population of antigens (e.g., proteins and other biologics, e.g., in a tissue). Thus, under designated immunoassay conditions, the specified antibodies bind to a particular antigen and do not bind in a significant amount to other antigens present in the sample. Specific binding to an antigen under such conditions may require an antibody that is selected for its specificity for a particular antigen. For example, anti-CD44 antibodies can specifically bind to CD44, and do not exhibit comparable binding (e.g., do not exhibit detectable binding) to other proteins present in a tissue sample. See Harlow and Lane (1988) Antibodies, A Laboratory Manual, Cold Spring Harbor Publications, New York, for a description of immunoassay formats and conditions that can be used to determine specific immunoreactivity.

DETAILED DESCRIPTION

Antibodies that specifically bind to tumor associated antigen CD44 and antibodies that specifically bind to tumor associated antigen EphA2 are disclosed herein, as well as related compositions and methods of use thereof. Methods of use encompass cancer therapies, diagnostics, and screening methods.

Where the antibodies are specific for CD44, the antibodies contain at least one, two, or all three CDRs of the $V_H$ of the antibody from (e.g., obtained by the expression of) clone F2-1A6, F2-1H9, E8H11, E8H7, E8G12, E8F11, E8C9, D6G9, D6D3, D1C5, D1D1, HB8, HC2, HC4, HE3, HF1, or HH3. The antibodies also encompass those containing at least one, two, or all three CDRs of the $V_L$ of the antibody from clone F2-1A6, F2-1H9, E8H11, E8H7, E8G12, E8F11, E8C9, D6G9, D6D3, D1C5, D1D1, HB8, HC2, HC4, HE3, HF1, or HH3. The antibodies also encompass those containing at least one, two, or all three CDRs independently selected from each of the $V_L$ and the $V_H$ of an antibody from clone F2-1A6, F2-1H9, E8H11, E8H7, E8G12, E8F11, E8C9, D6G9, D6D3, D1C5, D1D1, HB8, HC2, HC4, HE3, HF1, or HH3. Alternately the antibodies compete for binding to CD44 with (e.g., bind to the same epitope as) and antibody from clone F2-1A6, F2-1H9, E8H11, E8H7, E8G12, E8F11, E8C9, D6G9, D6D3, D1C5, D1D1, HB8, HC2, HC4, HE3, HF1, or HH3.

Where the antibodies are specific for EphA2, the antibodies contain at least one, two or all three heavy chain ($V_H$) complementarity determining region(s) (CDR(s)) of an antibody from clone 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11. The antibodies also encompass those containing at least one, two or all three light chain ($V_L$) complementarity determining region(s) (CDR(s)) of an antibody from clone 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11. The antibodies also encompass those containing at least one, two, or all three CDRs independently selected from each of the $V_L$ and the $V_H$ of an antibody from clone 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11. Alternately the antibodies compete for binding to EphA2 with (e.g., bind to the same epitope as) and antibody from clone 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11.

An antibody of the present disclosure may also contain all $V_H$ CDRs and/or $V_L$ CDRs of an antibody from clone F2-1A6, F2-1H9, 2D6, D2-1A7, D2-1A9, D2-1B1, E8H11, E8H7, E8G12, E8F11, E8C9, D6G9, D6D3, D1C5, D1D1, HB8, HC2, HC4, HE3, HF1, HH3, A3H9, A3G3, A3D10, A3D1, A3C8, 1A3, 1A5, 1A8, 1A12, 1B2, 1C2, 1C7, 1D8, or 15H11. The antibodies may contain full-length $V_H$ chains of an antibody from clone F2-1A6, F2-1H9, 2D6, D2-1A7, D2-1A9, D2-1B1, E8H11, E8H7, E8G12, E8F11, E8C9, D6G9, D6D3, D1C5, D1D1, HB8, HC2, HC4, HE3, HF1, HH3, A3H9, A3G3, A3D10, A3D1, A3C8, 1A3, 1A5, 1A8, 1A12, 1B2, 1C2, 1C7, 1D8, or 15H11. The antibodies can also or alternatively contain full-length $V_L$ chains of an antibody from clone F2-1A6, F2-1H9, 2D6, D2-1A7, D2-1A9, D2-1B1, E8H11, E8H7, E8G12, E8F11, E8C9, D6G9, D6D3, D1C5, D1D1, HB8, HC2, HC4, HE3, HF1, HH3, A3H9, A3G3, A3D10, A3D1, A3C8, 1A3, 1A5, 1A8, 1A12, 1B2, 1C2, 1C7, 1D8, or 15H11.

The antibody may be a full length antibody (i.e., an antibody comprising at least one full-length $V_H$ sequence and at least one full length $V_L$ sequence) or a fragment such as a single chain Fv (scFv), a Fab, a $(Fab')_2$, an $(ScFv)_2$, and the like. The antibody may be an IgG (e.g., $IgG_2$) or any other isotype, or may be a bispecific antibody.

The antibodies may be conjugated, such as to an anticancer drug, a label, or to a moiety that improves or promotes serum half-life (e.g. poly(ethylene glycol) (PEG)), endocytosis, or another biological function or characteristic. The antibody may also be in a composition comprising a pharmaceutically acceptable excipient, e.g., a composition suitable for injection (e.g., in a unit dosage formulation). The present disclosure also provides compositions that include one or more different antibodies selected from the antibodies described herein and/or antibodies comprising one or more CDRs from these antibodies, and/or one or more antibodies comprising mutants or derivatives of these antibodies. The composition may include one or more antibodies, such as F2-1A6, F2-1H9, E8H11, E8H7, E8G12, E8F11, E8C9, D6G9, D6D3, D1C5, D1D1, HB8, HC2, HC4, HE3, HF1, HH3, 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11.

Methods of the present disclosure include those that provide for administering one or more subject antibodies as disclosed herein in an amount effective to treat a subject having cancer expressing the antigen(s) specifically bound by the subject antibody or antibodies. The antibodies provided by this disclosure can also be used for diagnosis/prognosis or imaging of cancer.

Nucleic acids provided herein encode one or more antibodies that are described herein. Host cells containing such nucleic acids are also provided herein, as well as those that produce the subject antibodies (e.g. by secretion). Kits are also provided for preparing compositions containing the subject antibodies or for carrying out the subject methods.

Antibodies

Preferred antibodies have a high affinity (e.g., exhibit $K_D$ values of $10^{-7}$ M or lower) to one or more of the tumor associated antigens (TAA), EphA2 or CD44, that are cell-surface exposed on cancer cells during at least some portion of the cell cycle. Antibodies having lower affinity (e.g., having $K_D$ values of from $10^{-5}$ M to $10^{-6}$ M) for EphA2 or CD44 are also contemplated. Cancer cells, for example, include those derived from breast cancer cells (e.g. MDAMB231) and others. The subject antibodies include those that are internalized into the cell upon binding to antigen, e.g., an antigen on the surface of a living mammalian cell, e.g. by endocytosis, such as receptor-mediated endocytosis.

The subject antibodies include those that competitively bind to an epitope of CD44 with an antibody from clone F2-1A6, F2-1H9, E8H11, E8H7, E8G12, E8F11, E8C9, D6G9, D6D3, D1C5, D1D1, HB8, HC2, HC4, HE3, HF1, or HH3. The antibodies also encompass those that competitively bind to an epitope on EphA2 with an antibody from clone 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11. The ability of a particular antibody to recognize the same epitope as another antibody can be determined by the ability of one antibody to competitively inhibit binding of the second antibody (e.g., competitively bind) to the antigen (e.g., as determined by competitive binding assays such as those disclosed in US patent publication No. 20090291085). Competitive inhibition of binding may also be referred to as cross-reactivity of antibodies.

Any of a number of competitive binding assays can be used to measure competition between two antibodies to the same antigen. For example, a sandwich ELISA assay can be used for this purpose. Means of assaying for cross-reactivity are well known to those of skill in the art (see, e.g., Dowbenko et al. (1988) *J. Virol.* 62: 4703-4711).

An antibody is considered to competitively inhibit binding of a second antibody to an antigen if binding of the second antibody to the antigen is reduced by at least 30%, usually at least about 40%, 50%, 60% or 75%, and often by at least about 90%, in the presence of the first antibody using any of the assays used to assess competitive binding.

This can be ascertained by providing one or more isolated target TAA(s), EphA2 and/or CD44, attached to a solid support and assaying the ability of an antibody to bind to the target TAA or to compete with an antibody described herein for binding to the target TAA (e.g. using surface plasmon resonance).

As noted above, the subject antibodies encompass those that compete with one or more of the following antibodies: 2D6, D2-1A7, D2-1A9, D2-1B1, F2-1A6, F2-1H9, E8H11, E8H7, E8G12, E8F11, E8C9, D6G9, D6D3, D1C5, D1D1, HB8, HC2, HC4, HE3, HF1, HH3, A3H9, A3G3, A3D10, A3D1, A3C8, 1A3, 1A5, 1A8, 1A12, 1B2, 1C2, 1C7, 1D8, and 15H11. In addition, the antibodies can have a binding affinity for EphA2 or CD44 comparable to or greater than about $1\times10^{-6}$ M (i.e., the antibodies can exhibit $K_D$ values lower than $10^{-6}$ M, e.g., about $10^{-7}$ M, $10^{-8}$ M, $10^{-9}$ M, $10^{-10}$ M or an even higher binding affinity such as a $K_D$ value of about $10^{-11}$ M or $10^{-12}$ M).

In a related embodiment, the subject antibodies encompass those that bind to the same epitope as F2-1A6 or F2-1H9 or to the epitope of 2D6, D2-1A7, D2-1A9, or D2-1B1, or to the epitope of E8H11, E8H7, E8G12, E8F11, E8C9, D6G9, D6D3, D1C5, D1D1, HB8, HC2, HC4, HE3, HF1, or HH3, or to the epitope of A3H9, A3G3, A3D10, A3D1, A3C8, 1A3, 1A5, 1A8, 1A12, 1B2, 1C2, 1C7, 1D8, or 15H11. Epitope mapping can be performed using pairs of antibodies at concentrations resulting in near saturation and at least 100 relative units (RU) of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU. Antibodies may be said to be cross-reactive if, when "injected" together they show an essentially additive increase (e.g. an increase by at least a factor of about 1.4, an increase by at least a factor of about 1.6, or an increase by at least a factor of about 1.8 or 2.)

Epitopes of antibodies can also be ascertained by a number of other standard techniques (see, e.g., Geysen et al (1987) *J. Immunol. Meth* 102:259-274). This technique involves the synthesis of large numbers of overlapping peptides of EphA2 or CD44. The synthesized peptides are then screened against one or more of the prototypical antibodies (e.g., 2D6, etc.) and the characteristic epitopes specifically bound by these antibodies can be identified by binding specificity and affinity. The epitopes thus identified can be conveniently used for competitive assays as described herein to identify cross-reacting antibodies.

The peptides for epitope mapping can be conveniently prepared using "Multipin" peptide synthesis techniques (see, e.g., Geysen et al (1987) *Science* 235:1184-1190). Using the known sequence of one or more EphA2 and/or CD44, overlapping polypeptide sequences can be synthesized individually in a sequential manner on plastic pins in an array of one or more 96-well microtest plate(s).

Anti-CD44

Antibodies of the present disclosure include those that specifically bind CD44. Anti-CD44 antibodies encompass those that competitively bind to an epitope (e.g. in domain 1) of CD44 with F2-1A6, F2-1H9, E8H11, E8H7, E8G12, E8F11, E8C9, D6G9, D6D3, D1C5, D1D1, HB8, HC2, HC4, HE3, HF1, or HH3. The epitope bound by anti-CD44 antibodies reside in a contiguous amino acid sequence of CD44 from residue position 21-169, as set forth below.

(SEQ ID NO: 1)

QIDLNITCRFAGVFHVEKNGRYSISRTEAADLCKAFNSTLPTMAQMEKAL

SIGFETCRYGFIEGHVVIPRIHPNSICAANNTGVYILTSNTSQYDTYCFN

ASAPPEEDCTSVTDLPNAFDGPITITIVNRDGTRYVQKGEYRTNPEDIY

The residue position numbers of CD44 are determined based on the sequence set forth in GenBank Accession No. NP_000601.3 or UniProt Accession No. P16070.

Antigens that share similar epitopes as CD44 can also be binding targets of subject antibodies. When bound to CD44, a subject antibody can be internalized by the cell expressing the CD44 protein.

Epitopes for which anti-CD44 antibodies have affinity are cell-surface exposed and solvent-accessible on many cancer cells, particularly on the plasma membrane of cells. The epitopes can be accessible to the subject antibodies when the cells are live. For example, the epitopes may be present on cancer cells derived from breast cancers, colon cancers, adenoma, head and neck squamous cell carcinoma (HNSCC), prostate cancers, pancreatic cancers, etc. Cancers cells for which anti-CD44 antibodies have affinity may also be from any cancer that is metastic and/or has metastatic potential.

Additional examples of subject antibodies encompass those that have the same binding specificities and comprise at least two CDRs that each independently shares at least about 80%, at least about 87%, at least about 93%, at least about 94%, or up to 100% amino acid sequence identity with the amino acid sequence of a $V_H$ CDR of antibodies shown in FIGS. 7, 44, and 45 (45A and 45B) and in tables below (e.g. $V_H$ CDR1 of F2-1A6, F2-1H9, E8H11, E8H7, E8G12, E8F11, E8C9, D6G9, D6D3, D1C5, D1D1, HB8, HC2, HC4, HE3, HF1, or HH3). The subject antibody can also include all three CDRs from any $V_H$ CDRs of each antibody shown in FIGS. 7, 44, and 45, such that each $V_H$ CDR in the subject antibody is selected from a single antibody shown in FIGS. 7, 44, and 45, or tables below (e.g., Table 1) and each $V_H$ CDR independently shares at least about 80%, at least about 87%, at least about 93%, at least about 94%, or up to 100% amino acid sequence identity with the amino acid sequence of the $V_H$ CDR of the antibody shown in FIG. 7, 44, or 45 or tables below (e.g., Table 1). For example, the heavy chain of a subject antibody can contain two $V_H$ CDRs or all three $V_H$ CDRs of F2-1A6. Alternatively, the heavy chain can contain two $V_H$ CDRs or all three $V_H$ CDRs of F2-1H9. As further examples, the heavy chain of a subject antibody can contain two $V_H$ CDRs or all three $V_H$ CDRs of any one of E8H11, E8H7, E8G12, E8F11, E8C9, D6G9, D6D3, D1C5, D1D1, HB8, HC2, HC4, HE3, HF1, and HH3.

Similarly for the light chain, a subject antibody will have the same binding specificity and can contain at least two CDRs that are each independently at least about 80%, at least about 87%, at least about 93%, at least about 94%, or up to 100% amino acid sequence identity with the amino acid sequence of a $V_L$ CDR of each antibody shown in FIGS. 7, 44, and 45 (45A and 45B) or tables below (e.g. $V_L$ CDR1 of F2-1A6; e.g., $V_L$ CDR1 of E8H11, E8H7, E8G12, E8F11, E8C9, D6G9, D6D3, D1C5, D1D1, HB8, HC2, HC4, HE3, HF1, or HH3). The subject antibody can also or alternatively include all three $V_L$ CDRs from any of the antibodies shown in FIGS. 7, 44, and 45, or tables below (e.g., Table 2) and each $V_L$ CDR independently shares at least about 80%, at least about 87%, at least about 93%, at least about 94%, or up to 100% amino acid sequence identity with the amino acid sequence of the $V_L$ CDR of the antibody shown in FIG. 7, 44, or 45, or tables below. For example, the light chain of a subject antibody can contain two $V_L$ CDRs or all three $V_L$ CDRs of F2-1A6. Alternatively, the light chain can contain two $V_L$ CDRs or all three $V_L$ CDRs of F2-1H9. As further examples, the light chain of a subject antibody can contain two $V_L$ CDRs or all three $V_L$ CDRs of E8H11, E8H7, E8G12, E8F11, E8C9, D6G9, D6D3, D1C5, D1D1, HB8, HC2, HC4, HE3, HF1, or HH3.

Optionally, antibodies can contain the same (i.e. 100% identity), similar, or different framework sequences (FR) in any of corresponding framework sequences in the heavy or light chain provided in FIGS. 7, 44, and 45 or tables below (e.g., Tables 1 and 2, below), so long as binding specificity is substantially maintained. Where the framework sequences are similar, the framework may be at least about 85%, at least about 86%, at least about 90%, at least about 93%, at least about 96%, at least about 98%, or up to 100% identity to a corresponding framework sequence in any of antibodies shown in FIGS. 7, 44, and 45 or tables below (e.g., Tables 1 and 2, below).

An antibody of the present disclosure may therefore contain a full-length $V_H$ and/or full length $V_L$ sequence that is at least 80% identity, at least 85%, at least 90%, at least 95%, up to 100% amino acid sequence identity to a full-length $V_H$ or $V_L$ sequence shown in FIG. 7, 44, or 45 or tables below. For example, a subject antibody can contain the full length $V_H$ and/or full length $V_L$ of F2-1A6. Alternatively, the subject antibody can contain the full length $V_H$ and/or full length $V_L$ of F2-1H9. As further examples, a subject antibody can contain the full length $V_H$ and/or full length $V_L$ of E8H11, E8H7, E8G12, E8F11, E8C9, D6G9, D6D3, D1C5, D1D1, HB8, HC2, HC4, HE3, HF1, or HH3. Examples of antibodies of the present disclosure that bind to CD44 are listed in tables below (e.g., Tables 1 and 2).

TABLE 1

Heavy chain FRs and CDRs of antibodies that specifically bind CD44

| clone | $V_H$ FR1 | $V_H$ CDR1 | $V_H$ FR2 |
|---|---|---|---|
| F2-1A6 | QVQLVQSGAEVKKPGESLKISCKGSGYSFT (SEQ ID NO: 2) | SYWIG (SEQ ID NO: 3) | WVRQMPGKGLEWMG (SEQ ID NO: 4) |
| F2-1H9 | QVQLQESGGGLVQPGGSLRLSCAASGFTFS (SEQ ID NO: 5) | SYRMH (SEQ ID NO: 6) | WVRQAPGKGLEWVA (SEQ ID NO: 7) |
| D1C5 | QVQLQQSGGGVVQPGRSLRLSCAASGFTFS (SEQ ID NO: 28) | SYGIH (SEQ ID NO: 36) | WVRQAPGKGLEWVA SEQ ID NO: 7) |
| D1D1 | QVQLVESGGGLVKPGGSLRLSCAASGFTFS (SEQ ID NO: 24) | TYTMS (SEQ ID NO: 65) | WARQAPGKGLEWVS (SEQ ID NO: 21) |
| HB8 | QVQLVESGGGVVQPGRSLRLSCAASGFTFS (SEQ ID NO: 131) | NYAMI (SEQ ID NO: 132) | WVRQAPGKGLEWVS (SEQ ID NO: 133) |
| HC2 | QVQRVESGGGVVQPGRSLRLSCAASGFTFS (SEQ ID NO: 134) | SYAMS (SEQ ID NO: 32) | WVRQAPGKGLEWVS (SEQ ID NO: 133) |
| HC4 | QVQLVESGGGLVQPGGSLRLSCAASGFTFS (SEQ ID NO: 74) | TLAMG (SEQ ID NO: 33) | WVRQAPGKGLEWVS (SEQ ID NO: 133) |
| HE3 | QVQLQESGGGLVKPGGSLRLSCEASGFTFS (SEQ ID NO: 433) | SYSMN (SEQ ID NO: 37) | WVRQAPGKGLEWVS (SEQ ID NO: 133) |
| HF1 | QVQLVESGGGLVQPGGSLRLSCAASGFTFS (SEQ ID NO: 74) | NYALI (SEQ ID NO: 78) | WVRQAPGKGLEWVS (SEQ ID NO: 133) |
| HH3 | QVQLQESGGGLVQPGGSLRLSCAASGFTFS (SEQ ID NO: 5) | SYAMS (SEQ ID NO: 32) | WVRQAPGKGLEWVS (SEQ ID NO: 133) |
| E8H11 | QVQLVESGGGVVQPGRSLRLSCAASGFTFS (SEQ ID NO: 131) | SYGMH (SEQ ID NO: 41) | WVRQAPGKGLEWVA (SEQ ID NO: 7) |
| E8H7 | QVQLQESGGGLVQPGGSLRLSCSASGFTFS (SEQ ID NO: 180) | SYAMH (SEQ ID NO: 29) | WVRQAPGKGLEYVS (SEQ ID NO: 181) |
| E8G12 | QVQLQQSGGGLVQPGGSLRLSCAASGFTFS (SEQ ID NO: 182) | SYAMS (SEQ ID NO: 32) | WVRQAPGKGLEWVS (SEQ ID NO: 133) |
| E8F11 | QVQLQQSGGGLVQPGGSLRLSCAASGFTFS (SEQ ID NO: 183) | SYAMS (SEQ ID NO: 32) | WVRQAPVKGLEWVS (SEQ ID NO: 184) |
| E8C9 | QVNLRESGGGLVKPGGSLRLSCAASGFTFS (SEQ ID NO: 185) | SYAMS (SEQ ID NO: 32) | WVRQAPGKGLEWVS (SEQ ID NO: 133) |
| D6G9 | QVQLQESGGGLVQPGGSLRLSCAASGFTFS (SEQ ID NO: 74) | SYAMG (SEQ ID NO: 186) | WVRQAPGKGLEWVS (SEQ ID NO: 133) |

TABLE 1-continued

| Heavy chain FRs and CDRs of antibodies that specifically bind CD44 | | | |
|---|---|---|---|
| D6D3 | QVQLQESGGGLVQPGGSLRLSCAASGFTFS (SEQ ID NO: 5) | SYAM (SEQ ID NO: 32) | WVRQAPGKGLEWVS (SEQ ID NO: 133) |
| clone | $V_H$ CDR2 | $V_H$ FR3 | |
| F2-1A6 | IIYPGDSDTRYSPSFQG (SEQ ID NO: 8) | QVTISADKSISTAYLQWSSLKASDTAMYYCAR (SEQ ID NO: 9) | |
| F2-1H9 | AVKQDGSEKYYLDSVKG (SEQ ID NO: 10) | RFTISRDNAKSSLYLQMDSLSVEDTAVYYCAR (SEQ ID NO: 11) | |
| D1C5 | VISYDGSNKYYADSVKG (SEQ ID NO: 45) | RFTISRDNSKNTLYLQMNSLRAEDTAVYYCAK (SEQ ID NO: 50) | |
| D1D1 | AI SADGAGTYYGDSVKG (SEQ ID NO: 82) | RFTVSRDNFKSTLYLQMNRLRAEDTAVYYCAK (SEQ ID NO: 139) | |
| HB8 | AITGGGGSTYYADSVKG (SEQ ID NO: 140) | RFTISRDNSKNTLYLQMNSLRAEDTALYYCAK (SEQ ID NO: 141) | |
| HC2 | AISGSGGSTYYADSVKG (SEQ ID NO: 142) | RFTISRDNSKNTLYLQMNSLRAEDTAVYYCAK (SEQ ID NO: 50) | |
| HC4 | AISGSGGSTYYADSVKG (SEQ ID NO: 142) | RFTISRDNSKNTLYLQMNSLRAEDTAVYYCAR (SEQ ID NO: 46) | |
| HE3 | AISGSGGSTYYADSVKG (SEQ ID NO: 142) | RFTISRDNSKNTLYLQMNSLRAEDTAVYYCAK (SEQ ID NO: 50) | |
| HF1 | AISGSGSGTYYADSVKG (SEQ ID NO: 143) | RFTISRDNSKNTLYLQMNTLRAEDTALYYCAK (SEQ ID NO: 144) | |
| HH3 | AITSSGGRTYYADSVRG (SEQ ID NO: 145) | RLTISRDNSKNTLYLQMNTLRAEDTAVYYCAK (SEQ ID NO: 146) | |
| E8H11 | VISYDGSNKYYADSVKG (SEQ ID NO: 45) | RFTISRDNSKNTLYLQMNSLRAEDTAVYYCAK (SEQ ID NO: 50) | |
| E8H7 | AISSNGGSTYYADSVKG (SEQ ID NO: 187) | RFTISRDNSKNTLYLQMSSLRAEDTAVYYCVA (SEQ ID NO: 188) | |
| H8G12 | AISGSGGSTYYADSVKG (SEQ ID NO: 142) | RFTISRDNSKNTLYLQMNSLRAEDTAVYYCAK (SEQ ID NO: 50) | |
| E8F11 | AISGSGGSTYYADSVKG (SEQ ID NO: 142) | RFTISRDNSKNTLYLQMNSLRIEDTAVYYCGR (SEQ ID NO: 189) | |
| E8C9 | VIS-DGSTTYYADSVKG (SEQ ID NO: 190) | RFTISRDNSKNMLYLQTNSLRAEDTAVYYCAK (SEQ ID NO: 191) | |
| D6G9 | AISASGGSTYYADSVKG (SEQ ID NO: 192) | RFTISRDNSKNTLYLQLNSLRAEDTAVYYCAK (SEQ ID NO: 193) | |
| D6D3 | AITSSGGRTYYADSVRG (SEQ ID NO: 145) | RLTISRDNSKNTLYLQMNTLRAEDTAVYYCAK (SEQ ID NO: 146) | |
| clone | $V_H$ CDR3 | $V_H$ FR4 | |
| F2-1A6 | RLHGPFYFDY (SEQ ID NO: 12) | WGQGTLVTVSS (SEQ ID NO: 13) | |
| F2-1H9 | GLRT (SEQ ID NO: 14) | MGQGTLVTVSS (SEQ ID NO: 15) | |
| D1C5 | GYGSGSYWSGAFDI (SEQ ID NO: 147) | WGQGTMVTVSS (SEQ ID NO: 43) | |
| D1D1 | LGGESYSAD (SEQ ID NO: 148) | WGQGTLVTVSS (SEQ ID NO: 13) | |
| HB8 | TLGRSTVATDY (SEQ ID NO: 149) | WGQGTLVTVSS (SEQ ID NO: 13) | |
| HC2 | GPGAAQDY (SEQ ID NO: 150) | WGQGTLVTVSS (SEQ ID NO: 13) | |
| HC4 | GAVGATTAFDY (SEQ ID NO: 151) | WGQGTLVTVSS (SEQ ID NO: 13) | |
| HE3 | VASSSSLGMDV (SEQ ID NO: 152) | WGQGTTVTVSS (SEQ ID NO: 153) | |
| HF1 | SVVGATSLDY (SEQ ID NO: 154) | WGQGTLVTVSS (SEQ ID NO: 13) | |
| HH3 | GIVGATAFDY (SEQ ID NO: 155) | WGQGTLVTVSS (SEQ ID NO: 13) | |
| E8H11 | DYGYCSGGSCYSPFDY (SEQ ID NO: 194) | WGQGTLVTVSS (SEQ ID NO: 13) | |
| E8H7 | RLEWL-----PLAWDY (SEQ ID NO: 195) | WGQGTLVTVSS (SEQ ID NO: 13) | |
| E8G12 | AARIAAR---PGPLDY (SEQ ID NO: 196) | WGQGTLVTVSS (SEQ ID NO: 13) | |
| E8F11 | H--LSSG----SSVDY (SEQ ID NO: 197) | WGQGTLVTVSS (SEQ ID NO: 13) | |
| E8C9 | AGPRTTV----TTVDS (SEQ ID NO: 198) | WGQGTLVTVSS (SEQ ID NO: 13) | |
| D6G9 | GLKDSSG------FDY (SEQ ID NO: 199) | WGQGTLVTVSS (SEQ ID NO: 13) | |
| D6D3 | GIVGATA------FDY (SEQ ID NO: 155) | WGQGTLVTVSS (SEQ ID NO: 13) | |

TABLE 2

Light chain FRs and CDRs of antibodies that specifically bind CD44

| clone | $V_L$ FR1 | $V_L$ CDR1 | $V_L$ FR2 |
|---|---|---|---|
| F2-1A6 | SELTQDPAVSVALGQTVRITC (SEQ ID NO: 16) | QGDSLRSYYAS (SEQ ID NO: 17) | WYQQKPGQAPLLVIY (SEQ ID NO: 18) |
| F2-1H9 | SELTQDPAVSVALGQTVRITC (SEQ ID NO: 16) | QGDSLRSYYAS (SEQ ID NO: 17) | WYQRKPGQAPLLVIY (SEQ ID NO: 19) |
| D1C5 | EIVLTQSPLSLPVTPGEPASISC (SEQ ID NO: 156) | RSSQSLLHTNGYNYLD (SEQ ID NO: 157 | WYLQKPGQSPQLLIY (SEQ ID NO: 158) |
| D1D1 | HVILTQDPAVSVALGQTVKITC (SEQ ID NO: 159) | QGDSLRSYYAS (SEQ ID NO: 17) | WYQQKPGQAPLLVLY (SEQ ID NO: 160) |
| HB8 | SELTQDPAVSVALGQTVRITC (SEQ ID NO: 16) | QGDSLRSYYAS (SEQ ID NO: 17) | WYQQKPGQAPVLVIY (SEQ ID NO: 70) |
| HC2 | QSVLTQDPAVSVALGQTVTITC (SEQ ID NO: 161) | QGDSLRSYYAS (SEQ ID NO: 17) | WYQQKPGQAPVLVIY (SEQ ID NO: 70) |
| HC4 | SELTQDPAVSVALGQTVKITC (SEQ ID NO: 51) | QGDSLRSYYAS (SEQ ID NO: 17) | WYQQKPGQAPVLVIY (SEQ ID NO: 70) |
| HE3 | SELTQDPAVSVALGQTVRITC (SEQ ID NO: 16) | QGDSLRSYYAS (SEQ ID NO: 17) | WYQQKPGQAPVLVIY (SEQ ID NO: 70) |
| HF1 | QSVLTQDPAVSVALGQTVRITC (SEQ ID NO: 162) | QGDSLRDYYAS (SEQ ID NO: 163) | WYKQKPGQAPLLVFF (SEQ ID NO: 164) |
| HH3 | SELTQDPAVSVALGQTVRITC (SEQ ID NO: 16) | QGDSLRSYYAS (SEQ ID NO: 17) | WYQQKPGQAPVLVIY (SEQ ID NO: 70) |
| E8H11 | NFMLTQDPAVSVALGQTVRITC (SEQ ID NO: 200) | QGDSLRS---YYAS (SEQ ID NO: 17) | WYQQKPGQAPVLVIY (SEQ ID NO: 70) |
| E8H7 | S-ELTQDPAVSVALGQTVRITC (SEQ ID NO: 16) | QGDSLRS---YYAS (SEQ ID NO: 17) | WYQQKPGQAPVLVIY (SEQ ID NO: 70) |
| E8G12 | S-ELTQDPAVSVAVGQTVKITC (SEQ ID NO: 201) | QGDSLRN---YYAS (SEQ ID NO: 202) | WYQQKPRQAPVLVIY (SEQ ID NO: 203) |
| E8F11 | -SELTQPPSASGSPGQSVTISC (SEQ ID NO: 204) | TGTSSDVGGYNYVS (SEQ ID NO: 205) | WYQQRPGYAPKLMIY (SEQ ID NO: 206) |
| E8C9 | QSVLTQPPSVSGAPGQRVTISC (SEQ ID NO: 207) | TGSSSNIGAGYDVH (SEQ ID NO: 208) | WYQQLPGTAPKLLTY (SEQ ID NO: 209) |
| D6G9 | NFMLTQDPAVSVALGQTVRITC (SEQ ID NO: 200) | QGDSLRS---YYAS (SEQ ID NO: 17) | WYQQKPGQAPVLVIY (SEQ ID NO: 70) |
| D6D3 | S-ELTQDPAVSVALGQTVRITC (SEQ ID NO: 16) | QGDSLRS---YYAS (SEQ ID NO: 17) | WYQQKPGQAPVLVIY (SEQ ID NO: 70) |

| clone | $V_L$ CDR2 | $V_L$ FR3 |
|---|---|---|
| F2-1A6 | GKNIRPS (SEQ ID NO: 20) | GIPDRFSGSSSGNTASLTITGAQAEDEADYYC (SEQ ID NO: 23) |
| F2-1H9 | GKNIRPS (SEQ ID NO: 20) | GIPDRFSGSSSGNTASLIITGAQAEDEADYYC (SEQ ID NO: 22) |
| D1C5 | LGSNRAS (SEQ ID NO: 165) | GVPDRFSGSGSGTDFTLKISRVEAEDVGVYYC (SEQ ID NO: 166) |
| D1D1 | GENNRPS (SEQ ID NO: 71) | GIPDRFSGSGSGNTASLTITGAQAEDEADYYC (SEQ ID NO: 167) |
| HB8 | GKNNRPS (SEQ ID NO: 168) | GIPDRFSGSSSGNTASLTITGAQAEDEADYYC (SEQ ID NO: 23) |
| HC2 | GKNNRPS (SEQ ID NO: 168) | GIPDRFSGSSSGNTASLTITGAQAEDEADYYC (SEQ ID NO: 23) |
| HC4 | GKNNRPS (SEQ ID NO: 168) | GIPDRFSGSSSGNTASLTITGAQAEDEADYYC (SEQ ID NO: 23) |
| HE3 | GKNNRPS (SEQ ID NO: 168) | GIPDRFSGSSSGNTASLTITGARAEDEADYYC (SEQ ID NO: 169) |
| HF1 | GKSNRPS (SEQ ID NO: 170) | GIPNRFSGSTSGSTATLTVTGAQAEDEADYFC (SEQ ID NO: 171) |
| HH3 | GKNNRPS (SEQ ID NO: 168) | GIPDRFSGSSSGNTASLTITGAQAEDEADYYC (SEQ ID NO: 23) |
| E8H11 | GKNNRPS (SEQ ID NO: 168) | GIPDRFSGSSSGNTASLTITGAQAEDEADYYC (SEQ ID NO: 23) |
| E8H7 | GKNNRPS (SEQ ID NO: 168) | GIPDRFSGSSSGNTASLTITGAQAEDEADYYC (SEQ ID NO: 23) |
| E8G12 | GKNNRPS (SEQ ID NO: 168) | GIPDRFSGSSSGNTASLTITGAQAEDEADYYC (SEQ ID NO: 23) |
| E8F11 | DVSNRPS (SEQ ID NO: 210) | GVSNRFSGSKSGNSASLDISGLQSEDEADYYC (SEQ ID NO: 211) |
| E8C9 | GNSNRPS (SEQ ID NO: 212) | GVPDRFSGSKSGTSASLAITGLQAEDEADYYR (SEQ ID NO: 213) |
| D6C9 | GKNNRPS (SEQ ID NO: 168) | GIPDRFSGSSSGNTASLTITGAQAEDEADYYC (SEQ ID NO: 23) |
| D6D3 | GKNNRPS (SEQ ID NO: 168) | GIPDRFSGSSSGNTASLTITGAQAEDEADYYC (SEQ ID NO: 23) |

| clone | $V_L$ CDR3 | $V_L$ FR4 |
|---|---|---|
| F2-1A6 | NSRDSSGNHVV (SEQ ID NO: 23) | FGGGTKLTVLG (SEQ ID NO: 27) |
| F2-1H9 | NSRDSSANQM (SEQ ID NO: 25) | FGGGTKLTVLG (SEQ ID NO: 27) |

TABLE 2-continued

Light chain FRs and CDRs of antibodies that specifically bind CD44

| | | |
|---|---|---|
| D1C5 | MQGRQSPLT (SEQ ID NO: 172) | FGGGTKVEIKR (SEQ ID NO: 84) |
| D1D1 | HSRDSSGKYV (SEQ ID NO: 173) | FGVGTKVTVLG (SEQ ID NO: 174) |
| HB8 | NSRDSSGNPHVV (SEQ ID NO: 175) | FGGGTKLTVLG (SEQ ID NO: 27) |
| HC2 | NSRDSSGNHVV (SEQ ID NO: 23) | FGGGTKVTVLG (SEQ ID NO: 80) |
| HC4 | NSRDSSGNHLV (SEQ ID NO: 176) | FGGGTKLTVLG (SEQ ID NO: 27) |
| HE3 | TSRDSSGKQLV (SEQ ID NO: 177) | FGGGTKLTVLG (SEQ ID NO: 27) |
| HFI | SSRDSSGRLIL (SEQ ID NO: 178) | FGGGTKLTVLG (SEQ ID NO: 27) |
| HH3 | NSRDSSGNSVV (SEQ ID NO: 179) | FGGGTKVTVLG (SEQ ID NO: 80) |
| E8H11 | HSRDSSGN-YL (SEQ ID NO: 214) | FGGGTKLTVLG (SEQ ID NO: 27) |
| E8H7 | NSRDSSGNHKV (SEQ ID NO: 215) | FGGGTKLTVLG (SEQ ID NO: 27) |
| E8G12 | NSRDRSNNHLL (SEQ ID NO: 216) | FGGGTKLTVLG (SEQ ID NO: 27) |
| E8F11 | AAWDDSLREFL (SEQ ID NO: 217) | FGTGTKVTVLG (SEQ ID NO: 218) |
| E8C9 | SAWDSSLFNWV (SEQ ID NO: 219) | FGGGTKLTVLG (SEQ ID NO: 27) |
| D6G9 | NSRDSSAKRVV (SEQ ID NO: 220) | FGGGTKVTVLG (SEQ ID NO: 80) |
| D6D3 | NSRDSSGNSVV (SEQ ID NO: 179) | FGGGTKVTVLG (SEQ ID NO: 80) |

Anti-EphA2

Antibodies of the present disclosure include those that specifically bind EphA2. Anti-EphA2 antibodies encompass those that competitively bind to an epitope (e.g. on the extracellular domain) of EphA2 with 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11. The epitope bound by anti-EphA2 antibodies reside in a contiguous amino acid sequence of EphA2 from residue position 25 to 534, as set forth below.

(SEQ ID NO: 26)
QGKEVVLLDFAAAGGELGWLTHPYGKGWDLMQNIMNDMPIYMYSVCNVMS

GDQDNWLRTNWVYRGEAERIFIELKFTVRDCNSFPGGASSCKETFNLYYA

ESDLDYGTNFQKRLFTKIDTIAPDEITVSSDFEARHVKLNVEERSVGPLT

RKGFYLAFQDIGACVALLSVRVYYKKCPELLQGLAHFPETIAGSDAPSLA

TVAGTCVDHAVVPPGGEEPRMHCAVDGEWLVPIGQCLCQAGYEKVEDACQ

ACSPGFFKFEASESPCLECPEHTLPSPEGATSCECEEGFFRAPQDPASMP

CTRPPSAPHYLTAVGMGAKVELRWTPPQDSGGREDIVYSVTCEQCWPESG

ECGPCEASVRYSEPPHGLTRTSVTVSDLEPHMNYTFTVEARNGVSGLVTS

RSFRTASVSINQTEPPKVRLEGRSTTSLSVSWSIPPPQQSRVWKYEVTYR

KKGDSNSYNVRRTEGFSVTLDDLAPDTTYLVQVQALTQEGQGAGSKVHEF

QTLSPEGSGN

The residue position numbers of EphA2 are determined based on the sequence set forth in GenBank Accession No. NP_004422.2 or UniProt Accession No. P29317.

Anti-EphA2 antibodies also encompass those that competitively bind to the ligand binding site of EphA2. For example, antibodies 2D6, D2-1A7, and D2-1A9 compete with Ephrin A1, the natural ligand of EphA2, for binding to EphA2. Thus, the subject antibodies can also compete with Ephrin A1 for binding to an epitope of EphA2.

Antigens that comprise epitopes that are similar to the epitopes of EphA2 can also be binding targets of subject antibodies. When bound to an antigen on a cell surface (e.g. EphA2), certain of the subject antibodies will be internalized by the cell.

Epitopes for which anti-EphA2 antibodies have affinity are cell-surface exposed and solvent-accessible on many cancer cells, particularly on the plasma membrane of cells. The epitopes can be accessible to the subject antibodies when the cells are live. The cancer cells can include those derived from tissue of epithelial in origin. For example, the epitopes can be found on cancer cells derived from breast cancers, skin cancers (e.g. melanoma), lung cancers, prostate cancers, colon cancers, and/or ovarian cancers. Other cancers cells for which anti-EphA2 antibodies have affinity may be liver cancer, esophageal squamous cell carcinoma, epidermoid cancer, pancreatic cancer, glioblastomas, neuroblastomas, and/or other neural cancers, for example.

Additional examples of subject antibodies encompass those that have the same binding specificities and contain at least two CDRs that each independently shares at least about 80%, at least about 87%, at least about 93%, at least about 94%, or up to 100% amino acid sequence identity with the amino acid sequence of a $V_H$ CDR of antibodies shown in FIGS. 8, 46, and 47, and in tables below (e.g. $V_H$ CDR1 of 2D6; or $V_H$ of CDR1 of A3H9, A3G3, A3D10, A3D1, A3C8, 1A3, 1A5, 1A8, 1A12, 1B2, 1C2, 1C7, 1D8, or 15E11). The subject antibody can also include all three CDRs from any $V_H$ of any antibody shown in FIGS. 8, 46, and 47, such that each $V_H$ CDR in the subject antibody is selected from a single antibody shown in FIG. 8, 46, or 47 or tables below (e.g., Table 3) and each $V_H$ CDR independently shares at least about 80%, at least about 87%, at least about 93%, at least about 94%, or up to 100% amino acid sequence identity with the amino acid sequence of the corresponding $V_H$ CDR of an antibody shown in FIGS. 8, 46, and 47 or in tables below. For example, the heavy chain of a subject antibody can contain at least two $V_H$ CDRs or all three $V_H$ CDRs of 2D6. Alternatively, the heavy chain can contain at least two $V_H$ CDRs or all three $V_H$ CDRs of D2-1A7. Other examples include a heavy chain that contains at least two $V_H$ CDRs or all three $V_H$ CDRs of D2-1A9 and a heavy chain that contains at least two $V_H$ CDRs or all three $V_H$ CDRs of D2-1B1. As further examples, the heavy chain of a subject antibody can contain at least two $V_H$ CDRs or all three $V_H$ CDRs of A3H9, A3G3, A3D10, A3D1, A3C8, 1A3, 1A5, 1A8, 1A12, 1B2, 1C2, 1C7, 1D8, or 15H11.

Similarly for the light chain, a subject antibody can contain at least two CDRs that are each independently at least about 80%, at least about 87%, at least about 93%, at least about 94%, or up to 100% amino acid sequence identity with the amino acid sequence of a $V_L$ CDR of an antibody shown in FIG. 8, 46, or 47 or tables below (e.g. $V_L$ CDR1 of 2D6; or $V_L$ of CDR1 of A3H9, A3G3, A3D10, A3D1, A3C8, 1A3, 1A5, 1A8, 1A12, 1B2, 1C2, 1C7, 1D8, or 15H11). The subject antibody can also or alternatively include all three $V_L$ CDRs from any of antibodies shown in FIGS. 8, 46, and 47 or tables below (e.g., Table 4) and each $V_L$ CDR independently shares at least about 80%, at least about 87%, at least about 93%, at least about 94%, or up to 100% amino acid sequence identity with the amino acid sequence of a $V_L$ CDR of an antibody shown in FIG. 8, 46, or 47 or tables below. For example, the light chain of a subject antibody can contain two $V_L$ CDRs or all three $V_L$ CDRs of 2D6. Alternatively, the light chain can contain two $V_L$ CDRs or all three $V_L$ CDRs of D2-1A7. Other examples include a light chain that contains two $V_L$ CDRs or all three $V_L$ CDRs of D2-1A9 and a light chain that contains two $V_L$ CDRs or all three $V_L$ CDRs of D2-1B1. As further examples, the light chain of a subject antibody can contain two $V_L$ CDRs or all three $V_L$ CDRs of A3H9, A3G3, A3D10, A3D1, A3C8, 1A3, 1A5, 1A8, 1A12, 1B2, 1C2, 1C7, 1D8, or 15H11.

Optionally, antibodies can contain the exactly the same (i.e. 100% identity), similar, or different framework sequences (FR) in any of corresponding framework sequences in the heavy or light chain provided in FIGS. 8, 46, and 47 or tables below (e.g., Tables 3 and 4). Where the framework sequences are similar, the framework may be at least about 85%, at least about 86%, at least about 90%, at least about 93%, at least about 96%, at least about 98%, or up to 100% identity to a corresponding framework sequence in any of antibodies shown in FIGS. 8, 46, and 47 or tables below.

An antibody of the present disclosure may therefore contain a full-length $V_H$ and/or full length $V_L$ sequence that is at least 80% identity, at least 85%, at least 90%, at least 95%, up to 100% amino acid sequence identity to a full-length $V_H$ or $V_L$ sequence shown in FIG. 8, 46, or 47 or tables below. For example, a subject antibody can contain the full length $V_H$ and/or full length $V_L$ of 2D6. Alternatively, the subject antibody can contain the full length $V_H$ and/or full length $V_L$ of D2-1A7. Other examples include an antibody containing the full length $V_H$ and/or full length $V_L$ of D2-1A9 and an antibody containing the full length $V_H$ and/or full length $V_L$ of D2-1B1. Further examples include an antibody containing the full length $V_H$ and/or full length $V_L$ of A3H9, A3G3, A3D10, A3D1, A3C8, 1A3, 1A5, 1A8, 1A12, 1B2, 1C2, 1C7, 1D8, or 15H11. Examples of antibodies of the present disclosure that bind to EphA2 are listed in tables below.

TABLE 3

Heavy chain FRs and CDRs of antibodies that specifically bind EphA2

| clone | $V_H$ FR1 | $V_H$ CDR1 | $V_H$ FR2 |
|---|---|---|---|
| 2D6 | QVQLQESGGGLVQPGGSLRLSCAASGFTFS (SEQ ID NO: 5) | SYAMS (SEQ ID NO: 32) | WVRQAPGKGLDWVS (SEQ ID NO: 53) |
| D2-1A7 | QVQLQQSGGGVVQPGRSLRLSCAASGFTFS (SEQ ID NO: 28) | SYAMH (SEQ ID NO: 29) | WVRQAPGKGLEWVA (SEQ ID NO: 7) |
| D2-1A9 | QVQLVESGGGLIQPGGSLKLSCAASGFTVS (SEQ ID NO: 30) | NSYMS (SEQ ID NO: 31) | WVRQAPGKGLEWVA (SEQ ID NO: 7) |
| D2-1B1 | QVQLQESGGGVVQPGRSLRLSCAASGFTFS (SEQ ID NO: 54) | SYGMH (SEQ ID NO: 41) | WVRQAPGKGLEWVA (SEQ ID NO: 7) |
| A3H9 | QVLLVESGGGVVQAGASLRVSCAASGFSLT (SEQ ID NO: 126) | SYGMH (SEQ ID NO: 41) | WVRQAPGKGLEWVA (SEQ ID NO: 7) |
| A3G3 | QVQLVESGGGVVQPGRSLRLSCAASGFTFS (SEQ ID NO: 131) | SYAMG (SEQ ID NO: 186) | WVRQAPGKGLEWVA (SEQ ID NO: 7) |
| A3D10 | LVQLVQSGGGLVKPGGSLRLSCAASGFTFS (SEQ ID NO: 434) | TYSMN (SEQ ID NO: 222) | WVRQAPGKGLEWVS (SEQ ID NO: 133) |
| A3D1 | QVQLVQSGGGLVQPGGSLRLSCAASGFTFS (SEQ ID NO: 182) | SYGMH (SEQ ID NO: 41) | WVRQAPGKGLEWVA (SEQ ID NO: 7) |
| A3C8 | QLQLVESGGGLVQPGGSLRLSCAASGFTFS (SEQ ID NO: 223) | SYAMN (SEQ ID NO: 224) | WVRQAPGKGLEWVS (SEQ ID NO: 133) |
| 1A3 | QVQLQQSGPGLVKPSQTLSLTCAISGDSVS (SEQ ID NO: 225) | SNSAA (SEQ ID NO: 226) | WNWIRQSPSRGLEWLG (SEQ ID NO: 227) |
| 1A5 | QVQLQESGGGVVQPGGSLRLSCAASGFTFS (SEQ ID NO: 228) | NYAMH (SEQ ID NO: 229) | WVRQAPGKGLEYVS (SEQ ID NO: 181) |

TABLE 3-continued

Heavy chain FRs and CDRs of antibodies that specifically bind EphA2

| | | | |
|---|---|---|---|
| 1A8 | QVQLQQSGGGLVQPGGSLRLSCSASGFTFS (SEQ ID NO: 230) | NYAIH (SEQ ID NO: 231) | WVRQAPGKGLEYVS (SEQ ID NO: 181) |
| 1A12 | QVQLQESGGGLVQPGGFLRLSCAASGFTFS (SEQ ID NO: 232) | SYGMH (SEQ ID NO: 41) | WVRQTPGKGLEWVS (SEQ ID NO: 233) |
| 1B2 | QVQLVESGGGVVQPGRSLRLSCAASGFTFS (SEQ ID NO: 131) | SYGMH (SEQ ID NO: 41) | WVRQAPGKGLEWVA (SEQ ID NO: 7) |
| 1C2 | QVQLQESGGGLVKPGGSLRLSCAGSGFIFN (SEQ ID NO: 234) | TYSMN (SEQ ID NO: 222) | WVRQSPGKGLEWVS (SEQ ID NO: 235) |
| 1C7 | QVQLVESGGGVVQPGRSLRLSCAASGFTFS (SEQ ID NO: 131) | SYGMH (SEQ ID NO: 41) | WVRQAPGKGLEWVS (SEQ ID NO: 133) |
| 1D8 | QVQLVESGGGLIQPGGSLRLSCAASGFTVS (SEQ ID NO: 236) | SNYMS (SEQ ID NO: 237) | WVRQAPGKGLEWVS (SEQ ID NO: 133) |
| clone | $V_H$ CDR2 | $V_H$ FR3 | |
| 2D6 | IIYNGDNTYYADSVKG (SEQ ID NO: 34) | RFTISRDNSKNSLYLQMNSLRAEDTAVYYCAR (SEQ ID NO: 35) | |
| D2-1A7 | VISYDGSNKYYADSVKG (SEQ ID NO: 45) | RFTISRDNSKNTLYLQMNSLRAEDTAVYYCAR (SEQ ID NO: 46) | |
| D2-1A9 | VIYSAGNTYYADSVKG (SEQ ID NO: 38) | RFTISRDTSNNTVHLQMNSLRPEDTAVYYCAR (SEQ ID NO: 39) | |
| D2-1B1 | VISYDGSNKYYADSVKG (SEQ ID NO: 45) | RFTISRDNSKNTLYLQMNSLRAEDTAVYYCAK (SEQ ID NO: 50) | |
| A3H9 | FISSDGSDKYYVDSVKG (SEQ ID NO: 238) | RFTISRDTSKNMMYLQMNSLTTEDTAVYYCAK (SEQ ID NO: 239) | |
| A3G3 | VIYRDGHGYYADSVKG (SEQ ID NO: 240) | RFTVSRDSSENTVYLQMNSLRAEDTAIYYCAS (SEQ ID NO: 241) | |
| A3D10 | SISSSSSYIYYADSVKG (SEQ ID NO: 242) | RFTISRDNANNSLYLQMNSLRAEDTAVYYCAR (SEQ ID NO: 243) | |
| A3D1 | VIWYDGSNKYYADSVKG (SEQ ID NO: 244) | RFTISRDNSRNTLYLEMNSLRAEDTAVYYCVK (SEQ ID NO: 245) | |
| A3C8 | AISGSGGNTYYADSVKG (SEQ ID NO: 246) | RFTISRDNSNNALYLQMNSLRVEDTAVYYCAR (SEQ ID NO: 247) | |
| 1A3 | RTYYRSKWYNDYAVSVKS (SEQ ID NO: 248) | RITINPDTSKNLFSLQLNSVTPEDTALYYCAR (SEQ ID NO: 249) | |
| 1A5 | SISSNGGGTYYADSVKG (SEQ ID NO: 250) | RFTISRDDAKNTLYLQLNSLRDEDTAVYYCAK (SEQ ID NO: 251) | |
| 1A8 | AINSNGGSTYYADSVKG (SEQ ID NO: 252) | RSIISRDNSMNTVYLQMSSLRAEDTAVYYCVK (SEQ ID NO: 253) | |
| 1A12 | YISSSSSYTNYADSVKG (SEQ ID NO: 254) | RFTISRDNSKNTLYLQMNSLRAEDTAVYYCAR (SEQ ID NO: 46) | |
| 1B2 | VISYDGSNKYYADSVKG (SEQ ID NO: 45) | RFTISRDNSKNTLYLQMNSLRAEDTAVYYCAR (SEQ ID NO: 46) | |
| 1C2 | STGGSGKNTFYADSVRG (SEQ ID NO: 255) | RFTISRDNAKNSLYLQMNSLRAEDTAVYYCAR (SEQ ID NO: 256) | |
| 1C7 | YISSSGSYTNYADSVKG (SEQ ID NO: 257) | RFTISRDNAKNTLYLQMNSLRAEDTAVYYCAK (SEQ ID NO: 258) | |
| 1D8 | VIYSGGSTYYADSVKG (SEQ ID NO: 259) | RFTISRDNSKNTLYLQMNSLRAEDTAVYYCAR (SEQ ID NO: 46) | |
| clone | $V_H$ CDR3 | $V_H$ FR4 | |
| 2D6 | WSGTSYDY (SEQ ID NO: 62) | WGQGTLVTVSS (SEQ ID NO: 13) | |
| D2-1A7 | ASVGATGPFDI (SEQ ID NO: 42) | WGQGTMVTVSS (SEQ ID NO: 43) | |
| D2-1A9 | EGSFGYDY (SEQ ID NO: 44) | RGQGTLVTVSS (SEQ ID NO: 75) | |
| D2-1B1 | VIAGGAYYGSADY (SEQ ID NO: 76) | WGQGTLVTVSS (SEQ ID NO: 13) | |
| A3H9 | DWGSNWYLFDY (SEQ ID NO: 260) | WGQGTLVTVSS (SEQ ID NO: 13) | |
| A3G3 | HDYAGNPAGSASGY (SEQ ID NO: 261) | WGQGTLVTVSS (SEQ ID NO: 13) | |
| A3D10 | GNTVAQRLDVFDY (SEQ ID NO: 262) | WGQGTLVTVSS (SEQ ID NO: 13) | |
| A3D1 | DRQPDGRWPFDL (SEQ ID NO: 263) | WGQGTLVTVSS (SEQ ID NO: 13) | |
| A3C8 | DASYYADDY (SEQ ID NO: 264) | WGQGTLVTVSS (SEQ ID NO: 13) | |
| 1A3 | EEDYSGFQH (SEQ ID NO: 265) | WGQGTLVTVSS (SEQ ID NO: 13) | |

TABLE 3-continued

Heavy chain FRs and CDRs of antibodies that specifically bind EphA2

| | | |
|---|---|---|
| 1A5 | DYFGSIDY (SEQ ID NO: 266) | WGQGTLVTVSS (SEQ ID NO: 13) |
| 1A8 | EENGSGFDS (SEQ ID NO: 267) | WGQGTLVTVSS (SEQ ID NO: 13) |
| 1A12 | DNWYFDL (SEQ ID NO: 268) | WGRGTLVTVSS (SEQ ID NO: 269) |
| 1B2 | ALYYDEALDY (SEQ ID NO: 270) | WGQGTLVTVSS (SEQ ID NO: 13) |
| 1C2 | EDSSGSFDY (SEQ ID NO: 271) | WGQGTLVTVSS (SEQ ID NO: 13) |
| 1C7 | VRGWDGDYLDY (SEQ ID NO: 272) | WGQGTLVTVSS (SEQ ID NO: 13) |
| 1D8 | GGFSGYDYFDY (SEQ ID NO: 273) | WGQGTLVTVSS (SEQ ID NO: 13) |

TABLE 4

Light chain FRs and CDRs of antibodies that specifically bind EphA2

| clone | $V_L$ FR1 | $V_L$ CDR1 | $V_L$ FR2 |
|---|---|---|---|
| 2D6 | SELTQDPAVSVALGQTVRITC (SEQ ID NO: 16) | QGDSLRSYYAS (SEQ ID NO: 17) | WYQQKPGQAPLLVIY (SEQ ID NO: 18) |
| D2-1A7 | SELTQDPAVSVALGQTVSITC (SEQ ID NO: 47) | QGDSLRSYYAS (SEQ ID NO: 17) | WYQQKPGQAPLLVIY (SEQ ID NO: 18) |
| D2-1A9 | DIVMTQSPGTLSLSPGERATLSC (SEQ ID NO: 48) | RASQSVSSSFLG (SEQ ID NO: 49) | WYQQKPGQAPRLLIY (SEQ ID NO: 77) |
| D2-1B1 | SELTQDPAVSVALGQTVKITC (SEQ ID NO: 51) | QGDSLRTYYAS (SEQ ID NO: 52) | WYQQKPGQAPVLVIY (SEQ ID NO: 70) |
| A3H9 | SVLTQPPSASETPGQRVTISC (SEQ ID NO: 291) | SGSSSNIGANTVH (SEQ ID NO: 292) | WYQQFPGTAPKLLIY (SEQ ID NO: 293) |
| A3G3 | SALTQPASVSGSPGQSVTISC (SEQ ID NO: 294) | TGTSSDVGGYDYVS (SEQ ID NO: 295) | WYQQHPGKAPKLVMY (SEQ ID NO: 296) |
| A3D10 | SVLTQPPSVSGAPGQRVTISC (SEQ ID NO: 297) | TGGSSNVGAGFDVH (SEQ ID NO: 298) | WYQQLPGTAPKLLIY (SEQ ID NO: 299) |
| A3D1 | SALTQPASVSGSPGQSVTISC (SEQ ID NO: 300) | TGANSDLGGYNYVS (SEQ ID NO: 301) | WYQHHPAKAPKLIIY (SEQ ID NO: 302) |
| A3C8 | SELTQDPAVSVALGQTVRITC (SEQ ID NO: 16) | QGDSLKSYYAS (SEQ ID NO: 303) | WYQQKPGQAPVLVIY (SEQ ID NO: 70) |
| 1A3 | QSALTQPASVSGSPGQSITISC (SEQ ID NO: 304) | TGTSSDVGGYNYVS (SEQ ID NO: 205) | WYQQHPGKAPKLMIY (SEQ ID NO: 435) |
| 1A5 | PELTQDPAVSVALGQTVTITC (SEQ ID NO: 436) | QGDSLRSYYAS (SEQ ID NO: 17) | WYQQKPGQAPLLVIY (SEQ ID NO: 18) |
| 1A8 | EIVLTQSPSSVSASVGDRVTITC (SEQ ID NO: 437) | RASQDISKWLA (SEQ ID NO: 438) | WYQQRPGKVPRLLIY (SEQ ID NO: 439) |
| 1A12 | DVVMTQSPSTLSASVGDRVSITC (SEQ ID NO: 440) | RASESISRWLA (SEQ ID NO: 441) | WYQQKPGKAPKALIY (SEQ ID NO: 442) |
| 1B2 | EIVLTQSPSSLSASVGDRVTITC (SEQ ID NO: 443) | RASQDMSRWLA (SEQ ID NO: 444) | WYQQKPGKAPKLLIH (SEQ ID NO: 445) |
| 1C2 | DIQMTQSPSTLSASIGDRVTITC (SEQ ID NO: 446) | RASEGIYHWLA (SEQ ID NO: 447) | WYQQKPGKAPKLLIY (SEQ ID NO: 448) |
| 1C7 | DIQMTQSPSLLSASVGDRVTITC (SEQ ID NO: 449) | RASQGINNYLA (SEQ ID NO: 221) | WYQQKPGKAPKLLIY (SEQ ID NO: 448) |
| 1D8 | QSVLTQPPSVSGAPGQRVTISC (SEQ ID NO: 207) | TGSSSNIGAGYDVH (SEQ ID NO: 208) | WYQQLPGTAPKLLIY (SEQ ID NO: 299) |

TABLE 4-continued

Light chain FRs and CDRs of antibodies that specifically bind EphA2

| clone | $V_L$ CDR2 | $V_L$ FR3 |
|---|---|---|
| 2D6 | GENNRPS (SEQ ID NO: 71) | GIPDRFSGSSSGNTASLTITGAQAEDEADYYC (SEQ ID NO: 23) |
| D2-1A7 | GENNRPS (SEQ ID NO: 71) | GIPDRFSGSSSGNTASLTITGAQAEDEADYYC (SEQ ID NO: 23) |
| D2-1A9 | GASSRAT (SEQ ID NO: 55) | GIPDRFSGSGSGTDFTLTISRLEPEDFAVYYC (SEQ ID NO: 56) |
| D2-1B1 | GENSRPS (SEQ ID NO: 57) | GIPDRFSGSSSGNTASLTITGAQAEDEADYYC (SEQ ID NO: 23) |
| A3H9 | SYSQRPS (SEQ ID NO: 395) | GVPDRFSDSKSGTSASLAISGLQSEDEADYYC (SEQ ID NO: 396) |
| A3G3 | SHNQRSS (SEQ ID NO: 397) | GVPDRFSGSKSGNSASLDISGLQSEDEADYYR (SEQ ID NO: 398) |
| A3D10 | GDKNRPS (SEQ ID NO: 399) | GVPDRFSGSRSGTSASLAITGLQAEDEADYYC (SEQ ID NO: 400) |
| A3D1 | EVNNRPS (SEQ ID NO: 401) | GVSHRFSGSKSANTASLTISGLQAEDEADYYC (SEQ ID NO: 402) |
| A3C8 | GKNNRPS (SEQ ID NO: 168) | GIPDRFSGSSSGNTASLTITGAQAEDEADYYC (SEQ ID NO: 23) |
| 1A3 | EGSKRPS (SEQ ID NO: 403) | GVPERFSGSNSGNTATLTIGRVEAGDEADYYC (SEQ ID NO: 404) |
| 1A5 | GKNIRPS (SEQ ID NO: 20) | GIPDRFSGSSSGNSASLTITGAQAEDEADYYC (SEQ ID NO: 405) |
| 1A8 | SASSLQS (SEQ ID NO: 406) | GVPSRFSGSGSGTDFTLTISSLQPEDFASYFC (SEQ ID NO: 407) |
| 1A12 | KASSLES (SEQ ID NO: 408) | GVPSRFSGSGSATEFTLTINSLQPDDFATYYC (SEQ ID NO: 409) |
| 1B2 | SASTLQS (SEQ ID NO: 410) | GVPSRFSGSGSGTEFTLTISSLQPEDFATYYC (SEQ ID NO: 411) |
| 1C2 | KASSLAS (SEQ ID NO: 412) | GAPSRFSGSGSGTDFTLTISSLQPDDFATYYC (SEQ ID NO: 413) |
| 1C7 | AASTLQS (SEQ ID NO: 414) | GVPSRFSGSGSGTEFTLTISGLQPEDFATYYC (SEQ ID NO: 415) |
| 1D8 | VNSNRPS (SEQ ID NO: 94) | GVPDRFSGSKSGTSASLAITGLQAEDEADYYC (SEQ ID NO: 95) |

| clone | $V_L$ CDR3 | $V_L$ FR4 |
|---|---|---|
| 2D6 | HSRDSSGTHLRV (SEQ ID NO: 79) | FGGGTKVTVLG (SEQ ID NO: 80) |
| D2-1A7 | NSRDSSGTHLTV (SEQ ID NO: 60) | FGGGTKLTVLG (SEQ ID NO: 27) |
| D2-1A9 | QQYGISPLT (SEQ ID NO: 61) | FGGGTKVEIKR (SEQ ID NO: 84) |
| D2-1B1 | HSRDSSGTHLRV (SEQ ID NO: 79) | FGGGTKLTVLG (SEQ ID NO: 27) |
| A3H9 | AAWDDILNGWV (SEQ ID NO: 274) | FGGGTKVTVLG (SEQ ID NO: 80) |
| A3G3 | AAWDDSLSEFL (SEQ ID NO: 275) | FGTGTKLTVLG (SEQ ID NO: 276) |
| A3D10 | QAYDSSLRGSV (SEQ ID NO: 277) | FGGGTKLTVLG (SEQ ID NO: 27) |
| A3D1 | SSYRSGGTYV (SEQ ID NO: 278) | FGTGTKLTVLG (SEQ ID NO: 276) |
| A3C8 | HSRDSSGNHPVV (SEQ ID NO: 279) | FGGGTKVTVLG (SEQ ID NO: 80) |
| 1A3 | QAWDSTSDHVV (SEQ ID NO: 280) | FGGGTKVTVLG (SEQ ID NO: 80) |
| 1A5 | HSRDSSGTHLRV (SEQ ID NO: 79) | FGGGTKLTVLG (SEQ ID NO: 27) |
| 1A8 | QQASVFPVT (SEQ ID NO: 281) | FGGGTKLEIKR (SEQ ID NO: 282) |
| 1A12 | QQYSSYPLT (SEQ ID NO: 283) | FGQGTKVDIKR (SEQ ID NO: 284) |
| 1B2 | QQLGVYPLT (SEQ ID NO: 285) | IGGGTKVEIKR (SEQ ID NO: 286) |
| 1C2 | QQYHTISRT (SEQ ID NO: 287) | FGPXTKLEIKR (SEQ ID NO: 288) |
| 1C7 | QNLNSYPLT (SEQ ID NO: 289) | FGGGTKVEIKR (SEQ ID NO: 84) |
| 1D8 | QSYDSSLSGWV (SEQ ID NO: 290) | FGGGTKLTVLG (SEQ ID NO: 27) |

It will be appreciated that the amino acid sequence of a CDR can also be defined using alternative systems, which will be readily apparent to and applied by the ordinarily skilled artisan (see, "Sequences of Proteins of Immunological Interest," E. Kabat et al., U.S. Department of Health and Human Services, (1991 and Lefranc et al. IMGT, the international ImMunoGeneTics information system. *Nucl. Acids Res.,* 2005, 33, D593-D597)). A detailed discussion of the IMGTS system, including how the IMGTS system was formulated and how it compares to other systems, is provided on the World Wide Web at www(dot)imgt.cines.fr/textes/IMGTScientificChart/Numbering/IMGTnumberingsTable.html. All amino acid sequences of CDR in the present disclosure are defined according to Kabat et al., supra, unless otherwise indicated.

The variable chains disclosed herein can be joined directly or through a linker (e.g., $(Gly_4Ser)_3$, SEQ ID NO: 81) to form a single-chain antibody. Details on linkers are discussed later below.

Method of Antibody Production

Using the information provided herein, the anti-CD44 and anti-EphA2 antibodies of the present disclosure are prepared using standard techniques well known to those of skill in the art.

For example, the nucleic acid sequences provided in FIG. 9 can be used to express the subject antibodies. Alternatively, the polypeptide sequences provided herein (see, e.g., tables above and/or FIGS. 7, 8, 9, and 44-47) can be used to determine appropriate nucleic acid sequences encoding the antibodies and the nucleic acids sequences then used to express one or more antibodies specific for EphA2 or CD44. The nucleic acid sequence(s) can be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12:6159-6168) or manually synthesized using, for example, the solid phase phosphoramidite triester method described by Beaucage et. al. (1981) *Tetrahedron Letts.* 22(20): 1859-1862.

Once a nucleic acid encoding a subject antibody is synthesized it can be amplified and/or cloned according to standard methods. Molecular cloning techniques to achieve these ends are known in the art. A wide variety of cloning and in vitro amplification methods suitable for the construction of recombinant nucleic acids are known to persons of skill in the art and are the subjects of numerous textbooks and laboratory manuals.

Expression of natural or synthetic nucleic acids encoding the antibodies of the present disclosure can be achieved by operably linking a nucleic acid encoding the antibody to a promoter (which is either constitutive or inducible), and incorporating the construct into an expression vector to generate a recombinant expression vector. The vectors can be suitable for replication and integration in prokaryotes, eukaryotes, or both. Typical cloning vectors contain functionally appropriately oriented transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, e.g., as found in shuttle vectors, and selection markers for both prokaryotic and eukaryotic systems.

To obtain high levels of expression of a cloned nucleic acid it is common to construct expression plasmids which typically contain a strong promoter to direct transcription, a ribosome binding site for translational initiation, and a transcription/translation terminator, each in functional orientation to each other and to the protein-encoding sequence. Examples of regulatory regions suitable for this purpose in *E. coli* are the promoter and operator region of the *E. coli* tryptophan biosynthetic pathway, the leftward promoter of phage lambda ($P_L$), and the L-arabinose (araBAD) operon. The inclusion of selection markers in DNA vectors transformed in *E. coli* is also useful. Examples of such markers include genes specifying resistance to ampicillin, tetracycline, or chloramphenicol. Expression systems for expressing antibodies are available using, for example, *E. coli, Bacillus* sp. and *Salmonella. E. coli* systems may also be used.

The antibody gene(s) may also be subcloned into an expression vector that allows for the addition of a tag (e.g., a FLAG® tag, hexahistidine, and the like) at the C-terminal end or the N-terminal end of the antibody (e.g. scFv) to facilitate purification. Methods of transfecting and expressing genes in mammalian cells are known in the art. Transducing cells with nucleic acids can involve, for example, incubating lipidic microparticles containing nucleic acids with cells or incubating viral vectors containing nucleic acids with cells within the host range of the vector. The culture of cells used in the present disclosure, including cell lines and cultured cells from tissue (e.g., tumor) or blood samples is well known in the art.

Once the nucleic acid encoding a subject antibody is isolated and cloned, one can express the nucleic acid in a variety of recombinantly engineered cells known to those of skill in the art. Examples of such cells include bacteria, yeast, filamentous fungi, insect (e.g. those employing baculoviral vectors), and mammalian cells.

Isolation and purification of a subject antibody can be accomplished according to methods known in the art. For example, a protein can be isolated from a lysate of cells genetically modified to express the protein constitutively and/or upon induction, or from a synthetic reaction mixture, by immunoaffinity purification (or precipitation using Protein L or A), washing to remove non-specifically bound material, and eluting the specifically bound antibody. The isolated antibody can be further purified by dialysis and other methods normally employed in protein purification methods. In one embodiment, the antibody may be isolated using metal chelate chromatography methods. Antibodies of the present disclosure may contain modifications to facilitate isolation, as discussed above.

The subject antibodies may be prepared in substantially pure or isolated form (e.g., free from other polypeptides). The protein can present in a composition that is enriched for the polypeptide relative to other components that may be present (e.g., other polypeptides or other host cell components). Purified antibodies may be provided such that the antibody is present in a composition that is substantially free of other expressed proteins, e.g., less than 90%, usually less than 60% and more usually less than 50% of the composition is made up of other expressed proteins.

The antibodies produced by prokaryotic cells may require exposure to chaotropic agents for proper folding. During purification from *E. coli*, for example, the expressed protein can be optionally denatured and then renatured. This can be accomplished, e.g., by solubilizing the bacterially produced antibodies in a chaotropic agent such as guanidine HCl. The antibody is then renatured, either by slow dialysis or by gel filtration. Alternatively, nucleic acid encoding the antibodies may be operably linked to a secretion signal sequence such as pelB so that the antibodies are secreted into the periplasm in correctly-folded form.

The present disclosure also provides cells that produce subject antibodies, where suitable cells include eukaryotic cells, e.g., mammalian cells. The cells can be a hybrid cell or "hybridoma" that is capable of reproducing antibodies in vitro (e.g. monoclonal antibodies, such as IgG). For example, the present disclosure provides a recombinant host cell (also referred to herein as a "genetically modified host cell") that is genetically modified with one or more nucleic acids comprising nucleotide sequence encoding a subject antibody.

Techniques for creating recombinant DNA versions of the antigen-binding regions of antibody molecules which bypass the generation of hybridomas are also contemplated herein. DNA is cloned into a bacterial (e.g., bacteriophage), yeast (e.g. *Saccharomyces* or *Pichia*) insect or mammalian expression system, for example. One example of a suitable technique uses a bacteriophage lambda vector system having a leader sequence that causes the expressed antibody (e.g. Fab or scFv) to migrate to the periplasmic space (between the bacterial cell membrane and the cell wall) or to be secreted. One can rapidly generate a great numbers of functional fragments (e.g. scFv) for those which bind the tumor associated antigen.

Modification

The present disclosure encompasses antibodies and nucleic acids that are modified to provide a desired feature, e.g., to facilitate delivery to a specific type of tissue and/or cells in a subject, to increase serum half-life, to supplement anti-cancer activity, etc. The antibodies of the present disclosure can be provided with or without modification, and include human antibodies humanized antibodies and chimeric antibodies. One way to modify a subject antibody is to conjugate (e.g. link) one or more additional elements at the N- and/or C-terminus or to any amino acid (including an internal amino acid) of the antibody, where such additional elements include, e.g., another protein and/or a drug or carrier molecule.

A subject antibody modified with one or more additional elements retains the desired binding specificity, while exploiting properties of the one or more additional elements to impart an additional desired characteristic. For example, a subject antibody can be conjugated to a second molecule that aids in solubility, storage or other handling properties, cell permeability, half-life, reduction in immunogenicity, controls release and/or distribution such as by targeting a particular cell (e.g., neurons, leucocytes, tumor cells, etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking, imaging, and the like. More specifically, a subject antibody can be conjugated to a second molecule such as a peptide, polypeptide, dye, fluorophore, nucleic acid, carbohydrate, anti-cancer agent, lipid, radionuclide, and the like (e.g., at either the reducing or non-reducing end), such as the attachment of a lipid moiety, including N-fatty acyl groups such as N-lauroyl, N-oleoyl, fatty amines such as dodecyl amine, oleoyl amine, and the like.

For example, for antibodies that can be internalized into cells, the antibody or nucleic acids of the present disclosure may be further modified to increase or decrease the efficiency of delivery into cells. Gene delivery methods are also contemplated herein to deliver nucleic acids that direct expression of proteins (e.g., a subject antibody or other protein) in cells. The efficiency of cellular uptake (e.g. endocytosis) of antibodies can be increased or decreased by linking to peptides or proteins. For example, a given antibody can be linked to a ligand for a target receptor or large molecule that is more easily engulfed by endocytotic mechanisms, such as another antibody, where such an antibody is an "antibody conjugate." The conjugate payload (e.g., a ligand) can also be released by acid hydrolysis or enzymatic activity when the endocytotic vesicle fuses with lysosomes. To modify cellular uptake, the conjugate can include a ligand that retains the antibody on the surface of a cell, which can be useful as a control for (e.g., to decrease) cellular uptake, or in some instances decrease uptake in one cell type while increasing it in others.

Where the antibody is linked to another antibody, the antibody may be bispecific. As noted above, bispecific antibodies refer to antibodies that are specific for two different epitopes that may or may not be of the same antigen.

Other features of a conjugated antibody may include one where the conjugate reduces toxicity relative to unconjugated antibody. Another feature is that the conjugate may target a type of cell or organ (e.g. cancerous cell or cancerous tissue) more efficiently than an unconjugated antibody.

Additional examples include an antibody conjugated with one or more molecules that complement, potentiate, enhance or can otherwise operate synergistically in connection with the antibody. The antibody can have attached an anti-cancer drug, e.g., for delivery to a site of a cancer to further facilitate cell killing or clearance, e.g., an anti-proliferation moiety (e.g., VEGF antagonist, e.g., an anti-VEGF antibody), a toxin (e.g., ricin, *Pseudomonas* exotoxin A, and the like), a radionuclide (e.g. $^{90}Y$, $^{131}I$, $^{177}L$, $^{10}B$ for boron neutron capture, and the like), an anti-cancer agent, and/or an oligonucleotide (e.g. siRNA).

For example, an antibody may be formulated in a lipidic nanoparticle (e.g., a liposome) by covalent or non-covalent modifications. The antibody may be attached to the surface of a lipidic nanoparticle directly via an Fc region, for example. The antibody may also be covalently attached to a terminus of a polymer grafted at or inserted into the surface of a lipidic nanoparticle via a linker. Such conjugated lipidic nanoparticles may be referred to herein as "immunoliposomes". The subject antibodies in an immunoliposome can act as a targeting moiety enabling the immunoliposomes to specifically bind to CD44 and/or EphA2 on the surface of cancer cells. The immunoliposomes can be loaded with one or more of the anti-cancer agents, such as small molecule, peptide, and/or nucleic acid (e.g. siRNAs). Methods of making and loading lipidic nanoparticles, such as liposomes and immunoliposomes, are known in the art, e.g. US 20100068255, US 20100008978, US 20090171077, US 20090155272, US 20070116753, US 20070110798, US 20070031484, US 20060147513, US 20050112065, US 20040037874, US 20040209366, US 20030003143, U.S. Pat. No. 7,135,177, U.S. Pat. No. 7,022,336, U.S. Pat. No. 6,803,053, U.S. Pat. No. 6,528,087, U.S. Pat. No. 6,214,388, U.S. Pat. No. 6,210,707, U.S. Pat. No. 6,110,491, U.S. Pat. No. 5,980,935, U.S. Pat. No. 5,380,531, U.S. Pat. No. 7,507,407, U.S. Pat. No. 7,479,276, and U.S. Pat. No. 7,462,603.

The antibodies of the present disclosure can optionally be modified to provide for improved pharmacokinetic profile (e.g., by PEGylation, hyperglycosylation, and the like). Modifications that can enhance serum half-life are of interest. A subject antibody may be "PEGylated", as containing one or more poly(ethylene glycol) (PEG) moieties. Methods and reagents suitable for PEGylation of a protein are well known in the art and may be found in U.S. Pat. No. 5,849,860. PEG suitable for conjugation to a protein is generally soluble in water at room temperature, and has the general formula $R(O—CH_2—CH_2)_nO—R$, where R is hydrogen or a protective group such as an alkyl or an alkanol group, and where n is an integer from 1 to 1000. Where R is a protective group, it generally has from 1 to 8 carbons.

The PEG conjugated to the subject protein can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Where the subject antibody is to be isolated from a source, the subject protein can be conjugated to moieties the facilitate purification, such as members of specific binding pairs, e.g., biotin (member of biotin-avidin specific binding pair), a lectin, and the like. A subject protein can also be bound to (e.g., immobilized onto) a solid support, including, but not limited to, polystyrene plates or beads, magnetic beads, test strips, membranes, and the like.

Where the antibodies are to be detected in an assay, the subject proteins may also contain a detectable label, e.g., a radioisotope (e.g., $^{125}I$; $^{35}S$, and the like), an enzyme which generates a detectable product (e.g., luciferase, β-galactosidase, horse radish peroxidase, alkaline phosphatase, and the like), a fluorescent protein, a chromogenic protein, dye (e.g., fluorescein isothiocyanate, rhodamine, phycoerythrin, and the like); fluorescence emitting metals, e.g., $^{152}Eu$, or others of the lanthanide series, attached to the protein through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include antibodies specific for a subject protein, wherein the antibody may be detected via a secondary antibody; and members of specific binding pairs, e.g., biotin-avidin, and the like.

Any of the above elements that are used to modify the subject antibody may be linked to the antibody via a linker, e.g. a flexible linker. If present, the linker molecules are generally of sufficient length to permit the antibody and a linked carrier to allow some flexible movement between the antibody and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof.

Where the linkers are peptide, the linkers can be of any of a suitable of different lengths, such as from 1 amino acid (e.g., Gly) to 20 or more amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Flexible linkers include glycine polymers $(G)_n$, glycine-serine polymers (including, for example, $(GS)_n$, $GSGGS_n$ (SEQ ID NO: 83) and $GGGS_n$ (SEQ ID NO: 87), where n is an integer of at least one), glycine-alanine polymers, alanine-serine polymers, and other flexible linkers known in the art. Glycine and glycine-serine polymers may be used where relatively unstructured amino acids are of interest, and may serve as a neutral tether between components. Examples of flexible linkers include, but are not limited GGSG (SEQ ID NO:66), GGSGG (SEQ ID NO:67), GSGSG (SEQ ID NO: 68), GSGGG (SEQ ID NO: 69), GGGSG (SEQ ID NO: 88), GSSSG (SEQ ID NO: 89), and the like. The ordinarily skilled artisan will recognize that design of a peptide conjugated to any elements described above can include linkers that are all or partially flexible, such that the linker can include a flexible linker as well as one or more portions that confer less flexible structure.

Human Engineered Antibody

Where the antibodies of the present disclosure that binds CD44 or EphA2 are not human, the antibodies can be humanized. As used herein, a humanized antibody is a recombinant polypeptide that is derived from a non-human (e.g., rodent) antibody and has been modified to contain at least a portion of the framework and/or constant regions of a human antibody.

Humanized antibodies also encompass chimeric antibodies and CDR-grafted antibodies in which various regions may be derived from different species. Chimeric antibodies may be antibodies that include a variable region from any source linked to a human constant region. Thus, in chimeric antibodies, the variable region can be non-human, and the constant region is human. CDR-grafted antibodies are antibodies that include the CDRs from a non-human "donor" antibody linked to the framework region from a human "recipient" antibody. For example, an antibody of the present disclosure in a form of scFV may be linked to a human constant region (e.g. Fc region) to be made into a human immunoglobulin.

Fc Region

An antibody of the present disclosure that binds CD44 or EphA2 may contain an Fc region. The Fc region may be any of the naturally occurring isoforms found in human or other animals (e.g. derived from any classes or subclasses of immunoglobulins) and can optionally be further modified to have altered function. For example, the Fc region may be modified in one or more amino acid residue position to have increased effector functions, such as initiating cell-mediated cytotoxicity or activating complement activity (e.g. C1q binding or complement dependent cytotoxicity), downregulating cell-surface receptor, etc. Details of Fc variants that may be used as antibodies of the present disclosure may be found in, for example, U.S. Pat. No. 7,416,727, U.S. Pat. No. 7,371,826, U.S. Pat. No. 7,335,742, U.S. Pat. No. 7,355,008, U.S. Pat. No. 7,521,542, and U.S. Pat. No. 7,632,497.

Compositions

The subject compositions provide antibodies and/or nucleic acid encoding thereof, in which the antibodies bind to and are internalized by cancer cells. The compositions of the present disclosure find use in treating a subject (e.g., a human) containing cancer, and may be suitable for treatment during any stage of the disease. Compositions containing one, two, or more different antibodies can be provided as a pharmaceutical composition and administered to a mammal (e.g., to a human) in need thereof.

Compositions contemplated herein may contain one, two, three, or more different antibodies of the present disclosure (and/or nucleic acids encoding thereof). For example, the composition can contain one or more of the following: F2-1A6, F2-1H9, E8H11, E8H7, E8G12, E8F11, E8C9, D6G9, D6D3, D1C5, D1D1, HB8, HC2, HC4, HE3, HF1, HH3, 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11. The composition may optionally further include antibodies containing one or more CDRs from these antibodies, and/or one or more antibodies containing mutants or derivatives of these antibodies.

An example of a composition of the present disclosure may include any of the combinations described above or one or more of the antibodies disclosed in FIG. 7, 8, or 9, or FIGS. 44-47. Where the composition contains two or more antibodies, each antibody can be specific to the same or different epitopes or to epitopes on different antigens. For example, the composition may contain at least one antibody specific for the epitope of CD44 or EphA2 and another antibody specific for another cell-surface antigen, such as EGFR. The composition may also contain dual-specific, polyspecific antibodies, or nucleic acids encoding thereof.

The antibodies of the present disclosure can be used individually, and/or in combination with each other (e.g. to form bispecific or polyspecific antibodies), and/or in combination with other known anti-cancer agents (e.g. antibodies for cancer treatment). For example, a composition, such as a liposome, can comprise two or more antibodies, in which at least one of the antibodies is an antibody of the present disclosure. As described above, the liposome may contain one or more antibodies that are different than the subject antibodies. Such liposome may be dual-specific, polyspecific, etc, so that the liposome is specific for an additional epitope (e.g. an epitope in EGFR or HER2) in addition to the epitope of the subject antibody.

Combinations can be provided in a single formulation or can be provided as separate formulations in a kit, where the separate formulations may contain a single antibody or two antibodies. Such separate formulations of a kit may be combined prior to administration or administered by separate injection.

A subject pharmaceutical composition can be provided in a pharmaceutically acceptable excipient, which can be a solution such as an aqueous solution, e.g., a saline solution, or can be provided in powder form. A subject composition may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

A subject antibody, e.g., in the form of a pharmaceutically acceptable salt, can be formulated for oral, topical or parenteral administration for use in the methods described later below. In certain embodiments, e.g., where an antibody is administered as a liquid injectable, e.g., suitable for intravenous injection) an antibody formulation may be a sterile, non-pyrogenic aqueous solution comprising salts (e.g., to adjust tonicity) buffers, preservatives, amino acids, and other pharmaceutically acceptable carriers and excipients, and may be provided as a ready-to-use dosage form, or as a reconstitutable storage-stable powder or liquid composed of pharmaceutically acceptable carriers and excipients. Formulation for convection enhanced delivery may be as described in, e.g., US 20090208422.

Compositions of the present disclosure can include a therapeutically effective amount of a subject antibody, as well as any other compatible components, as needed. By "therapeutically effective amount" is meant that the administration of that amount to an individual, either in a single dose, as part of a series of the same or different antibody or compositions, is effective to reduce the proliferation and/or metastases of a cancerous cell in a subject or to provide any other detectable therapeutic benefit. Such therapeutically effective amount of an antibody and its impact on cell growth includes cooperative and/or synergistic inhibition of cell growth in conjunction with one or more other therapies (e.g., immunotherapy, chemotherapy, radiation therapy etc.). As noted below, the therapeutically effective amount can be adjusted in connection with dosing regimen and diagnostic analysis of the subject's condition (e.g., monitoring for the presence or absence of a cell surface epitopes using an antibody specific for CD44 and/or EphA2) and the like.

Amount and Dosage

The exact dose will be ascertainable by one skilled in the art. The dosage can depend on a variety of factors including the strength of the particular compound employed, the condition of the subject, and the body weight of the subject, as well as the severity of the illness and the stage of the disease. The size of the dose will also be determined by the existence, nature, and extent of any adverse side-effects that might accompany the administration of a particular compound. As known in the art, adjustments based on age, body weight, sex, diet, time of administration, drug interaction and severity of condition may be necessary and will be ascertainable with routine experimentation by those skilled in the art. A therapeutically effective amount is also one in which the therapeutically beneficial effects outweigh any toxic or detrimental effects of the antibody or antibody fragment.

The amount of composition administered to a subject, e.g., a human, in the context of the present disclosure should be sufficient to effect a prophylactic or therapeutic response in the animal over a reasonable time frame, and varies depending upon the goal of the administration, the health and physical condition of the individual to be treated, age, the degree of resolution desired, the formulation of the antibody composition, the treating clinician's assessment of the medical situation, and other relevant factors. Thus it is expected that the amount will fall in a relatively broad range, but can nevertheless be routinely determined through various features of the subject such as note above.

As an example, a non-limiting range for a therapeutically or prophylactically effective amount of a subject antibody is from about 0.1 mg/kg to about 20 mg/kg, e.g., from about 1 mg/kg to about 10 mg/kg.

The concentration of an antibody in a pharmaceutical formulations can vary from less than about 0.1%, usually at or at least about 2% to as much as 20% to 50% or more by weight, and will be selected primarily by consideration of fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

Also, suitable doses and dosage regimens can be determined by comparisons to anticancer or immunosuppressive agents that are known to affect the desired growth inhibitory or immunosuppressive response. Such dosages include dosages which result in the low dose inhibition of cell growth, without significant side effects. In proper doses and with suitable administration of certain compounds, the compounds of the present disclosure can provide for a wide range of intracellular effects, e.g., from partial inhibition to essentially complete inhibition of cell growth. Dosage treatment may be a single dose schedule or a multiple dose schedule (e.g., including ramp and maintenance doses). As indicated below, a subject composition may be administered in conjunction with other agents, and thus doses and regiments can vary in this context as well to suit the needs of the subject.

Combination Therapy

Any of a wide variety of cancer therapies can be combined in a composition with a subject antibody. For example, agents used in chemotherapeutic treatment or biological response modifier treatment may be present in the pharmaceutical composition comprising the antibody, such as an immunoliposome. Certain agents that can be used in combination with the subject antibodies are briefly discussed below.

Chemotherapeutic agents are non-proteinaceous compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (e.g., vinca) alkaloids, nucleic acids, such as inhibitory nucleic acids (e.g. siRNA), and steroid hormones.

Antimetabolite agents include folic acid analogs, pyrimidine analogs, purine analogs, and adenosine deaminase inhibitors, for example.

Suitable natural products and their derivatives, (e.g., vinca alkaloids, antitumor antibiotics, enzymes, lymphokines, and epipodophyllotoxins) can be used as anti-cancer agents. For example, taxanes, such as paclitaxel, as well as any active taxane derivative such as docetaxel, or a taxane pro-drug such as is 2'-(2-(N,N'-diethylamino)propionyl)-paclitaxel, 7-(2-(N,N'-diethylamino)propionyl)-paclitaxel, 2'-(2-(N,N'-diethylamino)propionyl)-docetaxel or 7-(2-(N,N'-diethylamino)propionyl)-docetaxel, are suitable.

Other anti-proliferative cytotoxic agents are navelbene, CPT-11 (irinotecan), anastrazole, letrazole, capecitabine, reloxafine, cyclophosphamide, ifosamide, and droloxafine. Microtubule affecting agents that have antiproliferative activity are also suitable for use. Hormone modulators and steroids (including synthetic analogs) are suitable for use.

Diagnostic Methods

The present disclosure provides a method of detecting a tumor associated antigen (e.g. CD44 or EphA2) in a biological sample in a subject or in a sample isolated from a subject. The methods are useful to both diagnostic and prognostic purposes. A subject method generally involves contacting a sample containing a cell with an antibody of the present disclosure; and detecting binding of the antibody to a cell in the sample. The cell can be in vitro, where the cell is in a biological sample obtained from a subject suspected for having cancer cells, a subject undergoing cancer treatment, or a subject being tested for susceptibility to treatment. The cell can be in vivo, e.g., the cell is in a subject suspected for having cancer cells, a subject undergoing treatment, or a subject being tested for susceptibility to treatment.

Antibodies can be used to detect cells expressing CD44 and/or EphA2 in a biological sample of a subject having or suspected of having cancerous cells via immunodiagnostic techniques. Such diagnostics can be useful to identify patients amenable to the therapies disclosed later below, and/or to monitor response to therapy.

Suitable immunodiagnostic techniques include, but are not necessarily limited to, both in vitro and in vivo (imaging) methods. For example, anti-CD44 or anti-EphA2 antibodies can be detectably labeled, administered to a subject suspected of having a cancer characterized by cell surface expression of CD44 or EphA2, and bound detectably labeled antibody detected using imaging methods available in the art.

The phrase "in vivo imaging" as used herein refers to methods of detecting the presence of an antibody (e.g. detectably labeled 2D6) in whole, live mammal. Optically detectable proteins such as fluorescent antibodies and luciferases-conjugated antibodies may be detected by in vivo imaging. Methods for using luciferases for real-time imaging of luciferase expression in live animals can be readily adapted for use in the subject methods disclosed herein (e.g., Greer L F et al., *Luminescence* 2002, 17: 43-74). In vivo imaging of fluorescent proteins in live animals is described in, e.g., Hoffman, *Cell Death and Differentiation* 2002, 9:786-789. In vivo imaging may be used to provide 2-D as well as 3-D images of a mammal. Radiolabeled antibodies, for example, may be administered to a subject and the subject imaged with a gamma camera. Charge-coupled device cameras, CMOS, or 3D tomographers may used to carry out in vivo imaging. For example, Burdette J E *Journal of Mol. Endocrin.*, 40: 253-261, 2008, reviews utilizing computed tomography, magnetic resonance imaging, ultrasonography, positron emission tomography, single-photon emission computed tomography (SPECT), etc. The information from many in vivo imaging methods as those described above can provide information on cancer cells in the subject.

Where the methods are in vitro, the biological sample can be any sample in which a cancer cell may be present, including but not limited to, blood samples (including whole blood, serum, etc.), tissues, whole cells (e.g., intact cells), and tissue or cell extracts. For example, the assay can involve detection of CD44 and/or EphA2 on live cells or cells in a histological tissue sample. Particularly, detection can be assessed on an extracellular surface of a living cell. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Examples of assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detectable labels conjugated to the antibody. Labels include those that are fluorescent, chemiluminescent, radioactive, enzymatic and/or dye molecules, or other methods for detecting the formation of a complex between antigen in the sample and the antibody or antibodies reacted therewith.

Where a solid support is used, the solid support is usually first reacted with a solid phase component under suitable binding conditions such that the antibody is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies to a support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antibodies, are well known to those of ordinary skill in the art.

An ELISA method can be used, wherein the wells of a microtiter plate are coated with a subject antibody. A biological sample containing or suspected of containing CD44 and/or EphA2, is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound CD44 and/or EphA2 from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and the antigens form complexes under precipitating conditions. An antibody-coated particle can be contacted under suitable binding conditions with a biological sample suspected of containing the target antigen to provide for formation of particle-antibody-antigen complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

Alternatively, assays for cellular uptake in live cells can be another diagnostic technique to positively identify cancerous cells. Since the subject antibodies are specifically internalized by cells expressing CD44 and/or EphA2, the cells can be allowed for internalization of the antibodies and any antibodies that are not internalized be washed away (e.g. acid wash). The internalized antibodies may be detected via its label as contained with the cells (e.g. FACS, spectrometer, radioisotope counter, etc.). Internalizing antibodies may also be selected for as described in U.S. Pat. No. 7,045,283.

The diagnostic assays described herein can be used to determine whether a subject has a cancer that is more or less amenable to therapy using antibody-based therapy, as well as monitor the progress of treatment in a subject. It also may be used to assess the course of other combination therapies. Thus, the diagnostic assays can inform selection of therapy and treatment regimen by a clinician.

The above-described assay reagents, including the antibodies of the present disclosure, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Therapeutic Methods

A subject antibody finds therapeutic use in a variety of cancers. Subjects having, suspected of having, or at risk of developing cancer are contemplated for therapy and diagnosis described herein.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells (e.g. metastatic cancer cells); and/or (iii) relief, that is, causing the regression of clinical symptoms.

A variety of subjects are treatable according to the methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

In a related embodiment, the subject being treated possesses cells that express (e.g. overexpresses) a tumor associated antigen, CD44 and/or EphA2. The antigen is expressed on the cancer cell surface and is often present at a higher level than a corresponding non-cancerous cell. This aspect can be beneficial in the context of the methods of the present disclosure in that cells expressing or presenting CD44 and/or EphA2 can be amenable to treatment with an antibody of the present disclosure. The antibody can be administered to a subject, for example, where therapy is initiated at a point where presence of the antigen is not detectable, and thus is not intended to be limiting. It is also possible to initiate antibody therapy prior to the first sign of disease symptoms, at the first sign of possible disease, or prior to or after diagnosis of a disease.

Prodrugs of the antibody composition of the present disclosure are also contemplated in the methods described herein. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003).

Cancer

The antibody compositions may be advantageously used in an anti-cancer therapy, particularly where the cancerous cells present EphA2 and/or CD44 on an extracellularly accessible cell surface. One example is a cancer that presents an epitope bound by F2-1A6, F2-1H9, E8H11, E8H7, E8G12, E8F11, E8C9, D6G9, D6D3, D1C5, D1D1, HB8, HC2, HC4, HE3, HF1, HH3, 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11.

Antibody compositions described herein can be administered to a subject (e.g. a human patient) to reduce proliferation of cancerous cells, e.g., to reduce tumor size, reduce cancer load, reduce metastasis, and/or improve the clinical outcome in patients. For example, antibody compositions can be used to disrupt the cell cycle of the cancer cell, and facilitate entry of the cell into apoptosis. The methods relating to cancer contemplated herein include, for example, use of antibody therapy alone or in combination with anti-cancer vaccine or therapy.

Cancers particularly amenable to antibody therapy can be identified by methods similar to the diagnostic methods described above and others known in the art.

Types of Cancer

Where the anti-cancer therapy comprises administration of an antibody composition described previously, the anti-cancer therapy can be particularly directed to cancerous cells expressing cell-surface accessible and/or solvent-exposed epitopes bound by the subject antibodies, including metastatic cancer.

Examples of cancers presenting epitopes of CD44 that can be treated by the subject methods include cancers of the breast (e.g. basal cell breast cancer), colon, prostate, pancreas, etc. as well as adenoma and head and neck squamous cell carcinoma (HNSCC). Other cancers amenable to treatment can also be any cancer that is metastic and/or has metastatic potential.

Examples of cancers presenting epitopes of EphA2 include but not limited to cancer cells of epithelial origin. For example, the cancer cells can be derived from breast (e.g. basal cell breast cancer), skin (e.g. melanoma), lung, prostate, colon, and/or ovary. Other cancers cells for which anti-EphA2 antibodies have affinity may be liver cancer, esophageal squamous cell carcinoma, epidermoid cancer, pancreatic cancer, glioblastoma, neuroblastomas, and/or other neural cancers, for example.

It should be noted that while EphA2 or CD44 may be expressed at higher levels on a cancer cell compared to a non-cancerous cell, this is not a limitation of the therapies disclosed herein.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Other examples of cancers that can be amenable to treatment using a methods disclosed herein include, but are not limited to, cancers of epithelial and neuroectodermal origin. Examples of epithelial origin include, but are not limited to, small cell lung cancer, cancers of the breast, eye lens, colon, pancreas, kidney, liver, ovary, and bronchial epithelium. The methods of the present disclosure may be used to treat cancer cells known to overexpress CD44 and/or EphA2.

Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults.

Combinations with Other Cancer Therapies

As noted above, another feature of the methods is that an antibody can be administered to the subject in combination with one or more other therapies. Such therapy may be combined in a composition or be conjugated to the subject antibodies. In addition to being physically combined with antibodies disclosed herein (e.g, as a conjugate or in a liposome or other lipidic nanoparticle), one or more anti-cancer agents, may be administered in conjunction with, either simultaneously or before or after, administration of an antibody disclosed herein.

A therapy or treatment other than administration of antibody composition can be administered anywhere from simultaneously, to up to 5 hours or more, e.g., 10 hours, 15 hours, 20 hours or more, prior to or after administration of a subject antibody. A subject antibody and other therapeutic intervention are administered or applied sequentially, e.g., where a subject antibody is administered before or after another therapeutic treatment. A subject antibody and other therapy are administered simultaneously, e.g., where a subject antibody and a second therapy are administered at the same time, e.g., when the second therapy is a drug it can be administered along with a subject antibody as two separate formulations or combined into a single composition that is administered to the subject. Regardless of whether administered sequentially or simultaneously, as illustrated above, the treatments are considered to be administered together or in combination for purposes of the present disclosure.

Additional standard anti-cancer therapeutics that may or may not be administered in conjunction with a subject antibody, include but not limited to immunotherapy, chemotherapeutic agents and surgery (e.g., as those described further below). In addition, therapeutic administration of a subject antibody can also be post-therapeutic treatment of the subject with an anti-cancer therapy, where the anti-cancer therapy can be, for example, surgery, radiation therapy, administration of chemotherapeutic agents, and the like. Antibodies other than those disclosed herein, particularly monoclonal antibodies that can provide for complement-mediated killing, and/or antibody-dependent cellular cytotoxicity-mediated killing, of a target cell may also be used.

For example, a subject antibody can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor), radiation therapy, bone marrow transplantation, biological response modifier treatment, and certain combinations of the foregoing. Radiation therapy includes, but is not limited to, X-rays or gamma rays that are delivered from either an externally applied source such as a beam, or by implantation of small radioactive sources.

Routes of Administration

In practicing the methods, routes of administration (path by which a subject antibody is brought into a subject) may vary, where representative routes of administration for a subject antibody are described in greater detail below. A subject antibody alone or in combinations described above can be administered systemically (e.g., by parenteral, intravenous, intramuscular, intrathecal, intraventricular, or subcutaneous administration) or locally (e.g., at a local tumor site, e.g., by intratumoral administration (e.g., into a solid tumor, into an involved lymph node in a lymphoma or leukemia, or by convection enhanced delivery, e.g. into the brain, e.g., as disclosed in US 20090209937), administration into a blood vessel supplying a solid tumor, etc.), into a body cavity or lumen, or into an organ. These different routes of administration may be carried out by injection or infusion.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Methods for preparing parenterally administrable compositions will be known or apparent to those skilled in the art and are described in more detail in such publications as *Remington's Pharmaceutical Science*, 15th ed., Mack Publishing Company, Easton, Pa. (1980).

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for topical administration may be presented as transdermal compositions or transdermal delivery devices ("patches"), creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing the antibody compositions. Similarly, unit dosage forms for injection or intravenous administration may comprise the antibody in a composition as a solution in sterile water, normal saline or another pharmaceutically acceptable carrier.

Administration of the therapy can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The antibody can also be administered as part of a combination therapy, in which at least one of an immunotherapy, a cancer chemotherapy or a radiation therapy is administered to the subject (as described in greater detail above).

Screening Methods

The present disclosure also provides methods to screen for antibodies specific for antigens expressed on the cell surface (e.g. tumor associated antigens), as well as for internalization into mammalian cells upon binding to cell surface antigen. Some such methods are well known, see, e.g., U.S. Pat. No. 6,794,128 and U.S. Pat. No. 7,045,283. In one embodiment, methods are disclosed for screening antibody libraries (e.g., phage display libraries) for antibodies that bind to particular antigen(s) and are internalized into cells upon antigen binding. The antibody may be selected for its binding to a TAA (e.g. CD44 and/or EphA2) of interest and/or to a cancer cell, for example. The methods comprise initial internalizing antibody selection by several iterated rounds of library screening comprising selection for internalization on at least one mammalian cell line. Next, the collection of phage that express internalizing antibodies was selected against one or more antigen(s) (e.g., yeast displayed antigen, e.g., antigen known to be associated with a mammalian cell type) to isolate phage displaying antibodies against the desired antigen(s). The method may be executed according to the phage display, yeast display, and internalization selection methods described in the examples below.

Briefly, non-immune human scFv phage library is optionally depleted with control cells that do not express (e.g., do not appreciably express) the antigen(s) to be selected against to get rid of antibodies that may be nonspecifically interacting with cancer cells. The optionally depleted library is incubated with the live cancer cells of interest. The cancer cells may be derived from a known source or an unknown source. The cancer cells can also be derived exclusively from one cell line or one tumor or from a plurality of different cell lines or a plurality of different tumors. The process selects for antibodies that are internalized into cells by allowing the cells to endocytose the antibodies and stripping the cells of surface bound antibodies before proceeding to recover the phage from the cells. During panning and selection, the internalized phage are recovered from cell lysates and amplified. Multiple successive selection rounds (e.g. two or more) ensure selection of phage displaying a polypeptide that acts as a specific internalizing antibody for the cancer of interest.

Optionally before incubation with the yeast library, the selected phage may be depleted with control yeasts (e.g. yeasts that are not expressing an antigen of interest and/or expressing an irrelevant protein). The phage previously selected for cancer cell internalization are then incubated with yeast displaying one or more TAAs of interest (e.g. an extracellular domain of EphA2). The yeast incubated with the phage for further selection can express a plurality of TAAs, each being a different peptide fragment of the same full-length protein and/or each derived from different TAA. Where the yeast display a plurality of TAA, the antibodies specific for different TAA may be selected in parallel. The TAA may also encompass known tumor associated antigen and/or antigen whose cancer association is yet to be verified (e.g. suspected of being associated with cancer). After incubation, the phage bound to yeast displaying TAA of interest is eluted. Multiple successive rounds (e.g. two or more) may be carried out against the yeast library.

The stringency of the selection against yeast library can increase over each successive round (e.g. two or more). Many techniques well known in the art may be employed to increase the specificity of the recovered phage. Examples include increased wash times, increased detergent concentrations, increased salt concentrations, and inclusion of known macromolecular inhibitors (e.g. BPTI, Ecotin, and/or previously identified antibody inhibitors). Characterization of antibodies may include ELISAs and inhibition assays. Details on the assays to be performed in the method for selecting and isolating a polypeptide that can act as an anti-TAA agent are known in the art.

Compared to the use of phage to display antigens, the use of a simple eukaryote such as yeast for antigen display can result in a greater proportion of antigens being displayed in their proper conformation.

Kits and Systems

Also provided are kits and systems that find use in practicing the methods, as described above. For example, kits and systems may include one or more of the compositions described herein, such as an anti-CD44 and/or anti-EphA2 antibody (e.g. 2D6, D2-1A7, D2-1A9, D2-1B1, A3H9, A3G3, A3D10, A3D1, A3C8, 1A3, 1A5, 1A8, 1A12, 1B2, 1C2, 1C7, 1D8, or 15H11; or F2-1A6, F2-1H9, E8H11, E8H7, E8G12, E8F11, E8C9, D6G9, D6D3, D1C5, D1D1, HB8, HC2, HC4, HE3, HF1, or HH3), a nucleic acid encoding the same (especially a nucleic acid encoding a CDR of a heavy and/or light chain of any subject antibodies described above), or a cell containing the same. Other optional components of the kit include: buffers, etc., for administering the subject antibody, and/or for performing a diagnostic assay. The recombinant nucleic acids of the kit may also have restrictions sites, multiple cloning sites, primer sites, etc to facilitate their ligation to constant regions of nucleic acids. The various components of the kit may be present in separate containers or certain compatible components may be precombined into a single container, as desired.

The kits and systems for practicing the methods may include one or more pharmaceutical formulations that include the antibody compositions described herein. As such, the kits may include a single pharmaceutical composition present as one or more unit dosages. The kits may also include two or more separate pharmaceutical compositions.

In addition to the above components, the kits may further include instructions for practicing the methods. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

A kit may be provided for use in treating a host suffering from a cellular proliferative disease. This kit includes a pharmaceutical composition comprising antibody specific for EphA2 or CD44, and instructions for the effective use of the pharmaceutical composition in a method of treating a host suffering from a cancerous condition by inhibiting the growth of a cancer cell in a subject. Such instructions may include not only the appropriate handling properties, dosing regiment and method of administration, and the like, but can further include instructions to optionally screen the subject for a CD44- and/or EphA2-associated disease. This aspect can assist the practitioner of the kit in gauging the potential responsiveness of the subject to treatment with an antibody of the present disclosure, including timing and duration of treatment relative to the type and growth stage of the cancer. Thus in another embodiment, the kit may further include an antibody or other reagent for detecting an epitope of EphA2 or CD44 on an extracellularly accessible surface of a cancer cell. In another embodiment, the kit includes antibody that comprises a conjugate with a detectable label, such as a fluorophore.

The term "system" as employed herein refers to a collection of antibodies described herein and one or more second therapeutic agents, present in single or disparate compositions that are brought together for the purpose of practicing the methods. For example, separately obtained antibody specific to a TAA and chemotherapy dosage forms brought together and coadministered to a subject are a system according to the present disclosure.

EXAMPLES

The following examples are offered to illustrate, but not to limit any embodiments provided by the present disclosure.

The following methods and materials were used in the present example.

Methods and Materials

Cell Lines, Media, Antibodies and Full-Length cDNA Clones.

Breast cancer cell lines MCF7, T47D, MDAMB453, MDAMB231, human mammary epithelial cell (HMEC), and SUM52PE were obtained from the ATCC and Clontech (HMEC), or from collections developed in the laboratories of Dr. Steve Ethier (SUM52PE). The cell lines were cultured using conditions described previously (Neve R M et al. (2006) *Cancer Cell* 10:515-27). Yeast strain EBY100 was grown in YPD medium (*Current Protocols in Molecular Biology*, John Wiley and Sons, Chapter 13.1.2). EBY100 transfected with expression vector pYD2 (Razai A et al. (2005) *J Mol Biol* 351:158-69) was selected on SD-CAA medium (*Current Protocols, Chapter* 13). The Aga2p antigen fusion was expressed on the yeast surface by induction in SG-CAA medium (identical to SD-CAA medium except the glucose is replaced by galactose) at 20° C. for 24-48 hr as described previously (Feldhaus M J et al. (2003) *Nat Biotechnol* 21:163-70). Bacteria strain *E. coli* DH5α and TG1 were used for the preparation of plasmid DNA and the expression of soluble scFv antibodies respectively. SV5 antibody was purified from hybridoma supernatant using Protein G and directly labeled with ALEXA FLUOR® 488 or ALEXA FLUOR® 647 using a kit provided by the manufacturer (Invitrogen; Carlsbad, Calif.). Biotin conjugated rabbit anti-fd bacteriophage was purchased from Sigma and used to detect phage antibodies. Monoclonal antibody D7 against EphA2 ECD was purchased from Upstate Biotech, polyclonal goat anti-EphA2 and recombinant mouse Ephrin A1 with human Fc fusion protein from R&D Systems, anti-CD44 antibody for Western Blotting from NeoMarkers, and monoclonal anti-CD44 recognizing link domain from Abcam. The full-length cDNA of EphA2 and CD44 was obtained from the ATCC.

The phage library used in the examples below contains non-immune human single-chain Fv antibodies (scFv). Briefly, the library was generated by first constructing a cDNA library from RNAs of human spleen cells and peripheral blood lymphocytes. Heavy chain and light chain repertoires were joined to form the scFV gene repertoire. The single chain Fv (scFv) gene repertoire from a naïve phagemid antibody library was subcloned into a true phage vector to create a multivalently displayed scFv phage library. For details, see Sheets M D et al. (1998) *Proc Natl Acad Sci USA* 95:6157-62 and O'Connell D et al. (2002) *J Mol Biol* 321:49-56.

Antigen and Antigen Domains Displayed on the Yeast Surface.

Primers annealing to antigen cDNA and having a 25-mer overlapping sequence with pYD2/NcoI-NotI-digested vector were designed to amplify antigen domains by PCR using Pfu polymerase. After gel purification, the amplified antigen fragment and NcoI-NotI digested pYD2 vector were used to transform LiAc-treated EBY100 cells by gap repair (Gietz R D et al. (1991) *Yeast* 7:253-63; Orr-Weaver T L et al. (1983) *Proc Natl Acad Sci USA* 80:4417-21). The transformation mixes were cultured and subcultured in SD-CAA, and induced by culturing in SG-CAA medium for 24-48 hours at 18° C. To validate antigen display, anti-EphA2 (R&D) and recombinant mouse Ephrin A1 (R&D) were analyzed for binding to yeast displayed EphA2 ECD, and anti-CD44 antibody (Abcam) was analyzed for binding to CD44 domain 1 by flow cytometry. Briefly, the induced yeast cells ($10^6$ cells) with specific displayed antigen domains were incubated with monoclonal or polyclonal antibodies (1 μg/ml) for 1 h at 4° C., detected using anti-goat PE conjugate for anti-EphA2, anti-human (Fc specific) for rEphrinA1-human Fc fusion protein, and anti-rabbit PE for anti-CD44 respectively, and co-stained with SV5-ALEXA FLUOR® 647 dye.

Optimization of Elution Buffer for Phage Antibody Selection.

Different elution buffer including phosphate buffered saline, pH 7.4 (PBS), 40 mM 2-mercaptoethylamine (2-MEA), 1 mM dithiolthreitol (DTT), 100 mM triethylamine (TEA) and 100 mM Glycine/150 mM NaCl/0.1% BSA/0.5% polysorbate 20/TWEEN® 20 were evaluated for their ability to elute bound phage form the yeast surface. The elution time was 1 hour at 37° C. for PBS, 2-MEA and DTT, and 2 minutes at RT for TEA and glycine. After neutralizing with 10 mM cysteine for 2-MEA and DTT elution, and ½ volume of 1M Tris-HCl (pH 7.4) for TEA and glycine elutions, the eluted mixture was used to infect exponentially growing *E. coli* TG1 cells, and the titer of phage determined by serial dilution and plating on tetracycline resistant media.

Selection of Phage Antibodies Specific to Yeast Displayed Antigen Domains.

Human mammary epithelial cell (HMEC), luminal breast cancer cell line SUM52PE, T47D, and MDAMB453 were used to deplete the phage library of nonspecific binders by incubating $10^{12}$ phage particles (Sheets M D et al. (1998) *Proc Natl Acad Sci USA* 95:6157-62; Huie M A et al. (2001) *Proc Natl Acad Sci USA* 98: 2682-7) with $10^8$ cells for 4 h at 4° C. The depleted phage library was then incubated with $5\times10^6$ basal breast cancer cell line MDAMB231 cells for 1 h at 4° C., followed by washing with cold PBS and incubation with 37° C.-prewarmed medium/10% FBS for 30 mM at 37° C. to enable the receptor mediated endocytosis of phage particles. The cell surface was stripped by three incubations of five minutes with 4 ml of glycine buffer (150 mM NaCl, 0.1 M glycine, pH 2.5). The cells were then trypsinized, washed with PBS, lysed with 1 ml of 100 mM TEA for four minutes at 4° C. and neutralized with 0.5 ml of 1M Tris (pH 7.4). Internalized phage (TEA lysate) was amplified for further selections.

After two rounds of selection on MDAMB231 cells, the polyclonal phage antibodies were used to select phage antibodies specific to yeast displayed antigens EphA2 (Y-EphA2) and CD44 link domain (Y-CD44 D1). The induced yeast cells displaying an irrelevant protein were used to deplete the non-specific binders by incubating $2.5\times10^{11}$ phage particles with $10^9$ yeast cells for 2 h at 4° C. The filtered supernatant containing the depleted phage library was then incubated with $2\times10^7$ yeast-cells displaying specific antigen domain for 1 h at 4° C. Yeast cells were washed with cold PBS ten times and pelleted by centrifugation. The bound phage antibodies were eluted by incubating yeast cells with 1 ml of 100 mM Glycine/150 mM NaCl/0.1% BSA/0.5% polysorbate 20/TWEEN® 20, neutralized with 0.5 ml of 1M Tris-HCl (pH 7.4), and amplified for another round of selection. In the second round of selection, $2\times10^7$ yeast cells were used for both antigens, while $2.1\times10^{12}$ phage particles from the first round selection were used for CD44 domain 1 compared to $3.4\times10^{11}$ used for EphA2. Two rounds of selection were performed.

Characterization of Phage Antibodies.

After two rounds of selection, individual phage antibodies were prepared by growing single colonies in 96-well microtiter plates as described (O'Connell D et al. (2002) *J Mol Biol* 321:49-56). Binding of each phage antibody to yeast displayed antigen was determined by incubation of $10^5$ yeast cells with 100 μl phage supernatant diluted in FACS buffer (PBS with 1 mM $MgCl_2$, 0.1 mM $CaCl_2$ and 0.3% BSA) for 2 h at 4° C. in conical 96-well microtiter plates, followed by incubation with biotinylated anti-fd antibody and streptavidin-phycoerythrin conjugate (PE) (Jackson), and analyzed using a FACS LSRII (Becton Dickinson). The number of unique phage antibodies was determined by patterns of BstNI digestion of 18 scFv genes amplified by PCR from phage-infected bacteria (Marks, J D et al. (1991) *J Mol Biol* 222:581-97) and confirmed by DNA sequencing.

For binding to breast cancer cells and Ephrin A1 competition experiments, $5\times10^4$ MDAMB231 cells were incubated with $10^8$ phage antibodies in the presence of recombinant mouse Ephrin A1 (R&D) at concentration of 0 to 1000 ng/ml for 2 h at 4° C. The bound phage antibodies were detected by incubating cells with biotin conjugated anti-fd antibody (1 μg/ml) (Sigma) for 30 min at 4° C. and streptavidin-PE (Jackson) followed by flow cytometry analysis.

Immunoprecipitation and Western Blot Using scFv Antibodies.

MDAMB231 cell extracts were prepared using 1 ml of lysis buffer per T75 culture flask, containing 0.5% NP40, 50 mM Tris (pH 7.4), 150 mM NaCl, 2 mM DTT, and protease inhibitor cocktail (Sigma). Soluble scFv antibodies with a $(His)_6$ tag at the C-terminal were generated by subcloning scFv genes from the phage vector into the expression vector pUC119mycHis (Schier R et al. (1995) *Immunotechnology* 1:73-81), followed by purification from the periplasmic fraction of *E. coli* TG1 by IMAC[51] using a Ni-NTA column (Qiagen) and gel filtration (Schier R et al. (1996) *J Mol Biol* 255:28-43). Cell extracts were incubated with scFv at 26 μg/ml for 2 h at 4° C. before the immune complexes were captured on Ni-NTA agarose. The agarose captured immune complexes were then washed 5 times in lysis buffer and heated to 94° C. for 4 min in non-reducing protein loading buffer. Immunoprecipitates were resolved by SDS-PAGE and analyzed by Western Blotting using anti-EphA2 (Upstate) and anti-CD44 (NeoMarkers) antibodies.

Immunofluorescence.

MDAMB231 cells were grown on coverslips to 70% of confluence in 12 well-plates and incubated with $10^{11}$ phage antibodies for three hours at 37° C. The coverslips were washed once with PBS, three times for five minutes with glycine buffer (50 mM glycine (pH 2.5), 150 mM NaCl), neutralized with PEM (80 mM Potassium PIPES (pH 6.8), 5 mM EGTA (pH 7), 2 mM $MgCl_2$), and fixed with PEM containing 4% (W/V) paraformaldehyde for 30 min on ice. Cells were quenched with 0.1 M $NH_4Cl$, permeabilized with 0.5% 4-octylphenol polyethoxylate/TRITON™ X-100, and blocked with 5% non-fat dry milk in TBS-T buffer overnight at 4° C. After blocking endogenous biotin with Avidin-Biotin Kit (Lab Vision), intracellular phages were detected with biotinylated anti-fd polyclonal antibody (Sigma) and streptavidin TEXAS RED® (sulforhodamine 101 acid chloride) dye (Amersham). Coverslips were inverted on a slide on mounting medium and microscopic images were taken with a Zeiss LSM 510 laser scanning microscope (Zeiss, Germany).

Example 1

Display of Tumor Associated Antigens on the Surface of Yeast

Two TAA (CD44 and EphA2) are overexpressed in basal breast cancers (Hamilton S R et al. (2007) *J Biol Chem* 282:16667-80) and were selected for display on the surface of *Sachromyces cerevisiae*. For yeast surface display, the full-length extracellular domain (ECD) of EphA2 (aa 1-510) and the link domain of CD44 (aa 1-149) (domain 1) were cloned into the yeast display vector pYD2 for (C-terminal) fusion to Aga2 (Razai A et al. (2005) *J Mol Biol* 351:158-69). Vector DNA was used to transform EBY100, and cell surface display was induced. Both extracellular domains of CD44 and EphA2 were well displayed on the yeast surface as quantitated by a monoclonal antibody to a C-terminal epitope tag (FIG. 1). Specific binding to yeast displayed EphA2 and CD44 extracellular domains of the EphA2 natural ligand Ephrin A1, and antibodies to EphA2 and CD44 suggests that the domains are not only displayed but displayed in a form that can bind to ligand and can be specifically recognized by antibodies (FIG. 1).

Example 2

Figure 2:
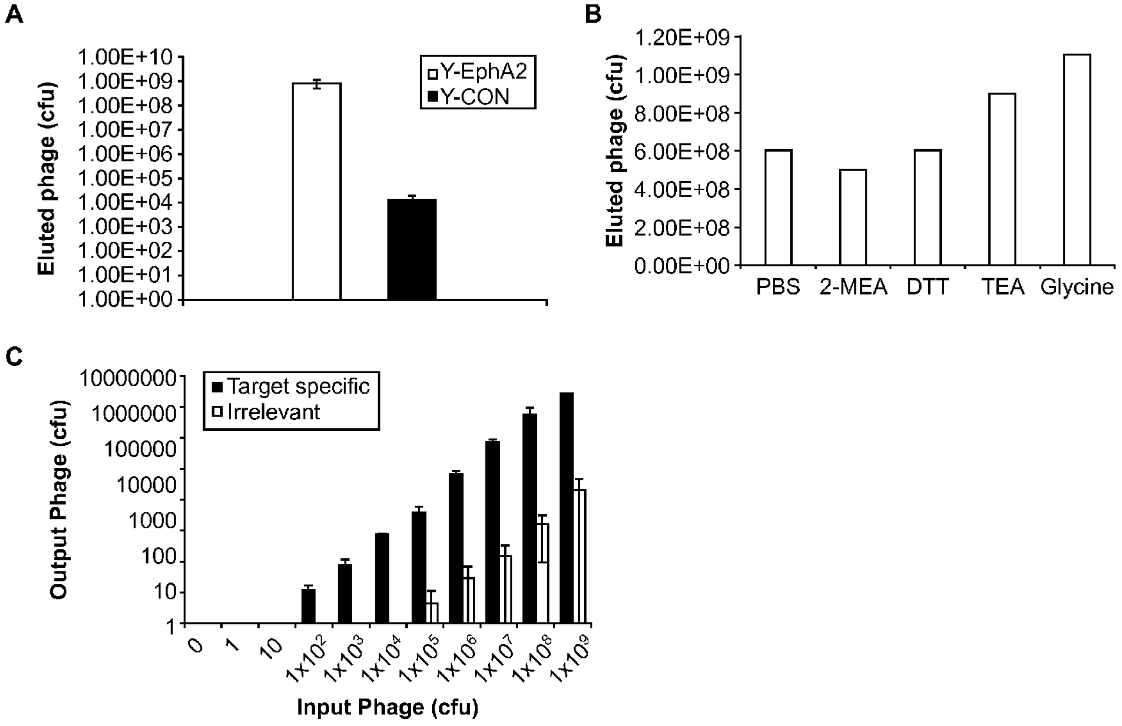
FIG. 2. Recovery of phage antibodies from yeast displayed antigens. Panel A, Comparison of the recovery of a phage antibody known to bind EphA2 (2D6) from yeast displaying EphA2 ECD (Y-EphA2) versus yeast displaying an irrelevant protein (Y-CON). A total of $10^{11}$ anti-EphA2 phage antibody 2D6 were incubated with each of the yeast displayed antigens. Panel B, Impact of the elution buffer on the titer of EphA2 phage antibody eluted from the surface of yeast displaying EphA2 ECD. A total of $10^{11}$ anti-EphA2 phage antibody 2D6 were incubated with each of the yeast displayed antigen proteins prior to elution. Panel C, The impact of input phage titer on the eluted phage titer. The indicated titer of anti-EphA2 phage antibody 2D6 was incubated with yeast displayed EphA2 ECD or an irrelevant yeast displayed protein and the titer of eluted phage determined.

Efficient Recovery of Antigen Specific Phage Antibodies from Yeast Cell Surface Displayed Antigen A scFv phage antibody that specifically bound to EphA2 was used to study the ability to select phage antibodies on yeast displayed antigen. Approximately $10^{11}$ phage particles displaying anti-EphA2 human scFv 2D6 were incubated with $10^8$ yeast cells displaying the target antigen EphA2 ECD (Y-EphA2). As a control, an identical number of anti-EphA2 phage antibodies were incubated with $10^8$ yeast cells displaying an irrelevant scFv (Y-CON). The recovery of anti-EphA2 phage antibody from yeast displaying the EphA2 ECD was more than $10^4$ fold higher than the recovery of anti-EphA2 phage antibody from yeast displaying the scFv (FIG. 2, panel A). To determine the optimal buffer to elute phage antibodies from the yeast surface, different buffers (PBS, 2-MEA, DTT, triethylamine (TEA) and glycine) were evaluated. Although yeast surface display of TAA results from the disulfide linkage between the Aga2 and Aga1 proteins on the yeast surface, reducing agents, including 2-MEA and DTT, resulted in poorer recovery of viable phage antibodies than spontaneous dissociation of phage by incubation in PBS (FIG. 2, panel B). In contrast, elution with high pH TEA buffer or low pH glycine buffer increased the number of viable phage recovered approximately two fold, with low pH glycine being the optimal elution buffer of those studied. This elution buffer was used for subsequent studies.

To determine the minimum frequency of a specific antibody within a library that can be enriched and selected, phage displayed anti-EphA2 antibodies were serially diluted from $10^9$ to $10^0$ cfu and then mixed with $10^9$ helper phage VCSM13. Phage mixtures were incubated with $10^7$ yeast cells displaying the EphA2 ECD or with yeast displaying the CD44 domain 1, followed by washing, elution and titration of the recovered phages. With an input of $10^2$ specific phage particles, about 12 phage were recovered from yeast cells displaying EphA2, while an input of at least $10^5$ phage were required before phage were present in the output when selected on CD44 (FIG. 2, panel C). The average recovery of phage antibodies was $6.5\times10^{-2}$ for the specific antigen-antibody pair, and $6.5\times10^{-5}$ for the mismatched pair (Table 5), respectively. This high recovery ratio for specific compared to non-specific phage suggested that it would be possible to enrich and select phage antibodies on yeast displayed antigen.

TABLE 5

Recovery of specific phage antibody from yeast displayed antigens. The indicated yeast displayed antigen was incubated with $10^9$ phage and the titer of bound phage determined. Results are expressed as the ratio of output/input phage.

| Ag:Ab | PhAb Output/Input |
|---|---|
| Y-EphA2 ECD:PhAb-EphA2 | $6 \times 10^{-2}$ |
| Y-CD44 D1:PhAb-CD44 | $7 \times 10^{-2}$ |
| Y-EphA2 ECD:PhAb-CD44 | $3 \times 10^{-5}$ |
| Y-CD44 D1:PhAb-EphA2 | $1 \times 10^{-6}$ |

Y = yeast displayed antigen; PhAb = phage displayed antibody.

Example 3

Figure 3:
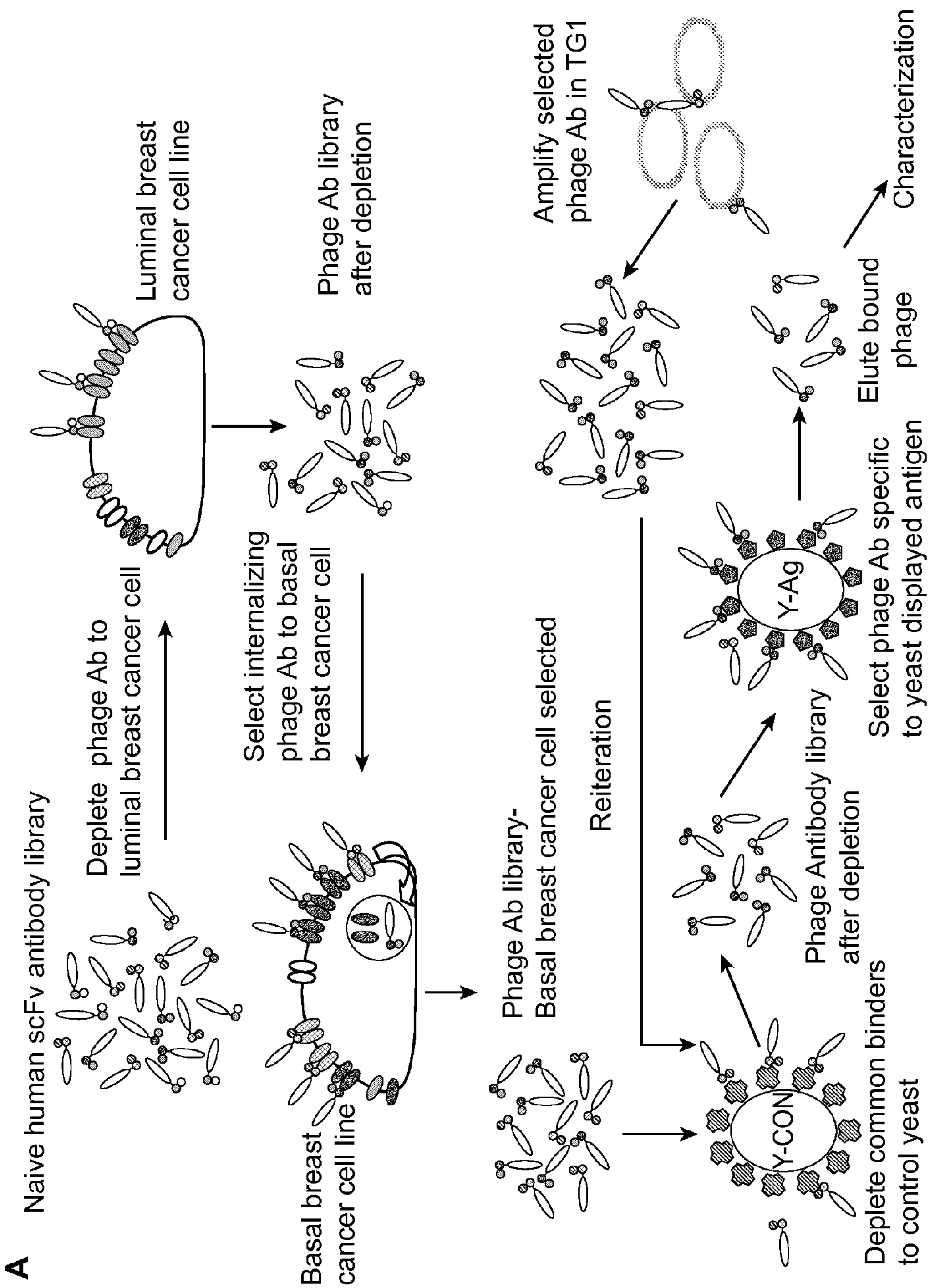
FIG. 3. Strategy for selecting internalizing antigen specific phage antibodies. Panel A, After two rounds of selection for internalization on the basal breast cancer cell line MDAMB231, the pool of phage antibodies was first incubated with irrelevant control yeast to remove any yeast binding antibodies followed by panning on yeast displaying either EphA2 ECD or CD44 domain 1. Panel B, The binding signal of the polyclonal phage antibody pool to EphA2 ECD or CD44 domain 1 after 2 rounds of panning was measured by using flow cytometry. The irrelevant control yeast was stained with unselected phage antibody library (R0), round 1 (R1) and round 2 (R2) polyclonal phage. Panel C, Frequency of antigen specific phage antibodies after one and two rounds of selection on yeast displayed antigen. Binding frequency was determined by analyzing 96 randomly picked phage antibodies for binding to yeast displayed antigen by flow cytometry. The induced yeast cells displaying an irrelevant protein, EphA2-ECD or CD44 domain 1 were stained with un-selected phage library (R0) and polyclonal phages from R1 and R2 respectively. The un-induced yeast cells (yeast only), irrelevant phage antibody (phage control) and the un-selected phage antibody library were used as control.
Figure 3:
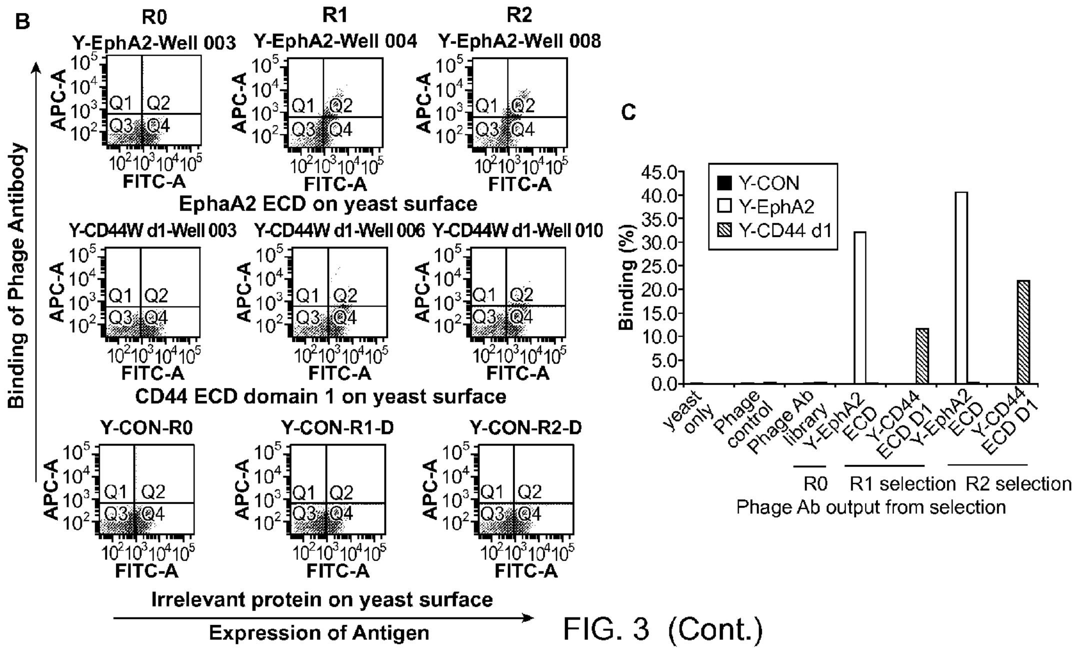

Selection of Antigen Specific Phage Antibodies on Yeast Cells Displaying Tumor Antigens The strategy used to select internalizing phage antibodies to specific tumor antigens is shown in FIG. 3. To ensure that phage antibodies bound tumor antigens as presented on the surface of human tumor cells and could be internalized upon antigen binding, a starting phage library was used. The polyclonal phage output after the second round of selection of a non-immune human scFv phage library (O'Connell D et al. (2002) *J Mol Biol* 321:49-56) was selected for endocytosis into MDAMB231 tumor cells. Based on the fact that basal subtype breast cancer cells over-express EphA2 (Neve R M et al. (2006) *Cancer Cell* 10:515-27) and CD44 (Hamilton S R et al. (2007) *J Biol Chem* 282:16667-80), the phage output of selection on the basal subtype breast cancer cell line MDAMB231 was selected independently on yeast displayed EphA2 ECD (aa 25-534) and CD44 domain 1 (aa 21-169). To remove phage antibodies that bound to irrelevant proteins on the yeast surface, $2.5 \times 10^{11}$ phage from the second round output of the MDAMB231 selection were incubated first with $1 \times 10^9$ yeast cells displaying the scFv 4E17 (Y-CON). Then, the depleted phage library was incubated with $2 \times 10^7$ yeast cells displaying the relevant antigen (Y—Ag) (FIG. 3, panel A).

For both EphA2 ECD and CD44 domain 1 selections, the number of phage recovered from each yeast cell in the second round of selection increased over 40 fold compared to the first round (Table 6), suggesting enrichment for phage binding yeast displayed tumor antigens. This was verified by using polyclonal phage to stain the yeast displayed antigens. From both the first and second round of selections, polyclonal phage antibodies showed specific binding to the antigen domain that was used for selection, with stronger staining after the second round of selection (FIG. 3, panel B). In contrast, prior to selection, the input phage antibody library gave no signal above background on yeast cells displaying either EphA2 or CD44. Binding was specific for the yeast displayed antigen, since the polyclonal phage did not bind yeast cells displaying an irrelevant protein (the scFv 4E17) (FIG. 3, panel B). To determine the frequency of binding phage antibodies, 96 individual clones were picked, phage produced, and the phage analyzed for binding to the yeast displayed tumor antigen. After one round and two rounds of selection, 31/96 (32.2%) and 39/96 (40.6%) of the clones from EphA2 selection bound yeast cells displaying EphA2 ECD, and 11/96 (11.7%) and 21/96 (21.9%) of the clones from CD44 selection bound yeast displayed CD44, respectively (FIG. 3, panel C)

TABLE 6

Phage display scFv antibody selection on yeast displayed antigens. Phage input and output ratios during the first and second rounds of selection on yeast displayed antigens.

| Antigen | Input (cfu) | Output (cfu) | Output/Input | Phage/Yeast |
|---|---|---|---|---|
| | Round 1 selection | | | |
| EphA2-ECD | $2.5 \times 10^{11}$ | $3.6 \times 10^6$ | $1.3 \times 10^{-5}$ | 0.18 |
| CD44-ECD D1 | $2.5 \times 10^{11}$ | $9.8 \times 10^6$ | $3.9 \times 10^{-5}$ | 0.49 |
| | Round 2 selection | | | |
| EphA2-ECD | $3.4 \times 10^{11}$ | $2.4 \times 10^8$ | $7 \times 10^{-4}$ | 12 |
| CD44-ECD D1 | $2.1 \times 10^{12}$ | $4.3 \times 10^8$ | $2 \times 10^{-4}$ | 20 |

Example 4

Identification and Characterization of Phage Antibodies

Individual phage antibodies from the second round of selection that bound the yeast displayed tumor antigen were analyzed by PCR fingerprinting and DNA sequencing of the scFv genes. The results are shown in FIG. 9, where the nucleic acid and amino acid sequences for each of the isolated clones are shown. The sense strand is shown as the top strand of the nucleic acid sequences in FIG. 9. The CDRs and framework regions are identified based on the Kabat database for each antibody as shown in FIGS. 7 and 8.

Figure 4:
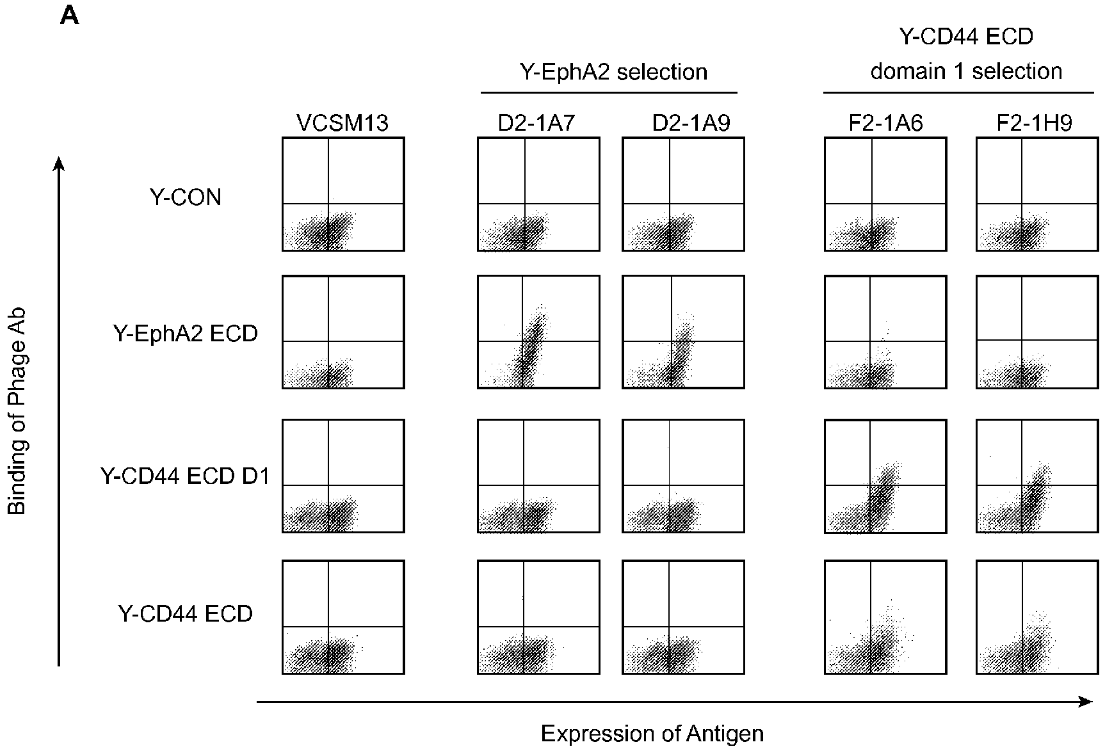
FIG. 4. Binding specificity of monoclonal phage antibodies from yeast antigen biopanning. Panel A, Binding of monoclonal phage antibodies to yeast displayed antigen domains as determined by flow cytometry. The induced yeast cells displaying an irrelevant protein (Y-CON), EphA2-ECD (Y-EphA2 ECD), CD44 link domain (Y-CD44 ECD D1) and CD44 full length ECD (Y-CD44 ECD) were stained with monoclonal phage antibodies isolated from Y-EphA2 and Y-CD44 D1 selections. Panel B shows the binding of monoclonal phage antibodies to MDAMB231 cells as determined by flow cytometry. Panel C shows the differential binding of monoclonal phage antibodies to breast cancer cell lines including luminal breast cancer cell lines SUM52PE and MCF7, and basal breast cancer cell line MDAMB231.
Figure 4:
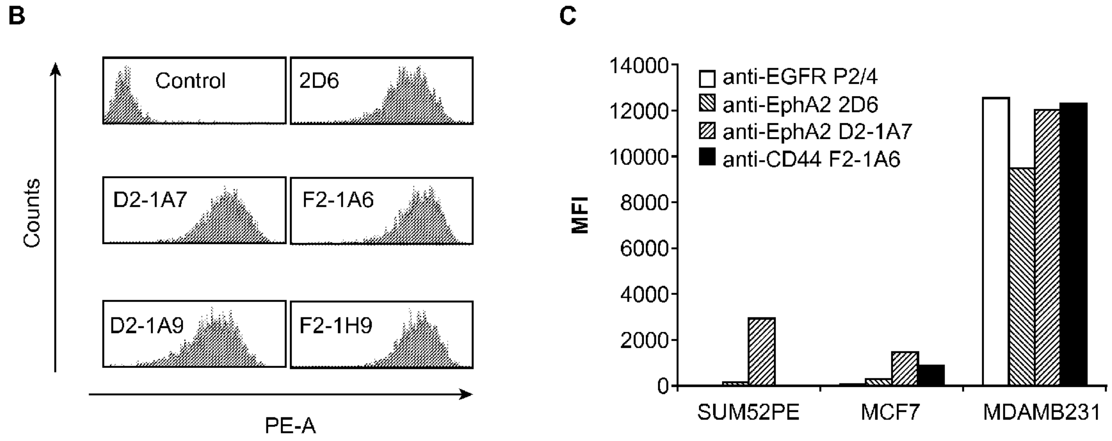

Three unique human scFv antibodies (D2-1A7, D2-1A9 and D2-1B1) were identified which bound to EphA2, and two unique scFv (F2-1A6 and F2-1H9) were identified which bound to CD44 ECD domain 1. Characterization of each of these scFv on yeast displayed EphA2-ECD (Y-EphA2 ECD), CD44 ECD domain 1 (Y-CD44 ECD D1) and full-length ECD (Y-CD44 ECD), and scFv 4E17 (Y-CON) indicated that each scFv was specific for its target antigen (FIG. 4, panel A). Each unique phage antibody was also analyzed for its ability to bind the original selecting tumor cell line MDAMB231 by flow cytometry. Each phage antibody strongly stained MDAMB231 cells (FIG. 4, panel B). Since the initial selection of the phage antibody library aimed to target cell surface receptors specific to basal subtype breast cancer cells, the binding of the selected mAbs to basal and luminal breast cancer cell lines was determined. Each mAb was relatively specific for basal breast cancer cell lines compared to luminal breast cancer cell lines (FIG. 4, panel C).

Example 5

Binding Specificity of Phage Antibodies

Figure 5:
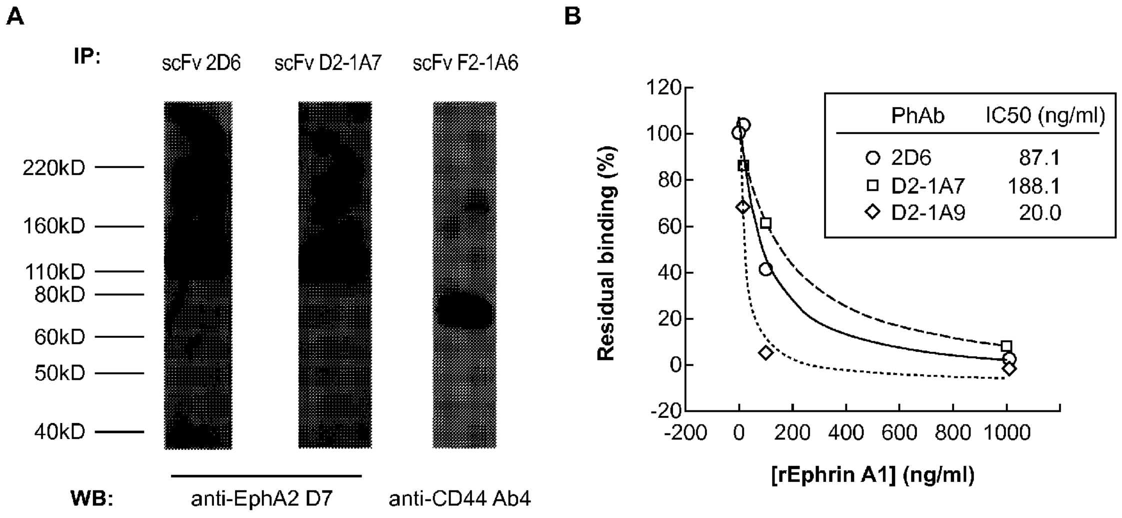
FIG. 5. Characterization of scFv antibodies by western-blot and flow cytometry. Panel A, Anti-EphA2 scFv 2D6 or D2-1A7 and anti-CD44 scFv F2-1A6 were used to immunoprecipitate their target antigen from MDAMB231 cells. Antigen was detected by Western blotting using either anti-EphA2 antibody D7 (Upstate Biotech, Billerica) or anti-CD44 antibody Ab-4 (NeoMarkers, Fremont). Panel B, EphA2 antibodies D2-1A7, D2-1A9, and 2D6 compete with ephrin A1 for binding to MDAMB231 cells. The ability of phage antibodies D2-1A7, D2-1A9, and 2D6 that bind to MDAMB231 cells in the presence of increasing concentrations of the EphA2 ligand ephrin A1 was determined by flow cytometry.

The binding of the identified EphA2 and CD44 antibodies to native antigens was also confirmed by immunoprecipitation of the receptors from cell extracts of MDAMB231 cells followed by Western blotting with murine monoclonal antibodies specific to EphA2 and CD44 (FIG. 5, panel A). The specificity of the EphA2 mAbs was further studied. The ability of each of the EphA2 mAbs was evaluated for its ability to compete with the natural ligand, ephrin A1 for binding to EphA2 on the surface of MDAMB231 cells. Although the 1050 of ephrin A1 for phage antibodies D2-1A7 and D2-1A9 at the given concentration differed by 9-fold, 1 μg/ml ephrin A1 can fully block the cell binding of both D2-1A7 and D2-1A9 phage antibodies (FIG. 5, panel B), indicating that these two antibodies bind epitopes which overlap with Ephrin A1.

Example 6

Phage Antibodies are Internalized by MDAMB231 Cells

Figure 6:
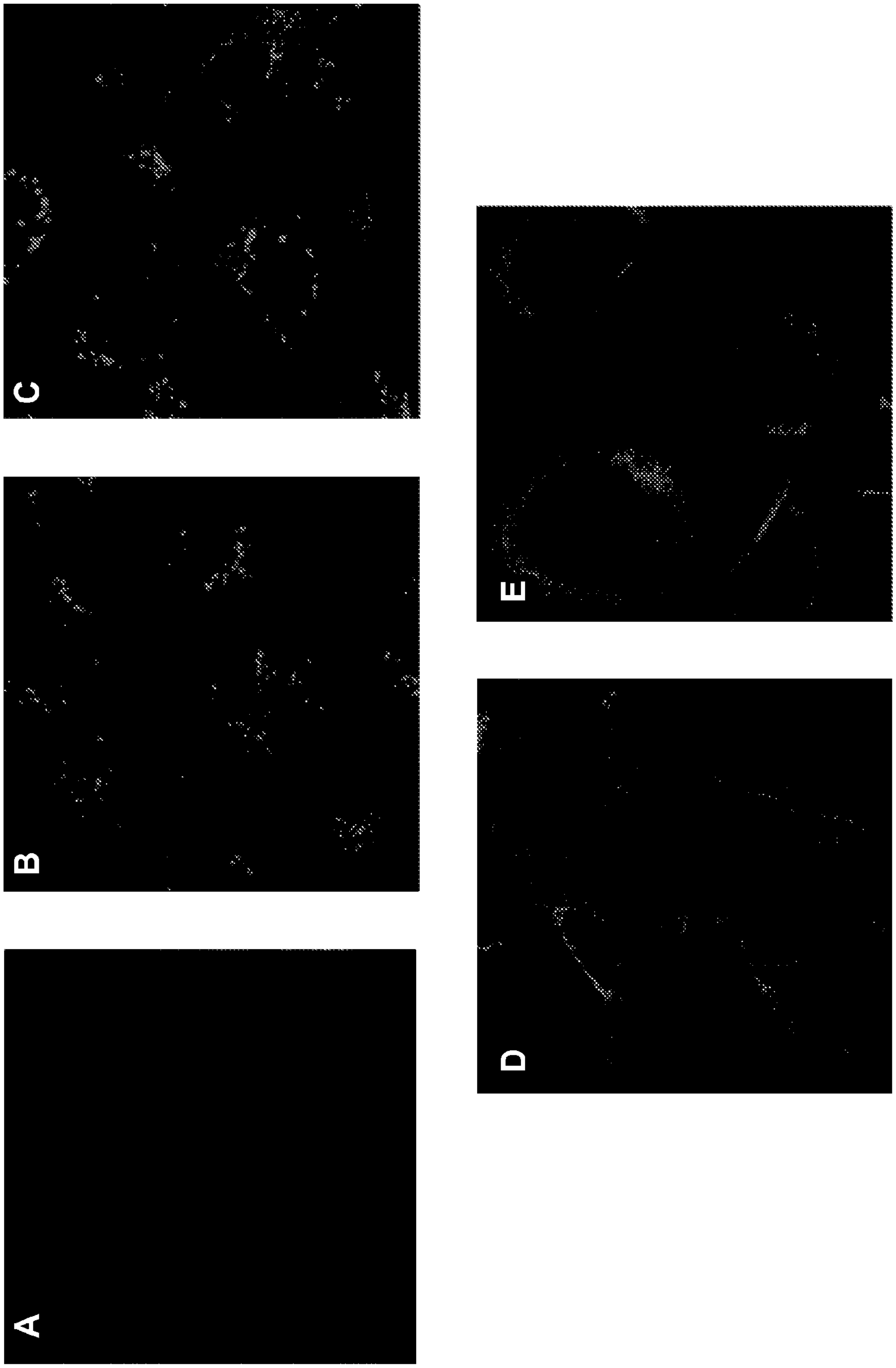
FIG. 6. Phage antibodies specific to EphA2 and CD44 are endocytosed by MDAMB231 cells. Cultured cells were incubated with irrelevant phage (panel A), anti-EphA2 phage D2-1A7 (panel B) and D2-1A9 (panel C), anti-CD44 phage F2-1A6 (panels D and E) for 3 hr at 37° C. followed by Glycine buffer wash. Endocytosis was determined by detection of intracellular phage with anti-fd antibody, and analyzing by confocal microscopy.

Since the phage antibodies identified by yeast display antigen biopanning were originally selected for the ability to be endocytosed into MDAMB231 cells (FIG. 3, panel A), it was anticipated that they would be internalized efficiently. To determine whether D2-1A7, D2-1A9 and F2-1A6 phage antibodies were endocytosed, the phage antibodies were incubated with MDAMB231 cells at 37° C. to allow receptor mediated endocytosis, the surface bound phage removed by stripping with low pH buffer, and the internalized phage stained with anti-fd antibody and observed using confocal microscopy (FIG. 6). Both D2-1A7 and D2-1A9 anti-EphA2 antibodies gave strong intracellular staining, a control phage gave no staining, and F2-1A6 anti-CD44 antibody gave a different staining pattern than the anti-EphA2 phage.

Example 7

Fd Phage and Phagemid Antibodies Specific for CD44 or EphA2

To select antigen specific antibodies without the use of mammalian cells, the non-immune human scFv phage library (Sheets, 1998; Huie, 2001) was incubated with yeast-displayed tumor associated antigens (TAAs) without prior selection on cancer cells. Specifically, $10^{12}$ fd-phage particles (Huie et al. (2001) supra) or $10^{13}$ phagemid-phage particles (Sheets et al (1998) supra) were first incubated with $10^{10}$ yeast cells displaying an irrelevant protein for 2 h at 4° C. to remove phage antibodies binding common yeast proteins. The depleted phage library was then incubated with $10^8$ yeast cells displaying a specific antigen domain for 2 h at 4° C. (for example EphA2 or CD44). Yeast cells were washed with cold PBS ten times and pelleted by centrifugation. The bound phage antibodies were eluted by incubating yeast cells with 1 ml of 100 mM Glycine/150 mM NaCl/0.1% BSA/0.5% polysorbate 20/TWEEN® 20, neutralized with 0.5 ml of 1M Tris-HCl (pH 7.4), and amplified for another round of selection. In the second round of selection, $2\times10^7$ yeast cells were used for both antigens, while phage particles from the first round selection were used as the input phage library with $10^{11}$ phage for fd library and $10^{12}$ for phagemid library respectively. Two rounds of selection were performed to enrich phage antibodies specific to the TAA used for selection. If two rounds of selection didn't enrich TAA specific antibodies, a third round of selection was performed, following the same protocol as the second round of selection.

The method for screening and characterization of monoclonal phage antibodies was the same as that described in Examples 4 and 5.

Five fd phage antibodies, designated E8H11, E8H7, E8G12, E8F11, and E8C9, were raised to CD44 link domain and were specific for CD44 link domain. Two fd phage antibodies, designated D6G9 and D6D3, were raised to the CD44s (standard form), and were specific for the CD44s.

Two phagemid antibodies, designated D1C5 and D1D1, were raised to the CD44 link domain, and were specific for the CD44 link domain. Six phagemid antibodies, designated HB8, HC2, HC4, HE3, HF1, and HH3, were raised to CD44s and were specific for CD44s.

Five fd phage antibodies, designated A3H9, A3G3, A3D10, A3D1, and A3C8 were raised to EphA2 and were specific for EphA2. Eight phagemid antibodies, designated 1A3, 1A5, 1A8, 1A12, 1B2, 1C2, 1C7, and 1D8, were raised to EphA2 and were specific for EphA2.

Another fd phage antibody, designated 15H11, was raised to EphA2 and was specific to EphA2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. While the subject antibody, method, and composition have been particularly shown and described with references to preferred embodiments thereof, it will be understood by those skilled in the art that various changes in form and details may be made therein without departing from the scope of the invention encompassed by the appended claims.

What is claimed is:

1. A conjugated monoclonal antibody comprising a monoclonal antibody attached to a polymer comprising poly (ethylene glycol) (PEG), wherein the monoclonal antibody specifically binds an epitope of ephrinA receptor A2 (EphA2) that is specifically bound by a monoclonal antibody comprising:

a variable heavy chain ($V_H$) polypeptide comprising:

a $V_H$ CDR1 comprising the amino acid sequence SYAMH (SEQ ID NO:29), a $V_H$ CDR2 comprising the amino acid sequence VISYDGSNKYYADSVKG (SEQ ID NO: 45), and a $V_H$ CDR3 comprising the amino acid sequence ASVGATGPFDI (SEQ ID NO: 42); and a variable light chain ($V_L$) polypeptide comprising:

a $V_L$ CDR1 comprising the amino acid sequence QGDSLRSYYAS (SEQ ID NO:17), a $V_L$ CDR2 comprising the amino acid sequence GENNRPS (SEQ ID NO:71), and a $V_L$ CDR3 comprising the amino acid sequence NSRDSSGTHLTV (SEQ ID NO: 60).

2. The conjugated monoclonal antibody of claim 1, wherein the monoclonal antibody is covalently bound to the polymer.

3. The conjugated monoclonal antibody of claim 1, wherein the monoclonal antibody is covalently bound to a terminus of the polymer.

4. The conjugated monoclonal antibody of claim 1, wherein the monoclonal antibody comprises an Fc region and the Fc region of the monoclonal antibody is attached to the polymer.

5. The conjugated monoclonal antibody of claim 1, wherein the variable heavy chain ($V_H$) polypeptide and the variable light chain ($V_L$) polypeptide of the monoclonal antibody are joined in a single chain Fv (scFv).

6. The conjugated monoclonal antibody of claim 1, wherein the polymer is soluble in water at room temperature.

7. The conjugated monoclonal antibody of claim 5, wherein the conjugated scFv is characterized by one or more of the following:

the scFv is covalently bound to a terminus of the polymer;

the scFv is covalently bound to a terminus of the polymer via a linker; and the polymer is soluble in water at room temperature.

8. The conjugated monoclonal antibody of claim 1, wherein the conjugated monoclonal antibody is a human, humanized, or chimeric monoclonal antibody.

9. A composition comprising a pharmaceutically acceptable carrier and a conjugated monoclonal antibody of claim 1.

10. The composition of claim 9, wherein said composition is formulated for parenteral administration.

11. The conjugated monoclonal antibody of claim 5, wherein the variable light chain ($V_L$) polypeptide and the variable heavy chain ($V_H$) polypeptide of the scFv are human or humanized.

12. The conjugated monoclonal antibody of claim 7, wherein the variable light chain ($V_L$) polypeptide and the variable heavy chain ($V_H$) polypeptide of the scFv are human or humanized.

13. A composition comprising a pharmaceutically acceptable carrier and a conjugated monoclonal antibody of claim 11.

14. The composition of claim 13, wherein said composition is formulated for parenteral administration.

15. A composition comprising a pharmaceutically acceptable carrier and a conjugated monoclonal antibody of claim 12.

16. The composition of claim 15, wherein said composition is formulated for parenteral administration.

17. The conjugated monoclonal antibody of claim 1, wherein the monoclonal antibody is an IgG, Fab, $F(ab')_2$, or $(scFv')_2$.

* * * * *

UNITED STATES PATENT AND TRADEMARK OFFICE

CERTIFICATE OF CORRECTION

PATENT NO. : 9,446,125 B2
APPLICATION NO. : 14/829077
DATED : September 20, 2016
INVENTOR(S) : Yu Zhou It is certified that error appears in the above-identified patent and that said Letters Patent is hereby corrected as shown below:

On the Title Page

Please correct the Assignee as follows:
"THE REGENTS OF THE UNIVERSITY OF CALIFORNIA, BERKE, Oakland, CA (US)" to read --THE REGENTS OF THE UNIVERSITY OF CALIFORNIA, Oakland, CA (US)--

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 433

<210> SEQ ID NO 1
<211> LENGTH: 149
<212> TYPE: PRT
<213> ORGANISM: artificial sequence
<220> FEATURE:
<223> OTHER INFORMATION: synthetic polypeptide

<400> SEQUENCE: 1

Gln Ile Asp Leu Asn Ile Thr Cys Arg Phe Ala Gly Val Phe His Val
1               5                   10                  15

Glu Lys Asn Gly Arg Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Arg Tyr Gly Phe Ile Glu Gly
```

```
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

Thr Asp Leu Pro Asn Ala Phe Asp Gly Pro Ile Thr Ile Thr Ile Val
        115                 120                 125

Asn Arg Asp Gly Thr Arg Tyr Val Gln Lys Gly Glu Tyr Arg Thr Asn
    130                 135                 140

Pro Glu Asp Ile Tyr
145


<210> SEQ ID NO 2
<211> LENGTH: 30
<212> TYPE: PRT
<213> ORGANISM: artificial sequence
<220> FEATURE:
<223> OTHER INFORMATION: synthetic polypeptide

<400> SEQUENCE: 2

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr
            20                  25                  30


<210> SEQ ID NO 3
<211> LENGTH: 5
<212> TYPE: PRT
<213> ORGANISM: artificial sequence
<220> FEATURE:
<223> OTHER INFORMATION: synthetic polypeptide

<400> SEQUENCE: 3

Ser Tyr Trp Ile Gly
 1               5


<210> SEQ ID NO 4
<211> LENGTH: 14
<212> TYPE: PRT
<213> ORGANISM: artificial sequence
<220> FEATURE:
<223> OTHER INFORMATION: synthetic polypeptide

<400> SEQUENCE: 4

Trp Val Arg Gln Met Pro Gly Lys Gly Leu Glu Trp Met Gly
 1               5                  10


<210> SEQ ID NO 5
<211> LENGTH: 30
<212> TYPE: PRT
<213> ORGANISM: artificial sequence
<220> FEATURE:
<223> OTHER INFORMATION: synthetic polypeptide

<400> SEQUENCE: 5

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser
            20                  25                  30
```

<210> SEQ ID NO 6
<211> LENGTH: 5
<212> TYPE: PRT
<213> ORGANISM: artificial sequence
<220> FEATURE:
<223> OTHER INFORMATION: synthetic polypeptide

<400> SEQUENCE: 6

Ser Tyr Arg Met His
 1               5

<210> SEQ ID NO 7
<211> LENGTH: 14
<212> TYPE: PRT
<213> ORGANISM: artificial sequence
<220> FEATURE:
<223> OTHER INFORMATION: synthetic polypeptide

<400> SEQUENCE: 7

Trp Val Arg Gln Ala Pro Gly Lys Gly Leu Glu Trp Val Ala
 1               5                   10

<210> SEQ ID NO 8
<211> LENGTH: 17
<212> TYPE: PRT
<213> ORGANISM: artificial sequence
<220> FEATURE:
<223> OTHER INFORMATION: synthetic polypeptide

<400> SEQUENCE: 8

Ile Ile Tyr Pro Gly Asp Ser Asp Thr Arg Tyr Ser Pro Ser Phe Gln
 1               5                   10                  15

Gly

<210> SEQ ID NO 9
<211> LENGTH: 32
<212> TYPE: PRT
<213> ORGANISM: artificial sequence
<220> FEATURE:
<223> OTHER INFORMATION: synthetic polypeptide

<400> SEQUENCE: 9

Gln Val Thr Ile Ser Ala Asp Lys Ser Ile Ser Thr Ala Tyr Leu Gln
 1               5                   10                  15

Trp Ser Ser Leu Lys Ala Ser Asp Thr Ala Met Tyr Tyr Cys Ala Arg
            20                  25                  30

<210> SEQ ID NO 10
<211> LENGTH: 17
<212> TYPE: PRT
<213> ORGANISM: artificial sequence
<220> FEATURE:
<223> OTHER INFORMATION: synthetic polypeptide

<400> SEQUENCE: 10

Ala Val Lys Gln Asp Gly Ser Glu Lys Tyr Tyr Leu Asp Ser Val Lys
 1               5                   10                  15

Gly

<210> SEQ ID NO 11
<211> LENGTH: 32
<212> TYPE: PRT
<213> ORGANISM: artificial sequence
<220> FEATURE:
<223> OTHER INFORMATION: synthetic polypeptide

<400> SEQUENCE: 11

Arg Phe Thr Ile Ser Arg Asp Asn Ala Lys Ser Ser Leu Tyr Leu Gln
 1               5                   10                  15

Met Asp Ser Leu Ser Val Glu Asp Thr Ala Val Tyr Tyr Cys Ala Arg
            20                  25                  30

<210> SEQ ID NO 12
<211> LENGTH: 10
<212> TYPE: PRT
<213> ORGANISM: artificial sequence
<220> FEATURE:
<223> OTHER INFORMATION: synthetic polypeptide

<400> SEQUENCE: 12

Arg Leu His Gly Pro Phe Tyr Phe Asp Tyr
 1               5                   10

<210> SEQ ID NO 13
<211> LENGTH: 11
<212> TYPE: PRT
<213> ORGANISM: artificial sequence
<220> FEATURE:
<223> OTHER INFORMATION: synthetic polypeptide

<400> SEQUENCE: 13

Trp Gly Gln Gly Thr Leu Val Thr Val Ser Ser
 1               5                   10

<210> SEQ ID NO 14
<211> LENGTH: 4
<212> TYPE: PRT
<213> ORGANISM: artificial sequence
<220> FEATURE:
<223> OTHER INFORMATION: synthetic polypeptide

<400> SEQUENCE: 14

Gly Leu Arg Thr
 1

<210> SEQ ID NO 15
<211> LENGTH: 11
<212> TYPE: PRT
<213> ORGANISM: artificial sequence
<220> FEATURE:
<223> OTHER INFORMATION: synthetic polypeptide

<400> SEQUENCE: 15

Met Gly Gln Gly Thr Leu Val Thr Val Ser Ser
 1               5                   10

<210> SEQ ID NO 16
<211> LENGTH: 21
<212> TYPE: PRT
<213> ORGANISM: artificial sequence
<220> FEATURE:
<223> OTHER INFORMATION: synthetic polypeptide

<400> SEQUENCE: 16

Ser Glu Leu Thr Gln Asp Pro Ala Val Ser Val Ala Leu Gly Gln Thr
 1               5                   10                  15

Val Arg Ile Thr Cys
            20

<210> SEQ ID NO 17
<211> LENGTH: 11

<212> TYPE: PRT
<213> ORGANISM: artificial sequence
<220> FEATURE:
<223> OTHER INFORMATION: synthetic polypeptide

<400> SEQUENCE: 17

Gln Gly Asp Ser Leu Arg Ser Tyr Tyr Ala Ser
1 5 10

<210> SEQ ID NO 18
<211> LENGTH: 15
<212> TYPE: PRT
<213> ORGANISM: artificial sequence
<220> FEATURE:
<223> OTHER INFORMATION: synthetic polypeptide

<400> SEQUENCE: 18

Trp Tyr Gln Gln Lys Pro Gly Gln Ala Pro Leu Leu Val Ile Tyr
1 5 10 15

<210> SEQ ID NO 19
<211> LENGTH: 15
<212> TYPE: PRT
<213> ORGANISM: artificial sequence
<220> FEATURE:
<223> OTHER INFORMATION: synthetic polypeptide

<400> SEQUENCE: 19

Trp Tyr Gln Arg Lys Pro Gly Gln Ala Pro Leu Leu Val Ile Tyr
1 5 10 15

<210> SEQ ID NO 20
<211> LENGTH: 7
<212> TYPE: PRT
<213> ORGANISM: artificial sequence
<220> FEATURE:
<223> OTHER INFORMATION: synthetic polypeptide

<400> SEQUENCE: 20

Gly Lys Asn Ile Arg Pro Ser
1 5

<210> SEQ ID NO 21
<211> LENGTH: 14
<212> TYPE: PRT
<213> ORGANISM: artificial sequence
<220> FEATURE:
<223> OTHER INFORMATION: synthetic polypeptide

<400> SEQUENCE: 21

Trp Ala Arg Gln Ala Pro Gly Lys Gly Leu Glu Trp Val Ser
1 5 10

<210> SEQ ID NO 22
<211> LENGTH: 32
<212> TYPE: PRT
<213> ORGANISM: artificial sequence
<220> FEATURE:
<223> OTHER INFORMATION: synthetic polypeptide

<400> SEQUENCE: 22

Gly Ile Pro Asp Arg Phe Ser Gly Ser Ser Ser Gly Asn Thr Ala Ser
1 5 10 15

Leu Ile Ile Thr Gly Ala Gln Ala Glu Asp Glu Ala Asp Tyr Tyr Cys
20 25 30

<210> SEQ ID NO 23
<211> LENGTH: 32
<212> TYPE: PRT
<213> ORGANISM: artificial sequence
<220> FEATURE:
<223> OTHER INFORMATION: synthetic polypeptide

<400> SEQUENCE: 23

```
Gly Ile Pro Asp Arg Phe Ser Gly Ser Ser Ser Gly Asn Thr Ala Ser
 1               5                  10                  15

Leu Thr Ile Thr Gly Ala Gln Ala Glu Asp Glu Ala Asp Tyr Tyr Cys
            20                  25                  30
```

<210> SEQ ID NO 24
<211> LENGTH: 30
<212> TYPE: PRT
<213> ORGANISM: artificial sequence
<220> FEATURE:
<223> OTHER INFORMATION: synthetic polypeptide

<400> SEQUENCE: 24

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser
            20                  25                  30
```

<210> SEQ ID NO 25
<211> LENGTH: 10
<212> TYPE: PRT
<213> ORGANISM: artificial sequence
<220> FEATURE:
<223> OTHER INFORMATION: synthetic polypeptide

<400> SEQUENCE: 25

```
Asn Ser Arg Asp Ser Ser Ala Asn Gln Met
 1               5                  10
```

<210> SEQ ID NO 26
<211> LENGTH: 510
<212> TYPE: PRT
<213> ORGANISM: artificial sequence
<220> FEATURE:
<223> OTHER INFORMATION: synthetic polypeptide

<400> SEQUENCE: 26

```
Gln Gly Lys Glu Val Val Leu Leu Asp Phe Ala Ala Ala Gly Gly Glu
 1               5                  10                  15

Leu Gly Trp Leu Thr His Pro Tyr Gly Lys Gly Trp Asp Leu Met Gln
            20                  25                  30

Asn Ile Met Asn Asp Met Pro Ile Tyr Met Tyr Ser Val Cys Asn Val
        35                  40                  45

Met Ser Gly Asp Gln Asp Asn Trp Leu Arg Thr Asn Trp Val Tyr Arg
    50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
            100                 105                 110

Arg Leu Phe Thr Lys Ile Asp Thr Ile Ala Pro Asp Glu Ile Thr Val
        115                 120                 125

Ser Ser Asp Phe Glu Ala Arg His Val Lys Leu Asn Val Glu Glu Arg
```

-continued

```
    130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys Lys
                165                 170                 175

Cys Pro Glu Leu Leu Gln Gly Leu Ala His Phe Pro Glu Thr Ile Ala
            180                 185                 190

Gly Ser Asp Ala Pro Ser Leu Ala Thr Val Ala Gly Thr Cys Val Asp
        195                 200                 205

His Ala Val Val Pro Pro Gly Gly Glu Glu Pro Arg Met His Cys Ala
    210                 215                 220

Val Asp Gly Glu Trp Leu Val Pro Ile Gly Gln Cys Leu Cys Gln Ala
225                 230                 235                 240

Gly Tyr Glu Lys Val Glu Asp Ala Cys Gln Ala Cys Ser Pro Gly Phe
                245                 250                 255

Phe Lys Phe Glu Ala Ser Glu Ser Pro Cys Leu Glu Cys Pro Glu His
            260                 265                 270

Thr Leu Pro Ser Pro Glu Gly Ala Thr Ser Cys Glu Cys Glu Glu Gly
        275                 280                 285

Phe Phe Arg Ala Pro Gln Asp Pro Ala Ser Met Pro Cys Thr Arg Pro
    290                 295                 300

Pro Ser Ala Pro His Tyr Leu Thr Ala Val Gly Met Gly Ala Lys Val
305                 310                 315                 320

Glu Leu Arg Trp Thr Pro Pro Gln Asp Ser Gly Gly Arg Glu Asp Ile
                325                 330                 335

Val Tyr Ser Val Thr Cys Glu Gln Cys Trp Pro Glu Ser Gly Glu Cys
            340                 345                 350

Gly Pro Cys Glu Ala Ser Val Arg Tyr Ser Glu Pro Pro His Gly Leu
        355                 360                 365

Thr Arg Thr Ser Val Thr Val Ser Asp Leu Glu Pro His Met Asn Tyr
    370                 375                 380

Thr Phe Thr Val Glu Ala Arg Asn Gly Val Ser Gly Leu Val Thr Ser
385                 390                 395                 400

Arg Ser Phe Arg Thr Ala Ser Val Ser Ile Asn Gln Thr Glu Pro Pro
                405                 410                 415

Lys Val Arg Leu Glu Gly Arg Ser Thr Thr Ser Leu Ser Val Ser Trp
            420                 425                 430

Ser Ile Pro Pro Pro Gln Gln Ser Arg Val Trp Lys Tyr Glu Val Thr
        435                 440                 445

Tyr Arg Lys Lys Gly Asp Ser Asn Ser Tyr Asn Val Arg Arg Thr Glu
    450                 455                 460

Gly Phe Ser Val Thr Leu Asp Asp Leu Ala Pro Asp Thr Thr Tyr Leu
465                 470                 475                 480

Val Gln Val Gln Ala Leu Thr Gln Glu Gly Gln Gly Ala Gly Ser Lys
                485                 490                 495

Val His Glu Phe Gln Thr Leu Ser Pro Glu Gly Ser Gly Asn
            500                 505                 510
```

<210> SEQ ID NO 27
<211> LENGTH: 11
<212> TYPE: PRT
<213> ORGANISM: artificial sequence
<220> FEATURE:
<223> OTHER INFORMATION: synthetic polypeptide

<400> SEQUENCE: 27

Phe Gly Gly Gly Thr Lys Leu Thr Val Leu Gly
1 5 10

<210> SEQ ID NO 28
<211> LENGTH: 30
<212> TYPE: PRT
<213> ORGANISM: artificial sequence
<220> FEATURE:
<223> OTHER INFORMATION: synthetic polypeptide

<400> SEQUENCE: 28

Gln Val Gln Leu Gln Gln Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 29
<211> LENGTH: 5
<212> TYPE: PRT
<213> ORGANISM: artificial sequence
<220> FEATURE:
<223> OTHER INFORMATION: synthetic polypeptide

<400> SEQUENCE: 29

Ser Tyr Ala Met His
1 5

<210> SEQ ID NO 30
<211> LENGTH: 30
<212> TYPE: PRT
<213> ORGANISM: artificial sequence
<220> FEATURE:
<223> OTHER INFORMATION: synthetic polypeptide

<400> SEQUENCE: 30

Gln Val Gln Leu Val Glu Ser Gly Gly Gly Leu Ile Gln Pro Gly Gly
1 5 10 15

Ser Leu Lys Leu Ser Cys Ala Ala Ser Gly Phe Thr Val Ser
20 25 30

<210> SEQ ID NO 31
<211> LENGTH: 5
<212> TYPE: PRT
<213> ORGANISM: artificial sequence
<220> FEATURE:
<223> OTHER INFORMATION: synthetic polypeptide

<400> SEQUENCE: 31

Asn Ser Tyr Met Ser
1 5

<210> SEQ ID NO 32
<211> LENGTH: 5
<212> TYPE: PRT
<213> ORGANISM: artificial sequence
<220> FEATURE:
<223> OTHER INFORMATION: synthetic polypeptide

<400> SEQUENCE: 32

Ser Tyr Ala Met Ser
1 5

<210> SEQ ID NO 33
<211> LENGTH: 5

-continued

<212> TYPE: PRT
<213> ORGANISM: artificial sequence
<220> FEATURE:
<223> OTHER INFORMATION: synthetic polypeptide

<400> SEQUENCE: 33

Thr Leu Ala Met Gly
1 5

<210> SEQ ID NO 34
<211> LENGTH: 16
<212> TYPE: PRT
<213> ORGANISM: artificial sequence
<220> FEATURE:
<223> OTHER INFORMATION: synthetic polypeptide

<400> SEQUENCE: 34

Ile Ile Tyr Asn Gly Asp Asn Thr Tyr Tyr Ala Asp Ser Val Lys Gly
1 5 10 15

<210> SEQ ID NO 35
<211> LENGTH: 32
<212> TYPE: PRT
<213> ORGANISM: artificial sequence
<220> FEATURE:
<223> OTHER INFORMATION: synthetic polypeptide

<400> SEQUENCE: 35

Arg Phe Thr Ile Ser Arg Asp Asn Ser Lys Asn Ser Leu Tyr Leu Gln
1 5 10 15

Met Asn Ser Leu Arg Ala Glu Asp Thr Ala Val Tyr Tyr Cys Ala Arg
20 25 30

<210> SEQ ID NO 36
<211> LENGTH: 5
<212> TYPE: PRT
<213> ORGANISM: artificial sequence
<220> FEATURE:
<223> OTHER INFORMATION: synthetic polypeptide

<400> SEQUENCE: 36

Ser Tyr Gly Ile His
1 5

<210> SEQ ID NO 37
<211> LENGTH: 5
<212> TYPE: PRT
<213> ORGANISM: artificial sequence
<220> FEATURE:
<223> OTHER INFORMATION: synthetic polypeptide

<400> SEQUENCE: 37

Ser Tyr Ser Met Asn
1 5

<210> SEQ ID NO 38
<211> LENGTH: 16
<212> TYPE: PRT
<213> ORGANISM: artificial sequence
<220> FEATURE:
<223> OTHER INFORMATION: synthetic polypeptide

<400> SEQUENCE: 38

Val Ile Tyr Ser Ala Gly Asn Thr Tyr Tyr Ala Asp Ser Val Lys Gly
1 5 10 15

-continued

<210> SEQ ID NO 39
<211> LENGTH: 32
<212> TYPE: PRT
<213> ORGANISM: artificial sequence
<220> FEATURE:
<223> OTHER INFORMATION: synthetic polypeptide

<400> SEQUENCE: 39

```
Arg Phe Thr Ile Ser Arg Asp Thr Ser Asn Asn Thr Val His Leu Gln
 1               5                  10                  15

Met Asn Ser Leu Arg Pro Glu Asp Thr Ala Val Tyr Tyr Cys Ala Arg
            20                  25                  30
```

<210> SEQ ID NO 40
<211> LENGTH: 11
<212> TYPE: PRT
<213> ORGANISM: artificial sequence
<220> FEATURE:
<223> OTHER INFORMATION: synthetic polypeptide

<400> SEQUENCE: 40

```
Asn Ser Arg Asp Ser Ser Gly Asn His Val Val
 1               5                  10
```

<210> SEQ ID NO 41
<211> LENGTH: 5
<212> TYPE: PRT
<213> ORGANISM: artificial sequence
<220> FEATURE:
<223> OTHER INFORMATION: synthetic polypeptide

<400> SEQUENCE: 41

```
Ser Tyr Gly Met His
 1               5
```

<210> SEQ ID NO 42
<211> LENGTH: 11
<212> TYPE: PRT
<213> ORGANISM: artificial sequence
<220> FEATURE:
<223> OTHER INFORMATION: synthetic polypeptide

<400> SEQUENCE: 42

```
Ala Ser Val Gly Ala Thr Gly Pro Phe Asp Ile
 1               5                  10
```

<210> SEQ ID NO 43
<211> LENGTH: 11
<212> TYPE: PRT
<213> ORGANISM: artificial sequence
<220> FEATURE:
<223> OTHER INFORMATION: synthetic polypeptide

<400> SEQUENCE: 43

```
Trp Gly Gln Gly Thr Met Val Thr Val Ser Ser
 1               5                  10
```

<210> SEQ ID NO 44
<211> LENGTH: 8
<212> TYPE: PRT
<213> ORGANISM: artificial sequence
<220> FEATURE:
<223> OTHER INFORMATION: synthetic polypeptide

<400> SEQUENCE: 44

```
Glu Gly Ser Phe Gly Tyr Asp Tyr
 1               5
```

<210> SEQ ID NO 45
<211> LENGTH: 17
<212> TYPE: PRT
<213> ORGANISM: artificial sequence
<220> FEATURE:
<223> OTHER INFORMATION: synthetic polypeptide

<400> SEQUENCE: 45

Val Ile Ser Tyr Asp Gly Ser Asn Lys Tyr Tyr Ala Asp Ser Val Lys
1 5 10 15

Gly

<210> SEQ ID NO 46
<211> LENGTH: 32
<212> TYPE: PRT
<213> ORGANISM: artificial sequence
<220> FEATURE:
<223> OTHER INFORMATION: synthetic polypeptide

<400> SEQUENCE: 46

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 47
<211> LENGTH: 21
<212> TYPE: PRT
<213> ORGANISM: artificial sequence
<220> FEATURE:
<223> OTHER INFORMATION: synthetic polypeptide

<400> SEQUENCE: 47

Ser Glu Leu Thr Gln Asp Pro Ala Val Ser Val Ala Leu Gly Gln Thr
1 5 10 15

Val Ser Ile Thr Cys
20

<210> SEQ ID NO 48
<211> LENGTH: 23
<212> TYPE: PRT
<213> ORGANISM: artificial sequence
<220> FEATURE:
<223> OTHER INFORMATION: synthetic polypeptide

<400> SEQUENCE: 48

Asp Ile Val Met Thr Gln Ser Pro Gly Thr Leu Ser Leu Ser Pro Gly
1 5 10 15

Glu Arg Ala Thr Leu Ser Cys
20

<210> SEQ ID NO 49
<211> LENGTH: 12
<212> TYPE: PRT
<213> ORGANISM: artificial sequence
<220> FEATURE:
<223> OTHER INFORMATION: synthetic polypeptide

<400> SEQUENCE: 49

Arg Ala Ser Gln Ser Val Ser Ser Ser Phe Leu Gly
1 5 10

<210> SEQ ID NO 50

<211> LENGTH: 32
<212> TYPE: PRT
<213> ORGANISM: artificial sequence
<220> FEATURE:
<223> OTHER INFORMATION: synthetic polypeptide

<400> SEQUENCE: 50

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Lys
20 25 30

<210> SEQ ID NO 51
<211> LENGTH: 21
<212> TYPE: PRT
<213> ORGANISM: artificial sequence
<220> FEATURE:
<223> OTHER INFORMATION: synthetic polypeptide

<400> SEQUENCE: 51

Ser Glu Leu Thr Gln Asp Pro Ala Val Ser Val Ala Leu Gly Gln Thr
1 5 10 15

Val Lys Ile Thr Cys
20

<210> SEQ ID NO 52
<211> LENGTH: 11
<212> TYPE: PRT
<213> ORGANISM: artificial sequence
<220> FEATURE:
<223> OTHER INFORMATION: synthetic polypeptide

<400> SEQUENCE: 52

Gln Gly Asp Ser Leu Arg Thr Tyr Tyr Ala Ser
1 5 10

<210> SEQ ID NO 53
<211> LENGTH: 14
<212> TYPE: PRT
<213> ORGANISM: artificial sequence
<220> FEATURE:
<223> OTHER INFORMATION: synthetic polypeptide

<400> SEQUENCE: 53

Trp Val Arg Gln Ala Pro Gly Lys Gly Leu Asp Trp Val Ser
1 5 10

<210> SEQ ID NO 54
<211> LENGTH: 30
<212> TYPE: PRT
<213> ORGANISM: artificial sequence
<220> FEATURE:
<223> OTHER INFORMATION: synthetic polypeptide

<400> SEQUENCE: 54

Gln Val Gln Leu Gln Glu Ser Gly Gly Gly Val Val Gln Pro Gly Arg
1 5 10 15

Ser Leu Arg Leu Ser Cys Ala Ala Ser Gly Phe Thr Phe Ser
20 25 30

<210> SEQ ID NO 55
<211> LENGTH: 7
<212> TYPE: PRT
<213> ORGANISM: artificial sequence
<220> FEATURE:
<223> OTHER INFORMATION: synthetic polypeptide -continued

<400> SEQUENCE: 55

Gly Ala Ser Ser Arg Ala Thr
1 5

<210> SEQ ID NO 56
<211> LENGTH: 32
<212> TYPE: PRT
<213> ORGANISM: artificial sequence
<220> FEATURE:
<223> OTHER INFORMATION: synthetic polypeptide

<400> SEQUENCE: 56

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 57
<211> LENGTH: 7
<212> TYPE: PRT
<213> ORGANISM: artificial sequence
<220> FEATURE:
<223> OTHER INFORMATION: synthetic polypeptide

<400> SEQUENCE: 57

Gly Glu Asn Ser Arg Pro Ser
1 5

<210> SEQ ID NO 58
<211> LENGTH: 243
<212> TYPE: PRT
<213> ORGANISM: artificial sequence
<220> FEATURE:
<223> OTHER INFORMATION: synthetic polypeptide

<400> SEQUENCE: 58

Gln Val Gln Leu Gln Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Ser Ser Leu Arg Ala Glu Asp Thr Ala Val Tyr Tyr Cys
85 90 95

Val Ala Arg Leu Glu Trp Leu Pro Leu Ala Trp Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Ser Glu Leu Thr Gln Asp Pro Ala Val
130 135 140

Ser Val Ala Leu Gly Gln Thr Val Arg Ile Thr Cys Gln Gly Asp Ser
145 150 155 160

Leu Arg Ser Tyr Tyr Ala Ser Trp Tyr Gln Gln Lys Pro Gly Gln Ala
165 170 175

Pro Val Leu Val Ile Tyr Gly Lys Asn Asn Arg Pro Ser Gly Ile Pro

-continued

```
        180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Cys Asn Ser Arg
    210                 215                 220

Asp Ser Ser Gly Asn His Lys Val Phe Gly Gly Gly Thr Lys Leu Thr
225                 230                 235                 240

Val Leu Gly
```

```
<210> SEQ ID NO 59
<211> LENGTH: 729
<212> TYPE: DNA
<213> ORGANISM: Artificial Sequence
<220> FEATURE:
<223> OTHER INFORMATION: synthetic polynucleotide

<400> SEQUENCE: 59

caggtgcagc tgcaggagtc gggggaggc ttggtccagc ctgggggtc cctgagactc      60

tcctgttcag cctctggatt caccttcagt agctatgcta tgcactgggt ccgccaggct    120

ccagggaagg gactggaata tgtttcagct attagtagta atggggtag cacatactac     180

gcagactccg tgaagggcag attcaccatc tccagagaca attccaagaa cacgctgtat    240

cttcaaatga gcagtctgag agctgaggac acggctgtgt attactgtgt cgcgcgtttg    300

gagtggttac cactagcctg ggactactgg ggccagggca ccctggtcac cgtctcctca    360

ggtggaggcg gttcaggcgg aggtggctct ggcggtggcg gatcgtctga gctgactcag    420

gaccctgctg tgtctgtggc cttgggacag acagtcagga tcacatgcca aggagacagc    480

ctcagaagct attatgcaag ctggtaccag cagaagccag gacaggcccc tgtacttgtc    540

atctatggta aaaacaaccg gccctcaggg atcccagacc gattctctgg ctccagctca    600

ggaaacacag cttccttgac catcactggg gctcaggcgg aagatgaggc tgactattac    660

tgtaactccc gggacagcag tggtaaccat aaggtgttcg gcggagggac caagctgacc    720

gtcctaggt                                                            729


<210> SEQ ID NO 60
<211> LENGTH: 12
<212> TYPE: PRT
<213> ORGANISM: artificial sequence
<220> FEATURE:
<223> OTHER INFORMATION: synthetic polypeptide

<400> SEQUENCE: 60

Asn Ser Arg Asp Ser Ser Gly Thr His Leu Thr Val
 1               5                  10


<210> SEQ ID NO 61
<211> LENGTH: 9
<212> TYPE: PRT
<213> ORGANISM: artificial sequence
<220> FEATURE:
<223> OTHER INFORMATION: synthetic polypeptide

<400> SEQUENCE: 61

Gln Gln Tyr Gly Ile Ser Pro Leu Thr
 1               5


<210> SEQ ID NO 62
<211> LENGTH: 8
<212> TYPE: PRT
```

<213> ORGANISM: artificial sequence
<220> FEATURE:
<223> OTHER INFORMATION: synthetic polypeptide

<400> SEQUENCE: 62

Trp Ser Gly Thr Ser Tyr Asp Tyr
1 5

<210> SEQ ID NO 63
<211> LENGTH: 245
<212> TYPE: PRT
<213> ORGANISM: artificial sequence
<220> FEATURE:
<223> OTHER INFORMATION: synthetic polypeptide

<400> SEQUENCE: 63

Gln Val Gln Leu Gln Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Val Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ile Glu Asp Thr Ala Val Tyr Tyr Cys
85 90 95

Gly Arg His Leu Ser Ser Gly Ser Ser Val Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Ser Glu Leu Thr Gln Pro Pro Ser Ala Ser
130 135 140

Gly Ser Pro Gly Gln Ser Val Thr Ile Ser Cys Thr Gly Thr Ser Ser
145 150 155 160

Asp Val Gly Gly Tyr Asn Tyr Val Ser Trp Tyr Gln Gln Arg Pro Gly
165 170 175

Tyr Ala Pro Lys Leu Met Ile Tyr Asp Val Ser Asn Arg Pro Ser Gly
180 185 190

Val Ser Asn Arg Phe Ser Gly Ser Lys Ser Gly Asn Ser Ala Ser Leu
195 200 205

Asp Ile Ser Gly Leu Gln Ser Glu Asp Glu Ala Asp Tyr Tyr Cys Ala
210 215 220

Ala Trp Asp Asp Ser Leu Arg Glu Phe Leu Phe Gly Thr Gly Thr Lys
225 230 235 240

Val Thr Val Leu Gly
245

<210> SEQ ID NO 64
<211> LENGTH: 735
<212> TYPE: DNA
<213> ORGANISM: artificial sequence
<220> FEATURE:
<223> OTHER INFORMATION: synthetic polynucleotide

<400> SEQUENCE: 64
caggtacagc tgcagcagtc aggggaggc ttggtccagc ctggggggtc cctgagactc 60

```
tcctgtgcag cctctggatt cacctttagc agctatgcca tgagctgggt ccgccaggct    120

ccagtgaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag aattgaggac acggctgtct attactgtgg gagacatctt    300

agtagcggct cgagcgttga ctactggggc cagggaaccc tggtcaccgt ctcctcaggt    360

ggaggcggtt caggcggagg tggctctggc ggtggcggat cgtctgagct gactcagcct    420

ccctccgcgt ccgggtctcc tggacagtca gtcaccatct cctgcactgg aaccagcagt    480

gacgttggtg gttataacta tgtctcctgg taccaacagc gcccaggcta cgccccccaaa    540

ctcatgattt atgatgtcag taatcggccc tcaggggttt ctaatcgctt ctctggctcc    600

aagtctggca actcagcctc cctggacatc agtgggctcc agtctgagga tgaggctgat    660

tactattgtg cagcatggga tgacagcctg cgtgaatttc tctttggaac tgggaccaag    720

gtcaccgtcc taggt                                                      735
```

<210> SEQ ID NO 65
<211> LENGTH: 5
<212> TYPE: PRT
<213> ORGANISM: artificial sequence
<220> FEATURE:
<223> OTHER INFORMATION: synthetic polypeptide

<400> SEQUENCE: 65

```
Thr Tyr Thr Met Ser
 1               5
```

<210> SEQ ID NO 66
<211> LENGTH: 4
<212> TYPE: PRT
<213> ORGANISM: artificial sequence
<220> FEATURE:
<223> OTHER INFORMATION: synthetic polypeptide

<400> SEQUENCE: 66

```
Gly Gly Ser Gly
 1
```

<210> SEQ ID NO 67
<211> LENGTH: 5
<212> TYPE: PRT
<213> ORGANISM: artificial sequence
<220> FEATURE:
<223> OTHER INFORMATION: synthetic polypeptide

<400> SEQUENCE: 67

```
Gly Gly Ser Gly Gly
 1               5
```

<210> SEQ ID NO 68
<211> LENGTH: 5
<212> TYPE: PRT
<213> ORGANISM: artificial sequence
<220> FEATURE:
<223> OTHER INFORMATION: synthetic polypeptide

<400> SEQUENCE: 68

```
Gly Ser Gly Ser Gly
 1               5
```

<210> SEQ ID NO 69
<211> LENGTH: 5

<212> TYPE: PRT
<213> ORGANISM: artificial sequence
<220> FEATURE:
<223> OTHER INFORMATION: synthetic polypeptide

<400> SEQUENCE: 69

Gly Ser Gly Gly Gly
1 5

<210> SEQ ID NO 70
<211> LENGTH: 15
<212> TYPE: PRT
<213> ORGANISM: artificial sequence
<220> FEATURE:
<223> OTHER INFORMATION: synthetic polypeptide

<400> SEQUENCE: 70

Trp Tyr Gln Gln Lys Pro Gly Gln Ala Pro Val Leu Val Ile Tyr
1 5 10 15

<210> SEQ ID NO 71
<211> LENGTH: 7
<212> TYPE: PRT
<213> ORGANISM: artificial sequence
<220> FEATURE:
<223> OTHER INFORMATION: synthetic polypeptide

<400> SEQUENCE: 71

Gly Glu Asn Asn Arg Pro Ser
1 5

<210> SEQ ID NO 72
<211> LENGTH: 247
<212> TYPE: PRT
<213> ORGANISM: artificial sequence
<220> FEATURE:
<223> OTHER INFORMATION: synthetic polypeptide

<400> SEQUENCE: 72

Gln Val Asn Leu Arg Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Val Ile Ser Asp Gly Ser Thr Thr Tyr Tyr Ala Asp Ser Val Lys
50 55 60

Gly Arg Phe Thr Ile Ser Arg Asp Asn Ser Lys Asn Met Leu Tyr Leu
65 70 75 80

Gln Thr Asn Ser Leu Arg Ala Glu Asp Thr Ala Val Tyr Tyr Cys Ala
85 90 95

Lys Ala Gly Pro Arg Thr Thr Val Thr Thr Val Asp Ser Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gln Ser Val Leu Thr Gln Pro Pro Ser
130 135 140

Val Ser Gly Ala Pro Gly Gln Arg Val Thr Ile Ser Cys Thr Gly Ser
145 150 155 160

Ser Ser Asn Ile Gly Ala Gly Tyr Asp Val His Trp Tyr Gln Gln Leu
165 170 175

```
Pro Gly Thr Ala Pro Lys Leu Leu Thr Tyr Gly Asn Ser Asn Arg Pro
            180                 185                 190

Ser Gly Val Pro Asp Arg Phe Ser Gly Ser Lys Ser Gly Thr Ser Ala
        195                 200                 205

Ser Leu Ala Ile Thr Gly Leu Gln Ala Glu Asp Glu Ala Asp Tyr Tyr
    210                 215                 220

Arg Ser Ala Trp Asp Ser Ser Leu Phe Asn Trp Val Phe Gly Gly Gly
225                 230                 235                 240

Thr Lys Leu Thr Val Leu Gly
                245
```

<210> SEQ ID NO 73
<211> LENGTH: 741
<212> TYPE: DNA
<213> ORGANISM: artificial sequence
<220> FEATURE:
<223> OTHER INFORMATION: synthetic polynucleotide

<400> SEQUENCE: 73

```
caggtcaact taagggagtc tgggggaggc ctggtcaagc ctgggggtc cctgagactc      60

tcctgtgcag cctctggatt cacctttagc agctatgcca tgagctgggt ccgccaggct     120

ccagggaagg ggctggagtg ggtctcagtc attagtgatg gtagtaccac atattacgca     180

gactccgtga agggccggtt caccatctcc agagacaatt ccaagaacat gctgtatctg     240

caaacgaaca gcctgagagc cgaggacacg gccgtatatt actgtgcgaa agccggccct     300

cgaactacag taactacggt tgactcctgg ggccagggaa ccctggtcac cgtctcctca     360

ggtggaggcg gttcaggcgg aggtggctct ggcggtggcg gatcgcagtc tgtgctgact     420

cagccgccct cagtgtctgg ggccccaggg cagagggtca ccatctcctg cactgggagc     480

agctccaaca tcggggcagg ttatgatgta cactggtacc agcagcttcc aggaacagcc     540

cccaaactcc tcacctatgg taacagcaat cggccctcag ggtccctga ccgattctct      600

ggctccaagt ctggcacctc agcctccctg gccatcactg ggctccaggc tgaggatgag     660

gctgactatt accgctcagc atgggacagc agcctcttta attgggtgtt cggcggaggg     720

accaagctga ccgtcctagg t                                               741
```

<210> SEQ ID NO 74
<211> LENGTH: 30
<212> TYPE: PRT
<213> ORGANISM: artificial sequence
<220> FEATURE:
<223> OTHER INFORMATION: synthetic polypeptide

<400> SEQUENCE: 74

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser
            20                  25                  30
```

<210> SEQ ID NO 75
<211> LENGTH: 11
<212> TYPE: PRT
<213> ORGANISM: artificial sequence
<220> FEATURE:
<223> OTHER INFORMATION: synthetic polypeptide

<400> SEQUENCE: 75

```
Arg Gly Gln Gly Thr Leu Val Thr Val Ser Ser
 1               5                  10
```

<210> SEQ ID NO 76
<211> LENGTH: 13
<212> TYPE: PRT
<213> ORGANISM: artificial sequence
<220> FEATURE:
<223> OTHER INFORMATION: synthetic polypeptide

<400> SEQUENCE: 76

Val Ile Ala Gly Gly Ala Tyr Tyr Gly Ser Ala Asp Tyr
1 5 10

<210> SEQ ID NO 77
<211> LENGTH: 15
<212> TYPE: PRT
<213> ORGANISM: artificial sequence
<220> FEATURE:
<223> OTHER INFORMATION: synthetic polypeptide

<400> SEQUENCE: 77

Trp Tyr Gln Gln Lys Pro Gly Gln Ala Pro Arg Leu Leu Ile Tyr
1 5 10 15

<210> SEQ ID NO 78
<211> LENGTH: 5
<212> TYPE: PRT
<213> ORGANISM: artificial sequence
<220> FEATURE:
<223> OTHER INFORMATION: synthetic polypeptide

<400> SEQUENCE: 78

Asn Tyr Ala Leu Ile
1 5

<210> SEQ ID NO 79
<211> LENGTH: 12
<212> TYPE: PRT
<213> ORGANISM: artificial sequence
<220> FEATURE:
<223> OTHER INFORMATION: synthetic polypeptide

<400> SEQUENCE: 79

His Ser Arg Asp Ser Ser Gly Thr His Leu Arg Val
1 5 10

<210> SEQ ID NO 80
<211> LENGTH: 11
<212> TYPE: PRT
<213> ORGANISM: artificial sequence
<220> FEATURE:
<223> OTHER INFORMATION: synthetic polypeptide

<400> SEQUENCE: 80

Phe Gly Gly Gly Thr Lys Val Thr Val Leu Gly
1 5 10

<210> SEQ ID NO 81
<211> LENGTH: 15
<212> TYPE: PRT
<213> ORGANISM: artificial sequence
<220> FEATURE:
<223> OTHER INFORMATION: synthetic polypeptide

<400> SEQUENCE: 81

Gly Gly Gly Gly Ser Gly Gly Gly Gly Ser Gly Gly Gly Gly Ser
1 5 10 15

<210> SEQ ID NO 82
<211> LENGTH: 17
<212> TYPE: PRT
<213> ORGANISM: artificial sequence
<220> FEATURE:
<223> OTHER INFORMATION: synthetic polypeptide

<400> SEQUENCE: 82

Ala Ile Ser Ala Asp Gly Ala Gly Thr Tyr Tyr Gly Asp Ser Val Lys
1 5 10 15

Gly

<210> SEQ ID NO 83
<211> LENGTH: 5
<212> TYPE: PRT
<213> ORGANISM: artificial sequence
<220> FEATURE:
<223> OTHER INFORMATION: synthetic polypeptide

<400> SEQUENCE: 83

Gly Ser Gly Gly Ser
1 5

<210> SEQ ID NO 84
<211> LENGTH: 11
<212> TYPE: PRT
<213> ORGANISM: artificial sequence
<220> FEATURE:
<223> OTHER INFORMATION: synthetic polypeptide

<400> SEQUENCE: 84

Phe Gly Gly Gly Thr Lys Val Glu Ile Lys Arg
1 5 10

<210> SEQ ID NO 85
<211> LENGTH: 243
<212> TYPE: PRT
<213> ORGANISM: artificial sequence
<220> FEATURE:
<223> OTHER INFORMATION: synthetic polypeptide

<400> SEQUENCE: 85

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Gly Trp Val Arg Gln Ala Pro Gly Lys Gly Leu Glu Trp Val
35 40 45

Ser Ala Ile Ser Ala Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Leu Asn Ser Leu Arg Ala Glu Asp Thr Ala Val Tyr Tyr Cys
85 90 95

Ala Lys Gly Leu Lys Asp Ser Ser Gly Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Asn Phe Met Leu Thr Gln Asp Pro Ala Val
130 135 140

Ser Val Ala Leu Gly Gln Thr Val Arg Ile Thr Cys Gln Gly Asp Ser 145 150 155 160

Leu Arg Ser Tyr Tyr Ala Ser Trp Tyr Gln Gln Lys Pro Gly Gln Ala
165 170 175

Pro Val Leu Val Ile Tyr Gly Lys Asn Asn Arg Pro Ser Gly Ile Pro
180 185 190

Asp Arg Phe Ser Gly Ser Ser Ser Gly Asn Thr Ala Ser Leu Thr Ile
195 200 205

Thr Gly Ala Gln Ala Glu Asp Glu Ala Asp Tyr Tyr Cys Asn Ser Arg
210 215 220

Asp Ser Ser Ala Lys Arg Val Val Phe Gly Gly Gly Thr Lys Val Thr
225 230 235 240

Val Leu Gly

<210> SEQ ID NO 86
<211> LENGTH: 729
<212> TYPE: DNA
<213> ORGANISM: artificial sequence
<220> FEATURE:
<223> OTHER INFORMATION: synthetic polynucleotide

<400> SEQUENCE: 86
caggtgcagc tggtggagtc tgggggaggc ttggtacagc caggggggtc cctgagactc 60
tcctgtgcag cctctggatt cacctttagc agctatgcca tgggctgggt ccgccaggct 120
ccagggaagg ggctggagtg ggtctcagct attagtgcta gtggtggtag cacatattac 180
gcagactccg tgaagggccg gttcaccatc tccagagaca attccaagaa cacgctgtat 240
ttgcaactga acagcctgag agccgaggac acggccgtat attactgtgc aaaaggattg 300
aaagatagta gtggttttga ctactggggc cagggaaccc tggtcactgt ctcctcaggt 360
ggaggcggtt caggcggagg tggctctggc ggtggcggat cgaattttat gctgactcag 420
gaccctgctg tgtctgtggc cttgggacag acagtcagga tcacatgcca aggagacagc 480
ctcagaagct attatgcaag ctggtaccag cagaagccag gacaggcccc tgtacttgtc 540
atctatggta aaaacaaccg gccctcaggg atcccagacc gattctctgg ctccagctca 600
ggaaacacag cttccttgac catcactggg gctcaggcgg aagatgaggc tgactattac 660
tgtaactccc gggacagcag tgccaaacgg gtggtattcg gcggagggac caaggtcacc 720
gtcctaggt 729

<210> SEQ ID NO 87
<211> LENGTH: 4
<212> TYPE: PRT
<213> ORGANISM: artificial sequence
<220> FEATURE:
<223> OTHER INFORMATION: synthetic polypeptide

<400> SEQUENCE: 87

Gly Gly Gly Ser
1

<210> SEQ ID NO 88
<211> LENGTH: 5
<212> TYPE: PRT
<213> ORGANISM: artificial sequence
<220> FEATURE:
<223> OTHER INFORMATION: synthetic polypeptide

<400> SEQUENCE: 88

Gly Gly Gly Ser Gly 1 5

<210> SEQ ID NO 89
<211> LENGTH: 5
<212> TYPE: PRT
<213> ORGANISM: artificial sequence
<220> FEATURE:
<223> OTHER INFORMATION: synthetic polypeptide

<400> SEQUENCE: 89

Gly Ser Ser Ser Gly
1 5

<210> SEQ ID NO 90
<211> LENGTH: 248
<212> TYPE: PRT
<213> ORGANISM: artificial sequence
<220> FEATURE:
<223> OTHER INFORMATION: synthetic polypeptide

<400> SEQUENCE: 90

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Tyr Gly Tyr Cys Ser Gly Gly Ser Cys Tyr Ser Pro Phe
100 105 110

Asp Tyr Trp Gly Gln Gly Thr Leu Val Thr Val Ser Ser Gly Gly Gly
115 120 125

Gly Ser Gly Gly Gly Gly Ser Gly Gly Gly Gly Ser Asn Phe Met Leu
130 135 140

Thr Gln Asp Pro Ala Val Ser Val Ala Leu Gly Gln Thr Val Arg Ile
145 150 155 160

Thr Cys Gln Gly Asp Ser Leu Arg Ser Tyr Tyr Ala Ser Trp Tyr Gln
165 170 175

Gln Lys Pro Gly Gln Ala Pro Val Leu Val Ile Tyr Gly Lys Asn Asn
180 185 190

Arg Pro Ser Gly Ile Pro Asp Arg Phe Ser Gly Ser Ser Ser Gly Asn
195 200 205

Thr Ala Ser Leu Thr Ile Thr Gly Ala Gln Ala Glu Asp Glu Ala Asp
210 215 220

Tyr Tyr Cys His Ser Arg Asp Ser Ser Gly Asn Tyr Leu Phe Gly Gly
225 230 235 240

Gly Thr Lys Leu Thr Val Leu Gly
245

<210> SEQ ID NO 91
<211> LENGTH: 744
<212> TYPE: DNA
<213> ORGANISM: artificial sequence
<220> FEATURE:

<223> OTHER INFORMATION: synthetic polynucleotide

<400> SEQUENCE: 91

```
caggtgcagc tggtggagtc tgggggaggc gtggtccagc ctgggaggtc cctgagactc      60

tcctgtgcag cctctggatt caccttcagt agctatggca tgcactgggt ccgccaggct     120

ccaggcaagg ggctggagtg ggtggcagtt atatcatatg atggaagtaa taaatactat     180

gcagactccg tgaagggccg attcaccatc tccagagaca attccaagaa cacgctgtat     240

ctgcaaatga acagcctgag agctgaggac acggctgtgt attactgtgc gaaagattat     300

ggctattgta gtggtggtag ctgctactcg ccctttgact actggggcca gggcaccctg     360

gtcaccgtct cctcaggtgg aggcggttca ggcggaggtg gctctggcgg tggcggatcg     420

aattttatgc tgactcagga ccctgctgtg tctgtggcct tgggacagac agtcaggatc     480

acatgccaag gagacagcct cagaagctat tatgcaagct ggtaccagca gaagccagga     540

caggcccctg tacttgtcat ctatggtaaa aacaaccggc cctcagggat cccagaccgg     600

ttctctggct ccagctcagg aaacacagct tccttgacca tcactggggc tcaggcggaa     660

gatgaggctg actattactg tcactcccgg gacagcagtg gtaactatct cttcggaggt     720

gggaccaagc tgaccgtcct aggt                                            744
```

<210> SEQ ID NO 92
<211> LENGTH: 245
<212> TYPE: PRT
<213> ORGANISM: artificial sequence
<220> FEATURE:
<223> OTHER INFORMATION: synthetic polypeptide

<400> SEQUENCE: 92

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Arg Ile Ala Ala Arg Pro Gly Pro Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Ser Glu Leu Thr Gln Asp Pro
    130                 135                 140

Ala Val Ser Val Ala Val Gly Gln Thr Val Lys Ile Thr Cys Gln Gly
145                 150                 155                 160

Asp Ser Leu Arg Asn Tyr Tyr Ala Ser Trp Tyr Gln Gln Lys Pro Arg
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Asn Thr Ala Ser Leu
        195                 200                 205
```

```
Thr Ile Thr Gly Ala Gln Ala Glu Asp Glu Ala Asp Tyr Tyr Cys Asn
    210                 215                 220

Ser Arg Asp Arg Ser Asn Asn His Leu Leu Phe Gly Gly Gly Thr Lys
225                 230                 235                 240

Leu Thr Val Leu Gly
                245
```

<210> SEQ ID NO 93
<211> LENGTH: 735
<212> TYPE: DNA
<213> ORGANISM: artificial sequence
<220> FEATURE:
<223> OTHER INFORMATION: synthetic polynucleotide

<400> SEQUENCE: 93

```
caggtgcagc tggtgcagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agctgaggac acggctgtgt attactgtgc gaaagcagcc     300

aggatagcag ctcgtcctgg accccttgac tactggggcc agggaaccct ggtcaccgtc     360

tcctcaggtg gaggcggttc aggcggaggt ggctctggcg gtggcggatc gtctgagctg     420

actcaggacc ctgctgtgtc tgtggccgtg ggacagacag tcaagatcac atgccaagga     480

gacagcctca gaaactatta tgcaagctgg taccagcaga agccaagaca ggcccctgta     540

cttgtcatct atggtaaaaa caaccggccc tcagggatcc cagaccgatt ctctggctcc     600

agctcaggaa acacagcttc cttgaccatc actggggctc aggcggaaga tgaggctgac     660

tattactgta actcccggga cagaagtaat aaccatctac tattcggcgg agggaccaag     720

ctgaccgtcc taggt                                                      735
```

<210> SEQ ID NO 94
<211> LENGTH: 7
<212> TYPE: PRT
<213> ORGANISM: artificial sequence
<220> FEATURE:
<223> OTHER INFORMATION: synthetic polypeptide

<400> SEQUENCE: 94

```
Val Asn Ser Asn Arg Pro Ser
 1               5
```

<210> SEQ ID NO 95
<211> LENGTH: 32
<212> TYPE: PRT
<213> ORGANISM: artificial sequence
<220> FEATURE:
<223> OTHER INFORMATION: synthetic polypeptide

<400> SEQUENCE: 95

```
Gly Val Pro Asp Arg Phe Ser Gly Ser Lys Ser Gly Thr Ser Ala Ser
 1               5                  10                  15

Leu Ala Ile Thr Gly Leu Gln Ala Glu Asp Glu Ala Asp Tyr Tyr Cys
            20                  25                  30
```

<210> SEQ ID NO 96
<211> LENGTH: 119
<212> TYPE: PRT
<213> ORGANISM: artificial sequence
<220> FEATURE:
<223> OTHER INFORMATION: synthetic polypeptide

<400> SEQUENCE: 96

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Leu His Gly Pro Phe Tyr Phe Asp Tyr Trp Gly Gln Gly
            100                 105                 110

Thr Leu Val Thr Val Ser Ser
        115
```

<210> SEQ ID NO 97
<211> LENGTH: 113
<212> TYPE: PRT
<213> ORGANISM: artificial sequence
<220> FEATURE:
<223> OTHER INFORMATION: synthetic polypeptide

<400> SEQUENCE: 97

```
Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Arg Met His Trp Val Arg Gln Ala Pro Gly Lys Gly Leu Glu Trp Val
        35                  40                  45

Ala Ala Val Lys Gln Asp Gly Ser Glu Lys Tyr Tyr Leu Asp Ser Val
    50                  55                  60

Lys Gly Arg Phe Thr Ile Ser Arg Asp Asn Ala Lys Ser Ser Leu Tyr
65                  70                  75                  80

Leu Gln Met Asp Ser Leu Ser Val Glu Asp Thr Ala Val Tyr Tyr Cys
                85                  90                  95

Ala Arg Gly Leu Arg Thr Met Gly Gln Gly Thr Leu Val Thr Val Ser
            100                 105                 110

Ser
```

<210> SEQ ID NO 98
<211> LENGTH: 108
<212> TYPE: PRT
<213> ORGANISM: artificial sequence
<220> FEATURE:
<223> OTHER INFORMATION: synthetic polypeptide

<400> SEQUENCE: 98

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Leu Leu Val Ile Tyr Gly
```

```
        35                  40                  45

Lys Asn Ile Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Leu Gly
            100                 105


<210> SEQ ID NO 99
<211> LENGTH: 107
<212> TYPE: PRT
<213> ORGANISM: artificial sequence
<220> FEATURE:
<223> OTHER INFORMATION: synthetic polypeptide

<400> SEQUENCE: 99

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
            20                  25                  30

Trp Tyr Gln Arg Lys Pro Gly Gln Ala Pro Leu Leu Val Ile Tyr Gly
        35                  40                  45

Lys Asn Ile Arg Pro Ser Gly Ile Pro Asp Arg Phe Ser Gly Ser Ser
    50                  55                  60

Ser Gly Asn Thr Ala Ser Leu Ile Ile Thr Gly Ala Gln Ala Glu Asp
65                  70                  75                  80

Glu Ala Asp Tyr Tyr Cys Asn Ser Arg Asp Ser Ser Ala Asn Gln Met
                85                  90                  95

Phe Gly Gly Gly Thr Lys Leu Thr Val Leu Gly
            100                 105


<210> SEQ ID NO 100
<211> LENGTH: 116
<212> TYPE: PRT
<213> ORGANISM: artificial sequence
<220> FEATURE:
<223> OTHER INFORMATION: synthetic polypeptide

<400> SEQUENCE: 100

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Asp Trp Val
        35                  40                  45

Ser Ile Ile Tyr Asn Gly Asp Asn Thr Tyr Tyr Ala Asp Ser Val Lys
    50                  55                  60

Gly Arg Phe Thr Ile Ser Arg Asp Asn Ser Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Trp Ser Gly Thr Ser Tyr Asp Tyr Trp Gly Gln Gly Thr Leu Val
            100                 105                 110

Thr Val Ser Ser
        115
```

<210> SEQ ID NO 101
<211> LENGTH: 120
<212> TYPE: PRT
<213> ORGANISM: artificial sequence
<220> FEATURE:
<223> OTHER INFORMATION: synthetic polypeptide

<400> SEQUENCE: 101

Gln Val Gln Leu Gln Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ala Ser Val Gly Ala Thr Gly Pro Phe Asp Ile Trp Gly Gln
100 105 110

Gly Thr Met Val Thr Val Ser Ser
115 120

<210> SEQ ID NO 102
<211> LENGTH: 116
<212> TYPE: PRT
<213> ORGANISM: artificial sequence
<220> FEATURE:
<223> OTHER INFORMATION: synthetic polypeptide

<400> SEQUENCE: 102

Gln Val Gln Leu Val Glu Ser Gly Gly Gly Leu Ile Gln Pro Gly Gly
1 5 10 15

Ser Leu Lys Leu Ser Cys Ala Ala Ser Gly Phe Thr Val Ser Asn Ser
20 25 30

Tyr Met Ser Trp Val Arg Gln Ala Pro Gly Lys Gly Leu Glu Trp Val
35 40 45

Ala Val Ile Tyr Ser Ala Gly Asn Thr Tyr Tyr Ala Asp Ser Val Lys
50 55 60

Gly Arg Phe Thr Ile Ser Arg Asp Thr Ser Asn Asn Thr Val His Leu
65 70 75 80

Gln Met Asn Ser Leu Arg Pro Glu Asp Thr Ala Val Tyr Tyr Cys Ala
85 90 95

Arg Glu Gly Ser Phe Gly Tyr Asp Tyr Arg Gly Gln Gly Thr Leu Val
100 105 110

Thr Val Ser Ser
115

<210> SEQ ID NO 103
<211> LENGTH: 122
<212> TYPE: PRT
<213> ORGANISM: artificial sequence
<220> FEATURE:
<223> OTHER INFORMATION: synthetic polypeptide

<400> SEQUENCE: 103

Gln Val Gln Leu Gln Glu Ser Gly Gly Gly Val Val Gln Pro Gly Arg

```
 1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Gly Gly Ala Tyr Tyr Gly Ser Ala Asp Tyr Trp
            100                 105                 110

Gly Gln Gly Thr Leu Val Thr Val Ser Ser
        115                 120


<210> SEQ ID NO 104
<211> LENGTH: 109
<212> TYPE: PRT
<213> ORGANISM: artificial sequence
<220> FEATURE:
<223> OTHER INFORMATION: synthetic polypeptide

<400> SEQUENCE: 104

Ser Glu Leu Thr Gln Asp Pro Ala Val Ser Val Ala Leu Gly Gln Thr
 1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Leu Leu Val Ile Tyr Gly
        35                  40                  45

Glu Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys His Ser Arg Asp Ser Ser Gly Thr His Leu
                85                  90                  95

Arg Val Phe Gly Gly Gly Thr Lys Val Thr Val Leu Gly
            100                 105


<210> SEQ ID NO 105
<211> LENGTH: 109
<212> TYPE: PRT
<213> ORGANISM: artificial sequence
<220> FEATURE:
<223> OTHER INFORMATION: synthetic polypeptide

<400> SEQUENCE: 105

Ser Glu Leu Thr Gln Asp Pro Ala Val Ser Val Ala Leu Gly Gln Thr
 1               5                   10                  15

Val Ser Ile Thr Cys Gln Gly Asp Ser Leu Arg Ser Tyr Tyr Ala Ser
            20                  25                  30

Trp Tyr Gln Gln Lys Pro Gly Gln Ala Pro Leu Leu Val Ile Tyr Gly
        35                  40                  45

Glu Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80
```

Glu Ala Asp Tyr Tyr Cys Asn Ser Arg Asp Ser Ser Gly Thr His Leu
                 85                  90                  95

Thr Val Phe Gly Gly Gly Thr Lys Leu Thr Val Leu Gly
            100                 105

<210> SEQ ID NO 106
<211> LENGTH: 109
<212> TYPE: PRT
<213> ORGANISM: artificial sequence
<220> FEATURE:
<223> OTHER INFORMATION: synthetic polypeptide

<400> SEQUENCE: 106

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Phe Leu Gly Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ile Ser Pro
                85                  90                  95

Leu Thr Phe Gly Gly Gly Thr Lys Val Glu Ile Lys Arg
            100                 105

<210> SEQ ID NO 107
<211> LENGTH: 109
<212> TYPE: PRT
<213> ORGANISM: artificial sequence
<220> FEATURE:
<223> OTHER INFORMATION: synthetic polypeptide

<400> SEQUENCE: 107

Ser Glu Leu Thr Gln Asp Pro Ala Val Ser Val Ala Leu Gly Gln Thr
1               5                   10                  15

Val Lys Ile Thr Cys Gln Gly Asp Ser Leu Arg Thr Tyr Tyr Ala Ser
                20                  25                  30

Trp Tyr Gln Gln Lys Pro Gly Gln Ala Pro Val Leu Val Ile Tyr Gly
            35                  40                  45

Glu Asn Ser Arg Pro Ser Gly Ile Pro Asp Arg Phe Ser Gly Ser Ser
        50                  55                  60

Ser Gly Asn Thr Ala Ser Leu Thr Ile Thr Gly Ala Gln Ala Glu Asp
65                  70                  75                  80

Glu Ala Asp Tyr Tyr Cys His Ser Arg Asp Ser Ser Gly Thr His Leu
                85                  90                  95

Arg Val Phe Gly Gly Gly Thr Lys Leu Thr Val Leu Gly
            100                 105

<210> SEQ ID NO 108
<211> LENGTH: 720
<212> TYPE: DNA
<213> ORGANISM: artificial sequence
<220> FEATURE:
<223> OTHER INFORMATION: synthetic polynucleotide

<400> SEQUENCE: 108
caggtgcagc tgcaggagtc ggggggaggc ttggtacagc ctggggggtc cctgagactc       60

```
tcctgtgcag cctctggatt cacctttagc agctatgcca tgagctgggt ccgccaggct    120

ccagggaagg ggctggactg ggtctcaatt atttataacg gggataacac atactacgca    180

gactccgtga agggccgatt caccatctcc agagacaatt ccaagaactc actgtatctt    240

caaatgaaca gcctgagagc cgaggacacg gccgtctatt actgtgcgag atggagtggg    300

acctcctacg actactgggg ccagggcacc ctggtcaccg tctcctcagg tggaggcggt    360

tcaggcggag gtggctctgg cggtggcgga tcgtctgagc tgactcagga ccctgctgtg    420

tctgtggcct tgggacagac agtcaggatc acatgccaag gagacagtct cagaagttat    480

tatgcaagct ggtaccagca gaagccagga caggcccctc tacttgtcat ctatggtgaa    540

aacaaccggc cctcagggat cccagaccga ttctctggct ccagctcagg aaacacagct    600

tccttgacca tcactggggc tcaggcggaa gatgaggctg actattactg tcactcccgg    660

gacagcagtg gtacccatct aagggtgttc ggcggaggga ccaaggtcac cgtcctaggt    720
```

```
<210> SEQ ID NO 109
<211> LENGTH: 720
<212> TYPE: DNA
<213> ORGANISM: artificial sequence
<220> FEATURE:
<223> OTHER INFORMATION: synthetic polynucleotide

<400> SEQUENCE: 109

gtccacgtcg acgtcctcag ccccccctccg aaccatgtcg gaccccccag ggactctgag     60

aggacacgtc ggagacctaa gtggaaatcg tcgatacggt actcgaccca ggcggtccga    120

ggtcccttcc ccgacctgac ccagagttaa taaatattgc ccctattgtg tatgatgcgt    180

ctgaggcact tcccggctaa gtggtagagg tctctgttaa ggttcttgag tgacatagaa    240

gtttacttgt cggactctcg gctcctgtgc cggcagataa tgacacgctc tacctcaccc    300

tggaggatgc tgatgacccc ggtcccgtgg gaccagtggc agaggagtcc acctccgcca    360

agtccgcctc caccgagacc gccaccgcct agcagactcg actgagtcct gggacgacac    420

agacaccgga accctgtctg tcagtcctag tgtacggttc ctctgtcaga gtcttcaata    480

atacgttcga ccatggtcgt cttcggtcct gtccggggag atgaacagta gataccactt    540

ttgttggccg ggagtcccta gggtctggct aagagaccga ggtcgagtcc tttgtgtcga    600

aggaactggt agtgaccccg agtccgcctt ctactccgac tgataatgac agtgagggcc    660

ctgtcgtcac catgggtaga ttcccacaag ccgcctccct ggttccagtg gcaggatcca    720
```

```
<210> SEQ ID NO 110
<211> LENGTH: 240
<212> TYPE: PRT
<213> ORGANISM: artificial sequence
<220> FEATURE:
<223> OTHER INFORMATION: synthetic polypeptide

<400> SEQUENCE: 110

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Asp Trp Val
        35                  40                  45

Ser Ile Ile Tyr Asn Gly Asp Asn Thr Tyr Tyr Ala Asp Ser Val Lys
    50                  55                  60
```

-continued

```
Gly Arg Phe Thr Ile Ser Arg Asp Asn Ser Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Trp Ser Gly Thr Ser Tyr Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Glu Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys His Ser Arg Asp Ser Ser Gly
    210                 215                 220

Thr His Leu Arg Val Phe Gly Gly Gly Thr Lys Val Thr Val Leu Gly
225                 230                 235                 240
```

<210> SEQ ID NO 111
<211> LENGTH: 732
<212> TYPE: DNA
<213> ORGANISM: artificial sequence
<220> FEATURE:
<223> OTHER INFORMATION: synthetic polynucleotide

<400> SEQUENCE: 111

```
caggtacagc tgcagcagtc aggggaggc gtggtccagc ctgggaggtc cctgagactc      60

tcctgtgcag cctctggatt caccttcagt agctatgcta tgcactgggt ccgccaggct    120

ccaggcaagg ggctggagtg ggtggcagtt atatcatatg atggaagcaa taaatactac    180

gcagactccg tgaagggccg attcaccatc tccagagaca attccaagaa cacgctgtat    240

ctgcaaatga acagcctgag agctgaggac acggctgtgt attactgtgc gagagctagc    300

gtcggggcta cggggccttt tgatatctgg ggccaaggga caatggtcac cgtctcttca    360

ggtggaggcg gttcaggcgg aggtggctct ggcggtggcg gatcgtctga gctgactcag    420

gaccctgctg tgtctgtggc cttgggacag acagtcagca tcacatgcca aggagacagc    480

ctcagaagct attatgcaag ctggtaccag cagaagccag gacaggcccc tctacttgtc    540

atctatggtg aaaacaaccg gccctcaggg atcccagacc gattttctgg ctccagctca    600

ggaaacacag cttccttgac catcactggg gctcaggcgg aagatgaggc tgactattac    660

tgtaactccc gggacagcag tggtacgcat ttgacggtgt tcggcggagg gaccaagctg    720

accgtcctag gt                                                         732
```

<210> SEQ ID NO 112
<211> LENGTH: 732
<212> TYPE: DNA
<213> ORGANISM: artificial sequence
<220> FEATURE:
<223> OTHER INFORMATION: synthetic polynucleotide

<400> SEQUENCE: 112

```
gtccatgtcg acgtcgtcag tccccctccg caccaggtcg gaccctccag ggactctgag     60

aggacacgtc ggagacctaa gtggaagtca tcgatacgat acgtgaccca ggcggtccga    120

ggtccgttcc ccgacctcac ccaccgtcaa tatagtatac taccttcgtt atttatgatg    180

cgtctgaggc acttcccggc taagtggtag aggtctctgt taaggttctt gtgcgacata    240

gacgtttact tgtcggactc tcgactcctg tgccgacaca taatgacacg ctctcgatcg    300

cagccccgat gccccggaaa actatagacc ccggttccct gttaccagtg gcagagaagt    360

ccacctccgc caagtccgcc tccaccgaga ccgccaccgc ctagcagact cgactgagtc    420

ctgggacgac acagacaccg gaaccctgtc tgtcagtcgt agtgtacggt tcctctgtcg    480

gagtcttcga taatacgttc gaccatggtc gtcttcggtc ctgtccgggg agatgaacag    540

tagataccac ttttgttggc cgggagtccc tagggtctgg ctaaaagacc gaggtcgagt    600

cctttgtgtc gaaggaactg gtagtgaccc cgagtccgcc ttctactccg actgataatg    660

acattgaggg ccctgtcgtc accatgcgta aactgccaca agccgcctcc ctggttcgac    720

tggcaggatc ca                                                         732
```

<210> SEQ ID NO 113
<211> LENGTH: 244
<212> TYPE: PRT
<213> ORGANISM: artificial sequence
<220> FEATURE:
<223> OTHER INFORMATION: synthetic polypeptide

<400> SEQUENCE: 113

```
Gln Val Gln Leu Gln Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Val Gly Ala Thr Gly Pro Phe Asp Ile Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Ser Glu Leu Thr Gln Asp Pro Ala Val
    130                 135                 140

Ser Val Ala Leu Gly Gln Thr Val Ser Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Leu Leu Val Ile Tyr Gly Glu Asn Asn Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Cys Asn Ser Arg
    210                 215                 220

Asp Ser Ser Gly Thr His Leu Thr Val Phe Gly Gly Gly Thr Lys Leu
```

225 230 235 240

Thr Val Leu Gly

<210> SEQ ID NO 114
<211> LENGTH: 720
<212> TYPE: DNA
<213> ORGANISM: artificial sequence
<220> FEATURE:
<223> OTHER INFORMATION: synthetic polynucleotide

<400> SEQUENCE: 114
caggtgcagc tggtggagtc tggaggaggc ttgatccagc ctggggggtc cctgaaactc 60
tcctgtgcag cctctgggtt caccgtcagt aacagctaca tgagctgggt ccgccaggct 120
ccagggaagg ggctggagtg ggtcgcagtt atttatagcg ctggtaacac atactacgca 180
gactccgtga agggccgatt caccatctcc agagacactt ccaacaacac ggtgcatctt 240
caaatgaaca gcctgagacc cgaagacacg gccgtgtatt actgtgcgag agagggcagc 300
tttggttacg actacagggg ccagggaacc ctggtcaccg tctcctcagg tggaggcggt 360
tcaggcggag gtggctctgg cggtggcgga tcggacatcg tgatgaccca gtctccaggc 420
accctgtctt tgtctccagg ggaaagagcc accctctcct gcagggccag tcagagtgtt 480
agcagcagct tcttaggctg gtaccaacag aaacctggcc aggctcccag gctcctcatc 540
tatggtgcat ccagcagggc cactggcatc ccagacaggt tcagtggcag tgggtctggg 600
acagacttca ctctcaccat cagcagactg gagcctgaag attttgcagt gtattactgt 660
cagcagtatg gtatctcacc gctcactttc ggcggaggga ccaaggtgga aatcaaacgt 720

<210> SEQ ID NO 115
<211> LENGTH: 720
<212> TYPE: DNA
<213> ORGANISM: artificial sequence
<220> FEATURE:
<223> OTHER INFORMATION: synthetic polynucleotide

<400> SEQUENCE: 115
gtccacgtcg accacctcag acctcctccg aactaggtcg gacccccag ggactttgag 60 aggacacgtc ggagacccaa gtggcagtca ttgtcgatgt actcgaccca ggcggtccga 120
ggtcccttcc ccgacctcac ccagcgtcaa taaatatcgc gaccattgtg tatgatgcgt 180
ctgaggcact tcccggctaa gtggtagagg tctctgtgaa ggttgttgtg ccacgtagaa 240
gtttacttgt cggactctgg gcttctgtgc cggcacataa tgacacgctc tctcccgtcg 300
aaaccaatgc tgatgtcccc ggtcccttgg gaccagtggc agaggagtcc acctccgcca 360
agtccgcctc caccgagacc gccaccgcct agcctgtagc actactgggt cagaggtccg 420
tgggacagaa acagaggtcc cctttctcgg tgggagagga cgtcccggtc agtctcacaa 480
tcgtcgtcga agaatccgac catggttgtc tttggaccgg tccgagggtc cgaggagtag 540
ataccacgta ggtcgtcccg gtgaccgtag ggtctgtcca agtcaccgtc acccagaccc 600
tgtctgaagt gagagtggta gtcgtctgac ctcggacttc taaaacgtca cataatgaca 660
gtcgtcatac catagagtgg cgagtgaaag ccgcctccct ggttccacct ttagtttgca 720

<210> SEQ ID NO 116
<211> LENGTH: 240
<212> TYPE: PRT
<213> ORGANISM: artificial sequence
<220> FEATURE:
<223> OTHER INFORMATION: synthetic polypeptide

<400> SEQUENCE: 116

```
Gln Val Gln Leu Val Glu Ser Gly Gly Gly Leu Ile Gln Pro Gly Gly
 1               5                  10                  15

Ser Leu Lys Leu Ser Cys Ala Ala Ser Gly Phe Thr Val Ser Asn Ser
            20                  25                  30

Tyr Met Ser Trp Val Arg Gln Ala Pro Gly Lys Gly Leu Glu Trp Val
        35                  40                  45

Ala Val Ile Tyr Ser Ala Gly Asn Thr Tyr Tyr Ala Asp Ser Val Lys
    50                  55                  60

Gly Arg Phe Thr Ile Ser Arg Asp Thr Ser Asn Asn Thr Val His Leu
65                  70                  75                  80

Gln Met Asn Ser Leu Arg Pro Glu Asp Thr Ala Val Tyr Tyr Cys Ala
                85                  90                  95

Arg Glu Gly Ser Phe Gly Tyr Asp Tyr Arg Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asp Ile Val Met Thr Gln Ser Pro Gly Thr Leu Ser Leu
    130                 135                 140

Ser Pro Gly Glu Arg Ala Thr Leu Ser Cys Arg Ala Ser Gln Ser Val
145                 150                 155                 160

Ser Ser Ser Phe Leu Gly Trp Tyr Gln Gln Lys Pro Gly Gln Ala Pro
                165                 170                 175

Arg Leu Leu Ile Tyr Gly Ala Ser Ser Arg Ala Thr Gly Ile Pro Asp
            180                 185                 190

Arg Phe Ser Gly Ser Gly Ser Gly Thr Asp Phe Thr Leu Thr Ile Ser
        195                 200                 205

Arg Leu Glu Pro Glu Asp Phe Ala Val Tyr Tyr Cys Gln Gln Tyr Gly
    210                 215                 220

Ile Ser Pro Leu Thr Phe Gly Gly Gly Thr Lys Val Glu Ile Lys Arg
225                 230                 235                 240
```

<210> SEQ ID NO 117
<211> LENGTH: 738
<212> TYPE: DNA
<213> ORGANISM: artificial sequence
<220> FEATURE:
<223> OTHER INFORMATION: synthetic polynucleotide

<400> SEQUENCE: 117

```
caggtgcagc tgcaggagtc gggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaaagtaata    300

gcggggggg cttactatgg ttcagctgac tactggggcc agggaaccct ggtcaccgtc    360

tcctcaggtg gaggcggttc aggcggaggt ggctctggcg gtggcggatc gtctgagctg    420

actcaggacc ctgctgtgtc tgtggccttg ggacagacag tcaagatcac atgccaagga    480

gacagcctca gaacctatta tgcaagctgg taccagcaga agccaggaca ggcccctgta    540

cttgtcatct atggtgaaaa cagccggccc tccgggatcc cagaccgatt ctctggctcc    600

agctcaggaa acacagcttc cttgaccatc actggggctc aggcggaaga tgaggctgac    660
```

```
tattactgtc actcccggga cagcagtggt acccatctaa gggtgttcgg cggagggacc    720

aagctgaccg tcctaggt                                                  738


<210> SEQ ID NO 118
<211> LENGTH: 738
<212> TYPE: DNA
<213> ORGANISM: artificial sequence
<220> FEATURE:
<223> OTHER INFORMATION: synthetic polynucleotide

<400> SEQUENCE: 118

gtccacgtcg acgtcctcag ccccctccg caccaggtcg gaccctccag ggactctgag      60

aggacacgtc ggagacctaa gtggaagtca tcgataccgt acgtgaccca ggcggtccga    120

ggtccgttcc ccgacctcac ccaccgtcaa tatagtatac taccttcatt atttatgata    180

cgtctgaggc acttcccggc taagtggtag aggtctctgt taaggttctt gtgcgacata    240

gacgtttact tgtcggactc tcgactcctg tgccgacaca taatgacacg ctttcattat    300

cgcccccccc gaatgatacc aagtcgactg atgaccccgg tcccttggga ccagtggcag    360

aggagtccac ctccgccaag tccgcctcca ccgagaccgc caccgcctag cagactcgac    420

tgagtcctgg gacgacacag acaccggaac cctgtctgtc agttctagtg tacggttcct    480

ctgtcggagt cttggataat acgttcgacc atggtcgtct tcggtcctgt ccggggacat    540

gaacagtaga taccactttt gtcggccggg aggccctagg gtctggctaa gagaccgagg    600

tcgagtcctt tgtgtcgaag gaactggtag tgaccccgag tccgccttct actccgactg    660

ataatgacag tgagggccct gtcgtcacca tgggtagatt cccacaagcc gcctccctgg    720

ttcgactggc aggatcca                                                  738


<210> SEQ ID NO 119
<211> LENGTH: 246
<212> TYPE: PRT
<213> ORGANISM: artificial sequence
<220> FEATURE:
<223> OTHER INFORMATION: synthetic polypeptide

<400> SEQUENCE: 119

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Gly Gly Ala Tyr Tyr Gly Ser Ala Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Ser Glu Leu Thr Gln Asp Pro
    130                 135                 140

Ala Val Ser Val Ala Leu Gly Gln Thr Val Lys Ile Thr Cys Gln Gly
```

```
145                 150                 155                 160

Asp Ser Leu Arg Thr Tyr Tyr Ala Ser Trp Tyr Gln Gln Lys Pro Gly
                165                 170                 175

Gln Ala Pro Val Leu Val Ile Tyr Gly Glu Asn Ser Arg Pro Ser Gly
            180                 185                 190

Ile Pro Asp Arg Phe Ser Gly Ser Ser Ser Gly Asn Thr Ala Ser Leu
        195                 200                 205

Thr Ile Thr Gly Ala Gln Ala Glu Asp Glu Ala Asp Tyr Tyr Cys His
    210                 215                 220

Ser Arg Asp Ser Ser Gly Thr His Leu Arg Val Phe Gly Gly Gly Thr
225                 230                 235                 240

Lys Leu Thr Val Leu Gly
                245
```

<210> SEQ ID NO 120
<211> LENGTH: 726
<212> TYPE: DNA
<213> ORGANISM: artificial sequence
<220> FEATURE:
<223> OTHER INFORMATION: synthetic polynucleotide

<400> SEQUENCE: 120

```
caggtgcagc tggtgcagtc tggggcagag gtgaaaaagc ccggggagtc tctgaagatc     60

tcctgtaagg gttctggata cagctttacc agttactgga tcggctgggt gcgccagatg    120

cccgggaaag gcctggagtg gatggggatc atctatcctg gtgactctga taccagatac    180

agcccgtcct tccaaggcca ggtcaccatc tcagccgaca agtccatcag caccgcctac    240

ctgcagtgga gcagcctcaa ggcctcggac accgccatgt attactgtgc gaggcgacta    300

cacggacctt tctactttga ctactggggc cagggaaccc tggtcaccgt ctcctcaggt    360

ggaggcggtt caggcggagg tggctctggc ggtggcggat cgtctgagct gactcaggac    420

cctgctgtgt ctgtggcctt gggacagaca gtcagaatca catgccaagg agacagcctc    480

agaagctatt atgcaagttg gtaccagcag aagccaggac aggcccctct ccttgtcatc    540

tatggtaaaa acatccggcc ctcagggatc ccagaccgat tctctggctc cagctcagga    600

aacacagctt ccttgaccat cactggggct caggcggaag atgaggctga ctattactgt    660

aactcccggg acagcagtgg taaccatgtg gtattcggcg gagggaccaa gctgaccgtc    720

ctaggt                                                               726
```

<210> SEQ ID NO 121
<211> LENGTH: 726
<212> TYPE: DNA
<213> ORGANISM: artificial sequence
<220> FEATURE:
<223> OTHER INFORMATION: synthetic polynucleotide

<400> SEQUENCE: 121

```
gtccacgtcg accacgtcag accccgtctc cactttttcg ggcccctcag agacttctag     60

aggacattcc caagacctat gtcgaaatgg tcaatgacct agccgaccca cgcggtctac    120

gggccctttc cggacctcac ctacccctag tagataggac cactgagact atggtctatg    180

tcgggcagga aggttccggt ccagtggtag agtcggctgt tcaggtagtc gtggcggatg    240

gacgtcacct cgtcggagtt ccggagcctg tggcggtaca taatgacacg ctccgctgat    300

gtgcctggaa agatgaaact gatgaccccg gtcccttggg accagtggca gaggagtcca    360

cctccgccaa gtccgcctcc accgagaccg ccaccgccta gcagactcga ctgagtcctg    420
```

ggacgacaca gacaccggaa ccctgtctgt cagtcttagt gtacggttcc tctgtcggag 480
tcttcgataa tacgttcaac catggtcgtc ttcggtcctg tccggggaga ggaacagtag 540
ataccatttt tgtaggccgg gagtccctag ggtctggcta agagaccgag gtcgagtcct 600
ttgtgtcgaa ggaactggta gtgaccccga gtccgccttc tactccgact gataatgaca 660
ttgagggccc tgtcgtcacc attggtacac cataagccgc ctccctggtt cgactggcag 720
gatcca 726

<210> SEQ ID NO 122
<211> LENGTH: 242
<212> TYPE: PRT
<213> ORGANISM: artificial sequence
<220> FEATURE:
<223> OTHER INFORMATION: synthetic polypeptide

<400> SEQUENCE: 122

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Arg Leu His Gly Pro Phe Tyr Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Ser Glu Leu Thr Gln Asp Pro Ala Val Ser
130 135 140

Val Ala Leu Gly Gln Thr Val Arg Ile Thr Cys Gln Gly Asp Ser Leu
145 150 155 160

Arg Ser Tyr Tyr Ala Ser Trp Tyr Gln Gln Lys Pro Gly Gln Ala Pro
165 170 175

Leu Leu Val Ile Tyr Gly Lys Asn Ile Arg Pro Ser Gly Ile Pro Asp
180 185 190

Arg Phe Ser Gly Ser Ser Ser Gly Asn Thr Ala Ser Leu Thr Ile Thr
195 200 205

Gly Ala Gln Ala Glu Asp Glu Ala Asp Tyr Tyr Cys Asn Ser Arg Asp
210 215 220

Ser Ser Gly Asn His Val Val Phe Gly Gly Gly Thr Lys Leu Thr Val
225 230 235 240

Leu Gly

<210> SEQ ID NO 123
<211> LENGTH: 705
<212> TYPE: DNA
<213> ORGANISM: artificial sequence
<220> FEATURE:
<223> OTHER INFORMATION: synthetic polynucleotide

<400> SEQUENCE: 123

```
caggtgcagc tgcaggagtc gggggggaggc ttggtccagc ctgggggggtc cctgagactc     60

tcctgtgcag cctctggatt cacctttagt agctatcgga tgcactgggt ccgccaggct    120

ccagggaagg ggctggagtg ggtggccgcc gtaaagcaag atggaagtga gaagtactat    180

ttggactctg tgaagggccg attcaccatc tccagagaca acgccaagag ctcactgtat    240

ctgcaaatgg acagcctgag cgtcgaggac acggccgtct attactgtgc gagaggtctg    300

cgtaccatgg gccagggcac cctggtcacc gtctcctcag gtggaggcgg ttcaggcgga    360

ggtggctctg gcggtggcgg atcgtctgag ctgactcagg accctgctgt gtctgtggcc    420

ttgggacaga cagtcaggat cacatgccaa ggagacagcc tcagaagcta ttatgcaagt    480

tggtaccagc ggaagccagg acaggcccct ctccttgtca tctatggtaa aaacatccgg    540

ccctcaggga tcccagaccg attctctggc tccagctcag gaaacacagc ttccttgatc    600

atcactgggg ctcaggcgga agatgaggct gactattact gtaattctcg ggacagcagt    660

gctaaccaga tgttcggcgg agggaccaag ctgaccgtcc taggt                    705
```

<210> SEQ ID NO 124
<211> LENGTH: 705
<212> TYPE: DNA
<213> ORGANISM: artificial sequence
<220> FEATURE:
<223> OTHER INFORMATION: synthetic polynucleotide

<400> SEQUENCE: 124

```
gtccacgtcg acgtcctcag cccccctccg aaccaggtcg gaccccccag ggactctgag     60

aggacacgtc ggagacctaa gtggaaatca tcgatagcct acgtgaccca ggcggtccga    120

ggtcccttcc ccgacctcac ccaccggcgg catttcgttc taccttcact cttcatgata    180

aacctgagac acttcccggc taagtggtag aggtctctgt tgcggttctc gagtgacata    240

gacgtttacc tgtcggactc gcagctcctg tgccggcaga taatgacacg ctctccagac    300

gcatggtacc cggtcccgtg ggaccagtgg cagaggagtc cacctccgcc aagtccgcct    360

ccaccgagac cgccaccgcc tagcagactc gactgagtcc tgggacgaca cagacaccgg    420

aaccctgtct gtcagtccta gtgtacggtt cctctgtcgg agtcttcgat aatacgttca    480

accatggtcg ccttcggtcc tgtccgggga gaggaacagt agataccatt tttgtaggcc    540

gggagtccct agggtctggc taagagaccg aggtcgagtc ctttgtgtcg aaggaactag    600

tagtgacccc gagtccgcct tctactccga ctgataatga cattaagagc cctgtcgtca    660

cgattggtct acaagccgcc tccctggttc gactggcagg atcca                    705
```

<210> SEQ ID NO 125
<211> LENGTH: 235
<212> TYPE: PRT
<213> ORGANISM: artificial sequence
<220> FEATURE:
<223> OTHER INFORMATION: synthetic polypeptide

<400> SEQUENCE: 125

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met His Trp Val Arg Gln Ala Pro Gly Lys Gly Leu Glu Trp Val
        35                  40                  45

Ala Ala Val Lys Gln Asp Gly Ser Glu Lys Tyr Tyr Leu Asp Ser Val
```

```
    50                  55                  60

Lys Gly Arg Phe Thr Ile Ser Arg Asp Asn Ala Lys Ser Ser Leu Tyr
65                  70                  75                  80

Leu Gln Met Asp Ser Leu Ser Val Glu Asp Thr Ala Val Tyr Tyr Cys
                85                  90                  95

Ala Arg Gly Leu Arg Thr Met Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Ser Glu Leu Thr Gln Asp Pro Ala Val Ser Val Ala Leu Gly Gln Thr
    130                 135                 140

Val Arg Ile Thr Cys Gln Gly Asp Ser Leu Arg Ser Tyr Tyr Ala Ser
145                 150                 155                 160

Trp Tyr Gln Arg Lys Pro Gly Gln Ala Pro Leu Leu Val Ile Tyr Gly
                165                 170                 175

Lys Asn Ile Arg Pro Ser Gly Ile Pro Asp Arg Phe Ser Gly Ser Ser
            180                 185                 190

Ser Gly Asn Thr Ala Ser Leu Ile Ile Thr Gly Ala Gln Ala Glu Asp
        195                 200                 205

Glu Ala Asp Tyr Tyr Cys Asn Ser Arg Asp Ser Ser Ala Asn Gln Met
    210                 215                 220

Phe Gly Gly Gly Thr Lys Leu Thr Val Leu Gly
225                 230                 235


<210> SEQ ID NO 126
<211> LENGTH: 30
<212> TYPE: PRT
<213> ORGANISM: artificial sequence
<220> FEATURE:
<223> OTHER INFORMATION: synthetic polypeptide

<400> SEQUENCE: 126

Gln Val Leu Leu Val Glu Ser Gly Gly Gly Val Val Gln Ala Gly Ala
 1               5                  10                  15

Ser Leu Arg Val Ser Cys Ala Ala Ser Gly Phe Ser Leu Thr
            20                  25                  30


<210> SEQ ID NO 127
<211> LENGTH: 242
<212> TYPE: PRT
<213> ORGANISM: artificial sequence
<220> FEATURE:
<223> OTHER INFORMATION: synthetic polypeptide

<400> SEQUENCE: 127

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Ser Ser Gly Gly Arg Thr Tyr Tyr Ala Asp Ser Val
    50                  55                  60

Arg Gly Arg Leu Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95
```

```
Ala Lys Gly Ile Val Gly Ala Thr Ala Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Arg Asp
    210                 215                 220

Ser Ser Gly Asn Ser Val Val Phe Gly Gly Gly Thr Lys Val Thr Val
225                 230                 235                 240

Leu Gly


<210> SEQ ID NO 128
<211> LENGTH: 726
<212> TYPE: DNA
<213> ORGANISM: artificial sequence
<220> FEATURE:
<223> OTHER INFORMATION: synthetic polynucleotide

<400> SEQUENCE: 128

caggtgcagc tgcaggagtc ggggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagct attactagta gcggtggtag gacatactac     180

gcagactccg tgaggggccg gctcaccatc tccagagaca attccaagaa cacgctgtat     240

ctgcaaatga acaccctgag agccgaggac acggccgtat attactgtgc aaaaggaata     300

gtgggagcta ctgcctttga ctactggggc cagggaaccc tggtcaccgt ctcctcaggt     360

ggaggcggtt caggcggagg tggctctggc ggtggcggat cgtctgagct gactcaggac     420

cctgctgtgt ctgtggcctt gggacagaca gtcagaatca catgccaggg agacagcctc     480

agaagctatt atgcaagctg gtaccagcag aagccaggac aggcccctgt acttgtcatc     540

tatggtaaaa acaaccggcc ctcagggatc ccagaccgat tctctggctc cagctcagga     600

aacacagctt ccttgaccat cactggggct caggcggaag atgaggctga ctattactgt     660

aactcccggg acagcagtgg taactctgtg gtattcggcg gagggaccaa ggtcaccgtc     720

ctaggt                                                                726


<210> SEQ ID NO 129
<211> LENGTH: 246
<212> TYPE: PRT
<213> ORGANISM: artificial sequence
<220> FEATURE:
<223> OTHER INFORMATION: synthetic polypeptide

<400> SEQUENCE: 129

Gln Val Leu Leu Val Glu Ser Gly Gly Gly Val Val Gln Ala Gly Ala
 1               5                  10                  15

Ser Leu Arg Val Ser Cys Ala Ala Ser Gly Phe Ser Leu Thr Ser Tyr
```

```
            20                  25                  30

Gly Met His Trp Val Arg Gln Ala Pro Gly Lys Gly Leu Glu Trp Val
        35                  40                  45

Ala Phe Ile Ser Ser Asp Gly Ser Asp Lys Tyr Tyr Val Asp Ser Val
    50                  55                  60

Lys Gly Arg Phe Thr Ile Ser Arg Asp Thr Ser Lys Asn Met Met Tyr
65                  70                  75                  80

Leu Gln Met Asn Ser Leu Thr Thr Glu Asp Thr Ala Val Tyr Tyr Cys
                85                  90                  95

Ala Lys Asp Trp Gly Ser Asn Trp Tyr Leu Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Val Leu Thr Gln Pro Pro Ser
    130                 135                 140

Ala Ser Glu Thr Pro Gly Gln Arg Val Thr Ile Ser Cys Ser Gly Ser
145                 150                 155                 160

Ser Ser Asn Ile Gly Ala Asn Thr Val His Trp Tyr Gln Gln Phe Pro
                165                 170                 175

Gly Thr Ala Pro Lys Leu Leu Ile Tyr Ser Tyr Ser Gln Arg Pro Ser
            180                 185                 190

Gly Val Pro Asp Arg Phe Ser Asp Ser Lys Ser Gly Thr Ser Ala Ser
        195                 200                 205

Leu Ala Ile Ser Gly Leu Gln Ser Glu Asp Glu Ala Asp Tyr Tyr Cys
    210                 215                 220

Ala Ala Trp Asp Asp Ile Leu Asn Gly Trp Val Phe Gly Gly Gly Thr
225                 230                 235                 240

Lys Val Thr Val Leu Gly
                245
```

<210> SEQ ID NO 130
<211> LENGTH: 738
<212> TYPE: DNA
<213> ORGANISM: artificial sequence
<220> FEATURE:
<223> OTHER INFORMATION: synthetic polynucleotide

<400> SEQUENCE: 130

```
caggtgctgc tggtggagtc cgggggaggc gtggtccagg ccggggcatc cctgagagtc     60

tcctgtgcag catctggatt cagtttgact agctatggga tgcactgggt ccgccaggct    120

ccaggcaagg gactggagtg ggtggctttt atttcgtctg atggtagtga taagtactat    180

gtagactctg tgaagggccg attcaccatc tccagagaca cttccaagaa catgatgtat    240

ctgcaaatga acagcctgac aactgaggat acggctgtgt attactgtgc gaaagactgg    300

ggcagcaact ggtacctctt tgactactgg ggccagggaa ccctggtcac cgtctcctca    360

ggtggaggcg gttcaggcgg aggtggctct ggcggtggcg gatcgcagtc tgtgctgact    420

cagccaccct cagcgtctga gacccccggg cagagggtca ccatctcttg ttctggaagc    480

agctccaaca tcggagcgaa tactgtacac tggtaccagc agttcccagg aacggccccc    540

aaacttctca tctatagtta tagtcagcgg ccctcagggg tccctgaccg attctctgac    600

tccaagtctg gtacctcagc ctccctggcc atcagtgggc tccagtctga ggatgaggct    660

gattattact gtgcagcatg ggatgacatc ctgaatggtt gggtgttcgg cggagggacc    720

aaggtaaccg tcctaggt                                                  738
```

<210> SEQ ID NO 131
<211> LENGTH: 30
<212> TYPE: PRT
<213> ORGANISM: artificial sequence
<220> FEATURE:
<223> OTHER INFORMATION: synthetic polypeptide

<400> SEQUENCE: 131

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser
            20                  25                  30
```

<210> SEQ ID NO 132
<211> LENGTH: 5
<212> TYPE: PRT
<213> ORGANISM: artificial sequence
<220> FEATURE:
<223> OTHER INFORMATION: synthetic polypeptide

<400> SEQUENCE: 132

```
Asn Tyr Ala Met Ile
 1               5
```

<210> SEQ ID NO 133
<211> LENGTH: 14
<212> TYPE: PRT
<213> ORGANISM: artificial sequence
<220> FEATURE:
<223> OTHER INFORMATION: synthetic polypeptide

<400> SEQUENCE: 133

```
Trp Val Arg Gln Ala Pro Gly Lys Gly Leu Glu Trp Val Ser
 1               5                  10
```

<210> SEQ ID NO 134
<211> LENGTH: 30
<212> TYPE: PRT
<213> ORGANISM: artificial sequence
<220> FEATURE:
<223> OTHER INFORMATION: synthetic polypeptide

<400> SEQUENCE: 134

```
Gln Val Gln Arg Val Glu Ser Gly Gly Gly Val Val Gln Pro Gly Arg
 1               5                  10                  15

Ser Leu Arg Leu Ser Cys Ala Ala Ser Gly Phe Thr Phe Ser
            20                  25                  30
```

<210> SEQ ID NO 135
<211> LENGTH: 249
<212> TYPE: PRT
<213> ORGANISM: artificial sequence
<220> FEATURE:
<223> OTHER INFORMATION: synthetic polypeptide

<400> SEQUENCE: 135

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ala Val Ile Tyr Arg Asp Gly His Gly Tyr Tyr Ala Asp Ser Val Lys
```

```
    50                  55                  60

Gly Arg Phe Thr Val Ser Arg Asp Ser Ser Glu Asn Thr Val Tyr Leu
65                  70                  75                  80

Gln Met Asn Ser Leu Arg Ala Glu Asp Thr Ala Ile Tyr Tyr Cys Ala
                85                  90                  95

Ser His Asp Tyr Ala Gly Asn Pro Ala Gly Ser Ala Ser Gly Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gln Ser Ala Leu Thr Gln Pro
    130                 135                 140

Ala Ser Val Ser Ala Ser Pro Gly Gln Ser Ile Thr Ile Ser Cys Thr
145                 150                 155                 160

Gly Thr Ser Ser Asp Val Gly Gly Tyr Asp Tyr Val Ser Trp Tyr Gln
                165                 170                 175

Gln His Pro Gly Lys Ala Pro Lys Leu Val Met Tyr Ser His Asn Gln
            180                 185                 190

Arg Ser Ser Gly Val Pro Asp Arg Phe Ser Gly Ser Lys Ser Gly Asn
        195                 200                 205

Ser Ala Ser Leu Asp Ile Ser Gly Leu Gln Ser Glu Asp Glu Ala Asp
    210                 215                 220

Tyr Tyr Arg Ala Ala Trp Asp Asp Ser Leu Ser Glu Phe Leu Phe Gly
225                 230                 235                 240

Thr Gly Thr Lys Leu Thr Val Leu Gly
                245


<210> SEQ ID NO 136
<211> LENGTH: 747
<212> TYPE: DNA
<213> ORGANISM: artificial sequence
<220> FEATURE:
<223> OTHER INFORMATION: synthetic polynucleotide

<400> SEQUENCE: 136

caggtgcagc tggtggagtc cgggggaggc gtggtccagc ctgggaggtc cctgagactc      60

tcctgtgcag cctctggatt cacctttagc agctatgcca tggggtgggt ccgccaggct     120

ccaggcaagg ggctggagtg ggtggctgtt atttatagag atggtcacgg atattacgca     180

gactccgtga agggccgatt caccgtctcc agagacagtt ccgagaacac ggtgtatctt     240

caaatgaaca gcctgagagc cgaggacacg gccatatatt actgcgcgag ccatgactac     300

gctggtaatc ccgcaggctc ggcatctggc tactggggcc agggcaccct ggtcaccgtc     360

tcctcaggtg gaggcggttc aggcggaggt ggctctggcg gtggcggatc gcagtctgcc     420

ctgactcagc ctgcctccgt gtctgcgtct cctggacagt cgatcaccat ctcctgcact     480

ggaaccagca gtgatgttgg tggttatgac tatgtctcct ggtaccaaca gcacccaggc     540

aaagccccca aactcgtcat gtatagtcac aatcagcggt cctcaggggt ccctgaccga     600

ttctctggct ccaagtctgg caactcagcc tccctggaca tcagtgggct ccagtctgag     660

gatgaggctg attattaccg tgcagcatgg gatgacagcc tgagtgaatt tctcttcgga     720

actgggacca agctgaccgt cctaggt                                         747


<210> SEQ ID NO 137
<211> LENGTH: 249
<212> TYPE: PRT
<213> ORGANISM: artificial sequence
```

-continued

<220> FEATURE:
<223> OTHER INFORMATION: synthetic polypeptide

<400> SEQUENCE: 137

Leu Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Asn Asn Ser Leu Tyr
65 70 75 80

Leu Gln Met Asn Ser Leu Arg Ala Glu Asp Thr Ala Val Tyr Tyr Cys
85 90 95

Ala Arg Gly Asn Thr Val Ala Gln Arg Leu Asp Val Phe Asp Tyr Trp
100 105 110

Gly Gln Gly Thr Leu Val Thr Val Ser Ser Gly Gly Gly Gly Ser Gly
115 120 125

Gly Gly Gly Pro Gly Gly Gly Gly Ser Gln Ser Val Leu Thr Gln Pro
130 135 140

Pro Ser Val Ser Gly Ala Pro Gly Gln Arg Val Thr Ile Ser Cys Thr
145 150 155 160

Gly Gly Ser Ser Asn Val Gly Ala Gly Phe Asp Val His Trp Tyr Gln
165 170 175

Gln Leu Pro Gly Thr Ala Pro Lys Leu Leu Ile Tyr Gly Asp Lys Asn
180 185 190

Arg Pro Ser Gly Val Pro Asp Arg Phe Ser Gly Ser Arg Ser Gly Thr
195 200 205

Ser Ala Ser Leu Ala Ile Thr Gly Leu Gln Ala Glu Asp Glu Ala Asp
210 215 220

Tyr Tyr Cys Gln Ala Tyr Asp Ser Ser Leu Arg Gly Ser Val Phe Gly
225 230 235 240

Gly Gly Thr Lys Leu Thr Val Leu Gly
245

<210> SEQ ID NO 138
<211> LENGTH: 747
<212> TYPE: DNA
<213> ORGANISM: artificial sequence
<220> FEATURE:
<223> OTHER INFORMATION: synthetic polynucleotide

<400> SEQUENCE: 138
ctggtgcagc tggtgcagtc tgggggaggc ctggtcaagc ctggggggtc cctgagactc 60
tcctgtgcag cctctggatt caccttcagt acctatagca tgaactgggt ccgccaggct 120
ccagggaagg gcctggagtg ggtctcatcc attagtagta gtagtagtta catatactac 180
gcagactcag tgaagggccg attcaccatc tccagagaca acgccaacaa ctcactgtat 240
ctgcaaatga acagcctgag agccgaggac acggctgtct attactgtgc gagagggaat 300
acggtggccc aaagactgga cgtctttgac tactggggcc agggaaccct ggtcaccgtc 360
tcctcaggtg gaggcggttc aggcggaggt ggccctggcg gtggcggatc gcagtctgtg 420
ttgacgcagc cgccctcagt gtctggggcc ccagggcaga gggtcaccat ctcctgcact 480

```
gggggcagct ccaacgtcgg ggcaggtttt gatgtacact ggtaccagca gcttccagga    540

acagccccca aactcctcat ctatggtgac aagaatcggc cctcaggggt ccctgaccga    600

ttctctggct ccaggtctgg cacctcagcc tccctggcca tcactgggct ccaggctgag    660

gatgaggctg attattactg ccaggcctat gacagcagcc tgcgtggttc ggtattcggc    720

ggagggacca agctgaccgt cctaggt                                        747


<210> SEQ ID NO 139
<211> LENGTH: 32
<212> TYPE: PRT
<213> ORGANISM: artificial sequence
<220> FEATURE:
<223> OTHER INFORMATION: synthetic polypeptide

<400> SEQUENCE: 139

Arg Phe Thr Val Ser Arg Asp Asn Phe Lys Ser Thr Leu Tyr Leu Gln
1               5                   10                  15

Met Asn Arg Leu Arg Ala Glu Asp Thr Ala Val Tyr Tyr Cys Ala Lys
            20                  25                  30


<210> SEQ ID NO 140
<211> LENGTH: 17
<212> TYPE: PRT
<213> ORGANISM: artificial sequence
<220> FEATURE:
<223> OTHER INFORMATION: synthetic polypeptide

<400> SEQUENCE: 140

Ala Ile Thr Gly Gly Gly Gly Ser Thr Tyr Tyr Ala Asp Ser Val Lys
1               5                   10                  15

Gly


<210> SEQ ID NO 141
<211> LENGTH: 32
<212> TYPE: PRT
<213> ORGANISM: artificial sequence
<220> FEATURE:
<223> OTHER INFORMATION: synthetic polypeptide

<400> SEQUENCE: 141

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Leu Tyr Tyr Cys Ala Lys
            20                  25                  30


<210> SEQ ID NO 142
<211> LENGTH: 17
<212> TYPE: PRT
<213> ORGANISM: artificial sequence
<220> FEATURE:
<223> OTHER INFORMATION: synthetic polypeptide

<400> SEQUENCE: 142

Ala Ile Ser Gly Ser Gly Gly Ser Thr Tyr Tyr Ala Asp Ser Val Lys
1               5                   10                  15

Gly


<210> SEQ ID NO 143
<211> LENGTH: 17
<212> TYPE: PRT
<213> ORGANISM: artificial sequence
<220> FEATURE:
<223> OTHER INFORMATION: synthetic polypeptide
```

<400> SEQUENCE: 143

Ala Ile Ser Gly Ser Gly Ser Gly Thr Tyr Tyr Ala Asp Ser Val Lys
1               5                   10                  15

Gly

<210> SEQ ID NO 144
<211> LENGTH: 32
<212> TYPE: PRT
<213> ORGANISM: artificial sequence
<220> FEATURE:
<223> OTHER INFORMATION: synthetic polypeptide

<400> SEQUENCE: 144

Arg Phe Thr Ile Ser Arg Asp Asn Ser Lys Asn Thr Leu Tyr Leu Gln
1               5                   10                  15

Met Asn Thr Leu Arg Ala Glu Asp Thr Ala Leu Tyr Tyr Cys Ala Lys
            20                  25                  30

<210> SEQ ID NO 145
<211> LENGTH: 17
<212> TYPE: PRT
<213> ORGANISM: artificial sequence
<220> FEATURE:
<223> OTHER INFORMATION: synthetic polypeptide

<400> SEQUENCE: 145

Ala Ile Thr Ser Ser Gly Gly Arg Thr Tyr Tyr Ala Asp Ser Val Arg
1               5                   10                  15

Gly

<210> SEQ ID NO 146
<211> LENGTH: 32
<212> TYPE: PRT
<213> ORGANISM: artificial sequence
<220> FEATURE:
<223> OTHER INFORMATION: synthetic polypeptide

<400> SEQUENCE: 146

Arg Leu Thr Ile Ser Arg Asp Asn Ser Lys Asn Thr Leu Tyr Leu Gln
1               5                   10                  15

Met Asn Thr Leu Arg Ala Glu Asp Thr Ala Val Tyr Tyr Cys Ala Lys
            20                  25                  30

<210> SEQ ID NO 147
<211> LENGTH: 14
<212> TYPE: PRT
<213> ORGANISM: artificial sequence
<220> FEATURE:
<223> OTHER INFORMATION: synthetic polypeptide

<400> SEQUENCE: 147

Gly Tyr Gly Ser Gly Ser Tyr Trp Ser Gly Ala Phe Asp Ile
1               5                   10

<210> SEQ ID NO 148
<211> LENGTH: 9
<212> TYPE: PRT
<213> ORGANISM: artificial sequence
<220> FEATURE:
<223> OTHER INFORMATION: synthetic polypeptide

<400> SEQUENCE: 148

Leu Gly Gly Glu Ser Tyr Ser Ala Asp

-continued

```
 1               5


<210> SEQ ID NO 149
<211> LENGTH: 11
<212> TYPE: PRT
<213> ORGANISM: artificial sequence
<220> FEATURE:
<223> OTHER INFORMATION: synthetic polypeptide

<400> SEQUENCE: 149

Thr Leu Gly Arg Ser Thr Val Ala Thr Asp Tyr
 1               5                  10


<210> SEQ ID NO 150
<211> LENGTH: 8
<212> TYPE: PRT
<213> ORGANISM: artificial sequence
<220> FEATURE:
<223> OTHER INFORMATION: synthetic polypeptide

<400> SEQUENCE: 150

Gly Pro Gly Ala Ala Gln Asp Tyr
 1               5


<210> SEQ ID NO 151
<211> LENGTH: 11
<212> TYPE: PRT
<213> ORGANISM: artificial sequence
<220> FEATURE:
<223> OTHER INFORMATION: synthetic polypeptide

<400> SEQUENCE: 151

Gly Ala Val Gly Ala Thr Thr Ala Phe Asp Tyr
 1               5                  10


<210> SEQ ID NO 152
<211> LENGTH: 11
<212> TYPE: PRT
<213> ORGANISM: artificial sequence
<220> FEATURE:
<223> OTHER INFORMATION: synthetic polypeptide

<400> SEQUENCE: 152

Val Ala Ser Ser Ser Ser Leu Gly Met Asp Val
 1               5                  10


<210> SEQ ID NO 153
<211> LENGTH: 11
<212> TYPE: PRT
<213> ORGANISM: artificial sequence
<220> FEATURE:
<223> OTHER INFORMATION: synthetic polypeptide

<400> SEQUENCE: 153

Trp Gly Gln Gly Thr Thr Val Thr Val Ser Ser
 1               5                  10


<210> SEQ ID NO 154
<211> LENGTH: 10
<212> TYPE: PRT
<213> ORGANISM: artificial sequence
<220> FEATURE:
<223> OTHER INFORMATION: synthetic polypeptide

<400> SEQUENCE: 154

Ser Val Val Gly Ala Thr Ser Leu Asp Tyr
 1               5                  10
```

<210> SEQ ID NO 155
<211> LENGTH: 10
<212> TYPE: PRT
<213> ORGANISM: artificial sequence
<220> FEATURE:
<223> OTHER INFORMATION: synthetic polypeptide

<400> SEQUENCE: 155

Gly Ile Val Gly Ala Thr Ala Phe Asp Tyr
1 5 10

<210> SEQ ID NO 156
<211> LENGTH: 23
<212> TYPE: PRT
<213> ORGANISM: artificial sequence
<220> FEATURE:
<223> OTHER INFORMATION: synthetic polypeptide

<400> SEQUENCE: 156

Glu Ile Val Leu Thr Gln Ser Pro Leu Ser Leu Pro Val Thr Pro Gly
1 5 10 15

Glu Pro Ala Ser Ile Ser Cys
20

<210> SEQ ID NO 157
<211> LENGTH: 16
<212> TYPE: PRT
<213> ORGANISM: artificial sequence
<220> FEATURE:
<223> OTHER INFORMATION: synthetic polypeptide

<400> SEQUENCE: 157

Arg Ser Ser Gln Ser Leu Leu His Thr Asn Gly Tyr Asn Tyr Leu Asp
1 5 10 15

<210> SEQ ID NO 158
<211> LENGTH: 15
<212> TYPE: PRT
<213> ORGANISM: artificial sequence
<220> FEATURE:
<223> OTHER INFORMATION: synthetic polypeptide

<400> SEQUENCE: 158

Trp Tyr Leu Gln Lys Pro Gly Gln Ser Pro Gln Leu Leu Ile Tyr
1 5 10 15

<210> SEQ ID NO 159
<211> LENGTH: 22
<212> TYPE: PRT
<213> ORGANISM: artificial sequence
<220> FEATURE:
<223> OTHER INFORMATION: synthetic polypeptide

<400> SEQUENCE: 159

His Val Ile Leu Thr Gln Asp Pro Ala Val Ser Val Ala Leu Gly Gln
1 5 10 15

Thr Val Lys Ile Thr Cys
20

<210> SEQ ID NO 160
<211> LENGTH: 15
<212> TYPE: PRT
<213> ORGANISM: artificial sequence
<220> FEATURE:
<223> OTHER INFORMATION: synthetic polypeptide

<400> SEQUENCE: 160

Trp Tyr Gln Gln Lys Pro Gly Gln Ala Pro Leu Leu Val Leu Tyr
1 5 10 15

<210> SEQ ID NO 161
<211> LENGTH: 22
<212> TYPE: PRT
<213> ORGANISM: artificial sequence
<220> FEATURE:
<223> OTHER INFORMATION: synthetic polypeptide

<400> SEQUENCE: 161

Gln Ser Val Leu Thr Gln Asp Pro Ala Val Ser Val Ala Leu Gly Gln
1 5 10 15

Thr Val Thr Ile Thr Cys
20

<210> SEQ ID NO 162
<211> LENGTH: 22
<212> TYPE: PRT
<213> ORGANISM: artificial sequence
<220> FEATURE:
<223> OTHER INFORMATION: synthetic polypeptide

<400> SEQUENCE: 162

Gln Ser Val Leu Thr Gln Asp Pro Ala Val Ser Val Ala Leu Gly Gln
1 5 10 15

Thr Val Arg Ile Thr Cys
20

<210> SEQ ID NO 163
<211> LENGTH: 11
<212> TYPE: PRT
<213> ORGANISM: artificial sequence
<220> FEATURE:
<223> OTHER INFORMATION: synthetic polypeptide

<400> SEQUENCE: 163

Gln Gly Asp Ser Leu Arg Asp Tyr Tyr Ala Ser
1 5 10

<210> SEQ ID NO 164
<211> LENGTH: 15
<212> TYPE: PRT
<213> ORGANISM: artificial sequence
<220> FEATURE:
<223> OTHER INFORMATION: synthetic polypeptide

<400> SEQUENCE: 164

Trp Tyr Lys Gln Lys Pro Gly Gln Ala Pro Leu Leu Val Phe Phe
1 5 10 15

<210> SEQ ID NO 165
<211> LENGTH: 7
<212> TYPE: PRT
<213> ORGANISM: artificial sequence
<220> FEATURE:
<223> OTHER INFORMATION: synthetic polypeptide

<400> SEQUENCE: 165

Leu Gly Ser Asn Arg Ala Ser
1 5

<210> SEQ ID NO 166

<211> LENGTH: 32
<212> TYPE: PRT
<213> ORGANISM: artificial sequence
<220> FEATURE:
<223> OTHER INFORMATION: synthetic polypeptide

<400> SEQUENCE: 166

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 167
<211> LENGTH: 32
<212> TYPE: PRT
<213> ORGANISM: artificial sequence
<220> FEATURE:
<223> OTHER INFORMATION: synthetic polypeptide

<400> SEQUENCE: 167

Gly Ile Pro Asp Arg Phe Ser Gly Ser Gly Ser Gly Asn Thr Ala Ser
1 5 10 15

Leu Thr Ile Thr Gly Ala Gln Ala Glu Asp Glu Ala Asp Tyr Tyr Cys
20 25 30

<210> SEQ ID NO 168
<211> LENGTH: 7
<212> TYPE: PRT
<213> ORGANISM: artificial sequence
<220> FEATURE:
<223> OTHER INFORMATION: synthetic polypeptide

<400> SEQUENCE: 168

Gly Lys Asn Asn Arg Pro Ser
1 5

<210> SEQ ID NO 169
<211> LENGTH: 32
<212> TYPE: PRT
<213> ORGANISM: artificial sequence
<220> FEATURE:
<223> OTHER INFORMATION: synthetic polypeptide

<400> SEQUENCE: 169

Gly Ile Pro Asp Arg Phe Ser Gly Ser Ser Ser Gly Asn Thr Ala Ser
1 5 10 15

Leu Thr Ile Thr Gly Ala Arg Ala Glu Asp Glu Ala Asp Tyr Tyr Cys
20 25 30

<210> SEQ ID NO 170
<211> LENGTH: 7
<212> TYPE: PRT
<213> ORGANISM: artificial sequence
<220> FEATURE:
<223> OTHER INFORMATION: synthetic polypeptide

<400> SEQUENCE: 170

Gly Lys Ser Asn Arg Pro Ser
1 5

<210> SEQ ID NO 171
<211> LENGTH: 32
<212> TYPE: PRT
<213> ORGANISM: artificial sequence
<220> FEATURE:
<223> OTHER INFORMATION: synthetic polypeptide

<400> SEQUENCE: 171

Gly Ile Pro Asn Arg Phe Ser Gly Ser Thr Ser Gly Ser Thr Ala Thr
1 5 10 15

Leu Thr Val Thr Gly Ala Gln Ala Glu Asp Glu Ala Asp Tyr Phe Cys
20 25 30

<210> SEQ ID NO 172
<211> LENGTH: 9
<212> TYPE: PRT
<213> ORGANISM: artificial sequence
<220> FEATURE:
<223> OTHER INFORMATION: synthetic polypeptide

<400> SEQUENCE: 172

Met Gln Gly Arg Gln Ser Pro Leu Thr
1 5

<210> SEQ ID NO 173
<211> LENGTH: 10
<212> TYPE: PRT
<213> ORGANISM: artificial sequence
<220> FEATURE:
<223> OTHER INFORMATION: synthetic polypeptide

<400> SEQUENCE: 173

His Ser Arg Asp Ser Ser Gly Lys Tyr Val
1 5 10

<210> SEQ ID NO 174
<211> LENGTH: 11
<212> TYPE: PRT
<213> ORGANISM: artificial sequence
<220> FEATURE:
<223> OTHER INFORMATION: synthetic polypeptide

<400> SEQUENCE: 174

Phe Gly Val Gly Thr Lys Val Thr Val Leu Gly
1 5 10

<210> SEQ ID NO 175
<211> LENGTH: 12
<212> TYPE: PRT
<213> ORGANISM: artificial sequence
<220> FEATURE:
<223> OTHER INFORMATION: synthetic polypeptide

<400> SEQUENCE: 175

Asn Ser Arg Asp Ser Ser Gly Asn Pro His Val Val
1 5 10

<210> SEQ ID NO 176
<211> LENGTH: 11
<212> TYPE: PRT
<213> ORGANISM: artificial sequence
<220> FEATURE:
<223> OTHER INFORMATION: synthetic polypeptide

<400> SEQUENCE: 176

Asn Ser Arg Asp Ser Ser Gly Asn His Leu Val
1 5 10

<210> SEQ ID NO 177
<211> LENGTH: 11
<212> TYPE: PRT
<213> ORGANISM: artificial sequence
<220> FEATURE:
<223> OTHER INFORMATION: synthetic polypeptide

<400> SEQUENCE: 177

Thr Ser Arg Asp Ser Ser Gly Lys Gln Leu Val
1 5 10

<210> SEQ ID NO 178
<211> LENGTH: 11
<212> TYPE: PRT
<213> ORGANISM: artificial sequence
<220> FEATURE:
<223> OTHER INFORMATION: synthetic polypeptide

<400> SEQUENCE: 178

Ser Ser Arg Asp Ser Ser Gly Arg Leu Ile Leu
1 5 10

<210> SEQ ID NO 179
<211> LENGTH: 11
<212> TYPE: PRT
<213> ORGANISM: artificial sequence
<220> FEATURE:
<223> OTHER INFORMATION: synthetic polypeptide

<400> SEQUENCE: 179

Asn Ser Arg Asp Ser Ser Gly Asn Ser Val Val
1 5 10

<210> SEQ ID NO 180
<211> LENGTH: 30
<212> TYPE: PRT
<213> ORGANISM: artificial sequence
<220> FEATURE:
<223> OTHER INFORMATION: synthetic polypeptide

<400> SEQUENCE: 180

Gln Val Gln Leu Gln Glu Ser Gly Gly Gly Leu Val Gln Pro Gly Gly
1 5 10 15

Ser Leu Arg Leu Ser Cys Ser Ala Ser Gly Phe Thr Phe Ser
20 25 30

<210> SEQ ID NO 181
<211> LENGTH: 14
<212> TYPE: PRT
<213> ORGANISM: artificial sequence
<220> FEATURE:
<223> OTHER INFORMATION: synthetic polypeptide

<400> SEQUENCE: 181

Trp Val Arg Gln Ala Pro Gly Lys Gly Leu Glu Tyr Val Ser
1 5 10

<210> SEQ ID NO 182
<211> LENGTH: 30
<212> TYPE: PRT
<213> ORGANISM: artificial sequence
<220> FEATURE:
<223> OTHER INFORMATION: synthetic polypeptide

<400> SEQUENCE: 182

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 183
<211> LENGTH: 30
<212> TYPE: PRT
<213> ORGANISM: artificial sequence
<220> FEATURE:
<223> OTHER INFORMATION: synthetic polypeptide

<400> SEQUENCE: 183

```
Gln Val Gln Leu Gln Gln Ser Gly Gly Gly Leu Val Gln Pro Gly Gly
 1               5                  10                  15

Ser Leu Arg Leu Ser Cys Ala Ala Ser Gly Phe Thr Phe Ser
            20                  25                  30
```

<210> SEQ ID NO 184
<211> LENGTH: 14
<212> TYPE: PRT
<213> ORGANISM: artificial sequence
<220> FEATURE:
<223> OTHER INFORMATION: synthetic polypeptide

<400> SEQUENCE: 184

```
Trp Val Arg Gln Ala Pro Val Lys Gly Leu Glu Trp Val Ser
 1               5                  10
```

<210> SEQ ID NO 185
<211> LENGTH: 30
<212> TYPE: PRT
<213> ORGANISM: artificial sequence
<220> FEATURE:
<223> OTHER INFORMATION: synthetic polypeptide

<400> SEQUENCE: 185

```
Gln Val Asn Leu Arg Glu Ser Gly Gly Gly Leu Val Lys Pro Gly Gly
 1               5                  10                  15

Ser Leu Arg Leu Ser Cys Ala Ala Ser Gly Phe Thr Phe Ser
            20                  25                  30
```

<210> SEQ ID NO 186
<211> LENGTH: 5
<212> TYPE: PRT
<213> ORGANISM: artificial sequence
<220> FEATURE:
<223> OTHER INFORMATION: synthetic polypeptide

<400> SEQUENCE: 186

```
Ser Tyr Ala Met Gly
 1               5
```

<210> SEQ ID NO 187
<211> LENGTH: 17
<212> TYPE: PRT
<213> ORGANISM: artificial sequence
<220> FEATURE:
<223> OTHER INFORMATION: synthetic polypeptide

<400> SEQUENCE: 187

```
Ala Ile Ser Ser Asn Gly Gly Ser Thr Tyr Tyr Ala Asp Ser Val Lys
 1               5                  10                  15

Gly
```

<210> SEQ ID NO 188
<211> LENGTH: 32
<212> TYPE: PRT
<213> ORGANISM: artificial sequence
<220> FEATURE:

<223> OTHER INFORMATION: synthetic polypeptide

<400> SEQUENCE: 188

Arg Phe Thr Ile Ser Arg Asp Asn Ser Lys Asn Thr Leu Tyr Leu Gln
1 5 10 15

Met Ser Ser Leu Arg Ala Glu Asp Thr Ala Val Tyr Tyr Cys Val Ala
20 25 30

<210> SEQ ID NO 189
<211> LENGTH: 32
<212> TYPE: PRT
<213> ORGANISM: artificial sequence
<220> FEATURE:
<223> OTHER INFORMATION: synthetic polypeptide

<400> SEQUENCE: 189

Arg Phe Thr Ile Ser Arg Asp Asn Ser Lys Asn Thr Leu Tyr Leu Gln
1 5 10 15

Met Asn Ser Leu Arg Ile Glu Asp Thr Ala Val Tyr Tyr Cys Gly Arg
20 25 30

<210> SEQ ID NO 190
<211> LENGTH: 16
<212> TYPE: PRT
<213> ORGANISM: artificial sequence
<220> FEATURE:
<223> OTHER INFORMATION: synthetic polypeptide

<400> SEQUENCE: 190

Val Ile Ser Asp Gly Ser Thr Thr Tyr Tyr Ala Asp Ser Val Lys Gly
1 5 10 15

<210> SEQ ID NO 191
<211> LENGTH: 32
<212> TYPE: PRT
<213> ORGANISM: artificial sequence
<220> FEATURE:
<223> OTHER INFORMATION: synthetic polypeptide

<400> SEQUENCE: 191

Arg Phe Thr Ile Ser Arg Asp Asn Ser Lys Asn Met Leu Tyr Leu Gln
1 5 10 15

Thr Asn Ser Leu Arg Ala Glu Asp Thr Ala Val Tyr Tyr Cys Ala Lys
20 25 30

<210> SEQ ID NO 192
<211> LENGTH: 17
<212> TYPE: PRT
<213> ORGANISM: artificial sequence
<220> FEATURE:
<223> OTHER INFORMATION: synthetic polypeptide

<400> SEQUENCE: 192

Ala Ile Ser Ala Ser Gly Gly Ser Thr Tyr Tyr Ala Asp Ser Val Lys
1 5 10 15

Gly

<210> SEQ ID NO 193
<211> LENGTH: 32
<212> TYPE: PRT
<213> ORGANISM: artificial sequence
<220> FEATURE:
<223> OTHER INFORMATION: synthetic polypeptide

<400> SEQUENCE: 193

Arg Phe Thr Ile Ser Arg Asp Asn Ser Lys Asn Thr Leu Tyr Leu Gln
1 5 10 15

Leu Asn Ser Leu Arg Ala Glu Asp Thr Ala Val Tyr Tyr Cys Ala Lys
20 25 30

<210> SEQ ID NO 194
<211> LENGTH: 16
<212> TYPE: PRT
<213> ORGANISM: artificial sequence
<220> FEATURE:
<223> OTHER INFORMATION: synthetic polypeptide

<400> SEQUENCE: 194

Asp Tyr Gly Tyr Cys Ser Gly Gly Ser Cys Tyr Ser Pro Phe Asp Tyr
1 5 10 15

<210> SEQ ID NO 195
<211> LENGTH: 11
<212> TYPE: PRT
<213> ORGANISM: artificial sequence
<220> FEATURE:
<223> OTHER INFORMATION: synthetic polypeptide

<400> SEQUENCE: 195

Arg Leu Glu Trp Leu Pro Leu Ala Trp Asp Tyr
1 5 10

<210> SEQ ID NO 196
<211> LENGTH: 13
<212> TYPE: PRT
<213> ORGANISM: artificial sequence
<220> FEATURE:
<223> OTHER INFORMATION: synthetic polypeptide

<400> SEQUENCE: 196

Ala Ala Arg Ile Ala Ala Arg Pro Gly Pro Leu Asp Tyr
1 5 10

<210> SEQ ID NO 197
<211> LENGTH: 10
<212> TYPE: PRT
<213> ORGANISM: artificial sequence
<220> FEATURE:
<223> OTHER INFORMATION: synthetic polypeptide

<400> SEQUENCE: 197

His Leu Ser Ser Gly Ser Ser Val Asp Tyr
1 5 10

<210> SEQ ID NO 198
<211> LENGTH: 12
<212> TYPE: PRT
<213> ORGANISM: artificial sequence
<220> FEATURE:
<223> OTHER INFORMATION: synthetic polypeptide

<400> SEQUENCE: 198

Ala Gly Pro Arg Thr Thr Val Thr Thr Val Asp Ser
1 5 10

<210> SEQ ID NO 199
<211> LENGTH: 10
<212> TYPE: PRT
<213> ORGANISM: artificial sequence
<220> FEATURE:
<223> OTHER INFORMATION: synthetic polypeptide

<400> SEQUENCE: 199

Gly Leu Lys Asp Ser Ser Gly Phe Asp Tyr
1 5 10

<210> SEQ ID NO 200
<211> LENGTH: 22
<212> TYPE: PRT
<213> ORGANISM: artificial sequence
<220> FEATURE:
<223> OTHER INFORMATION: synthetic polypeptide

<400> SEQUENCE: 200

Asn Phe Met Leu Thr Gln Asp Pro Ala Val Ser Val Ala Leu Gly Gln
1 5 10 15

Thr Val Arg Ile Thr Cys
20

<210> SEQ ID NO 201
<211> LENGTH: 21
<212> TYPE: PRT
<213> ORGANISM: artificial sequence
<220> FEATURE:
<223> OTHER INFORMATION: synthetic polypeptide

<400> SEQUENCE: 201

Ser Glu Leu Thr Gln Asp Pro Ala Val Ser Val Ala Val Gly Gln Thr
1 5 10 15

Val Lys Ile Thr Cys
20

<210> SEQ ID NO 202
<211> LENGTH: 11
<212> TYPE: PRT
<213> ORGANISM: artificial sequence
<220> FEATURE:
<223> OTHER INFORMATION: synthetic polypeptide

<400> SEQUENCE: 202

Gln Gly Asp Ser Leu Arg Asn Tyr Tyr Ala Ser
1 5 10

<210> SEQ ID NO 203
<211> LENGTH: 15
<212> TYPE: PRT
<213> ORGANISM: artificial sequence
<220> FEATURE:
<223> OTHER INFORMATION: synthetic polypeptide

<400> SEQUENCE: 203

Trp Tyr Gln Gln Lys Pro Arg Gln Ala Pro Val Leu Val Ile Tyr
1 5 10 15

<210> SEQ ID NO 204
<211> LENGTH: 21
<212> TYPE: PRT
<213> ORGANISM: artificial sequence
<220> FEATURE:
<223> OTHER INFORMATION: synthetic polypeptide

<400> SEQUENCE: 204

Ser Glu Leu Thr Gln Pro Pro Ser Ala Ser Gly Ser Pro Gly Gln Ser
1 5 10 15

Val Thr Ile Ser Cys
20

<210> SEQ ID NO 205
<211> LENGTH: 14
<212> TYPE: PRT
<213> ORGANISM: artificial sequence
<220> FEATURE:
<223> OTHER INFORMATION: synthetic polypeptide

<400> SEQUENCE: 205

Thr Gly Thr Ser Ser Asp Val Gly Gly Tyr Asn Tyr Val Ser
1 5 10

<210> SEQ ID NO 206
<211> LENGTH: 15
<212> TYPE: PRT
<213> ORGANISM: artificial sequence
<220> FEATURE:
<223> OTHER INFORMATION: synthetic polypeptide

<400> SEQUENCE: 206

Trp Tyr Gln Gln Arg Pro Gly Tyr Ala Pro Lys Leu Met Ile Tyr
1 5 10 15

<210> SEQ ID NO 207
<211> LENGTH: 22
<212> TYPE: PRT
<213> ORGANISM: artificial sequence
<220> FEATURE:
<223> OTHER INFORMATION: synthetic polypeptide

<400> SEQUENCE: 207

Gln Ser Val Leu Thr Gln Pro Pro Ser Val Ser Gly Ala Pro Gly Gln
1 5 10 15

Arg Val Thr Ile Ser Cys
20

<210> SEQ ID NO 208
<211> LENGTH: 14
<212> TYPE: PRT
<213> ORGANISM: artificial sequence
<220> FEATURE:
<223> OTHER INFORMATION: synthetic polypeptide

<400> SEQUENCE: 208

Thr Gly Ser Ser Ser Asn Ile Gly Ala Gly Tyr Asp Val His
1 5 10

<210> SEQ ID NO 209
<211> LENGTH: 15
<212> TYPE: PRT
<213> ORGANISM: artificial sequence
<220> FEATURE:
<223> OTHER INFORMATION: synthetic polypeptide

<400> SEQUENCE: 209

Trp Tyr Gln Gln Leu Pro Gly Thr Ala Pro Lys Leu Leu Thr Tyr
1 5 10 15

<210> SEQ ID NO 210
<211> LENGTH: 7
<212> TYPE: PRT
<213> ORGANISM: artificial sequence
<220> FEATURE:
<223> OTHER INFORMATION: synthetic polypeptide

<400> SEQUENCE: 210

-continued

```
Asp Val Ser Asn Arg Pro Ser
 1               5


<210> SEQ ID NO 211
<211> LENGTH: 32
<212> TYPE: PRT
<213> ORGANISM: artificial sequence
<220> FEATURE:
<223> OTHER INFORMATION: synthetic polypeptide

<400> SEQUENCE: 211

Gly Val Ser Asn Arg Phe Ser Gly Ser Lys Ser Gly Asn Ser Ala Ser
 1               5                  10                  15

Leu Asp Ile Ser Gly Leu Gln Ser Glu Asp Glu Ala Asp Tyr Tyr Cys
            20                  25                  30


<210> SEQ ID NO 212
<211> LENGTH: 7
<212> TYPE: PRT
<213> ORGANISM: artificial sequence
<220> FEATURE:
<223> OTHER INFORMATION: synthetic polypeptide

<400> SEQUENCE: 212

Gly Asn Ser Asn Arg Pro Ser
 1               5


<210> SEQ ID NO 213
<211> LENGTH: 32
<212> TYPE: PRT
<213> ORGANISM: artificial sequence
<220> FEATURE:
<223> OTHER INFORMATION: synthetic polypeptide

<400> SEQUENCE: 213

Gly Val Pro Asp Arg Phe Ser Gly Ser Lys Ser Gly Thr Ser Ala Ser
 1               5                  10                  15

Leu Ala Ile Thr Gly Leu Gln Ala Glu Asp Glu Ala Asp Tyr Tyr Arg
            20                  25                  30


<210> SEQ ID NO 214
<211> LENGTH: 10
<212> TYPE: PRT
<213> ORGANISM: artificial sequence
<220> FEATURE:
<223> OTHER INFORMATION: synthetic polypeptide

<400> SEQUENCE: 214

His Ser Arg Asp Ser Ser Gly Asn Tyr Leu
 1               5                  10


<210> SEQ ID NO 215
<211> LENGTH: 11
<212> TYPE: PRT
<213> ORGANISM: artificial sequence
<220> FEATURE:
<223> OTHER INFORMATION: synthetic polypeptide

<400> SEQUENCE: 215

Asn Ser Arg Asp Ser Ser Gly Asn His Lys Val
 1               5                  10


<210> SEQ ID NO 216
<211> LENGTH: 11
<212> TYPE: PRT
<213> ORGANISM: artificial sequence
```

<220> FEATURE:
<223> OTHER INFORMATION: synthetic polypeptide

<400> SEQUENCE: 216

Asn Ser Arg Asp Arg Ser Asn Asn His Leu Leu
1 5 10

<210> SEQ ID NO 217
<211> LENGTH: 11
<212> TYPE: PRT
<213> ORGANISM: artificial sequence
<220> FEATURE:
<223> OTHER INFORMATION: synthetic polypeptide

<400> SEQUENCE: 217

Ala Ala Trp Asp Asp Ser Leu Arg Glu Phe Leu
1 5 10

<210> SEQ ID NO 218
<211> LENGTH: 11
<212> TYPE: PRT
<213> ORGANISM: artificial sequence
<220> FEATURE:
<223> OTHER INFORMATION: synthetic polypeptide

<400> SEQUENCE: 218

Phe Gly Thr Gly Thr Lys Val Thr Val Leu Gly
1 5 10

<210> SEQ ID NO 219
<211> LENGTH: 11
<212> TYPE: PRT
<213> ORGANISM: artificial sequence
<220> FEATURE:
<223> OTHER INFORMATION: synthetic polypeptide

<400> SEQUENCE: 219

Ser Ala Trp Asp Ser Ser Leu Phe Asn Trp Val
1 5 10

<210> SEQ ID NO 220
<211> LENGTH: 11
<212> TYPE: PRT
<213> ORGANISM: artificial sequence
<220> FEATURE:
<223> OTHER INFORMATION: synthetic polypeptide

<400> SEQUENCE: 220

Asn Ser Arg Asp Ser Ser Ala Lys Arg Val Val
1 5 10

<210> SEQ ID NO 221
<211> LENGTH: 11
<212> TYPE: PRT
<213> ORGANISM: artificial sequence
<220> FEATURE:
<223> OTHER INFORMATION: synthetic polypeptide

<400> SEQUENCE: 221

Arg Ala Ser Gln Gly Ile Asn Asn Tyr Leu Ala
1 5 10

<210> SEQ ID NO 222
<211> LENGTH: 5
<212> TYPE: PRT
<213> ORGANISM: artificial sequence
<220> FEATURE:

<223> OTHER INFORMATION: synthetic polypeptide

<400> SEQUENCE: 222

Thr Tyr Ser Met Asn
1 5

<210> SEQ ID NO 223
<211> LENGTH: 30
<212> TYPE: PRT
<213> ORGANISM: artificial sequence
<220> FEATURE:
<223> OTHER INFORMATION: synthetic polypeptide

<400> SEQUENCE: 223

Gln Leu Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 224
<211> LENGTH: 5
<212> TYPE: PRT
<213> ORGANISM: artificial sequence
<220> FEATURE:
<223> OTHER INFORMATION: synthetic polypeptide

<400> SEQUENCE: 224

Ser Tyr Ala Met Asn
1 5

<210> SEQ ID NO 225
<211> LENGTH: 30
<212> TYPE: PRT
<213> ORGANISM: artificial sequence
<220> FEATURE:
<223> OTHER INFORMATION: synthetic polypeptide

<400> SEQUENCE: 225

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser
20 25 30

<210> SEQ ID NO 226
<211> LENGTH: 5
<212> TYPE: PRT
<213> ORGANISM: artificial sequence
<220> FEATURE:
<223> OTHER INFORMATION: synthetic polypeptide

<400> SEQUENCE: 226

Ser Asn Ser Ala Ala
1 5

<210> SEQ ID NO 227
<211> LENGTH: 16
<212> TYPE: PRT
<213> ORGANISM: artificial sequence
<220> FEATURE:
<223> OTHER INFORMATION: synthetic polypeptide

<400> SEQUENCE: 227

Trp Asn Trp Ile Arg Gln Ser Pro Ser Arg Gly Leu Glu Trp Leu Gly
1 5 10 15

<210> SEQ ID NO 228
<211> LENGTH: 30
<212> TYPE: PRT
<213> ORGANISM: artificial sequence
<220> FEATURE:
<223> OTHER INFORMATION: synthetic polypeptide

<400> SEQUENCE: 228

Gln Val Gln Leu Gln Glu Ser Gly Gly Gly Val Val Gln Pro Gly Gly
1 5 10 15

Ser Leu Arg Leu Ser Cys Ala Ala Ser Gly Phe Thr Phe Ser
20 25 30

<210> SEQ ID NO 229
<211> LENGTH: 5
<212> TYPE: PRT
<213> ORGANISM: artificial sequence
<220> FEATURE:
<223> OTHER INFORMATION: synthetic polypeptide

<400> SEQUENCE: 229

Asn Tyr Ala Met His
1 5

<210> SEQ ID NO 230
<211> LENGTH: 30
<212> TYPE: PRT
<213> ORGANISM: artificial sequence
<220> FEATURE:
<223> OTHER INFORMATION: synthetic polypeptide

<400> SEQUENCE: 230

Gln Val Gln Leu Gln Gln Ser Gly Gly Gly Leu Val Gln Pro Gly Gly
1 5 10 15

Ser Leu Arg Leu Ser Cys Ser Ala Ser Gly Phe Thr Phe Ser
20 25 30

<210> SEQ ID NO 231
<211> LENGTH: 5
<212> TYPE: PRT
<213> ORGANISM: artificial sequence
<220> FEATURE:
<223> OTHER INFORMATION: synthetic polypeptide

<400> SEQUENCE: 231

Asn Tyr Ala Ile His
1 5

<210> SEQ ID NO 232
<211> LENGTH: 30
<212> TYPE: PRT
<213> ORGANISM: artificial sequence
<220> FEATURE:
<223> OTHER INFORMATION: synthetic polypeptide

<400> SEQUENCE: 232

Gln Val Gln Leu Gln Glu Ser Gly Gly Gly Leu Val Gln Pro Gly Gly
1 5 10 15

Phe Leu Arg Leu Ser Cys Ala Ala Ser Gly Phe Thr Phe Ser
20 25 30

<210> SEQ ID NO 233
<211> LENGTH: 14
<212> TYPE: PRT
<213> ORGANISM: artificial sequence
<220> FEATURE:

<223> OTHER INFORMATION: synthetic polypeptide

<400> SEQUENCE: 233

Trp Val Arg Gln Thr Pro Gly Lys Gly Leu Glu Trp Val Ser
1 5 10

<210> SEQ ID NO 234
<211> LENGTH: 30
<212> TYPE: PRT
<213> ORGANISM: artificial sequence
<220> FEATURE:
<223> OTHER INFORMATION: synthetic polypeptide

<400> SEQUENCE: 234

Gln Val Gln Leu Gln Glu Ser Gly Gly Gly Leu Val Lys Pro Gly Gly
1 5 10 15

Ser Leu Arg Leu Ser Cys Ala Gly Ser Gly Phe Ile Phe Asn
20 25 30

<210> SEQ ID NO 235
<211> LENGTH: 14
<212> TYPE: PRT
<213> ORGANISM: artificial sequence
<220> FEATURE:
<223> OTHER INFORMATION: synthetic polypeptide

<400> SEQUENCE: 235

Trp Val Arg Gln Ser Pro Gly Lys Gly Leu Glu Trp Val Ser
1 5 10

<210> SEQ ID NO 236
<211> LENGTH: 30
<212> TYPE: PRT
<213> ORGANISM: artificial sequence
<220> FEATURE:
<223> OTHER INFORMATION: synthetic polypeptide

<400> SEQUENCE: 236

Gln Val Gln Leu Val Glu Ser Gly Gly Gly Leu Ile Gln Pro Gly Gly
1 5 10 15

Ser Leu Arg Leu Ser Cys Ala Ala Ser Gly Phe Thr Val Ser
20 25 30

<210> SEQ ID NO 237
<211> LENGTH: 5
<212> TYPE: PRT
<213> ORGANISM: artificial sequence
<220> FEATURE:
<223> OTHER INFORMATION: synthetic polypeptide

<400> SEQUENCE: 237

Ser Asn Tyr Met Ser
1 5

<210> SEQ ID NO 238
<211> LENGTH: 17
<212> TYPE: PRT
<213> ORGANISM: artificial sequence
<220> FEATURE:
<223> OTHER INFORMATION: synthetic polypeptide

<400> SEQUENCE: 238

Phe Ile Ser Ser Asp Gly Ser Asp Lys Tyr Tyr Val Asp Ser Val Lys
1 5 10 15

Gly

<210> SEQ ID NO 239
<211> LENGTH: 32
<212> TYPE: PRT
<213> ORGANISM: artificial sequence
<220> FEATURE:
<223> OTHER INFORMATION: synthetic polypeptide

<400> SEQUENCE: 239

```
Arg Phe Thr Ile Ser Arg Asp Thr Ser Lys Asn Met Met Tyr Leu Gln
 1               5                  10                  15

Met Asn Ser Leu Thr Thr Glu Asp Thr Ala Val Tyr Tyr Cys Ala Lys
            20                  25                  30
```

<210> SEQ ID NO 240
<211> LENGTH: 16
<212> TYPE: PRT
<213> ORGANISM: artificial sequence
<220> FEATURE:
<223> OTHER INFORMATION: synthetic polypeptide

<400> SEQUENCE: 240

```
Val Ile Tyr Arg Asp Gly His Gly Tyr Tyr Ala Asp Ser Val Lys Gly
 1               5                  10                  15
```

<210> SEQ ID NO 241
<211> LENGTH: 32
<212> TYPE: PRT
<213> ORGANISM: artificial sequence
<220> FEATURE:
<223> OTHER INFORMATION: synthetic polypeptide

<400> SEQUENCE: 241

```
Arg Phe Thr Val Ser Arg Asp Ser Ser Glu Asn Thr Val Tyr Leu Gln
 1               5                  10                  15

Met Asn Ser Leu Arg Ala Glu Asp Thr Ala Ile Tyr Tyr Cys Ala Ser
            20                  25                  30
```

<210> SEQ ID NO 242
<211> LENGTH: 17
<212> TYPE: PRT
<213> ORGANISM: artificial sequence
<220> FEATURE:
<223> OTHER INFORMATION: synthetic polypeptide

<400> SEQUENCE: 242

```
Ser Ile Ser Ser Ser Ser Ser Tyr Ile Tyr Tyr Ala Asp Ser Val Lys
 1               5                  10                  15

Gly
```

<210> SEQ ID NO 243
<211> LENGTH: 32
<212> TYPE: PRT
<213> ORGANISM: artificial sequence
<220> FEATURE:
<223> OTHER INFORMATION: synthetic polypeptide

<400> SEQUENCE: 243

```
Arg Phe Thr Ile Ser Arg Asp Asn Ala Asn Asn Ser Leu Tyr Leu Gln
 1               5                  10                  15

Met Asn Ser Leu Arg Ala Glu Asp Thr Ala Val Tyr Tyr Cys Ala Arg
            20                  25                  30
```

<210> SEQ ID NO 244

<211> LENGTH: 17
<212> TYPE: PRT
<213> ORGANISM: artificial sequence
<220> FEATURE:
<223> OTHER INFORMATION: synthetic polypeptide

<400> SEQUENCE: 244

Val Ile Trp Tyr Asp Gly Ser Asn Lys Tyr Tyr Ala Asp Ser Val Lys
1 5 10 15

Gly

<210> SEQ ID NO 245
<211> LENGTH: 32
<212> TYPE: PRT
<213> ORGANISM: artificial sequence
<220> FEATURE:
<223> OTHER INFORMATION: synthetic polypeptide

<400> SEQUENCE: 245

Arg Phe Thr Ile Ser Arg Asp Asn Ser Arg Asn Thr Leu Tyr Leu Glu
1 5 10 15

Met Asn Ser Leu Arg Ala Glu Asp Thr Ala Val Tyr Tyr Cys Val Lys
20 25 30

<210> SEQ ID NO 246
<211> LENGTH: 17
<212> TYPE: PRT
<213> ORGANISM: artificial sequence
<220> FEATURE:
<223> OTHER INFORMATION: synthetic polypeptide

<400> SEQUENCE: 246

Ala Ile Ser Gly Ser Gly Gly Asn Thr Tyr Tyr Ala Asp Ser Val Lys
1 5 10 15

Gly

<210> SEQ ID NO 247
<211> LENGTH: 32
<212> TYPE: PRT
<213> ORGANISM: artificial sequence
<220> FEATURE:
<223> OTHER INFORMATION: synthetic polypeptide

<400> SEQUENCE: 247

Arg Phe Thr Ile Ser Arg Asp Asn Ser Asn Asn Ala Leu Tyr Leu Gln
1 5 10 15

Met Asn Ser Leu Arg Val Glu Asp Thr Ala Val Tyr Tyr Cys Ala Arg
20 25 30

<210> SEQ ID NO 248
<211> LENGTH: 18
<212> TYPE: PRT
<213> ORGANISM: artificial sequence
<220> FEATURE:
<223> OTHER INFORMATION: synthetic polypeptide

<400> SEQUENCE: 248

Arg Thr Tyr Tyr Arg Ser Lys Trp Tyr Asn Asp Tyr Ala Val Ser Val
1 5 10 15

Lys Ser

<210> SEQ ID NO 249
<211> LENGTH: 32
<212> TYPE: PRT

<213> ORGANISM: artificial sequence
<220> FEATURE:
<223> OTHER INFORMATION: synthetic polypeptide

<400> SEQUENCE: 249

Arg Ile Thr Ile Asn Pro Asp Thr Ser Lys Asn Leu Phe Ser Leu Gln
1 5 10 15

Leu Asn Ser Val Thr Pro Glu Asp Thr Ala Leu Tyr Tyr Cys Ala Arg
20 25 30

<210> SEQ ID NO 250
<211> LENGTH: 17
<212> TYPE: PRT
<213> ORGANISM: artificial sequence
<220> FEATURE:
<223> OTHER INFORMATION: synthetic polypeptide

<400> SEQUENCE: 250

Ser Ile Ser Ser Asn Gly Gly Gly Thr Tyr Tyr Ala Asp Ser Val Lys
1 5 10 15

Gly

<210> SEQ ID NO 251
<211> LENGTH: 32
<212> TYPE: PRT
<213> ORGANISM: artificial sequence
<220> FEATURE:
<223> OTHER INFORMATION: synthetic polypeptide

<400> SEQUENCE: 251

Arg Phe Thr Ile Ser Arg Asp Asp Ala Lys Asn Thr Leu Tyr Leu Gln
1 5 10 15

Leu Asn Ser Leu Arg Asp Glu Asp Thr Ala Val Tyr Tyr Cys Ala Lys
20 25 30

<210> SEQ ID NO 252
<211> LENGTH: 17
<212> TYPE: PRT
<213> ORGANISM: artificial sequence
<220> FEATURE:
<223> OTHER INFORMATION: synthetic polypeptide

<400> SEQUENCE: 252

Ala Ile Asn Ser Asn Gly Gly Ser Thr Tyr Tyr Ala Asp Ser Val Lys
1 5 10 15

Gly

<210> SEQ ID NO 253
<211> LENGTH: 32
<212> TYPE: PRT
<213> ORGANISM: artificial sequence
<220> FEATURE:
<223> OTHER INFORMATION: synthetic polypeptide

<400> SEQUENCE: 253

Arg Ser Ile Ile Ser Arg Asp Asn Ser Met Asn Thr Val Tyr Leu Gln
1 5 10 15

Met Ser Ser Leu Arg Ala Glu Asp Thr Ala Val Tyr Tyr Cys Val Lys
20 25 30

<210> SEQ ID NO 254
<211> LENGTH: 17
<212> TYPE: PRT
<213> ORGANISM: artificial sequence
<220> FEATURE:
<223> OTHER INFORMATION: synthetic polypeptide

<400> SEQUENCE: 254

Tyr Ile Ser Ser Ser Ser Ser Tyr Thr Asn Tyr Ala Asp Ser Val Lys
1 5 10 15

Gly

<210> SEQ ID NO 255
<211> LENGTH: 17
<212> TYPE: PRT
<213> ORGANISM: artificial sequence
<220> FEATURE:
<223> OTHER INFORMATION: synthetic polypeptide

<400> SEQUENCE: 255

Ser Thr Gly Gly Ser Gly Lys Asn Thr Phe Tyr Ala Asp Ser Val Arg
1 5 10 15

Gly

<210> SEQ ID NO 256
<211> LENGTH: 32
<212> TYPE: PRT
<213> ORGANISM: artificial sequence
<220> FEATURE:
<223> OTHER INFORMATION: synthetic polypeptide

<400> SEQUENCE: 256

Arg Phe Thr Ile Ser Arg Asp Asn Ala Lys Asn Ser Leu Tyr Leu Gln
1 5 10 15

Met Asn Ser Leu Arg Ala Glu Asp Thr Ala Val Tyr Tyr Cys Ala Arg
20 25 30

<210> SEQ ID NO 257
<211> LENGTH: 17
<212> TYPE: PRT
<213> ORGANISM: artificial sequence
<220> FEATURE:
<223> OTHER INFORMATION: synthetic polypeptide

<400> SEQUENCE: 257

Tyr Ile Ser Ser Ser Gly Ser Tyr Thr Asn Tyr Ala Asp Ser Val Lys
1 5 10 15

Gly

<210> SEQ ID NO 258
<211> LENGTH: 32
<212> TYPE: PRT
<213> ORGANISM: artificial sequence
<220> FEATURE:
<223> OTHER INFORMATION: synthetic polypeptide

<400> SEQUENCE: 258

Arg Phe Thr Ile Ser Arg Asp Asn Ala Lys Asn Thr Leu Tyr Leu Gln
1 5 10 15

Met Asn Ser Leu Arg Ala Glu Asp Thr Ala Val Tyr Tyr Cys Ala Lys
20 25 30

<210> SEQ ID NO 259
<211> LENGTH: 16
<212> TYPE: PRT
<213> ORGANISM: artificial sequence
<220> FEATURE:
<223> OTHER INFORMATION: synthetic polypeptide

<400> SEQUENCE: 259

Val Ile Tyr Ser Gly Gly Ser Thr Tyr Tyr Ala Asp Ser Val Lys Gly
1 5 10 15

<210> SEQ ID NO 260
<211> LENGTH: 11
<212> TYPE: PRT
<213> ORGANISM: artificial sequence
<220> FEATURE:
<223> OTHER INFORMATION: synthetic polypeptide

<400> SEQUENCE: 260

Asp Trp Gly Ser Asn Trp Tyr Leu Phe Asp Tyr
1 5 10

<210> SEQ ID NO 261
<211> LENGTH: 14
<212> TYPE: PRT
<213> ORGANISM: artificial sequence
<220> FEATURE:
<223> OTHER INFORMATION: synthetic polypeptide

<400> SEQUENCE: 261

His Asp Tyr Ala Gly Asn Pro Ala Gly Ser Ala Ser Gly Tyr
1 5 10

<210> SEQ ID NO 262
<211> LENGTH: 13
<212> TYPE: PRT
<213> ORGANISM: artificial sequence
<220> FEATURE:
<223> OTHER INFORMATION: synthetic polypeptide

<400> SEQUENCE: 262

Gly Asn Thr Val Ala Gln Arg Leu Asp Val Phe Asp Tyr
1 5 10

<210> SEQ ID NO 263
<211> LENGTH: 12
<212> TYPE: PRT
<213> ORGANISM: artificial sequence
<220> FEATURE:
<223> OTHER INFORMATION: synthetic polypeptide

<400> SEQUENCE: 263

Asp Arg Gln Pro Asp Gly Arg Trp Pro Phe Asp Leu
1 5 10

<210> SEQ ID NO 264
<211> LENGTH: 9
<212> TYPE: PRT
<213> ORGANISM: artificial sequence
<220> FEATURE:
<223> OTHER INFORMATION: synthetic polypeptide

<400> SEQUENCE: 264

Asp Ala Ser Tyr Tyr Ala Asp Asp Tyr
1 5

<210> SEQ ID NO 265
<211> LENGTH: 9
<212> TYPE: PRT
<213> ORGANISM: artificial sequence
<220> FEATURE:
<223> OTHER INFORMATION: synthetic polypeptide

<400> SEQUENCE: 265

Glu Glu Asp Tyr Ser Gly Phe Gln His
1 5

<210> SEQ ID NO 266
<211> LENGTH: 8
<212> TYPE: PRT
<213> ORGANISM: artificial sequence
<220> FEATURE:
<223> OTHER INFORMATION: synthetic polypeptide

<400> SEQUENCE: 266

Asp Tyr Phe Gly Ser Ile Asp Tyr
1 5

<210> SEQ ID NO 267
<211> LENGTH: 9
<212> TYPE: PRT
<213> ORGANISM: artificial sequence
<220> FEATURE:
<223> OTHER INFORMATION: synthetic polypeptide

<400> SEQUENCE: 267

Glu Glu Asn Gly Ser Gly Phe Asp Ser
1 5

<210> SEQ ID NO 268
<211> LENGTH: 7
<212> TYPE: PRT
<213> ORGANISM: artificial sequence
<220> FEATURE:
<223> OTHER INFORMATION: synthetic polypeptide

<400> SEQUENCE: 268

Asp Asn Trp Tyr Phe Asp Leu
1 5

<210> SEQ ID NO 269
<211> LENGTH: 11
<212> TYPE: PRT
<213> ORGANISM: artificial sequence
<220> FEATURE:
<223> OTHER INFORMATION: synthetic polypeptide

<400> SEQUENCE: 269

Trp Gly Arg Gly Thr Leu Val Thr Val Ser Ser
1 5 10

<210> SEQ ID NO 270
<211> LENGTH: 10
<212> TYPE: PRT
<213> ORGANISM: artificial sequence
<220> FEATURE:
<223> OTHER INFORMATION: synthetic polypeptide

<400> SEQUENCE: 270

Ala Leu Tyr Tyr Asp Glu Ala Leu Asp Tyr
1 5 10

<210> SEQ ID NO 271
<211> LENGTH: 9
<212> TYPE: PRT
<213> ORGANISM: artificial sequence
<220> FEATURE:
<223> OTHER INFORMATION: synthetic polypeptide

<400> SEQUENCE: 271

Glu Asp Ser Ser Gly Ser Phe Asp Tyr
1 5

<210> SEQ ID NO 272
<211> LENGTH: 11
<212> TYPE: PRT
<213> ORGANISM: artificial sequence
<220> FEATURE:
<223> OTHER INFORMATION: synthetic polypeptide

<400> SEQUENCE: 272

Val Arg Gly Trp Asp Gly Asp Tyr Leu Asp Tyr
1 5 10

<210> SEQ ID NO 273
<211> LENGTH: 11
<212> TYPE: PRT
<213> ORGANISM: artificial sequence
<220> FEATURE:
<223> OTHER INFORMATION: synthetic polypeptide

<400> SEQUENCE: 273

Gly Gly Phe Ser Gly Tyr Asp Tyr Phe Asp Tyr
1 5 10

<210> SEQ ID NO 274
<211> LENGTH: 11
<212> TYPE: PRT
<213> ORGANISM: artificial sequence
<220> FEATURE:
<223> OTHER INFORMATION: synthetic polypeptide

<400> SEQUENCE: 274

Ala Ala Trp Asp Asp Ile Leu Asn Gly Trp Val
1 5 10

<210> SEQ ID NO 275
<211> LENGTH: 11
<212> TYPE: PRT
<213> ORGANISM: artificial sequence
<220> FEATURE:
<223> OTHER INFORMATION: synthetic polypeptide

<400> SEQUENCE: 275

Ala Ala Trp Asp Asp Ser Leu Ser Glu Phe Leu
1 5 10

<210> SEQ ID NO 276
<211> LENGTH: 11
<212> TYPE: PRT
<213> ORGANISM: artificial sequence
<220> FEATURE:
<223> OTHER INFORMATION: synthetic polypeptide

<400> SEQUENCE: 276

Phe Gly Thr Gly Thr Lys Leu Thr Val Leu Gly
1 5 10

<210> SEQ ID NO 277
<211> LENGTH: 11
<212> TYPE: PRT
<213> ORGANISM: artificial sequence
<220> FEATURE:
<223> OTHER INFORMATION: synthetic polypeptide

<400> SEQUENCE: 277

Gln Ala Tyr Asp Ser Ser Leu Arg Gly Ser Val
1 5 10

<210> SEQ ID NO 278
<211> LENGTH: 10
<212> TYPE: PRT
<213> ORGANISM: artificial sequence
<220> FEATURE:
<223> OTHER INFORMATION: synthetic polypeptide

<400> SEQUENCE: 278

Ser Ser Tyr Arg Ser Gly Gly Thr Tyr Val
1 5 10

<210> SEQ ID NO 279
<211> LENGTH: 12
<212> TYPE: PRT
<213> ORGANISM: artificial sequence
<220> FEATURE:
<223> OTHER INFORMATION: synthetic polypeptide

<400> SEQUENCE: 279

His Ser Arg Asp Ser Ser Gly Asn His Pro Val Val
1 5 10

<210> SEQ ID NO 280
<211> LENGTH: 11
<212> TYPE: PRT
<213> ORGANISM: artificial sequence
<220> FEATURE:
<223> OTHER INFORMATION: synthetic polypeptide

<400> SEQUENCE: 280

Gln Ala Trp Asp Ser Thr Ser Asp His Val Val
1 5 10

<210> SEQ ID NO 281
<211> LENGTH: 9
<212> TYPE: PRT
<213> ORGANISM: artificial sequence
<220> FEATURE:
<223> OTHER INFORMATION: synthetic polypeptide

<400> SEQUENCE: 281

Gln Gln Ala Ser Val Phe Pro Val Thr
1 5

<210> SEQ ID NO 282
<211> LENGTH: 11
<212> TYPE: PRT
<213> ORGANISM: artificial sequence
<220> FEATURE:
<223> OTHER INFORMATION: synthetic polypeptide

<400> SEQUENCE: 282

Phe Gly Gly Gly Thr Lys Leu Glu Ile Lys Arg
1 5 10

<210> SEQ ID NO 283
<211> LENGTH: 9
<212> TYPE: PRT
<213> ORGANISM: artificial sequence
<220> FEATURE:
<223> OTHER INFORMATION: synthetic polypeptide

<400> SEQUENCE: 283

Gln Gln Tyr Ser Ser Tyr Pro Leu Thr 1 5

<210> SEQ ID NO 284
<211> LENGTH: 11
<212> TYPE: PRT
<213> ORGANISM: artificial sequence
<220> FEATURE:
<223> OTHER INFORMATION: synthetic polypeptide

<400> SEQUENCE: 284

Phe Gly Gln Gly Thr Lys Val Asp Ile Lys Arg
1 5 10

<210> SEQ ID NO 285
<211> LENGTH: 9
<212> TYPE: PRT
<213> ORGANISM: artificial sequence
<220> FEATURE:
<223> OTHER INFORMATION: synthetic polypeptide

<400> SEQUENCE: 285

Gln Gln Leu Gly Val Tyr Pro Leu Thr
1 5

<210> SEQ ID NO 286
<211> LENGTH: 11
<212> TYPE: PRT
<213> ORGANISM: artificial sequence
<220> FEATURE:
<223> OTHER INFORMATION: synthetic polypeptide

<400> SEQUENCE: 286

Ile Gly Gly Gly Thr Lys Val Glu Ile Lys Arg
1 5 10

<210> SEQ ID NO 287
<211> LENGTH: 9
<212> TYPE: PRT
<213> ORGANISM: artificial sequence
<220> FEATURE:
<223> OTHER INFORMATION: synthetic polypeptide

<400> SEQUENCE: 287

Gln Gln Tyr His Thr Ile Ser Arg Thr
1 5

<210> SEQ ID NO 288
<211> LENGTH: 11
<212> TYPE: PRT
<213> ORGANISM: artificial sequence
<220> FEATURE:
<223> OTHER INFORMATION: synthetic polypeptide
<220> FEATURE:
<221> NAME/KEY: VARIANT
<222> LOCATION: (4)...(4)
<223> OTHER INFORMATION: xxa=any amino acid

<400> SEQUENCE: 288

Phe Gly Pro Xaa Thr Lys Leu Glu Ile Lys Arg
1 5 10

<210> SEQ ID NO 289
<211> LENGTH: 9
<212> TYPE: PRT
<213> ORGANISM: artificial sequence
<220> FEATURE:
<223> OTHER INFORMATION: synthetic polypeptide

<400> SEQUENCE: 289

Gln Asn Leu Asn Ser Tyr Pro Leu Thr
1 5

<210> SEQ ID NO 290
<211> LENGTH: 11
<212> TYPE: PRT
<213> ORGANISM: artificial sequence
<220> FEATURE:
<223> OTHER INFORMATION: synthetic polypeptide

<400> SEQUENCE: 290

Gln Ser Tyr Asp Ser Ser Leu Ser Gly Trp Val
1 5 10

<210> SEQ ID NO 291
<211> LENGTH: 21
<212> TYPE: PRT
<213> ORGANISM: artificial sequence
<220> FEATURE:
<223> OTHER INFORMATION: synthetic polypeptide

<400> SEQUENCE: 291

Ser Val Leu Thr Gln Pro Pro Ser Ala Ser Glu Thr Pro Gly Gln Arg
1 5 10 15

Val Thr Ile Ser Cys
20

<210> SEQ ID NO 292
<211> LENGTH: 13
<212> TYPE: PRT
<213> ORGANISM: artificial sequence
<220> FEATURE:
<223> OTHER INFORMATION: synthetic polypeptide

<400> SEQUENCE: 292

Ser Gly Ser Ser Ser Asn Ile Gly Ala Asn Thr Val His
1 5 10

<210> SEQ ID NO 293
<211> LENGTH: 15
<212> TYPE: PRT
<213> ORGANISM: artificial sequence
<220> FEATURE:
<223> OTHER INFORMATION: synthetic polypeptide

<400> SEQUENCE: 293

Trp Tyr Gln Gln Phe Pro Gly Thr Ala Pro Lys Leu Leu Ile Tyr
1 5 10 15

<210> SEQ ID NO 294
<211> LENGTH: 21
<212> TYPE: PRT
<213> ORGANISM: artificial sequence
<220> FEATURE:
<223> OTHER INFORMATION: synthetic polypeptide

<400> SEQUENCE: 294

Ser Ala Leu Thr Gln Pro Ala Ser Val Ser Ala Ser Pro Gly Gln Ser
1 5 10 15

Ile Thr Ile Ser Cys
20

<210> SEQ ID NO 295
<211> LENGTH: 14

<212> TYPE: PRT
<213> ORGANISM: artificial sequence
<220> FEATURE:
<223> OTHER INFORMATION: synthetic polypeptide

<400> SEQUENCE: 295

Thr Gly Thr Ser Ser Asp Val Gly Gly Tyr Asp Tyr Val Ser
1 5 10

<210> SEQ ID NO 296
<211> LENGTH: 15
<212> TYPE: PRT
<213> ORGANISM: artificial sequence
<220> FEATURE:
<223> OTHER INFORMATION: synthetic polypeptide

<400> SEQUENCE: 296

Trp Tyr Gln Gln His Pro Gly Lys Ala Pro Lys Leu Val Met Tyr
1 5 10 15

<210> SEQ ID NO 297
<211> LENGTH: 21
<212> TYPE: PRT
<213> ORGANISM: artificial sequence
<220> FEATURE:
<223> OTHER INFORMATION: synthetic polypeptide

<400> SEQUENCE: 297

Ser Val Leu Thr Gln Pro Pro Ser Val Ser Gly Ala Pro Gly Gln Arg
1 5 10 15

Val Thr Ile Ser Cys
20

<210> SEQ ID NO 298
<211> LENGTH: 14
<212> TYPE: PRT
<213> ORGANISM: artificial sequence
<220> FEATURE:
<223> OTHER INFORMATION: synthetic polypeptide

<400> SEQUENCE: 298

Thr Gly Gly Ser Ser Asn Val Gly Ala Gly Phe Asp Val His
1 5 10

<210> SEQ ID NO 299
<211> LENGTH: 15
<212> TYPE: PRT
<213> ORGANISM: artificial sequence
<220> FEATURE:
<223> OTHER INFORMATION: synthetic polypeptide

<400> SEQUENCE: 299

Trp Tyr Gln Gln Leu Pro Gly Thr Ala Pro Lys Leu Leu Ile Tyr
1 5 10 15

<210> SEQ ID NO 300
<211> LENGTH: 21
<212> TYPE: PRT
<213> ORGANISM: artificial sequence
<220> FEATURE:
<223> OTHER INFORMATION: synthetic polypeptide

<400> SEQUENCE: 300

Ser Ala Leu Thr Gln Pro Ala Ser Val Ser Gly Ser Pro Gly Gln Ser
1 5 10 15

Val Thr Ile Ser Cys

20

<210> SEQ ID NO 301
<211> LENGTH: 14
<212> TYPE: PRT
<213> ORGANISM: artificial sequence
<220> FEATURE:
<223> OTHER INFORMATION: synthetic polypeptide

<400> SEQUENCE: 301

Thr Gly Ala Asn Ser Asp Leu Gly Gly Tyr Asn Tyr Val Ser
1 5 10

<210> SEQ ID NO 302
<211> LENGTH: 15
<212> TYPE: PRT
<213> ORGANISM: artificial sequence
<220> FEATURE:
<223> OTHER INFORMATION: synthetic polypeptide

<400> SEQUENCE: 302

Trp Tyr Gln His His Pro Ala Lys Ala Pro Lys Leu Ile Ile Tyr
1 5 10 15

<210> SEQ ID NO 303
<211> LENGTH: 11
<212> TYPE: PRT
<213> ORGANISM: artificial sequence
<220> FEATURE:
<223> OTHER INFORMATION: synthetic polypeptide

<400> SEQUENCE: 303

Gln Gly Asp Ser Leu Lys Ser Tyr Tyr Ala Ser
1 5 10

<210> SEQ ID NO 304
<211> LENGTH: 22
<212> TYPE: PRT
<213> ORGANISM: artificial sequence
<220> FEATURE:
<223> OTHER INFORMATION: synthetic polypeptide

<400> SEQUENCE: 304

Gln Ser Ala Leu Thr Gln Pro Ala Ser Val Ser Gly Ser Pro Gly Gln
1 5 10 15

Ser Ile Thr Ile Ser Cys
20

<210> SEQ ID NO 305
<211> LENGTH: 247
<212> TYPE: PRT
<213> ORGANISM: artificial sequence
<220> FEATURE:
<223> OTHER INFORMATION: synthetic polypeptide

<400> SEQUENCE: 305

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

-continued

```
Lys Gly Arg Phe Thr Ile Ser Arg Asp Asn Ser Arg Asn Thr Leu Tyr
65                  70                  75                  80

Leu Glu Met Asn Ser Leu Arg Ala Glu Asp Thr Ala Val Tyr Tyr Cys
                85                  90                  95

Val Lys Asp Arg Gln Pro Asp Gly Arg Trp Pro Phe Asp Leu Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Val Thr Ile Ser Cys Thr Gly
145                 150                 155                 160

Ala Asn Ser Asp Leu Gly Gly Tyr Asn Tyr Val Ser Trp Tyr Gln His
                165                 170                 175

His Pro Ala Lys Ala Pro Lys Leu Ile Ile Tyr Glu Val Asn Asn Arg
            180                 185                 190

Pro Ser Gly Val Ser His Arg Phe Ser Gly Ser Lys Ser Ala Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Arg Ser Gly Gly Thr Tyr Val Phe Gly Thr Gly
225                 230                 235                 240

Thr Lys Leu Thr Val Leu Gly
                245
```

<210> SEQ ID NO 306
<211> LENGTH: 741
<212> TYPE: DNA
<213> ORGANISM: artificial sequence
<220> FEATURE:
<223> OTHER INFORMATION: synthetic polynucleotide

<400> SEQUENCE: 306

```
caggtgcagc tggtgcagtc tgggggaggc ttggtacagc ctggggggtc cctgagactc      60

tcctgtgcag cgtctggatt caccttcagt agctatggca tgcactgggt ccgccaggct     120

ccaggcaagg ggctggagtg ggtggcagtt atatggtatg atggaagtaa taaatactat     180

gcagactccg tgaagggccg attcaccatc tccagagaca attccaggaa cacattgtat     240

ttggaaatga acagcctgag ggccgaggac acggccgttt attattgtgt gaaagatcgt     300

caaccggacg ggagatggcc atttgactta tggggccagg gaaccctggt caccgtctcc     360

tcaggtggag gcggttcagg cggaggtggc tctggcggtg gcggatcgca gtctgccctg     420

actcagcctg cctccgtgtc ggggtctcct ggacagtcgg tcaccatctc ctgcacagga     480

gccaacagtg accttggtgg ttataactat gtctcctggt accaacatca cccagccaaa     540

gcccccaaac tcataattta tgaggtcaat aatcggccct caggggtttc tcatcgcttc     600

tctggctcca agtctgccaa cacggcctcc ctgaccatct ctgggctcca ggctgaggac     660

gaggctgatt attactgcag ctcatataga agcggcggca cttatgtttt cggaactggg     720

accaagctga ccgtcctagg t                                                741
```

<210> SEQ ID NO 307
<211> LENGTH: 242
<212> TYPE: PRT
<213> ORGANISM: artificial sequence
<220> FEATURE:
<223> OTHER INFORMATION: synthetic polypeptide

<400> SEQUENCE: 307

Gln Leu Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Ala Ile Ser Gly Ser Gly Gly Asn Thr Tyr Tyr Ala Asp Ser Val
50 55 60

Lys Gly Arg Phe Thr Ile Ser Arg Asp Asn Ser Asn Asn Ala Leu Tyr
65 70 75 80

Leu Gln Met Asn Ser Leu Arg Val Glu Asp Thr Ala Val Tyr Tyr Cys
85 90 95

Ala Arg Asp Ala Ser Tyr Tyr Ala Asp Asp Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Ser Glu Leu Thr Gln Asp Pro Ala Val Ser Val
130 135 140

Ala Leu Gly Gln Thr Val Arg Ile Thr Cys Gln Gly Asp Ser Leu Lys
145 150 155 160

Ser Tyr Tyr Ala Ser Trp Tyr Gln Gln Lys Pro Gly Gln Ala Pro Val
165 170 175

Leu Val Ile Tyr Gly Lys Asn Asn Arg Pro Ser Gly Ile Pro Asp Arg
180 185 190

Phe Ser Gly Ser Ser Ser Gly Asn Thr Ala Ser Leu Thr Ile Thr Gly
195 200 205

Ala Gln Ala Glu Asp Glu Ala Asp Tyr Tyr Cys His Ser Arg Asp Ser
210 215 220

Ser Gly Asn His Pro Val Val Phe Gly Gly Gly Thr Lys Val Thr Val
225 230 235 240

Leu Gly

<210> SEQ ID NO 308
<211> LENGTH: 726
<212> TYPE: DNA
<213> ORGANISM: artificial sequence
<220> FEATURE:
<223> OTHER INFORMATION: synthetic polynucleotide

<400> SEQUENCE: 308
cagttgcagc tggtggagtc tgggggaggc ttggtacagc ctggggggtc cctgagactc 60
tcctgtgcag cctctggatt cacttttagc agctatgcca tgaactgggt ccgccaggct 120
ccagggaagg ggctggagtg ggtctcagct attagtggta gtggtggtaa cacatactat 180
gcagactccg tgaagggccg gttcaccatc tccagagaca attccaacaa cgccctgtat 240
ctgcaaatga acagcctgag agtcgaggac acggctgtgt attactgtgc gagagatgcc 300
agttactatg ctgatgacta ctggggccag ggaaccctgg tcaccgtctc ctcaggtgga 360
ggcggttcag gcggaggtgg ctctggcggt ggcggatcgt ctgagctgac tcaggaccct 420
gctgtgtctg tggccttggg acagacagtc aggatcacat gccaaggaga cagcctcaaa 480
agctactatg caagttggta ccagcagaag ccaggacagg cccctgtact tgtcatctat 540
ggtaaaaaca accggccctc agggatccca gaccgattct ctggctccag ctcaggaaac 600
acagcttcct tgaccatcac tggggctcag gcggaagatg aggctgacta ttactgtcac 660
tcccgggaca gcagtggtaa ccatccggtg gtattcggcg gagggaccaa ggtcaccgtc 720
ctaggt 726

<210> SEQ ID NO 309
<211> LENGTH: 248
<212> TYPE: PRT
<213> ORGANISM: artificial sequence
<220> FEATURE:
<223> OTHER INFORMATION: synthetic polypeptide

<400> SEQUENCE: 309

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Leu Phe Ser Leu Gln Leu Asn Ser Val Thr Pro Glu Asp Thr Ala Leu
85 90 95

Tyr Tyr Cys Ala Arg Glu Glu Asp Tyr Ser Gly Phe Gln His Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Thr Ile Ser Cys Thr Gly
145 150 155 160

Thr Ser Ser Asp Val Gly Gly Tyr Asn Tyr Val Ser Trp Tyr Gln Gln
165 170 175

His Pro Gly Lys Ala Pro Lys Leu Met Ile Tyr Glu Gly Ser Lys Arg
180 185 190

Pro Ser Gly Val Pro Glu Arg Phe Ser Gly Ser Asn Ser Gly Asn Thr
195 200 205

Ala Thr Leu Thr Ile Gly Arg Val Glu Ala Gly Asp Glu Ala Asp Tyr
210 215 220

Tyr Cys Gln Ala Trp Asp Ser Thr Ser Asp His Val Val Phe Gly Gly
225 230 235 240

Gly Thr Lys Val Thr Val Leu Gly
245

<210> SEQ ID NO 310
<211> LENGTH: 744
<212> TYPE: DNA
<213> ORGANISM: artificial sequence
<220> FEATURE:
<223> OTHER INFORMATION: synthetic polynucleotide

<400> SEQUENCE: 310
caggtacagc tgcagcagtc aggtccagga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac gtccaagaac 240
ctcttctccc tgcagctgaa ctctgtgact cccgaggaca cggctctgta ttactgtgca 300
agagaggagg attacagtgg cttccagcac tggggccagg gcaccctggt caccgtctct 360
tcaggtggag gcggttcagg cggaggtggc tctggcggtg gcggatcgca gtctgctctg 420
actcagcctg cctccgtgtc tgggtctcct ggacagtcga tcaccatctc ctgcactgga 480
accagcagtg acgttggtgg ttataactat gtctcctggt atcaacagca cccaggcaaa 540
gcccccaaac tcatgattta tgagggcagt aagcggccct caggggtccc tgagcgattc 600
tctggctcca actctgggaa cacggccacc ctgaccatcg gcagggtcga agccggggat 660
gaggccgact attactgtca ggcgtgggat agtactagtg atcatgtggt tttcggcgga 720
gggaccaagg tcaccgtcct aggt 744

<210> SEQ ID NO 311
<211> LENGTH: 241
<212> TYPE: PRT
<213> ORGANISM: artificial sequence
<220> FEATURE:
<223> OTHER INFORMATION: synthetic polypeptide

<400> SEQUENCE: 311

Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Tyr Val
        35                  40                  45

Ser Ser Ile Ser Ser Asn Gly Gly Gly Thr Tyr Tyr Ala Asp Ser Val
    50                  55                  60

Lys Gly Arg Phe Thr Ile Ser Arg Asp Asp Ala Lys Asn Thr Leu Tyr
65                  70                  75                  80

Leu Gln Leu Asn Ser Leu Arg Asp Glu Asp Thr Ala Val Tyr Tyr Cys
                85                  90                  95

Ala Lys Asp Tyr Phe Gly Ser Ile Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Pro Glu Leu Thr Gln Asp Pro Ala Val Ser Val Ala
    130                 135                 140

Leu Gly Gln Thr Val Thr Ile Thr Cys Gln Gly Asp Ser Leu Arg Ser
145                 150                 155                 160

Tyr Tyr Ala Ser Trp Tyr Gln Gln Lys Pro Gly Gln Ala Pro Leu Leu
                165                 170                 175

Val Ile Tyr Gly Lys Asn Ile Arg Pro Ser Gly Ile Pro Asp Arg Phe
            180                 185                 190

Ser Gly Ser Ser Ser Gly Asn Ser Ala Ser Leu Thr Ile Thr Gly Ala
        195                 200                 205

Gln Ala Glu Asp Glu Ala Asp Tyr Tyr Cys His Ser Arg Asp Ser Ser
    210                 215                 220

Gly Thr His Leu Arg Val Phe Gly Gly Gly Thr Lys Leu Thr Val Leu
225                 230                 235                 240

Gly

-continued

<210> SEQ ID NO 312
<211> LENGTH: 723
<212> TYPE: DNA
<213> ORGANISM: artificial sequence
<220> FEATURE:
<223> OTHER INFORMATION: synthetic polynucleotide

<400> SEQUENCE: 312
caggtgcagc tgcaggagtc gggggaggc gtggtccagc ctggggggtc cctgagactc 60
tcctgtgcag cgtctggatt caccttcagt aactatgcta tgcactgggt ccgccaggct 120
ccagggaagg gactggaata tgtttcatct attagtagta atgggggtgg cacatattat 180
gcagactctg tgaagggcag attcaccatc tccagagacg acgccaagaa cacactgtat 240
ctacaactga acagtctgag agacgaggac acggctgtgt attactgcgc taaagattac 300
tttggttcta ttgactactg gggccaggga accctggtca ccgtctcctc aggtggaggc 360
ggttcaggcg gaggtggctc tggcggtggc ggatcgcctg agctgactca ggaccctgct 420
gtgtctgtgg ccttgggaca gacagtcacg atcacatgcc aaggagacag cctcagaagc 480
tattatgcaa gttggtacca gcagaagcca ggacaggccc ctctccttgt catctatggt 540
aaaaacatcc ggccctcagg gatcccagac cgattctctg gctccagctc aggaaactca 600
gcttccttga ccatcactgg ggctcaggcg gaagatgagg ctgactatta ctgtcactcc 660
cgggacagca gtggtaccca tctaagggta ttcggcggag ggaccaagct gaccgtccta 720
ggt 723

<210> SEQ ID NO 313
<211> LENGTH: 241
<212> TYPE: PRT
<213> ORGANISM: artificial sequence
<220> FEATURE:
<223> OTHER INFORMATION: synthetic polypeptide

<400> SEQUENCE: 313

Gln Val Gln Leu Gln Gln Ser Gly Gly Gly Leu Val Gln Pro Gly Gly
1 5 10 15

Ser Leu Arg Leu Ser Cys Ser Ala Ser Gly Phe Thr Phe Ser Asn Tyr
20 25 30

Ala Ile His Trp Val Arg Gln Ala Pro Gly Lys Gly Leu Glu Tyr Val
35 40 45

Ser Ala Ile Asn Ser Asn Gly Gly Ser Thr Tyr Tyr Ala Asp Ser Val
50 55 60

Lys Gly Arg Ser Ile Ile Ser Arg Asp Asn Ser Met Asn Thr Val Tyr
65 70 75 80

Leu Gln Met Ser Ser Leu Arg Ala Glu Asp Thr Ala Val Tyr Tyr Cys
85 90 95

Val Lys Glu Glu Asn Gly Ser Gly Phe Asp Ser Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Glu Ile Val Leu Thr Gln Ser Pro Ser Ser Val
130 135 140

Ser Ala Ser Val Gly Asp Arg Val Thr Ile Thr Cys Arg Ala Ser Gln
145 150 155 160

Asp Ile Ser Lys Trp Leu Ala Trp Tyr Gln Gln Arg Pro Gly Lys Val
165 170 175

```
Pro Arg Leu Leu Ile Tyr Ser Ala Ser Ser Leu Gln Ser Gly Val Pro
            180                185                190

Ser Arg Phe Ser Gly Ser Gly Ser Gly Thr Asp Phe Thr Leu Thr Ile
        195                200                205

Ser Ser Leu Gln Pro Glu Asp Phe Ala Ser Tyr Phe Cys Gln Gln Ala
    210                215                220

Ser Val Phe Pro Val Thr Phe Gly Gly Gly Thr Lys Leu Glu Ile Lys
225                230                235                240

Arg
```

<210> SEQ ID NO 314
<211> LENGTH: 723
<212> TYPE: DNA
<213> ORGANISM: artificial sequence
<220> FEATURE:
<223> OTHER INFORMATION: synthetic polynucleotide

<400> SEQUENCE: 314

```
caggtacagc tgcagcagtc aggggaggc ttggtccagc ctgggggtc cctgagactc      60

tcctgttcag cctctggatt caccttcagt aactatgcta ttcactgggt ccgccaggct    120

ccagggaagg gactggaata tgtttcagct attaatagta atgggggcag cacatactac    180

gcagactccg tgaagggcag atccatcatc tccagagaca attccatgaa cacggtgtat    240

cttcaaatga gcagtctgag agctgaggac acggctgtct attactgtgt gaaggaggag    300

aatggttcgg ggtttgactc ctggggccag ggcaccctgg tcaccgtctc ctcaggtgga    360

ggcggttcag gcggaggtgg ctctggcggt ggcggatcgg aaattgtgct gactcagtct    420

ccatcttccg tgtctgcttc tgtaggagac agagtcacca tcacttgtcg ggcgagtcag    480

gatataagca agtggttagc ctggtatcag cagagaccag ggaaagtccc tagactcctc    540

atttattctg catccagttt gcaaagtggg gtcccatcaa gattcagcgg cagtggatct    600

gggacagatt tcactctcac catcagcagc ctgcagcctg aagattttgc atcttatttt    660

tgtcaacagg ctagtgtttt cccggtcact ttcggcggag ggaccaagct ggagatcaaa    720

cgt                                                                  723
```

<210> SEQ ID NO 315
<211> LENGTH: 239
<212> TYPE: PRT
<213> ORGANISM: artificial sequence
<220> FEATURE:
<223> OTHER INFORMATION: synthetic polypeptide

<400> SEQUENCE: 315

```
Gln Val Gln Leu Gln Glu Ser Gly Gly Gly Leu Val Gln Pro Gly Gly
 1               5                  10                  15

Phe Leu Arg Leu Ser Cys Ala Ala Ser Gly Phe Thr Phe Ser Ser Tyr
            20                  25                  30

Gly Met His Trp Val Arg Gln Thr Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Tyr Phe Asp Leu Trp Gly Arg Gly Thr Leu Val
```

100 105 110

Thr Val Ser Ser Gly Gly Gly Gly Ser Gly Gly Gly Gly Ser Gly Gly
115 120 125

Gly Gly Ser Asp Val Val Met Thr Gln Ser Pro Ser Thr Leu Ser Ala
130 135 140

Ser Val Gly Asp Arg Val Ser Ile Thr Cys Arg Ala Ser Glu Ser Ile
145 150 155 160

Ser Arg Trp Leu Ala Trp Tyr Gln Gln Lys Pro Gly Lys Ala Pro Lys
165 170 175

Ala Leu Ile Tyr Lys Ala Ser Ser Leu Glu Ser Gly Val Pro Ser Arg
180 185 190

Phe Ser Gly Ser Gly Ser Ala Thr Glu Phe Thr Leu Thr Ile Asn Ser
195 200 205

Leu Gln Pro Asp Asp Phe Ala Thr Tyr Tyr Cys Gln Gln Tyr Ser Ser
210 215 220

Tyr Pro Leu Thr Phe Gly Gln Gly Thr Lys Val Asp Ile Lys Arg
225 230 235

<210> SEQ ID NO 316
<211> LENGTH: 717
<212> TYPE: DNA
<213> ORGANISM: artificial sequence
<220> FEATURE:
<223> OTHER INFORMATION: synthetic polynucleotide

<400> SEQUENCE: 316
caggtgcagc tgcaggagtc gggggaggc ttggtccagc ctgggggtt cctgagactc 60 tcctgtgcag cgtctggatt caccttcagc agctatggca tgcactgggt ccgccagact 120
ccagggaagg ggctggagtg ggtttcatac attagtagta gtagtagtta cacaaactac 180
gcagactctg tgaagggccg gttcaccatc tccagagaca attccaagaa cacgctgtat 240
ctgcagatga acagcctgag agctgaggac acggctgtgt attactgtgc gagagataac 300
tggtacttcg atctctgggg ccgtggcacc ctggtcaccg tctcctcagg tggaggcggt 360
tcaggcggag gtggctctgg cggtggcgga tcggatgttg tgatgactca gtctccttcc 420
accctgtctg catctgtagg agacagagtc agtatcactt gccgggccag tgagagtatt 480
agtaggtggt tggcctggta tcagcagaaa ccaggaaaag cccctaaggc cctgatctat 540
aaggcatcta gtttagaaag tggggtccca tcaaggttca gcggcagtgg atctgcgaca 600
gagttcactc tcaccatcaa cagcctgcag cctgatgatt ttgcaactta ttactgccaa 660
cagtatagta gttatccgtt gacgttcggc caagggacca aagtggatat caaacgt 717

<210> SEQ ID NO 317
<211> LENGTH: 242
<212> TYPE: PRT
<213> ORGANISM: artificial sequence
<220> FEATURE:
<223> OTHER INFORMATION: synthetic polypeptide

<400> SEQUENCE: 317

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

```
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Tyr Tyr Asp Glu Ala Leu Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Asp Met Ser Arg Trp Leu Ala Trp Tyr Gln Gln Lys Pro Gly Lys
                165                 170                 175

Ala Pro Lys Leu Leu Ile His Ser Ala Ser Thr Leu Gln Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Glu Asp Phe Ala Thr Tyr Tyr Cys Gln Gln
    210                 215                 220

Leu Gly Val Tyr Pro Leu Thr Ile Gly Gly Gly Thr Lys Val Glu Ile
225                 230                 235                 240

Lys Arg
```

```
<210> SEQ ID NO 318
<211> LENGTH: 726
<212> TYPE: DNA
<213> ORGANISM: artificial sequence
<220> FEATURE:
<223> OTHER INFORMATION: synthetic polynucleotide

<400> SEQUENCE: 318

caggtgcagc tggtggagtc tgggggaggc gtggtccaac ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gagagccctg    300

tactatgatg aagcccttga ctactggggc cagggaaccc tggtcaccgt ctcttcaggt    360

ggaggcggtt caggcggagg tggctctggc ggtggcggat cggaaattgt gttgacgcag    420

tctccatcct cactgtctgc atctgtagga gacagagtca ccatcacttg tcgggcgagt    480

caggatatga gcaggtggtt agcctggtat cagcagaaac cagggaaagc ccctaagctc    540

ctgatccatt ctgcatccac tttgcaaagt ggggtcccat caagattcag cggcagtgga    600

tctgggacag aattcactct gacaataagc agcctgcagc ctgaagattt tgcaacttac    660

tattgtcaac aacttggcgt ttacccgctc actatcggcg gggggaccaa ggtggaaatc    720

aaacgt                                                               726

<210> SEQ ID NO 319
<211> LENGTH: 241
<212> TYPE: PRT
<213> ORGANISM: artificial sequence
```

```
<220> FEATURE:
<223> OTHER INFORMATION: synthetic polypeptide
<220> FEATURE:
<221> NAME/KEY: VARIANT
<222> LOCATION: (234)...(234)
<223> OTHER INFORMATION: Xaa = any amino acid

<400> SEQUENCE: 319

Gln Val Gln Leu Gln Glu Ser Gly Gly Gly Leu Val Lys Pro Gly Gly
 1               5                  10                  15

Ser Leu Arg Leu Ser Cys Ala Gly Ser Gly Phe Ile Phe Asn Thr Tyr
            20                  25                  30

Ser Met Asn Trp Val Arg Gln Ser Pro Gly Lys Gly Leu Glu Trp Val
        35                  40                  45

Ser Ser Thr Gly Gly Ser Gly Lys Asn Thr Phe Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ser Ser Gly Ser Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Thr Leu
    130                 135                 140

Ser Ala Ser Ile Gly Asp Arg Val Thr Ile Thr Cys Arg Ala Ser Glu
145                 150                 155                 160

Gly Ile Tyr His Trp Leu Ala Trp Tyr Gln Gln Lys Pro Gly Lys Ala
                165                 170                 175

Pro Lys Leu Leu Ile Tyr Lys Ala Ser Ser Leu Ala Ser Gly Ala Pro
            180                 185                 190

Ser Arg Phe Ser Gly Ser Gly Ser Gly Thr Asp Phe Thr Leu Thr Ile
        195                 200                 205

Ser Ser Leu Gln Pro Asp Asp Phe Ala Thr Tyr Tyr Cys Gln Gln Tyr
    210                 215                 220

His Thr Ile Ser Arg Thr Phe Gly Pro Xaa Thr Lys Leu Glu Ile Lys
225                 230                 235                 240

Arg


<210> SEQ ID NO 320
<211> LENGTH: 723
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (700)...(700)
<223> OTHER INFORMATION: n= a,t,c, or g

<400> SEQUENCE: 320

caggtgcagc tgcaggagtc gggggaggc ctggtcaagc ctgggggtc cctgagactc      60

tcctgtgcag gctctggatt catcttcaat acctatagca tgaactgggt ccgccagtct    120

ccagggaagg ggctggagtg ggtctcgtcc actggtggta gtggtaaaaa cacattttat    180

gcagactcag tgaggggccg attcaccatc tccagagaca acgccaagaa ctcactgtat    240

ctgcaaatga acagcctgag agccgaagac acggctgtat attactgtgc gagagaggat    300
```

```
agtagtggtt cctttgacta ctggggccag gggaccctgg tcaccgtctc ctcaggtgga    360

ggcggttcag gcggaggtgg ctctggcggt ggcggatcgg acatccagat gacccagtct    420

ccttccaccc tgtctgcatc tattggagac agagtcacca tcacctgccg ggccagtgag    480

ggtatttatc actggttggc ctggtatcag cagaagccag ggaaagcccc taaactcctg    540

atctataagg cctctagttt agccagtggg gccccatcaa ggttcagcgg cagtggatct    600

gggacagatt tcactctcac catcagcagc ctgcagcctg atgattttgc aacttattac    660

tgccagcaat atcatactat ttcgaggacg ttcggcccan ggaccaagct ggagatcaaa    720

cgt                                                                   723
```

```
<210> SEQ ID NO 321
<211> LENGTH: 243
<212> TYPE: PRT
<213> ORGANISM: artificial sequence
<220> FEATURE:
<223> OTHER INFORMATION: synthetic polypeptide

<400> SEQUENCE: 321

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Tyr Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Gly Trp Asp Gly Asp Tyr Leu Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Ala Gly Ser Asp Ile Gln Met Thr Gln Ser Pro Ser
    130                 135                 140

Leu Leu Ser Ala Ser Val Gly Asp Arg Val Thr Ile Thr Cys Arg Ala
145                 150                 155                 160

Ser Gln Gly Ile Asn Asn Tyr Leu Ala Trp Tyr Gln Gln Lys Pro Gly
                165                 170                 175

Lys Ala Pro Lys Leu Leu Ile Tyr Ala Ala Ser Thr Leu Gln Ser Gly
            180                 185                 190

Val Pro Ser Arg Phe Ser Gly Ser Gly Ser Gly Thr Glu Phe Thr Leu
        195                 200                 205

Thr Ile Ser Gly Leu Gln Pro Glu Asp Phe Ala Thr Tyr Tyr Cys Gln
    210                 215                 220

Asn Leu Asn Ser Tyr Pro Leu Thr Phe Gly Gly Gly Thr Lys Val Glu
225                 230                 235                 240

Ile Lys Arg


<210> SEQ ID NO 322
<211> LENGTH: 729
<212> TYPE: DNA
<213> ORGANISM: artificial sequence
```

<220> FEATURE:
<223> OTHER INFORMATION: synthetic polynucleotide

<400> SEQUENCE: 322
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtttcatac attagtagta gtggtagtta cacaaactac 180
gcagactctg tgaagggccg attcaccatc tccagagaca acgccaagaa cacgctgtat 240
ctgcaaatga acagcctgag agccgaggac acggccgtat attactgtgc gaaagtccgt 300
gggtgggacg gtgactactt agactactgg ggccagggaa ccctggtcac cgtctcctca 360
ggtggaggcg gttcaggcgg aggtggctct ggcggtgccg gatcggacat ccagatgacc 420
cagtctccat ccctcctgtc tgcatctgta ggagacagag tcaccatcac ttgccgggcc 480
agtcagggca ttaacaatta tttagcctgg tatcagcaaa aaccagggaa agcccctaaa 540
ctcctgatct atgctgcatc cactttgcaa agtggggtcc cgtcaaggtt cagcggcagt 600
ggatctggga cagaattcac tctcacaatc agcggcctgc agcctgaaga ttttgcaact 660
tattactgtc aaaaccttaa tagttacccg ctcactttcg gcggagggac caaggtggaa 720
atcaaacgt 729

<210> SEQ ID NO 323
<211> LENGTH: 246
<212> TYPE: PRT
<213> ORGANISM: artificial sequence
<220> FEATURE:
<223> OTHER INFORMATION: synthetic polypeptide

<400> SEQUENCE: 323

Gln Val Gln Leu Val Glu Ser Gly Gly Gly Leu Ile Gln Pro Gly Gly
1 5 10 15

Ser Leu Arg Leu Ser Cys Ala Ala Ser Gly Phe Thr Val Ser Ser Asn
20 25 30

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Gly Phe Ser Gly Tyr Asp Tyr Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Ser Val Leu Thr Gln Pro Pro Ser Val
130 135 140

Ser Gly Ala Pro Gly Gln Arg Val Thr Ile Ser Cys Thr Gly Ser Ser
145 150 155 160

Ser Asn Ile Gly Ala Gly Tyr Asp Val His Trp Tyr Gln Gln Leu Pro
165 170 175

Gly Thr Ala Pro Lys Leu Leu Ile Tyr Val Asn Ser Asn Arg Pro Ser
180 185 190

Gly Val Pro Asp Arg Phe Ser Gly Ser Lys Ser Gly Thr Ser Ala Ser
195 200 205

```
Leu Ala Ile Thr Gly Leu Gln Ala Glu Asp Glu Ala Asp Tyr Tyr Cys
    210                 215                 220

Gln Ser Tyr Asp Ser Ser Leu Ser Gly Trp Val Phe Gly Gly Gly Thr
225                 230                 235                 240

Lys Leu Thr Val Leu Gly
                245
```

<210> SEQ ID NO 324
<211> LENGTH: 738
<212> TYPE: DNA
<213> ORGANISM: artificial sequence
<220> FEATURE:
<223> OTHER INFORMATION: synthetic polynucleotide

<400> SEQUENCE: 324

```
caggtgcagc tggtggagtc tggaggaggg ttgatccagc ctgggggggtc cctgagactc     60

tcctgtgcag cctctgggtt caccgtcagt agcaactaca tgagctgggt ccgccaggct    120

ccagggaagg ggctggagtg ggtctcagtt atttatagcg gtggtagcac atactacgca    180

gactccgtga agggccgatt caccatctcc agagacaatt ccaagaacac gctgtatctt    240

caaatgaaca gcctgagagc cgaggacacg gccgtgtatt actgtgcgag aggtggattc    300

agtggctacg attactttga ctactggggc cagggaaccc tggtcaccgt ctcctcaggt    360

ggaggcggtt caggcggagg tggctctggc ggtggcggat cgcagtctgt gttgacgcag    420

ccgccctcag tgtctggggc cccagggcag agggtcacca tctcctgcac tgggagcagc    480

tccaacatcg gggcaggtta tgatgtacac tggtaccaac aacttccagg aacggccccc    540

aaactcctca tctatgttaa cagcaatcgg ccctcagggg tccctgaccg attctctggc    600

tccaagtctg gcacctcagc ctccctggcc atcactgggc tccaggctga ggatgaggct    660

gattattact gccagtccta tgacagcagc ctgagtggtt gggtgttcgg cggagggacc    720

aagctgaccg tcctaggt                                                  738
```

<210> SEQ ID NO 325
<211> LENGTH: 246
<212> TYPE: PRT
<213> ORGANISM: artificial sequence
<220> FEATURE:
<223> OTHER INFORMATION: synthetic polypeptide

<400> SEQUENCE: 325

```
Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Ala Tyr Tyr Asp Phe Trp Gly Gly Asp Tyr Phe Asp Tyr Trp
            100                 105                 110

Gly Gln Gly Thr Leu Val Thr Val Ser Ser Gly Gly Gly Gly Ser Gly
        115                 120                 125
```

```
Gly Gly Gly Ser Gly Gly Gly Gly Ser Ser Glu Leu Thr Gln Asp Pro
    130                 135                 140

Ala Val Ser Val Ala Leu Gly Glu Thr Val Thr Ile Thr Cys Gln Gly
145                 150                 155                 160

Asp Ile Leu Arg Gly Tyr Tyr Ala Ser Trp Tyr Gln Gln Lys Pro Gly
                165                 170                 175

Gln Ala Pro Ile Leu Val Ile Tyr Asn Lys Asn Asn Arg Pro Ser Gly
            180                 185                 190

Ile Pro Asp Arg Phe Ser Gly Ser Ser Ser Gly Asn Thr Ala Ser Leu
        195                 200                 205

Thr Ile Thr Gly Ala Gln Ala Glu Asp Glu Ala Asp Tyr Tyr Cys Asn
    210                 215                 220

Ser Arg Asp Ser Ser Ser Thr His Arg Gly Val Phe Gly Gly Gly Thr
225                 230                 235                 240

Lys Leu Thr Val Leu Gly
                245
```

<210> SEQ ID NO 326
<211> LENGTH: 738
<212> TYPE: DNA
<213> ORGANISM: artificial sequence
<220> FEATURE:
<223> OTHER INFORMATION: synthetic polynucleotide

<400> SEQUENCE: 326

```
caggtgcagc tgcaggagtc gggggaggc ctggtcaagc ctgggggtc cctgagactc      60

tcctgtgcag cctctggatt caccttcagt agctatagca tgaactgggt ccgccaggct    120

ccagggaagg ggctggagtg ggtctcatcc attagtagta gtagttacat atactacgca    180

gactcagtga agggccgatt caccatctcc agagacaacg ccaagaactc actgtatctg    240

caaatgaaca gcctgagagc cgaggacacg gctgtgtatt actgtgcgag aggggcctat    300

tacgattttt ggggtggtga ttactttgac tactggggcc agggcaccct ggtcaccgtc    360

tcctcaggtg gaggcggttc aggcggaggt ggctctggcg gtggcggatc gtctgagctg    420

actcaggacc ctgctgtgtc tgtggccttg ggagagacag tcacaatcac gtgccaagga    480

gacattctca gaggctatta tgcaagctgg taccagcaga agccaggaca ggcccctata    540

cttgtcatct ataataaaaa caaccggccc tcagggatcc cagaccgatt ctctggctcc    600

agctcaggaa acacagcttc cttgaccatc actggggctc aggcggaaga tgaggctgac    660

tattactgta actcccggga cagcagtagt acccatcgag ggtgttcgg cggagggacc     720

aagctgaccg tcctgggt                                                  738
```

<210> SEQ ID NO 327
<211> LENGTH: 251
<212> TYPE: PRT
<213> ORGANISM: artificial sequence
<220> FEATURE:
<223> OTHER INFORMATION: synthetic polypeptide

<400> SEQUENCE: 327

```
Gln Val Gln Leu Gln Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45
```

```
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Gly Ser Gly Ser Tyr Trp Ser Gly Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Leu Ser Leu Pro Val Thr Pro Gly Glu Pro Ala Ser Ile Ser
145                 150                 155                 160

Cys Arg Ser Ser Gln Ser Leu Leu His Thr Asn Gly Tyr Asn Tyr Leu
                165                 170                 175

Asp Trp Tyr Leu Gln Lys Pro Gly Gln Ser Pro Gln Leu Leu Ile Tyr
            180                 185                 190

Leu Gly Ser Asn Arg Ala Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Gly Arg Gln Ser Pro Leu Thr
225                 230                 235                 240

Phe Gly Gly Gly Thr Lys Val Glu Ile Lys Arg
                245                 250
```

<210> SEQ ID NO 328
<211> LENGTH: 753
<212> TYPE: DNA
<213> ORGANISM: artificial sequence
<220> FEATURE:
<223> OTHER INFORMATION: synthetic polynucleotide

<400> SEQUENCE: 328

```
caggtacagc tgcagcagtc aggggggaggc gtggtccagc ctgggaggtc cctgagactc     60

tcctgtgcag cctctggatt caccttcagt agctatggca ttcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaaaggctat    300

ggttcaggga gttattggtc gggtgctttt gatatctggg gccaagggac aatggtcacc    360

gtctcctcag gtggaggcgg ttcaggcgga ggtggctctg gcggtggcgg atcggaaatt    420

gtgttgacgc agtctccact ctccctgccc gtcacccctg gagagccggc ctccatctcc    480

tgcaggtcta gtcagagcct cctgcatact aatggataca actatttgga ttggtacctg    540

cagaagccag ggcagtctcc acaactcctg atctacttgg gttctaatcg ggcctccggg    600

gtccctgaca ggttcagtgg cagtggatca ggcacagatt ttacactgaa aatcagcaga    660

gtggaggctg aggatgttgg ggtttattac tgcatgcaag gtcgacaaag tccgctcact    720

ttcggcggag ggaccaaggt ggaaatcaaa cgt                                 753
```

<210> SEQ ID NO 329
<211> LENGTH: 241

<212> TYPE: PRT
<213> ORGANISM: artificial sequence
<220> FEATURE:
<223> OTHER INFORMATION: synthetic polypeptide

<400> SEQUENCE: 329

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ser Ala Ile Ser Ala Asp Gly Ala Gly Thr Tyr Tyr Gly Asp Ser Val
    50                  55                  60

Lys Gly Arg Phe Thr Val Ser Arg Asp Asn Phe Lys Ser Thr Leu Tyr
65                  70                  75                  80

Leu Gln Met Asn Arg Leu Arg Ala Glu Asp Thr Ala Val Tyr Tyr Cys
                85                  90                  95

Ala Lys Leu Gly Gly Glu Ser Tyr Ser Ala Asp Trp Gly Gln Gly Thr
            100                 105                 110

Leu Val Thr Val Ser Ser Ser Gly Gly Gly Ser Gly Gly Gly Gly Ser
        115                 120                 125

Gly Gly Gly Gly Ser His Val Ile Leu Thr Gln Asp Pro Ala Val Ser
    130                 135                 140

Val Ala Leu Gly Gln Thr Val Lys Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Leu Leu Val Leu Tyr Gly Glu Asn Asn Arg Pro Ser Gly Ile Pro Asp
            180                 185                 190

Arg Phe Ser Gly Ser Gly Ser Gly Asn Thr Ala Ser Leu Thr Ile Thr
        195                 200                 205

Gly Ala Gln Ala Glu Asp Glu Ala Asp Tyr Tyr Cys His Ser Arg Asp
    210                 215                 220

Ser Ser Gly Lys Tyr Val Phe Gly Val Gly Thr Lys Val Thr Val Leu
225                 230                 235                 240

Gly
```

<210> SEQ ID NO 330
<211> LENGTH: 723
<212> TYPE: DNA
<213> ORGANISM: artificial sequence
<220> FEATURE:
<223> OTHER INFORMATION: synthetic polynucleotide

<400> SEQUENCE: 330

```
caggtgcagc tggtcgagtc tgggggaggc ctggtcaagc ctgggggtc cctgagactc      60

tcctgtgcag cctctggatt caccttcagc acctatacca tgagctgggc ccgccaggct    120

ccagggaagg ggctggaatg ggtctcagct attagtgctg atggtgctgg cacatactac    180

ggagactccg tgaagggccg gttcaccgtc tccagagaca atttcaagag cacgctgtat    240

ctgcaaatga acagactgag agccgaagac acggccgtat attactgtgc gaagctgggc    300

ggtgagagct actctgccga ctggggccag ggcaccctgg tcaccgtctc ctcaagtgga    360

ggcggttcag gcggaggtgg ctctggcggt ggcggatcgc acgttatact gactcaggac    420

cctgctgtgt ctgtggcctt gggacagaca gtcaagatca catgccaagg agacagcctc    480
```

agaagctatt atgcaagctg gtaccagcag aagccaggac aggcccctct ccttgtcttg 540
tatggtgaaa acaaccggcc ctcagggatc ccagaccgat tctctggctc cggctcagga 600
aacacagctt ccttgaccat cactggggct caggcggaag atgaggctga ctattactgt 660
cactcccggg acagcagtgg gaagtatgtc ttcggagttg ggaccaaggt caccgtccta 720
ggt 723

<210> SEQ ID NO 331
<211> LENGTH: 244
<212> TYPE: PRT
<213> ORGANISM: artificial sequence
<220> FEATURE:
<223> OTHER INFORMATION: synthetic polypeptide

<400> SEQUENCE: 331

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Ala Met Ile Trp Val Arg Gln Ala Pro Gly Lys Gly Leu Glu Trp Val
35 40 45

Ser Ala Ile Thr Gly Gly Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Leu Tyr Tyr Cys
85 90 95

Ala Lys Thr Leu Gly Arg Ser Thr Val Ala Thr Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Ser Glu Leu Thr Gln Asp Pro Ala Val
130 135 140

Ser Val Ala Leu Gly Gln Thr Val Arg Ile Thr Cys Gln Gly Asp Ser
145 150 155 160

Leu Arg Ser Tyr Tyr Ala Ser Trp Tyr Gln Gln Lys Pro Gly Gln Ala
165 170 175

Pro Val Leu Val Ile Tyr Gly Lys Asn Asn Arg Pro Ser Gly Ile Pro
180 185 190

Asp Arg Phe Ser Gly Ser Ser Ser Gly Asn Thr Ala Ser Leu Thr Ile
195 200 205

Thr Gly Ala Gln Ala Glu Asp Glu Ala Asp Tyr Tyr Cys Asn Ser Arg
210 215 220

Asp Ser Ser Gly Asn Pro His Val Val Phe Gly Gly Gly Thr Lys Leu
225 230 235 240

Thr Val Leu Gly

<210> SEQ ID NO 332
<211> LENGTH: 732
<212> TYPE: DNA
<213> ORGANISM: artificial sequence
<220> FEATURE:
<223> OTHER INFORMATION: synthetic polynucleotide

<400> SEQUENCE: 332
caggtgcagt tggtggagtc tgggggaggc gtggtccagc ctgggaggtc cctgagactc 60

```
tcctgtgcag cctctggatt cacctttagc aactatgcca tgatctgggt ccgccaggct    120

ccagggaagg ggctggagtg ggtctcagct attactggtg gtggtggtag cacatactac    180

gcagactccg tgaagggccg gttcaccatc tccagagaca attccaagaa cacgctgtat    240

ctgcaaatga acagcctgag agccgaggac acggccttgt attattgtgc aaaaactttg    300

ggacgttcaa cagtggctac tgactactgg ggccagggca ccctggtcac cgtctcctca    360

ggtggaggcg gttcaggcgg aggtggctct ggcggtggcg gatcgtctga gctgactcag    420

gaccctgctg tgtctgtggc cttgggacag acagtcagga tcacatgcca aggagacagc    480

ctcagaagct attatgcaag ctggtaccag cagaagccag gacaggcccc tgtacttgtc    540

atctatggta aaaacaaccg gccctcaggg atcccagacc gattctctgg ctccagctca    600

ggaaacacag cttccttgac catcactggg gctcaggcgg aagatgaggc tgactattac    660

tgtaactccc gggacagcag tggtaaccct catgtggtat tcggcggagg gacaaagctg    720

accgtcctag gt                                                        732
```

```
<210> SEQ ID NO 333
<211> LENGTH: 241
<212> TYPE: PRT
<213> ORGANISM: artificial sequence
<220> FEATURE:
<223> OTHER INFORMATION: synthetic polypeptide

<400> SEQUENCE: 333

Gln Val Gln Arg Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Ala Ala Gln Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Ser Gly Gly Ser Gln Ser Val Leu Thr Gln Asp Pro Ala Val Ser Val
    130                 135                 140

Ala Leu Gly Gln Thr Val Thr Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Val Thr Val Leu
225                 230                 235                 240
```

Gly

<210> SEQ ID NO 334
<211> LENGTH: 723
<212> TYPE: DNA
<213> ORGANISM: artificial sequence
<220> FEATURE:
<223> OTHER INFORMATION: synthetic polynucleotide

<400> SEQUENCE: 334
caggtgcagc gggtggagtc tgggggaggc gtggtccagc ctgggaggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaaggcccg 300
ggggcagctc aagactactg gggccaggga accctggtca ccgtctcctc aggtggaggc 360
ggttcaggcg gaggtggctc tggcagtggc ggatcgcagt ctgtgttgac tcaggaccct 420
gctgtgtctg tggccttggg acagacagtc acgatcacat gccaaggaga cagcctcaga 480
agctattatg caagctggta ccagcagaag ccaggacagg cccctgtact tgtcatctat 540
ggtaaaaaca accggccctc agggatccca gaccgattct ctggctccag ctcaggaaac 600
acagcttcct tgaccatcac tggggctcag gcggaagatg aggctgacta ttactgtaac 660
tcccgggaca gcagtggtaa ccatgtggta ttcggcggag ggaccaaggt caccgtccta 720
ggt 723

<210> SEQ ID NO 335
<211> LENGTH: 243
<212> TYPE: PRT
<213> ORGANISM: artificial sequence
<220> FEATURE:
<223> OTHER INFORMATION: synthetic polypeptide

<400> SEQUENCE: 335

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Leu
20 25 30

Ala Met Gly Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Ala Val Gly Ala Thr Thr Ala Phe Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Ser Glu Leu Thr Gln Asp Pro Ala Val
130 135 140

Ser Val Ala Leu Gly Gln Thr Val Lys Ile Thr Cys Gln Gly Asp Ser
145 150 155 160

```
Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Cys Asn Ser Arg
    210                 215                 220

Asp Ser Ser Gly Asn His Leu Val Phe Gly Gly Gly Thr Lys Leu Thr
225                 230                 235                 240

Val Leu Gly
```

<210> SEQ ID NO 336
<211> LENGTH: 729
<212> TYPE: DNA
<213> ORGANISM: artificial sequence
<220> FEATURE:
<223> OTHER INFORMATION: synthetic polynucleotide

<400> SEQUENCE: 336

```
caggtgcagc tggtggagtc tgggggaggc ttggtacagc ctggggggtc cctgagactc      60

tcctgtgcag cctctggatt cacctttagc accttggcca tggggtgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agccgaagac acggccgtgt attactgtgc gagaggggcg     300

gtgggagcta ctaccgcctt tgactactgg ggccagggaa ccctggtcac cgtctcctcg     360

ggtggaggcg gttcaggcgg aggtggctct ggcggtggcg gatcgtctga gctgactcag     420

gaccctgctg tgtctgtggc cttgggacag acagtcaaga tcacatgcca aggagacagc     480

ctcagaagct attatgcaag ctggtaccag cagaagccag gacaggcccc tgtacttgtc     540

atctatggta aaaacaaccg gccctcaggg atcccagacc gattctctgg ctccagctca     600

gggaacacag cttccttgac catcactggg gctcaggcgg aagatgaggc tgactattac     660

tgtaactccc gggacagcag tggtaaccat ctcgtattcg gcggagggac caagctgacc     720

gtcctaggt                                                             729
```

<210> SEQ ID NO 337
<211> LENGTH: 243
<212> TYPE: PRT
<213> ORGANISM: artificial sequence
<220> FEATURE:
<223> OTHER INFORMATION: synthetic polypeptide

<400> SEQUENCE: 337

```
Gln Val Gln Leu Gln Glu Ser Gly Gly Gly Leu Val Lys Pro Gly Gly
 1               5                  10                  15

Ser Leu Arg Leu Ser Cys Glu Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Lys Val Ala Ser Ser Ser Ser Leu Gly Met Asp Val Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Arg Ala Glu Asp Glu Ala Asp Tyr Tyr Cys Thr Ser Arg
    210                 215                 220

Asp Ser Ser Gly Lys Gln Leu Val Phe Gly Gly Gly Thr Lys Leu Thr
225                 230                 235                 240

Val Leu Gly
```

<210> SEQ ID NO 338
<211> LENGTH: 729
<212> TYPE: DNA
<213> ORGANISM: artificial sequence
<220> FEATURE:
<223> OTHER INFORMATION: synthetic polynucleotide

<400> SEQUENCE: 338

```
caggtgcagc tgcaggagtc gggggaggc ctggtcaagc ctggggggtc cctgagactc     60

tcctgtgaag cctctggatt caccttcagt agctatagca tgaactgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtgt attactgtgc gaaagtggct    300

agcagctcgt cgctaggtat ggacgtctgg ggccaaggga ccacggtcac cgtctcctca    360

ggtggaggcg gttcaggcgg aggtggctct ggcggtggcg gatcgtctga gctgactcag    420

gaccctgctg tgtctgtggc cttgggacag acagtcagga tcacatgcca aggagacagc    480

ctcagaagct attatgcaag ctggtaccag cagaagccag gacaggcccc tgtacttgtc    540

atctatggta aaaacaaccg gccctcaggg atcccagacc gattctctgg ctccagctca    600

ggaaacacag cttccttgac catcactggg gctcgggcgg aggatgaggc tgactattac    660

tgtacgtccc gggacagcag tggtaagcaa ctggtgttcg gcggagggac caagctgacc    720

gtcctaggt                                                            729
```

<210> SEQ ID NO 339
<211> LENGTH: 243
<212> TYPE: PRT
<213> ORGANISM: artificial sequence
<220> FEATURE:
<223> OTHER INFORMATION: synthetic polypeptide
<220> FEATURE:
<221> NAME/KEY: VARIANT
<222> LOCATION: (13)...(13)
<223> OTHER INFORMATION: xxa=any amino acid

<400> SEQUENCE: 339

Gln Val Gln Leu Val Glu Ser Gly Gly Gly Leu Val Xaa Pro Gly Gly
1 5 10 15

Ser Leu Arg Leu Ser Cys Ala Ala Ser Gly Phe Thr Phe Ser Asn Tyr
20 25 30

Ala Leu Ile Trp Val Arg Gln Ala Pro Gly Lys Gly Leu Glu Trp Val
35 40 45

Ser Ala Ile Ser Gly Ser Gly Ser Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Thr Leu Arg Ala Glu Asp Thr Ala Leu Tyr Tyr Cys
85 90 95

Ala Lys Ser Val Val Gly Ala Thr Ser Leu Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gln Ser Val Leu Thr Gln Asp Pro Ala Val
130 135 140

Ser Val Ala Leu Gly Gln Thr Val Arg Ile Thr Cys Gln Gly Asp Ser
145 150 155 160

Leu Arg Asp Tyr Tyr Ala Ser Trp Tyr Lys Gln Lys Pro Gly Gln Ala
165 170 175

Pro Leu Leu Val Phe Phe Gly Lys Ser Asn Arg Pro Ser Gly Ile Pro
180 185 190

Asn Arg Phe Ser Gly Ser Thr Ser Gly Ser Thr Ala Thr Leu Thr Val
195 200 205

Thr Gly Ala Gln Ala Glu Asp Glu Ala Asp Tyr Phe Cys Ser Ser Arg
210 215 220

Asp Ser Ser Gly Arg Leu Ile Leu Phe Gly Gly Gly Thr Lys Leu Thr
225 230 235 240

Val Leu Gly

<210> SEQ ID NO 340
<211> LENGTH: 729
<212> TYPE: DNA
<213> ORGANISM: artificial sequence
<220> FEATURE:
<223> OTHER INFORMATION: synthetic polynucleotide

<400> SEQUENCE: 340
caggtgcagc tggtggagtc tgggggaggc ttggtatagc ctggggggtc cctgagactc 60
tcctgtgcag cctctggatt cacctttagc aactatgcct tgatctgggt ccgccaggct 120
ccagggaagg ggctggagtg ggtctccgct atcagtggta gtggtagtgg cacatactac 180
gcagactccg tgaagggccg gttcaccatc tccagagaca attccaagaa cacactgtat 240
ctgcaaatga acaccctgag agccgaagac acggccctat attactgtgc gaaatctgta 300
gtgggagcta cctctttgga ctactggggc cagggaaccc tggtcaccgt ctcctcaggt 360
ggaggcggtt caggcggagg tggctctggc ggtggcggat cgcagtctgt gctgactcag 420
gaccctgctg tgtctgtggc cttgggacag acagtcagga tcacatgtca aggagacagc 480
ctcagagact attatgcaag ctggtacaag cagaagccag gacaggcccc tctacttgtc 540
ttctttggta aaagcaatcg gccctcaggg atcccaaacc gattctctgg ctccacctca 600

-continued

```
ggaagcacag ctaccttgac cgtcactggg gctcaggcgg aagatgaggc tgactatttc    660

tgcagctctc gggacagcag tggtaggctt atcctattcg gcggagggac caagctgacc    720

gtcctaggt                                                            729


<210> SEQ ID NO 341
<211> LENGTH: 125
<212> TYPE: PRT
<213> ORGANISM: artificial sequence
<220> FEATURE:
<223> OTHER INFORMATION: synthetic polypeptide

<400> SEQUENCE: 341

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Gly Tyr Cys Ser Gly Gly Ser Cys Tyr Ser Pro Phe
            100                 105                 110

Asp Tyr Trp Gly Gln Gly Thr Leu Val Thr Val Ser Ser
        115                 120                 125


<210> SEQ ID NO 342
<211> LENGTH: 120
<212> TYPE: PRT
<213> ORGANISM: artificial sequence
<220> FEATURE:
<223> OTHER INFORMATION: synthetic polypeptide

<400> SEQUENCE: 342

Gln Val Gln Leu Gln Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Ala Arg Leu Glu Trp Leu Pro Leu Ala Trp Asp Tyr Trp Gly Gln
            100                 105                 110

Gly Thr Leu Val Thr Val Ser Ser
        115                 120


<210> SEQ ID NO 343
<211> LENGTH: 122
<212> TYPE: PRT
<213> ORGANISM: artificial sequence
```

<220> FEATURE:
<223> OTHER INFORMATION: synthetic polypeptide

<400> SEQUENCE: 343

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ala Ala Arg Ile Ala Ala Arg Pro Gly Pro Leu Asp Tyr Trp
100 105 110

Gly Gln Gly Thr Leu Val Thr Val Ser Ser
115 120

<210> SEQ ID NO 344
<211> LENGTH: 119
<212> TYPE: PRT
<213> ORGANISM: artificial sequence
<220> FEATURE:
<223> OTHER INFORMATION: synthetic polypeptide

<400> SEQUENCE: 344

Gln Val Gln Leu Gln Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Val Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ile Glu Asp Thr Ala Val Tyr Tyr Cys
85 90 95

Gly Arg His Leu Ser Ser Gly Ser Ser Val Asp Tyr Trp Gly Gln Gly
100 105 110

Thr Leu Val Thr Val Ser Ser
115

<210> SEQ ID NO 345
<211> LENGTH: 120
<212> TYPE: PRT
<213> ORGANISM: artificial sequence
<220> FEATURE:
<223> OTHER INFORMATION: synthetic polypeptide

<400> SEQUENCE: 345

Gln Val Asn Leu Arg Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

```
Ala Met Ser Trp Val Arg Gln Ala Pro Gly Lys Gly Leu Glu Trp Val
        35                  40                  45

Ser Val Ile Ser Asp Gly Ser Thr Thr Tyr Tyr Ala Asp Ser Val Lys
    50                  55                  60

Gly Arg Phe Thr Ile Ser Arg Asp Asn Ser Lys Asn Met Leu Tyr Leu
65                  70                  75                  80

Gln Thr Asn Ser Leu Arg Ala Glu Asp Thr Ala Val Tyr Tyr Cys Ala
                85                  90                  95

Lys Ala Gly Pro Arg Thr Thr Val Thr Thr Val Asp Ser Trp Gly Gln
            100                 105                 110

Gly Thr Leu Val Thr Val Ser Ser
        115                 120


<210> SEQ ID NO 346
<211> LENGTH: 119
<212> TYPE: PRT
<213> ORGANISM: artificial sequence
<220> FEATURE:
<223> OTHER INFORMATION: synthetic polypeptide

<400> SEQUENCE: 346

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Gly Leu Lys Asp Ser Ser Gly Phe Asp Tyr Trp Gly Gln Gly
            100                 105                 110

Thr Leu Val Thr Val Ser Ser
        115


<210> SEQ ID NO 347
<211> LENGTH: 119
<212> TYPE: PRT
<213> ORGANISM: artificial sequence
<220> FEATURE:
<223> OTHER INFORMATION: synthetic polypeptide

<400> SEQUENCE: 347

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Ser Ser Gly Gly Arg Thr Tyr Tyr Ala Asp Ser Val
    50                  55                  60

Arg Gly Arg Leu Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95
```

```
Ala Lys Gly Ile Val Gly Ala Thr Ala Phe Asp Tyr Trp Gly Gln Gly
            100                 105                 110

Thr Leu Val Thr Val Ser Ser
        115
```

<210> SEQ ID NO 348
<211> LENGTH: 108
<212> TYPE: PRT
<213> ORGANISM: artificial sequence
<220> FEATURE:
<223> OTHER INFORMATION: synthetic polypeptide

<400> SEQUENCE: 348

```
Asn Phe Met Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ser Ser Gly Asn Tyr
                85                  90                  95

Leu Phe Gly Gly Gly Thr Lys Leu Thr Val Leu Gly
            100                 105
```

<210> SEQ ID NO 349
<211> LENGTH: 108
<212> TYPE: PRT
<213> ORGANISM: artificial sequence
<220> FEATURE:
<223> OTHER INFORMATION: synthetic polypeptide

<400> SEQUENCE: 349

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Lys
                85                  90                  95

Val Phe Gly Gly Gly Thr Lys Leu Thr Val Leu Gly
            100                 105
```

<210> SEQ ID NO 350
<211> LENGTH: 108
<212> TYPE: PRT
<213> ORGANISM: artificial sequence
<220> FEATURE:
<223> OTHER INFORMATION: synthetic polypeptide

<400> SEQUENCE: 350

```
Ser Glu Leu Thr Gln Asp Pro Ala Val Ser Val Ala Val Gly Gln Thr
 1               5                  10                  15

Val Lys Ile Thr Cys Gln Gly Asp Ser Leu Arg Asn Tyr Tyr Ala Ser
            20                  25                  30

Trp Tyr Gln Gln Lys Pro Arg Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Arg Ser Asn Asn His Leu
                85                  90                  95

Leu Phe Gly Gly Gly Thr Lys Leu Thr Val Leu Gly
            100                 105


<210> SEQ ID NO 351
<211> LENGTH: 111
<212> TYPE: PRT
<213> ORGANISM: artificial sequence
<220> FEATURE:
<223> OTHER INFORMATION: synthetic polypeptide

<400> SEQUENCE: 351

Ser Glu Leu Thr Gln Pro Pro Ser Ala Ser Gly Ser Pro Gly Gln Ser
 1               5                  10                  15

Val Thr Ile Ser Cys Thr Gly Thr Ser Ser Asp Val Gly Gly Tyr Asn
            20                  25                  30

Tyr Val Ser Trp Tyr Gln Gln Arg Pro Gly Tyr Ala Pro Lys Leu Met
        35                  40                  45

Ile Tyr Asp Val Ser Asn Arg Pro Ser Gly Val Ser Asn Arg Phe Ser
    50                  55                  60

Gly Ser Lys Ser Gly Asn Ser Ala Ser Leu Asp Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Glu Phe Leu Phe Gly Thr Gly Thr Lys Val Thr Val Leu Gly
            100                 105                 110


<210> SEQ ID NO 352
<211> LENGTH: 112
<212> TYPE: PRT
<213> ORGANISM: artificial sequence
<220> FEATURE:
<223> OTHER INFORMATION: synthetic polypeptide

<400> SEQUENCE: 352

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Thr Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Arg Ser Ala Trp Asp Ser Ser
                85                  90                  95
```

Leu Phe Asn Trp Val Phe Gly Gly Gly Thr Lys Leu Thr Val Leu Gly
100 105 110

<210> SEQ ID NO 353
<211> LENGTH: 109
<212> TYPE: PRT
<213> ORGANISM: artificial sequence
<220> FEATURE:
<223> OTHER INFORMATION: synthetic polypeptide

<400> SEQUENCE: 353

Asn Phe Met Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Ala Lys Arg
85 90 95

Val Val Phe Gly Gly Gly Thr Lys Val Thr Val Leu Gly
100 105

<210> SEQ ID NO 354
<211> LENGTH: 108
<212> TYPE: PRT
<213> ORGANISM: artificial sequence
<220> FEATURE:
<223> OTHER INFORMATION: synthetic polypeptide

<400> SEQUENCE: 354

Ser Glu Leu Thr Gln Asp Pro Ala Val Ser Val Ala Leu Gly Gln Thr
1 5 10 15

Val Arg Ile Thr Cys Gln Gly Asp Ser Leu Arg Ser Tyr Tyr Ala Ser
20 25 30

Trp Tyr Gln Gln Lys Pro Gly Gln Ala Pro Val Leu Val Ile Tyr Gly
35 40 45

Lys Asn Asn Arg Pro Ser Gly Ile Pro Asp Arg Phe Ser Gly Ser Ser
50 55 60

Ser Gly Asn Thr Ala Ser Leu Thr Ile Thr Gly Ala Gln Ala Glu Asp
65 70 75 80

Glu Ala Asp Tyr Tyr Cys Asn Ser Arg Asp Ser Ser Gly Asn Ser Val
85 90 95

Val Phe Gly Gly Gly Thr Lys Val Thr Val Leu Gly
100 105

<210> SEQ ID NO 355
<211> LENGTH: 123
<212> TYPE: PRT
<213> ORGANISM: artificial sequence
<220> FEATURE:
<223> OTHER INFORMATION: synthetic polypeptide

<400> SEQUENCE: 355

Gln Val Gln Leu Gln Gln Ser Gly Gly Gly Val Val Gln Pro Gly Arg
1 5 10 15

```
Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Gly Ser Gly Ser Tyr Trp Ser Gly Ala Phe Asp Ile
            100                 105                 110

Trp Gly Gln Gly Thr Met Val Thr Val Ser Ser
        115                 120


<210> SEQ ID NO 356
<211> LENGTH: 118
<212> TYPE: PRT
<213> ORGANISM: artificial sequence
<220> FEATURE:
<223> OTHER INFORMATION: synthetic polypeptide

<400> SEQUENCE: 356

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ser Ala Ile Ser Ala Asp Gly Ala Gly Thr Tyr Tyr Gly Asp Ser Val
    50                  55                  60

Lys Gly Arg Phe Thr Val Ser Arg Asp Asn Phe Lys Ser Thr Leu Tyr
65                  70                  75                  80

Leu Gln Met Asn Arg Leu Arg Ala Glu Asp Thr Ala Val Tyr Tyr Cys
                85                  90                  95

Ala Lys Leu Gly Gly Glu Ser Tyr Ser Ala Asp Trp Gly Gln Gly Thr
            100                 105                 110

Leu Val Thr Val Ser Ser
        115


<210> SEQ ID NO 357
<211> LENGTH: 120
<212> TYPE: PRT
<213> ORGANISM: artificial sequence
<220> FEATURE:
<223> OTHER INFORMATION: synthetic polypeptide

<400> SEQUENCE: 357

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Ala Met Ile Trp Val Arg Gln Ala Pro Gly Lys Gly Leu Glu Trp Val
        35                  40                  45

Ser Ala Ile Thr Gly Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Leu Tyr Tyr Cys
                85                  90                  95

Ala Lys Thr Leu Gly Arg Ser Thr Val Ala Thr Asp Tyr Trp Gly Gln
            100                 105                 110

Gly Thr Leu Val Thr Val Ser Ser
        115                 120
```

<210> SEQ ID NO 358
<211> LENGTH: 117
<212> TYPE: PRT
<213> ORGANISM: artificial sequence
<220> FEATURE:
<223> OTHER INFORMATION: synthetic polypeptide

<400> SEQUENCE: 358

```
Gln Val Gln Arg Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Gly Ala Ala Gln Asp Tyr Trp Gly Gln Gly Thr Leu
            100                 105                 110

Val Thr Val Ser Ser
        115
```

<210> SEQ ID NO 359
<211> LENGTH: 120
<212> TYPE: PRT
<213> ORGANISM: artificial sequence
<220> FEATURE:
<223> OTHER INFORMATION: synthetic polypeptide

<400> SEQUENCE: 359

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Leu
            20                  25                  30

Ala Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Val Gly Ala Thr Thr Ala Phe Asp Tyr Trp Gly Gln
            100                 105                 110

Gly Thr Leu Val Thr Val Ser Ser
        115                 120
```

<210> SEQ ID NO 360
<211> LENGTH: 120
<212> TYPE: PRT
<213> ORGANISM: artificial sequence
<220> FEATURE:
<223> OTHER INFORMATION: synthetic polypeptide

<400> SEQUENCE: 360

```
Gln Val Gln Leu Gln Glu Ser Gly Gly Gly Leu Val Lys Pro Gly Gly
 1               5                  10                  15

Ser Leu Arg Leu Ser Cys Glu Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Ser Ser Ser Ser Leu Gly Met Asp Val Trp Gly Gln
            100                 105                 110

Gly Thr Thr Val Thr Val Ser Ser
        115                 120
```

<210> SEQ ID NO 361
<211> LENGTH: 119
<212> TYPE: PRT
<213> ORGANISM: artificial sequence
<220> FEATURE:
<223> OTHER INFORMATION: synthetic polypeptide
<220> FEATURE:
<221> NAME/KEY: VARIANT
<222> LOCATION: (13)...(13)
<223> OTHER INFORMATION: xxa=any amino acid

<400> SEQUENCE: 361

```
Gln Val Gln Leu Val Glu Ser Gly Gly Gly Leu Val Xaa Pro Gly Gly
 1               5                  10                  15

Ser Leu Arg Leu Ser Cys Ala Ala Ser Gly Phe Thr Phe Ser Asn Tyr
            20                  25                  30

Ala Leu Ile Trp Val Arg Gln Ala Pro Gly Lys Gly Leu Glu Trp Val
        35                  40                  45

Ser Ala Ile Ser Gly Ser Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Leu Tyr Tyr Cys
                85                  90                  95

Ala Lys Ser Val Val Gly Ala Thr Ser Leu Asp Tyr Trp Gly Gln Gly
            100                 105                 110

Thr Leu Val Thr Val Ser Ser
        115
```

<210> SEQ ID NO 362
<211> LENGTH: 113
<212> TYPE: PRT
<213> ORGANISM: artificial sequence
<220> FEATURE:
<223> OTHER INFORMATION: synthetic polypeptide

<400> SEQUENCE: 362

```
Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Arg Gln Ser Pro Leu Thr Phe Gly Gly Gly Thr Lys Val Glu Ile Lys
            100                 105                 110

Arg
```

<210> SEQ ID NO 363
<211> LENGTH: 108
<212> TYPE: PRT
<213> ORGANISM: artificial sequence
<220> FEATURE:
<223> OTHER INFORMATION: synthetic polypeptide

<400> SEQUENCE: 363

```
His Val Ile Leu Thr Gln Asp Pro Ala Val Ser Val Ala Leu Gly Gln
 1               5                  10                  15

Thr Val Lys Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Leu Tyr
        35                  40                  45

Gly Glu Asn Asn Arg Pro Ser Gly Ile Pro Asp Arg Phe Ser Gly Ser
    50                  55                  60

Gly Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ser Ser Gly Lys Tyr
                85                  90                  95

Val Phe Gly Val Gly Thr Lys Val Thr Val Leu Gly
            100                 105
```

<210> SEQ ID NO 364
<211> LENGTH: 109
<212> TYPE: PRT
<213> ORGANISM: artificial sequence
<220> FEATURE:
<223> OTHER INFORMATION: synthetic polypeptide

<400> SEQUENCE: 364

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
```

```
65                  70                  75                  80

Glu Ala Asp Tyr Tyr Cys Asn Ser Arg Asp Ser Ser Gly Asn Pro His
                85                  90                  95

Val Val Phe Gly Gly Gly Thr Lys Leu Thr Val Leu Gly
            100                 105
```

<210> SEQ ID NO 365
<211> LENGTH: 109
<212> TYPE: PRT
<213> ORGANISM: artificial sequence
<220> FEATURE:
<223> OTHER INFORMATION: synthetic polypeptide

<400> SEQUENCE: 365

```
Gln Ser Val Leu Thr Gln Asp Pro Ala Val Ser Val Ala Leu Gly Gln
 1               5                  10                  15

Thr Val Thr Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Val Thr Val Leu Gly
            100                 105
```

<210> SEQ ID NO 366
<211> LENGTH: 108
<212> TYPE: PRT
<213> ORGANISM: artificial sequence
<220> FEATURE:
<223> OTHER INFORMATION: synthetic polypeptide

<400> SEQUENCE: 366

```
Ser Glu Leu Thr Gln Asp Pro Ala Val Ser Val Ala Leu Gly Gln Thr
 1               5                  10                  15

Val Lys Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Leu
                85                  90                  95

Val Phe Gly Gly Gly Thr Lys Leu Thr Val Leu Gly
            100                 105
```

<210> SEQ ID NO 367
<211> LENGTH: 108
<212> TYPE: PRT
<213> ORGANISM: artificial sequence
<220> FEATURE:
<223> OTHER INFORMATION: synthetic polypeptide

<400> SEQUENCE: 367

Ser Glu Leu Thr Gln Asp Pro Ala Val Ser Val Ala Leu Gly Gln Thr
1 5 10 15

Val Arg Ile Thr Cys Gln Gly Asp Ser Leu Arg Ser Tyr Tyr Ala Ser
20 25 30

Trp Tyr Gln Gln Lys Pro Gly Gln Ala Pro Val Leu Val Ile Tyr Gly
35 40 45

Lys Asn Asn Arg Pro Ser Gly Ile Pro Asp Arg Phe Ser Gly Ser Ser
50 55 60

Ser Gly Asn Thr Ala Ser Leu Thr Ile Thr Gly Ala Arg Ala Glu Asp
65 70 75 80

Glu Ala Asp Tyr Tyr Cys Thr Ser Arg Asp Ser Ser Gly Lys Gln Leu
85 90 95

Val Phe Gly Gly Gly Thr Lys Leu Thr Val Leu Gly
100 105

<210> SEQ ID NO 368
<211> LENGTH: 109
<212> TYPE: PRT
<213> ORGANISM: artificial sequence
<220> FEATURE:
<223> OTHER INFORMATION: synthetic polypeptide

<400> SEQUENCE: 368

Gln Ser Val Leu Thr Gln Asp Pro Ala Val Ser Val Ala Leu Gly Gln
1 5 10 15

Thr Val Arg Ile Thr Cys Gln Gly Asp Ser Leu Arg Asp Tyr Tyr Ala
20 25 30

Ser Trp Tyr Lys Gln Lys Pro Gly Gln Ala Pro Leu Leu Val Phe Phe
35 40 45

Gly Lys Ser Asn Arg Pro Ser Gly Ile Pro Asn Arg Phe Ser Gly Ser
50 55 60

Thr Ser Gly Ser Thr Ala Thr Leu Thr Val Thr Gly Ala Gln Ala Glu
65 70 75 80

Asp Glu Ala Asp Tyr Phe Cys Ser Ser Arg Asp Ser Ser Gly Arg Leu
85 90 95

Ile Leu Phe Gly Gly Gly Thr Lys Leu Thr Val Leu Gly
100 105

<210> SEQ ID NO 369
<211> LENGTH: 120
<212> TYPE: PRT
<213> ORGANISM: artificial sequence
<220> FEATURE:
<223> OTHER INFORMATION: synthetic polypeptide

<400> SEQUENCE: 369

Gln Val Leu Leu Val Glu Ser Gly Gly Gly Val Val Gln Ala Gly Ala
1 5 10 15

Ser Leu Arg Val Ser Cys Ala Ala Ser Gly Phe Ser Leu Thr Ser Tyr
20 25 30

Gly Met His Trp Val Arg Gln Ala Pro Gly Lys Gly Leu Glu Trp Val
35 40 45

Ala Phe Ile Ser Ser Asp Gly Ser Asp Lys Tyr Tyr Val Asp Ser Val
50 55 60

Lys Gly Arg Phe Thr Ile Ser Arg Asp Thr Ser Lys Asn Met Met Tyr
65 70 75 80

Leu Gln Met Asn Ser Leu Thr Thr Glu Asp Thr Ala Val Tyr Tyr Cys

```
                85                  90                  95

Ala Lys Asp Trp Gly Ser Asn Trp Tyr Leu Phe Asp Tyr Trp Gly Gln
            100                 105                 110

Gly Thr Leu Val Thr Val Ser Ser
        115                 120


<210> SEQ ID NO 370
<211> LENGTH: 122
<212> TYPE: PRT
<213> ORGANISM: artificial sequence
<220> FEATURE:
<223> OTHER INFORMATION: synthetic polypeptide

<400> SEQUENCE: 370

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ala Val Ile Tyr Arg Asp Gly His Gly Tyr Tyr Ala Asp Ser Val Lys
    50                  55                  60

Gly Arg Phe Thr Val Ser Arg Asp Ser Ser Glu Asn Thr Val Tyr Leu
65                  70                  75                  80

Gln Met Asn Ser Leu Arg Ala Glu Asp Thr Ala Ile Tyr Tyr Cys Ala
                85                  90                  95

Ser His Asp Tyr Ala Gly Asn Pro Ala Gly Ser Ala Ser Gly Tyr Trp
            100                 105                 110

Gly Gln Gly Thr Leu Val Thr Val Ser Ser
        115                 120


<210> SEQ ID NO 371
<211> LENGTH: 122
<212> TYPE: PRT
<213> ORGANISM: artificial sequence
<220> FEATURE:
<223> OTHER INFORMATION: synthetic polypeptide

<400> SEQUENCE: 371

Leu Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Asn Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Thr Val Ala Gln Arg Leu Asp Val Phe Asp Tyr Trp
            100                 105                 110

Gly Gln Gly Thr Leu Val Thr Val Ser Ser
        115                 120


<210> SEQ ID NO 372
<211> LENGTH: 121
```

<212> TYPE: PRT
<213> ORGANISM: artificial sequence
<220> FEATURE:
<223> OTHER INFORMATION: synthetic polypeptide

<400> SEQUENCE: 372

```
Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Glu Met Asn Ser Leu Arg Ala Glu Asp Thr Ala Val Tyr Tyr Cys
                85                  90                  95

Val Lys Asp Arg Gln Pro Asp Gly Arg Trp Pro Phe Asp Leu Trp Gly
            100                 105                 110

Gln Gly Thr Leu Val Thr Val Ser Ser
        115                 120
```

<210> SEQ ID NO 373
<211> LENGTH: 118
<212> TYPE: PRT
<213> ORGANISM: artificial sequence
<220> FEATURE:
<223> OTHER INFORMATION: synthetic polypeptide

<400> SEQUENCE: 373

```
Gln Leu Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Asn Asn Ala Leu Tyr
65                  70                  75                  80

Leu Gln Met Asn Ser Leu Arg Val Glu Asp Thr Ala Val Tyr Tyr Cys
                85                  90                  95

Ala Arg Asp Ala Ser Tyr Tyr Ala Asp Asp Tyr Trp Gly Gln Gly Thr
            100                 105                 110

Leu Val Thr Val Ser Ser
        115
```

<210> SEQ ID NO 374
<211> LENGTH: 110
<212> TYPE: PRT
<213> ORGANISM: artificial sequence
<220> FEATURE:
<223> OTHER INFORMATION: synthetic polypeptide

<400> SEQUENCE: 374

```
Ser Val Leu Thr Gln Pro Pro Ser Ala Ser Glu Thr Pro Gly Gln Arg
 1               5                  10                  15

Val Thr Ile Ser Cys Ser Gly Ser Ser Ser Asn Ile Gly Ala Asn Thr
```

```
            20                  25                  30

Val His Trp Tyr Gln Gln Phe Pro Gly Thr Ala Pro Lys Leu Leu Ile
        35                  40                  45

Tyr Ser Tyr Ser Gln Arg Pro Ser Gly Val Pro Asp Arg Phe Ser Asp
    50                  55                  60

Ser Lys Ser Gly Thr Ser Ala Ser Leu Ala Ile Ser Gly Leu Gln Ser
65                  70                  75                  80

Glu Asp Glu Ala Asp Tyr Tyr Cys Ala Ala Trp Asp Asp Ile Leu Asn
                85                  90                  95

Gly Trp Val Phe Gly Gly Gly Thr Lys Val Thr Val Leu Gly
            100                 105                 110


<210> SEQ ID NO 375
<211> LENGTH: 111
<212> TYPE: PRT
<213> ORGANISM: artificial sequence
<220> FEATURE:
<223> OTHER INFORMATION: synthetic polypeptide

<400> SEQUENCE: 375

Ser Ala Leu Thr Gln Pro Ala Ser Val Ser Ala Ser Pro Gly Gln Ser
 1               5                  10                  15

Ile Thr Ile Ser Cys Thr Gly Thr Ser Ser Asp Val Gly Gly Tyr Asp
            20                  25                  30

Tyr Val Ser Trp Tyr Gln Gln His Pro Gly Lys Ala Pro Lys Leu Val
        35                  40                  45

Met Tyr Ser His Asn Gln Arg Ser Ser Gly Val Pro Asp Arg Phe Ser
    50                  55                  60

Gly Ser Lys Ser Gly Asn Ser Ala Ser Leu Asp Ile Ser Gly Leu Gln
65                  70                  75                  80

Ser Glu Asp Glu Ala Asp Tyr Tyr Arg Ala Ala Trp Asp Asp Ser Leu
                85                  90                  95

Ser Glu Phe Leu Phe Gly Thr Gly Thr Lys Leu Thr Val Leu Gly
            100                 105                 110


<210> SEQ ID NO 376
<211> LENGTH: 111
<212> TYPE: PRT
<213> ORGANISM: artificial sequence
<220> FEATURE:
<223> OTHER INFORMATION: synthetic polypeptide

<400> SEQUENCE: 376

Ser Val Leu Thr Gln Pro Pro Ser Val Ser Gly Ala Pro Gly Gln Arg
 1               5                  10                  15

Val Thr Ile Ser Cys Thr Gly Gly Ser Ser Asn Val Gly Ala Gly Phe
            20                  25                  30

Asp Val His Trp Tyr Gln Gln Leu Pro Gly Thr Ala Pro Lys Leu Leu
        35                  40                  45

Ile Tyr Gly Asp Lys Asn Arg Pro Ser Gly Val Pro Asp Arg Phe Ser
    50                  55                  60

Gly Ser Arg Ser Gly Thr Ser Ala Ser Leu Ala Ile Thr Gly Leu Gln
65                  70                  75                  80

Ala Glu Asp Glu Ala Asp Tyr Tyr Cys Gln Ala Tyr Asp Ser Ser Leu
                85                  90                  95

Arg Gly Ser Val Phe Gly Gly Gly Thr Lys Leu Thr Val Leu Gly
            100                 105                 110
```

<210> SEQ ID NO 377
<211> LENGTH: 110
<212> TYPE: PRT
<213> ORGANISM: artificial sequence
<220> FEATURE:
<223> OTHER INFORMATION: synthetic polypeptide

<400> SEQUENCE: 377

```
Ser Ala Leu Thr Gln Pro Ala Ser Val Ser Gly Ser Pro Gly Gln Ser
 1               5                  10                  15

Val Thr Ile Ser Cys Thr Gly Ala Asn Ser Asp Leu Gly Gly Tyr Asn
            20                  25                  30

Tyr Val Ser Trp Tyr Gln His His Pro Ala Lys Ala Pro Lys Leu Ile
        35                  40                  45

Ile Tyr Glu Val Asn Asn Arg Pro Ser Gly Val Ser His Arg Phe Ser
    50                  55                  60

Gly Ser Lys Ser Ala Asn Thr Ala Ser Leu Thr Ile Ser Gly Leu Gln
65                  70                  75                  80

Ala Glu Asp Glu Ala Asp Tyr Tyr Cys Ser Ser Tyr Arg Ser Gly Gly
                85                  90                  95

Thr Tyr Val Phe Gly Thr Gly Thr Lys Leu Thr Val Leu Gly
            100                 105                 110
```

<210> SEQ ID NO 378
<211> LENGTH: 109
<212> TYPE: PRT
<213> ORGANISM: artificial sequence
<220> FEATURE:
<223> OTHER INFORMATION: synthetic polypeptide

<400> SEQUENCE: 378

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Lys Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys His Ser Arg Asp Ser Ser Gly Asn His Pro
                85                  90                  95

Val Val Phe Gly Gly Gly Thr Lys Val Thr Val Leu Gly
            100                 105
```

<210> SEQ ID NO 379
<211> LENGTH: 121
<212> TYPE: PRT
<213> ORGANISM: artificial sequence
<220> FEATURE:
<223> OTHER INFORMATION: synthetic polypeptide

<400> SEQUENCE: 379

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
```

```
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Leu Phe Ser Leu Gln Leu Asn Ser Val Thr Pro Glu Asp Thr Ala Leu
                85                  90                  95

Tyr Tyr Cys Ala Arg Glu Glu Asp Tyr Ser Gly Phe Gln His Trp Gly
            100                 105                 110

Gln Gly Thr Leu Val Thr Val Ser Ser
        115                 120


<210> SEQ ID NO 380
<211> LENGTH: 117
<212> TYPE: PRT
<213> ORGANISM: artificial sequence
<220> FEATURE:
<223> OTHER INFORMATION: synthetic polypeptide

<400> SEQUENCE: 380

Gln Val Gln Leu Gln Glu Ser Gly Gly Gly Val Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Tyr Val
        35                  40                  45

Ser Ser Ile Ser Ser Asn Gly Gly Gly Thr Tyr Tyr Ala Asp Ser Val
    50                  55                  60

Lys Gly Arg Phe Thr Ile Ser Arg Asp Asp Ala Lys Asn Thr Leu Tyr
65                  70                  75                  80

Leu Gln Leu Asn Ser Leu Arg Asp Glu Asp Thr Ala Val Tyr Tyr Cys
                85                  90                  95

Ala Lys Asp Tyr Phe Gly Ser Ile Asp Tyr Trp Gly Gln Gly Thr Leu
            100                 105                 110

Val Thr Val Ser Ser
        115


<210> SEQ ID NO 381
<211> LENGTH: 118
<212> TYPE: PRT
<213> ORGANISM: artificial sequence
<220> FEATURE:
<223> OTHER INFORMATION: synthetic polypeptide

<400> SEQUENCE: 381

Gln Val Gln Leu Gln Gln Ser Gly Gly Gly Leu Val Gln Pro Gly Gly
 1               5                  10                  15

Ser Leu Arg Leu Ser Cys Ser Ala Ser Gly Phe Thr Phe Ser Asn Tyr
            20                  25                  30

Ala Ile His Trp Val Arg Gln Ala Pro Gly Lys Gly Leu Glu Tyr Val
        35                  40                  45

Ser Ala Ile Asn Ser Asn Gly Gly Ser Thr Tyr Tyr Ala Asp Ser Val
    50                  55                  60

Lys Gly Arg Ser Ile Ile Ser Arg Asp Asn Ser Met Asn Thr Val Tyr
65                  70                  75                  80

Leu Gln Met Ser Ser Leu Arg Ala Glu Asp Thr Ala Val Tyr Tyr Cys
                85                  90                  95
```

-continued

```
Val Lys Glu Glu Asn Gly Ser Gly Phe Asp Ser Trp Gly Gln Gly Thr
            100                 105                 110

Leu Val Thr Val Ser Ser
        115


<210> SEQ ID NO 382
<211> LENGTH: 116
<212> TYPE: PRT
<213> ORGANISM: artificial sequence
<220> FEATURE:
<223> OTHER INFORMATION: synthetic polypeptide

<400> SEQUENCE: 382

Gln Val Gln Leu Gln Glu Ser Gly Gly Gly Leu Val Gln Pro Gly Gly
 1               5                  10                  15

Phe Leu Arg Leu Ser Cys Ala Ala Ser Gly Phe Thr Phe Ser Ser Tyr
            20                  25                  30

Gly Met His Trp Val Arg Gln Thr Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Tyr Phe Asp Leu Trp Gly Arg Gly Thr Leu Val
            100                 105                 110

Thr Val Ser Ser
        115


<210> SEQ ID NO 383
<211> LENGTH: 119
<212> TYPE: PRT
<213> ORGANISM: artificial sequence
<220> FEATURE:
<223> OTHER INFORMATION: synthetic polypeptide

<400> SEQUENCE: 383

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Tyr Tyr Asp Glu Ala Leu Asp Tyr Trp Gly Gln Gly
            100                 105                 110

Thr Leu Val Thr Val Ser Ser
        115


<210> SEQ ID NO 384
<211> LENGTH: 118
<212> TYPE: PRT
<213> ORGANISM: artificial sequence
```

```
<220> FEATURE:
<223> OTHER INFORMATION: synthetic polypeptide

<400> SEQUENCE: 384

Gln Val Gln Leu Gln Glu Ser Gly Gly Gly Leu Val Lys Pro Gly Gly
1               5                   10                  15

Ser Leu Arg Leu Ser Cys Ala Gly Ser Gly Phe Ile Phe Asn Thr Tyr
            20                  25                  30

Ser Met Asn Trp Val Arg Gln Ser Pro Gly Lys Gly Leu Glu Trp Val
        35                  40                  45

Ser Ser Thr Gly Gly Ser Gly Lys Asn Thr Phe Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ser Ser Gly Ser Phe Asp Tyr Trp Gly Gln Gly Thr
            100                 105                 110

Leu Val Thr Val Ser Ser
        115


<210> SEQ ID NO 385
<211> LENGTH: 120
<212> TYPE: PRT
<213> ORGANISM: artificial sequence
<220> FEATURE:
<223> OTHER INFORMATION: synthetic polypeptide

<400> SEQUENCE: 385

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Tyr Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Gly Trp Asp Gly Asp Tyr Leu Asp Tyr Trp Gly Gln
            100                 105                 110

Gly Thr Leu Val Thr Val Ser Ser
        115                 120


<210> SEQ ID NO 386
<211> LENGTH: 119
<212> TYPE: PRT
<213> ORGANISM: artificial sequence
<220> FEATURE:
<223> OTHER INFORMATION: synthetic polypeptide

<400> SEQUENCE: 386

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30
```

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Gly Phe Ser Gly Tyr Asp Tyr Phe Asp Tyr Trp Gly Gln Gly
100 105 110

Thr Leu Val Thr Val Ser Ser
115

<210> SEQ ID NO 387
<211> LENGTH: 112
<212> TYPE: PRT
<213> ORGANISM: artificial sequence
<220> FEATURE:
<223> OTHER INFORMATION: synthetic polypeptide

<400> SEQUENCE: 387

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Gly Ser Lys Arg Pro Ser Gly Val Pro Glu Arg Phe
50 55 60

Ser Gly Ser Asn Ser Gly Asn Thr Ala Thr Leu Thr Ile Gly Arg Val
65 70 75 80

Glu Ala Gly Asp Glu Ala Asp Tyr Tyr Cys Gln Ala Trp Asp Ser Thr
85 90 95

Ser Asp His Val Val Phe Gly Gly Gly Thr Lys Val Thr Val Leu Gly
100 105 110

<210> SEQ ID NO 388
<211> LENGTH: 109
<212> TYPE: PRT
<213> ORGANISM: artificial sequence
<220> FEATURE:
<223> OTHER INFORMATION: synthetic polypeptide

<400> SEQUENCE: 388

Pro Glu Leu Thr Gln Asp Pro Ala Val Ser Val Ala Leu Gly Gln Thr
1 5 10 15

Val Thr Ile Thr Cys Gln Gly Asp Ser Leu Arg Ser Tyr Tyr Ala Ser
20 25 30

Trp Tyr Gln Gln Lys Pro Gly Gln Ala Pro Leu Leu Val Ile Tyr Gly
35 40 45

Lys Asn Ile Arg Pro Ser Gly Ile Pro Asp Arg Phe Ser Gly Ser Ser
50 55 60

Ser Gly Asn Ser Ala Ser Leu Thr Ile Thr Gly Ala Gln Ala Glu Asp
65 70 75 80

Glu Ala Asp Tyr Tyr Cys His Ser Arg Asp Ser Ser Gly Thr His Leu
85 90 95

Arg Val Phe Gly Gly Gly Thr Lys Leu Thr Val Leu Gly
100 105

<210> SEQ ID NO 389
<211> LENGTH: 108
<212> TYPE: PRT
<213> ORGANISM: artificial sequence
<220> FEATURE:
<223> OTHER INFORMATION: synthetic polypeptide

<400> SEQUENCE: 389

```
Glu Ile Val Leu Thr Gln Ser Pro Ser Ser Val Ser Ala Ser Val Gly
 1               5                  10                  15

Asp Arg Val Thr Ile Thr Cys Arg Ala Ser Gln Asp Ile Ser Lys Trp
            20                  25                  30

Leu Ala Trp Tyr Gln Gln Arg Pro Gly Lys Val Pro Arg Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Phe Cys Gln Gln Ala Ser Val Phe Pro Val
                85                  90                  95

Thr Phe Gly Gly Gly Thr Lys Leu Glu Ile Lys Arg
            100                 105
```

<210> SEQ ID NO 390
<211> LENGTH: 108
<212> TYPE: PRT
<213> ORGANISM: artificial sequence
<220> FEATURE:
<223> OTHER INFORMATION: synthetic polypeptide

<400> SEQUENCE: 390

```
Asp Val Val Met Thr Gln Ser Pro Ser Thr Leu Ser Ala Ser Val Gly
 1               5                  10                  15

Asp Arg Val Ser Ile Thr Cys Arg Ala Ser Glu Ser Ile Ser Arg Trp
            20                  25                  30

Leu Ala Trp Tyr Gln Gln Lys Pro Gly Lys Ala Pro Lys Ala Leu Ile
        35                  40                  45

Tyr Lys Ala Ser Ser Leu Glu Ser Gly Val Pro Ser Arg Phe Ser Gly
    50                  55                  60

Ser Gly Ser Ala Thr Glu Phe Thr Leu Thr Ile Asn Ser Leu Gln Pro
65                  70                  75                  80

Asp Asp Phe Ala Thr Tyr Tyr Cys Gln Gln Tyr Ser Ser Tyr Pro Leu
                85                  90                  95

Thr Phe Gly Gln Gly Thr Lys Val Asp Ile Lys Arg
            100                 105
```

<210> SEQ ID NO 391
<211> LENGTH: 108
<212> TYPE: PRT
<213> ORGANISM: artificial sequence
<220> FEATURE:
<223> OTHER INFORMATION: synthetic polypeptide

<400> SEQUENCE: 391

```
Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Asp Met Ser Arg Trp
            20                  25                  30
```

```
Leu Ala Trp Tyr Gln Gln Lys Pro Gly Lys Ala Pro Lys Leu Leu Ile
        35                  40                  45

His Ser Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Gly Val Tyr Pro Leu
                85                  90                  95

Thr Ile Gly Gly Gly Thr Lys Val Glu Ile Lys Arg
            100                 105


<210> SEQ ID NO 392
<211> LENGTH: 108
<212> TYPE: PRT
<213> ORGANISM: artificial sequence
<220> FEATURE:
<223> OTHER INFORMATION: synthetic polypeptide
<220> FEATURE:
<221> NAME/KEY: VARIANT
<222> LOCATION: (101)...(101)
<223> OTHER INFORMATION: xxa=any amino acid

<400> SEQUENCE: 392

Asp Ile Gln Met Thr Gln Ser Pro Ser Thr Leu Ser Ala Ser Ile Gly
 1               5                  10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr His Thr Ile Ser Arg
                85                  90                  95

Thr Phe Gly Pro Xaa Thr Lys Leu Glu Ile Lys Arg
            100                 105


<210> SEQ ID NO 393
<211> LENGTH: 108
<212> TYPE: PRT
<213> ORGANISM: artificial sequence
<220> FEATURE:
<223> OTHER INFORMATION: synthetic polypeptide

<400> SEQUENCE: 393

Asp Ile Gln Met Thr Gln Ser Pro Ser Leu Leu Ser Ala Ser Val Gly
 1               5                  10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Gln Asn Leu Asn Ser Tyr Pro Leu
                85                  90                  95

Thr Phe Gly Gly Gly Thr Lys Val Glu Ile Lys Arg
```

100 105

<210> SEQ ID NO 394
<211> LENGTH: 112
<212> TYPE: PRT
<213> ORGANISM: artificial sequence
<220> FEATURE:
<223> OTHER INFORMATION: synthetic polypeptide

<400> SEQUENCE: 394

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Val Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Trp Val Phe Gly Gly Gly Thr Lys Leu Thr Val Leu Gly
100 105 110

<210> SEQ ID NO 395
<211> LENGTH: 7
<212> TYPE: PRT
<213> ORGANISM: artificial sequence
<220> FEATURE:
<223> OTHER INFORMATION: synthetic polypeptide

<400> SEQUENCE: 395

Ser Tyr Ser Gln Arg Pro Ser
1 5

<210> SEQ ID NO 396
<211> LENGTH: 32
<212> TYPE: PRT
<213> ORGANISM: artificial sequence
<220> FEATURE:
<223> OTHER INFORMATION: synthetic polypeptide

<400> SEQUENCE: 396

Gly Val Pro Asp Arg Phe Ser Asp Ser Lys Ser Gly Thr Ser Ala Ser
1 5 10 15

Leu Ala Ile Ser Gly Leu Gln Ser Glu Asp Glu Ala Asp Tyr Tyr Cys
20 25 30

<210> SEQ ID NO 397
<211> LENGTH: 7
<212> TYPE: PRT
<213> ORGANISM: artificial sequence
<220> FEATURE:
<223> OTHER INFORMATION: synthetic polypeptide

<400> SEQUENCE: 397

Ser His Asn Gln Arg Ser Ser
1 5

<210> SEQ ID NO 398
<211> LENGTH: 32
<212> TYPE: PRT

<213> ORGANISM: artificial sequence
<220> FEATURE:
<223> OTHER INFORMATION: synthetic polypeptide

<400> SEQUENCE: 398

Gly Val Pro Asp Arg Phe Ser Gly Ser Lys Ser Gly Asn Ser Ala Ser
1 5 10 15

Leu Asp Ile Ser Gly Leu Gln Ser Glu Asp Glu Ala Asp Tyr Tyr Arg
20 25 30

<210> SEQ ID NO 399
<211> LENGTH: 7
<212> TYPE: PRT
<213> ORGANISM: artificial sequence
<220> FEATURE:
<223> OTHER INFORMATION: synthetic polypeptide

<400> SEQUENCE: 399

Gly Asp Lys Asn Arg Pro Ser
1 5

<210> SEQ ID NO 400
<211> LENGTH: 32
<212> TYPE: PRT
<213> ORGANISM: artificial sequence
<220> FEATURE:
<223> OTHER INFORMATION: synthetic polypeptide

<400> SEQUENCE: 400

Gly Val Pro Asp Arg Phe Ser Gly Ser Arg Ser Gly Thr Ser Ala Ser
1 5 10 15

Leu Ala Ile Thr Gly Leu Gln Ala Glu Asp Glu Ala Asp Tyr Tyr Cys
20 25 30

<210> SEQ ID NO 401
<211> LENGTH: 7
<212> TYPE: PRT
<213> ORGANISM: artificial sequence
<220> FEATURE:
<223> OTHER INFORMATION: synthetic polypeptide

<400> SEQUENCE: 401

Glu Val Asn Asn Arg Pro Ser
1 5

<210> SEQ ID NO 402
<211> LENGTH: 32
<212> TYPE: PRT
<213> ORGANISM: artificial sequence
<220> FEATURE:
<223> OTHER INFORMATION: synthetic polypeptide

<400> SEQUENCE: 402

Gly Val Ser His Arg Phe Ser Gly Ser Lys Ser Ala Asn Thr Ala Ser
1 5 10 15

Leu Thr Ile Ser Gly Leu Gln Ala Glu Asp Glu Ala Asp Tyr Tyr Cys
20 25 30

<210> SEQ ID NO 403
<211> LENGTH: 7
<212> TYPE: PRT
<213> ORGANISM: artificial sequence
<220> FEATURE:
<223> OTHER INFORMATION: synthetic polypeptide

<400> SEQUENCE: 403

```
Glu Gly Ser Lys Arg Pro Ser
 1               5


<210> SEQ ID NO 404
<211> LENGTH: 32
<212> TYPE: PRT
<213> ORGANISM: artificial sequence
<220> FEATURE:
<223> OTHER INFORMATION: synthetic polypeptide

<400> SEQUENCE: 404

Gly Val Pro Glu Arg Phe Ser Gly Ser Asn Ser Gly Asn Thr Ala Thr
 1               5                   10                  15

Leu Thr Ile Gly Arg Val Glu Ala Gly Asp Glu Ala Asp Tyr Tyr Cys
            20                  25                  30


<210> SEQ ID NO 405
<211> LENGTH: 32
<212> TYPE: PRT
<213> ORGANISM: artificial sequence
<220> FEATURE:
<223> OTHER INFORMATION: synthetic polypeptide

<400> SEQUENCE: 405

Gly Ile Pro Asp Arg Phe Ser Gly Ser Ser Ser Gly Asn Ser Ala Ser
 1               5                   10                  15

Leu Thr Ile Thr Gly Ala Gln Ala Glu Asp Glu Ala Asp Tyr Tyr Cys
            20                  25                  30


<210> SEQ ID NO 406
<211> LENGTH: 7
<212> TYPE: PRT
<213> ORGANISM: artificial sequence
<220> FEATURE:
<223> OTHER INFORMATION: synthetic polypeptide

<400> SEQUENCE: 406

Ser Ala Ser Ser Leu Gln Ser
 1               5


<210> SEQ ID NO 407
<211> LENGTH: 32
<212> TYPE: PRT
<213> ORGANISM: artificial sequence
<220> FEATURE:
<223> OTHER INFORMATION: synthetic polypeptide

<400> SEQUENCE: 407

Gly Val Pro Ser Arg Phe Ser Gly Ser Gly Ser Gly Thr Asp Phe Thr
 1               5                   10                  15

Leu Thr Ile Ser Ser Leu Gln Pro Glu Asp Phe Ala Ser Tyr Phe Cys
            20                  25                  30


<210> SEQ ID NO 408
<211> LENGTH: 7
<212> TYPE: PRT
<213> ORGANISM: artificial sequence
<220> FEATURE:
<223> OTHER INFORMATION: synthetic polypeptide

<400> SEQUENCE: 408

Lys Ala Ser Ser Leu Glu Ser
 1               5
```

-continued

<210> SEQ ID NO 409
<211> LENGTH: 32
<212> TYPE: PRT
<213> ORGANISM: artificial sequence
<220> FEATURE:
<223> OTHER INFORMATION: synthetic polypeptide

<400> SEQUENCE: 409

Gly Val Pro Ser Arg Phe Ser Gly Ser Gly Ser Ala Thr Glu Phe Thr
1 5 10 15

Leu Thr Ile Asn Ser Leu Gln Pro Asp Asp Phe Ala Thr Tyr Tyr Cys
20 25 30

<210> SEQ ID NO 410
<211> LENGTH: 7
<212> TYPE: PRT
<213> ORGANISM: artificial sequence
<220> FEATURE:
<223> OTHER INFORMATION: synthetic polypeptide

<400> SEQUENCE: 410

Ser Ala Ser Thr Leu Gln Ser
1 5

<210> SEQ ID NO 411
<211> LENGTH: 32
<212> TYPE: PRT
<213> ORGANISM: artificial sequence
<220> FEATURE:
<223> OTHER INFORMATION: synthetic polypeptide

<400> SEQUENCE: 411

Gly Val Pro Ser Arg Phe Ser Gly Ser Gly Ser Gly Thr Glu Phe Thr
1 5 10 15

Leu Thr Ile Ser Ser Leu Gln Pro Glu Asp Phe Ala Thr Tyr Tyr Cys
20 25 30

<210> SEQ ID NO 412
<211> LENGTH: 7
<212> TYPE: PRT
<213> ORGANISM: artificial sequence
<220> FEATURE:
<223> OTHER INFORMATION: synthetic polypeptide

<400> SEQUENCE: 412

Lys Ala Ser Ser Leu Ala Ser
1 5

<210> SEQ ID NO 413
<211> LENGTH: 32
<212> TYPE: PRT
<213> ORGANISM: artificial sequence
<220> FEATURE:
<223> OTHER INFORMATION: synthetic polypeptide

<400> SEQUENCE: 413

Gly Ala Pro Ser Arg Phe Ser Gly Ser Gly Ser Gly Thr Asp Phe Thr
1 5 10 15

Leu Thr Ile Ser Ser Leu Gln Pro Asp Asp Phe Ala Thr Tyr Tyr Cys
20 25 30

<210> SEQ ID NO 414
<211> LENGTH: 7
<212> TYPE: PRT
<213> ORGANISM: artificial sequence
<220> FEATURE:

<223> OTHER INFORMATION: synthetic polypeptide

<400> SEQUENCE: 414

Ala Ala Ser Thr Leu Gln Ser
1 5

<210> SEQ ID NO 415
<211> LENGTH: 32
<212> TYPE: PRT
<213> ORGANISM: artificial sequence
<220> FEATURE:
<223> OTHER INFORMATION: synthetic polypeptide

<400> SEQUENCE: 415

Gly Val Pro Ser Arg Phe Ser Gly Ser Gly Ser Gly Thr Glu Phe Thr
1 5 10 15

Leu Thr Ile Ser Gly Leu Gln Pro Glu Asp Phe Ala Thr Tyr Tyr Cys
20 25 30

<210> SEQ ID NO 416
<211> LENGTH: 744
<212> TYPE: DNA
<213> ORGANISM: artificial sequence
<220> FEATURE:
<223> OTHER INFORMATION: synthetic polynucleotide

<400> SEQUENCE: 416
acctaggacg gtgaccttgg tccctccgcc gaaaaccaca tgatcactag tactatccca 60
cgcctgacag taatagtcgg cctcatcccc ggcttcgacc ctgccgatgg tcagggtggc 120
cgtgttccca gagttggagc cagagaatcg ctcagggacc cctgagggcc gcttactgcc 180
ctcataaatc atgagtttgg gggctttgcc tgggtgctgt tgataccagg agacatagtt 240
ataaccacca acgtcactgc tggttccagt gcaggagatg gtgatcgact gtccaggaga 300
cccagacacg gaggcaggct gagtcagagc agactgcgat ccgccaccgc cagagccacc 360
tccgcctgaa ccgcctccac ctgaagagac ggtgaccagg gtgccctggc cccagtgctg 420
gaagccactg taatcctcct ctcttgcaca gtaatacaga gccgtgtcct cgggagtcac 480
agagttcagc tgcagggaga agaggttctt ggacgtgtct gggttgatgg ttattcgact 540
tttcacagat actgcataat cattatacca cttggacctg tagtatgtcc ttcccagcca 600
ctcaaggcct ctcgatgggg actgcctgat ccagttccaa gcagcactgt tgctagagac 660
actgtccccg gagatggcac aggtgagtga gagggtctgc gagggcttca ccagtcctgg 720
acctgactgc tgcagctgta cctg 744

<210> SEQ ID NO 417
<211> LENGTH: 723
<212> TYPE: DNA
<213> ORGANISM: artificial sequence
<220> FEATURE:
<223> OTHER INFORMATION: synthetic polynucleotide

<400> SEQUENCE: 417
acctaggacg gtcagcttgg tccctccgcc gaataccctt agatgggtac cactgctgtc 60
ccgggagtga cagtaatagt cagcctcatc ttccgcctga gccccagtga tggtcaagga 120
agctgagttt cctgagctgg agccagagaa tcggtctggg atccctgagg gccggatgtt 180
tttaccatag atgacaagga gaggggcctg tcctggcttc tgctggtacc aacttgcata 240
atagcttctg aggctgtctc cttggcatgt gatcgtgact gtctgtccca aggccacaga 300

-continued cacagcaggg tcctgagtca gctcaggcga tccgccaccg ccagagccac ctccgcctga 360
accgcctcca cctgaggaga cggtgaccag ggttccctgg ccccagtagt caatagaacc 420
aaagtaatct ttagcgcagt aatacacagc cgtgtcctcg tctctcagac tgttcagttg 480
tagatacagt gtgttcttgg cgtcgtctct ggagatggtg aatctgccct tcacagagtc 540
tgcataatat gtgccacccc cattactact aatagatgaa acatattcca gtcccttccc 600
tggagcctgg cggacccagt gcatagcata gttactgaag gtgaatccag acgctgcaca 660
ggagagtctc agggaccccc caggctggac cacgcctccc cccgactcct gcagctgcac 720
ctg 723

<210> SEQ ID NO 418
<211> LENGTH: 723
<212> TYPE: DNA
<213> ORGANISM: artificial sequence
<220> FEATURE:
<223> OTHER INFORMATION: synthetic polynucleotide

<400> SEQUENCE: 418
acgtttgatc tccagcttgg tccctccgcc gaaagtgacc gggaaaacac tagcctgttg 60
acaaaaataa gatgcaaaat cttcaggctg caggctgctg atggtgagag tgaaatctgt 120
cccagatcca ctgccgctga atcttgatgg gaccccactt tgcaaactgg atgcagaata 180
aatgaggagt ctagggactt tccctggtct ctgctgatac caggctaacc acttgcttat 240
atcctgactc gcccgacaag tgatggtgac tctgtctcct acagaagcag acacggaaga 300
tggagactga gtcagcacaa tttccgatcc gccaccgcca gagccacctc cgcctgaacc 360
gcctccacct gaggagacgg tgaccagggt gccctggccc caggagtcaa accccgaacc 420
attctcctcc ttcacacagt aatagacagc cgtgtcctca gctctcagac tgctcatttg 480
aagatacacc gtgttcatgg aattgtctct ggagatgatg gatctgccct tcacggagtc 540
tgcgtagtat gtgctgcccc cattactatt aatagctgaa acatattcca gtcccttccc 600
tggagcctgg cggacccagt gaatagcata gttactgaag gtgaatccag aggctgaaca 660
ggagagtctc agggaccccc caggctggac caagcctccc cctgactgct gcagctgtac 720
ctg 723

<210> SEQ ID NO 419
<211> LENGTH: 717
<212> TYPE: DNA
<213> ORGANISM: artificial sequence
<220> FEATURE:
<223> OTHER INFORMATION: synthetic polynucleotide

<400> SEQUENCE: 419
acgtttgata tccactttgg tcccttggcc gaacgtcaac ggataactac tatactgttg 60
gcagtaataa gttgcaaaat catcaggctg caggctgttg atggtgagag tgaactctgt 120
cgcagatcca ctgccgctga accttgatgg gaccccactt tctaaactag atgccttata 180
gatcagggcc ttaggggctt ttcctggttt ctgctgatac caggccaacc acctactaat 240
actctcactg gcccggcaag tgatactgac tctgtctcct acagatgcag acagggtgga 300
aggagactga gtcatcacaa catccgatcc gccaccgcca gagccacctc cgcctgaacc 360
gcctccacct gaggagacgg tgaccagggt gccacggccc cagagatcga agtaccagtt 420
atctctcgca cagtaataca cagccgtgtc ctcagctctc aggctgttca tctgcagata 480
cagcgtgttc ttggaattgt ctctggagat ggtgaaccgg cccttcacag agtctgcgta 540

```
gtttgtgtaa ctactactac tactaatgta tgaaacccac tccagcccct tccctggagt    600

ctggcggacc cagtgcatgc catagctgct gaaggtgaat ccagacgctg cacaggagag    660

tctcaggaac cccccaggct ggaccaagcc tccccccgac tcctgcagct gcacctg       717
```

```
<210> SEQ ID NO 420
<211> LENGTH: 726
<212> TYPE: DNA
<213> ORGANISM: artificial sequence
<220> FEATURE:
<223> OTHER INFORMATION: synthetic polynucleotide

<400> SEQUENCE: 420

acgtttgatt tccaccttgg tccccccgcc gatagtgagc gggtaaacgc caagttgttg     60

acaatagtaa gttgcaaaat cttcaggctg caggctgctt attgtcagag tgaattctgt    120

cccagatcca ctgccgctga atcttgatgg gaccccactt tgcaaagtgg atgcagaatg    180

gatcaggagc ttaggggctt tccctggttt ctgctgatac caggctaacc acctgctcat    240

atcctgactc gcccgacaag tgatggtgac tctgtctcct acagatgcag acagtgagga    300

tggagactgc gtcaacacaa tttccgatcc gccaccgcca gagccacctc cgcctgaacc    360

gcctccacct gaagagacgg tgaccagggt tccctggccc cagtagtcaa gggcttcatc    420

atagtacagg gctctcgcac agtaatacac agccgtgtcc tcagctctca ggctgttcat    480

ttgcagatac agcgtgttct tggaattgtc tctggagatg gtgaatcggc ccttcacgga    540

gtctgcatag tatttattac ttccatcata tgatataact gccacccact ccagcccctt    600

gcctggagcc tggcggaccc agtgcatgcc atagctactg aaggtgaatc cagaggctgc    660

acaggagagt ctcagggacc tcccaggttg gaccacgcct cccccagact ccaccagctg    720

cacctg                                                               726
```

```
<210> SEQ ID NO 421
<211> LENGTH: 723
<212> TYPE: DNA
<213> ORGANISM: artificial sequence
<220> FEATURE:
<223> OTHER INFORMATION: synthetic polynucleotide
<220> FEATURE:
<221> NAME/KEY: misc_feature
<222> LOCATION: (24)...(24)
<223> OTHER INFORMATION: n=a,t,c, org

<400> SEQUENCE: 421

acgtttgatc tccagcttgg tccntgggcc gaacgtcctc gaaatagtat gatattgctg     60

gcagtaataa gttgcaaaat catcaggctg caggctgctg atggtgagag tgaaatctgt    120

cccagatcca ctgccgctga accttgatgg ggccccactg gctaaactag aggccttata    180

gatcaggagt ttaggggctt tccctggctt ctgctgatac caggccaacc agtgataaat    240

accctcactg gcccggcagg tgatggtgac tctgtctcca atagatgcag acagggtgga    300

aggagactgg gtcatctgga tgtccgatcc gccaccgcca gagccacctc cgcctgaacc    360

gcctccacct gaggagacgg tgaccagggt cccctggccc cagtagtcaa aggaaccact    420

actatcctct ctcgcacagt aatatacagc cgtgtcttcg gctctcaggc tgttcatttg    480

cagatacagt gagttcttgg cgttgtctct ggagatggtg aatcggcccc tcactgagtc    540

tgcataaaat gtgtttttac cactaccacc agtggacgag acccactcca gccccttccc    600

tggagactgg cggacccagt tcatgctata ggtattgaag atgaatccag agcctgcaca    660
```

ggagagtctc agggaccccc caggcttgac caggcctccc cccgactcct gcagctgcac 720
ctg 723

<210> SEQ ID NO 422
<211> LENGTH: 729
<212> TYPE: DNA
<213> ORGANISM: artificial sequence
<220> FEATURE:
<223> OTHER INFORMATION: synthetic polynucleotide

<400> SEQUENCE: 422
acgtttgatt tccaccttgg tccctccgcc gaaagtgagc gggtaactat taaggttttg 60
acagtaataa gttgcaaaat cttcaggctg caggccgctg attgtgagag tgaattctgt 120
cccagatcca ctgccgctga accttgacgg gaccccactt tgcaaagtgg atgcagcata 180
gatcaggagt ttaggggctt tccctggttt ttgctgatac caggctaaat aattgttaat 240
gccctgactg gcccggcaag tgatggtgac tctgtctcct acagatgcag acaggaggga 300
tggagactgg gtcatctgga tgtccgatcc ggcaccgcca gagccacctc cgcctgaacc 360
gcctccacct gaggagacgg tgaccagggt tccctggccc cagtagtcta agtagtcacc 420
gtcccaccca cggactttcg cacagtaata tacggccgtg tcctcggctc tcaggctgtt 480
catttgcaga tacagcgtgt tcttggcgtt gtctctggag atggtgaatc ggcccttcac 540
agagtctgcg tagtttgtgt aactaccact actactaatg tatgaaaccc actccagccc 600
cttgcctgga gcctggcgga cccagtgcat gccatagcta ctgaaggtga atccagacgc 660
tgcacaggag agtctcaggg acctcccagg ctggaccacg cctcccccag actccaccag 720
ctgcacctg 729

<210> SEQ ID NO 423
<211> LENGTH: 738
<212> TYPE: DNA
<213> ORGANISM: artificial sequence
<220> FEATURE:
<223> OTHER INFORMATION: synthetic polynucleotide

<400> SEQUENCE: 423
acctaggacg gtcagcttgg tccctccgcc gaacacccaa ccactcaggc tgctgtcata 60
ggactggcag taataatcag cctcatcctc agcctggagc ccagtgatgg ccagggaggc 120
tgaggtgcca gacttggagc cagagaatcg gtcagggacc cctgagggcc gattgctgtt 180
aacatagatg aggagtttgg gggccgttcc tggaagttgt tggtaccagt gtacatcata 240
acctgccccg atgttggagc tgctcccagt gcaggagatg gtgaccctct gccctggggc 300
cccagacact gagggcggct gcgtcaacac agactgcgat ccgccaccgc cagagccacc 360
tccgcctgaa ccgcctccac ctgaggagac ggtgaccagg gttccctggc cccagtagtc 420
aaagtaatcg tagccactga atccacctct cgcacagtaa tacacggccg tgtcctcggc 480
tctcaggctg ttcatttgaa gatacagcgt gttcttggaa ttgtctctgg agatggtgaa 540
tcggcccttc acggagtctg cgtagtatgt gctaccaccg ctataaataa ctgagaccca 600
ctccagcccc ttccctggag cctggcggac ccagctcatg tagttgctac tgacggtgaa 660
cccagaggct gcacaggaga gtctcaggga ccccccaggc tggatcaacc ctcctccaga 720
ctccaccagc tgcacctg 738

<210> SEQ ID NO 424
<211> LENGTH: 738

<212> TYPE: DNA
<213> ORGANISM: artificial sequence
<220> FEATURE:
<223> OTHER INFORMATION: synthetic polynucleotide

<400> SEQUENCE: 424
acccaggacg gtcagcttgg tccctccgcc gaacacccct cgatgggtac tactgctgtc 60
ccgggagtta cagtaatagt cagcctcatc ttccgcctga gccccagtga tggtcaagga 120
agctgtgttt cctgagctgg agccagagaa tcggtctggg atccctgagg gccggttgtt 180
tttattatag atgacaagta taggggcctg tcctggcttc tgctggtacc agcttgcata 240
atagcctctg agaatgtctc cttggcacgt gattgtgact gtctctccca aggccacaga 300
cacagcaggg tcctgagtca gctcagacga tccgccaccg ccagagccac ctccgcctga 360
accgcctcca cctgaggaga cggtgaccag ggtgccctgg ccccagtagt caaagtaatc 420
accaccccaa aaatcgtaat aggcccctct cgcacagtaa tacacagccg tgtcctcggc 480
tctcaggctg ttcatttgca gatacagtga gttcttggcg ttgtctctgg agatggtgaa 540
tcggcccttc actgagtctg cgtagtatat gtaactacta ctactaatgg atgagaccca 600
ctccagcccc ttccctggag cctggcggac ccagttcatg ctatagctac tgaaggtgaa 660
tccagaggct gcacaggaga gtctcaggga ccccccaggc ttgaccaggc ctccccccga 720
ctcctgcagc tgcacctg 738

<210> SEQ ID NO 425
<211> LENGTH: 753
<212> TYPE: DNA
<213> ORGANISM: artificial sequence
<220> FEATURE:
<223> OTHER INFORMATION: synthetic polynucleotide

<400> SEQUENCE: 425
acgtttgatt tccaccttgg tccctccgcc gaaagtgagc ggactttgtc gaccttgcat 60
gcagtaataa accccaacat cctcagcctc cactctgctg attttcagtg taaaatctgt 120
gcctgatcca ctgccactga acctgtcagg gaccccggag gcccgattag aacccaagta 180
gatcaggagt tgtggagact gccctggctt ctgcaggtac caatccaaat agttgtatcc 240
attagtatgc aggaggctct gactagacct gcaggagatg gaggccggct ctccaggggt 300
gacgggcagg gagagtggag actgcgtcaa cacaatttcc gatccgccac cgccagagcc 360
acctccgcct gaaccgcctc cacctgagga gacggtgacc attgtccctt ggccccagat 420
atcaaaagca cccgaccaat aactccctga accatagcct ttcgcacagt aatacacagc 480
cgtgtcctca gctctcaggc tgttcatttg cagatacagc gtgttcttgg aattgtctct 540
ggagatggtg aatcggccct tcacggagtc tgcatagtat ttattacttc catcatatga 600
tataactgcc acccactcca gccccttgcc tggagcctgg cggacccagt gaatgccata 660
gctactgaag gtgaatccag aggctgcaca ggagagtctc agggacctcc caggctggac 720
cacgcctccc cctgactgct gcagctgtac ctg 753

<210> SEQ ID NO 426
<211> LENGTH: 723
<212> TYPE: DNA
<213> ORGANISM: artificial sequence
<220> FEATURE:
<223> OTHER INFORMATION: synthetic polypeptide

<400> SEQUENCE: 426
acctaggacg gtgaccttgg tcccaactcc gaagacatac ttcccactgc tgtcccggga 60
gtgacagtaa tagtcagcct catcttccgc ctgagcccca gtgatggtca aggaagctgt 120
gtttcctgag ccggagccag agaatcggtc tgggatccct gagggccggt tgttttcacc 180
atacaagaca aggagagggg cctgtcctgg cttctgctgg taccagcttg cataatagct 240
tctgaggctg tctccttggc atgtgatctt gactgtctgt cccaaggcca cagacacagc 300
agggtcctga gtcagtataa cgtgcgatcc gccaccgcca gagccacctc cgcctgaacc 360
gcctccactt gaggagacgg tgaccagggt gccctggccc cagtcggcag agtagctctc 420
accgcccagc ttcgcacagt aatatacggc cgtgtcttcg gctctcagtc tgttcatttg 480
cagatacagc gtgctcttga aattgtctct ggagacggtg aaccggccct tcacggagtc 540
tccgtagtat gtgccagcac catcagcact aatagctgag acccattcca gccccttccc 600
tggagcctgg cgggcccagc tcatggtata ggtgctgaag gtgaatccag aggctgcaca 660
ggagagtctc agggaccccc caggcttgac caggcctccc ccagactcga ccagctgcac 720
ctg 723

<210> SEQ ID NO 427
<211> LENGTH: 732
<212> TYPE: DNA
<213> ORGANISM: artificial sequence
<220> FEATURE:
<223> OTHER INFORMATION: synthetic polynucleotide

<400> SEQUENCE: 427
acctaggacg gtcagctttg tccctccgcc gaataccaca tgagggttac cactgctgtc 60
ccgggagtta cagtaatagt cagcctcatc ttccgcctga gccccagtga tggtcaagga 120
agctgtgttt cctgagctgg agccagagaa tcggtctggg atccctgagg gccggttgtt 180
tttaccatag atgacaagta caggggcctg tcctggcttc tgctggtacc agcttgcata 240
atagcttctg aggctgtctc cttggcatgt gatcctgact gtctgtccca aggccacaga 300
cacagcaggg tcctgagtca gctcagacga tccgccaccg ccagagccac ctccgcctga 360
accgcctcca cctgaggaga cggtgaccag ggtgccctgg ccccagtagt cagtagccac 420
tgttgaacgt cccaaagttt ttgcacaata atacaaggcc gtgtcctcgg ctctcaggct 480
gttcatttgc agatacagcg tgttcttgga attgtctctg gagatggtga accggccctt 540
cacggagtct gcgtagtatg tgctaccacc accaccagta atagctgaga cccactccag 600
ccccttccct ggagcctggc ggacccagat catggcatag ttgctaaagg tgaatccaga 660
ggctgcacag gagagtctca gggacctccc aggctggacc acgcctcccc cagactccac 720
caactgcacc tg 732

<210> SEQ ID NO 428
<211> LENGTH: 723
<212> TYPE: DNA
<213> ORGANISM: artificial sequence
<220> FEATURE:
<223> OTHER INFORMATION: synthetic polynucleotide

<400> SEQUENCE: 428
acctaggacg gtgaccttgg tccctccgcc gaataccaca tggttaccac tgctgtcccg 60
ggagttacag taatagtcag cctcatcttc cgcctgagcc ccagtgatgg tcaaggaagc 120
tgtgtttcct gagctggagc cagagaatcg gtctgggatc cctgagggcc ggttgttttt 180
accatagatg acaagtacag ggcctgtcc tggcttctgc tggtaccagc ttgcataata 240
gcttctgagg ctgtctcctt ggcatgtgat cgtgactgtc tgtcccaagg ccacagacac 300
agcagggtcc tgagtcaaca cagactgcga tccgccactg ccagagccac ctccgcctga 360
accgcctcca cctgaggaga cggtgaccag ggttccctgg ccccagtagt cttgagctgc 420
ccccgggcct ttcgcacagt aatatacggc cgtgtcctcg gctctcaggc tgttcatttg 480
cagatacagc gtgttcttgg aattgtctct ggagatggtg aaccggccct tcacggagtc 540
tgcgtagtat gtgctaccac cactaccact aatagctgag acccactcca gccccttccc 600
tggagcctgg cggacccagc tcatggcata gctgctaaag gtgaatccag aggctgcaca 660
ggagagtctc agggacctcc caggctggac cacgcctccc ccagactcca cccgctgcac 720
ctg 723

<210> SEQ ID NO 429
<211> LENGTH: 729
<212> TYPE: DNA
<213> ORGANISM: artificial sequence
<220> FEATURE:
<223> OTHER INFORMATION: synthetic polynucleotide

<400> SEQUENCE: 429
acctaggacg gtcagcttgg tccctccgcc gaatacgaga tggttaccac tgctgtcccg 60
ggagttacag taatagtcag cctcatcttc cgcctgagcc ccagtgatgg tcaaggaagc 120
tgtgttccct gagctggagc cagagaatcg gtctgggatc cctgagggcc ggttgttttt 180
accatagatg acaagtacag gggcctgtcc tggcttctgc tggtaccagc ttgcataata 240
gcttctgagg ctgtctcctt ggcatgtgat cttgactgtc tgtcccaagg ccacagacac 300
agcagggtcc tgagtcagct cagacgatcc gccaccgcca gagccacctc cgcctgaacc 360
gcctccaccc gaggagacgg tgaccagggt tccctggccc cagtagtcaa aggcggtagt 420
agctcccacc gcccctctcg cacagtaata cacggccgtg tcttcggctc tcaggctgtt 480
catttgcaga tacagcgtgt tcttggaatt gtctctggag atggtgaacc ggcccttcac 540
ggagtctgcg tagtatgtgc taccaccact accactaata gctgagaccc actccagccc 600
cttccctgga gcctggcgga cccaccccat ggccaaggtg ctaaaggtga atccagaggc 660
tgcacaggag agtctcaggg accccccagg ctgtaccaag cctcccccag actccaccag 720
ctgcacctg 729

<210> SEQ ID NO 430
<211> LENGTH: 729
<212> TYPE: DNA
<213> ORGANISM: artificial sequence
<220> FEATURE:
<223> OTHER INFORMATION: synthetic polynucleotide

<400> SEQUENCE: 430
acctaggacg gtcagcttgg tccctccgcc gaacaccagt tgcttaccac tgctgtcccg 60
ggacgtacag taatagtcag cctcatcctc cgcccgagcc ccagtgatgg tcaaggaagc 120
tgtgtttcct gagctggagc cagagaatcg gtctgggatc cctgagggcc ggttgttttt 180
accatagatg acaagtacag gggcctgtcc tggcttctgc tggtaccagc ttgcataata 240
gcttctgagg ctgtctcctt ggcatgtgat cctgactgtc tgtcccaagg ccacagacac 300
agcagggtcc tgagtcagct cagacgatcc gccaccgcca gagccacctc cgcctgaacc 360
gcctccacct gaggagacgg tgaccgtggt cccttggccc cagacgtcca tacctagcga 420
cgagctgcta gccactttcg cacagtaata cacggccgtg tcctcggctc tcaggctgtt 480
catttgcaga tacagcgtgt tcttggaatt gtctctggag atggtgaacc ggcccttcac 540
ggagtctgcg tagtatgtgc taccaccact accactaata gctgagaccc actccagccc 600
cttccctgga gcctggcgga cccagttcat gctatagcta ctgaaggtga atccagaggc 660
ttcacaggag agtctcaggg accccccagg cttgaccagg cctcccccg actcctgcag 720 ctgcacctg 729

<210> SEQ ID NO 431
<211> LENGTH: 729
<212> TYPE: DNA
<213> ORGANISM: artificial sequence
<220> FEATURE:
<223> OTHER INFORMATION: synthetic polynucleotide

<400> SEQUENCE: 431
acctaggacg gtcagcttgg tccctccgcc gaataggata agcctaccac tgctgtcccg 60
agagctgcag aaatagtcag cctcatcttc cgcctgagcc ccagtgacgg tcaaggtagc 120
tgtgcttcct gaggtggagc cagagaatcg gtttgggatc cctgagggcc gattgctttt 180
accaaagaag acaagtagag gggcctgtcc tggcttctgc ttgtaccagc ttgcataata 240
gtctctgagg ctgtctcctt gacatgtgat cctgactgtc tgtcccaagg ccacagacac 300
agcagggtcc tgagtcagca cagactgcga tccgccaccg ccagagccac ctccgcctga 360
accgcctcca cctgaggaga cggtgaccag ggttccctgg ccccagtagt ccaaagaggt 420
agctcccact acagatttcg cacagtaata tagggccgtg tcttcggctc tcagggtgtt 480
catttgcaga tacagtgtgt tcttggaatt gtctctggag atggtgaacc ggcccttcac 540
ggagtctgcg tagtatgtgc cactaccact accactgata gcggagaccc actccagccc 600
cttccctgga gcctggcgga cccagatcaa ggcatagttg ctaaaggtga atccagaggc 660
tgcacaggag agtctcaggg accccccagg ctataccaag cctcccccag actccaccag 720
ctgcacctg 729

<210> SEQ ID NO 432
<211> LENGTH: 726
<212> TYPE: DNA
<213> ORGANISM: artificial sequence
<220> FEATURE:
<223> OTHER INFORMATION: synthetic polynucleotide

<400> SEQUENCE: 432
acctaggacg gtgaccttgg tccctccgcc gaataccaca gagttaccac tgctgtcccg 60
ggagttacag taatagtcag cctcatcttc cgcctgagcc ccagtgatgg tcaaggaagc 120
tgtgtttcct gagctggagc cagagaatcg gtctgggatc cctgagggcc ggttgttttt 180
accatagatg acaagtacag gggcctgtcc tggcttctgc tggtaccagc ttgcataata 240
gcttctgagg ctgtctccct ggcatgtgat tctgactgtc tgtcccaagg ccacagacac 300
agcagggtcc tgagtcagct cagacgatcc gccaccgcca gagccacctc cgcctgaacc 360
gcctccacct gaggagacgg tgaccagggt tccctggccc cagtagtcaa aggcagtagc 420
tcccactatt ccttttgcac agtaatatac ggccgtgtcc tcggctctca gggtgttcat 480
ttgcagatac agcgtgttct tggaattgtc tctggagatg gtgagccggc ccctcacgga 540
gtctgcgtag tatgtcctac caccgctact agtaatagct gagacccact ccagcccctt 600
ccctggagcc tggcggaccc agctcatggc atagctgcta aaggtgaatc cagaggctgc 660

-continued

```
acaggagagt ctcagggacc ccccaggctg taccaagcct ccccccgact cctgcagctg    720

cacctg                                                                726


<210> SEQ ID NO 433
<211> LENGTH: 30
<212> TYPE: PRT
<213> ORGANISM: artificial sequence
<220> FEATURE:
<223> OTHER INFORMATION: synthetic polypeptide

<400> SEQUENCE: 433

Gln Val Gln Leu Gln Glu Ser Gly Gly Gly Leu Val Lys Pro Gly Gly
 1               5                  10                  15

Ser Leu Arg Leu Ser Cys Glu Ala Ser Gly Phe Thr Phe Ser
            20                  25                  30
```